(12) United States Patent
Braisted et al.

(10) Patent No.: US 6,271,198 B1
(45) Date of Patent: Aug. 7, 2001

(54) CONSTRAINED HELICAL PEPTIDES AND METHODS OF MAKING SAME

(75) Inventors: Andrew C. Braisted; J. Kevin Judice; Robert S. McDowell; J. Christopher Phelan, all of San Francisco; Melissa A. Starovasnik; James A. Wells, both of Burlingame, all of CA (US)

(73) Assignee: Genentech, Inc., South San Francisco, CA (US)

( * ) Notice: Subject to any disclaimer, the term of this patent is extended or adjusted under 35 U.S.C. 154(b) by 0 days.

(21) Appl. No.: 08/965,056

(22) Filed: Nov. 5, 1997

Related U.S. Application Data

(63) Continuation-in-part of application No. 08/876,698, filed on Jun. 16, 1997, now abandoned, and application No. 08/743,698, filed on Nov. 6, 1996.
(60) Provisional application No. 60/049,787, filed on Jun. 16, 1997, now abandoned.

(51) Int. Cl.$^7$ .................................................... A61K 38/00
(52) U.S. Cl. ................................. 514/2; 514/12; 514/13; 514/14; 514/15; 514/16; 514/17; 530/324; 530/325; 530/326; 530/327; 530/328; 530/329
(58) Field of Search ........................... 530/317, 324–329; 514/9, 11, 2, 12–17

(56) References Cited

U.S. PATENT DOCUMENTS

| | | |
|---|---|---|
| 5,141,867 | 8/1992 | Ivanoff et al. . |
| 5,440,013 | 8/1995 | Kahn . |
| 5,464,933 | 11/1995 | Bolognesi et al. . |
| 5,508,382 | 4/1996 | Ohaski et al. . |

FOREIGN PATENT DOCUMENTS

| | | |
|---|---|---|
| WO 89/01943 | 3/1989 | (WO) . |
| WO 91/15238 | 10/1991 | (WO) . |
| WO 91/15512 | 10/1991 | (WO) . |
| WO 92/09625 | 6/1992 | (WO) . |
| WO 94/02505 | 2/1994 | (WO) . |
| WO 94/03494 | 2/1994 | (WO) . |
| WO 94/16109 | 7/1994 | (WO) . |
| WO 94/29332 | 12/1994 | (WO) . |
| WO 95/31480 | 11/1995 | (WO) . |
| WO 95/34312 | 12/1995 | (WO) . |
| WO 96/19495 | 6/1996 | (WO) . |
| WO 96/20953 | 7/1996 | (WO) . |
| WO 96/40191 | 12/1996 | (WO) . |
| WO 97/00267 | 1/1997 | (WO) . |
| WO 97/12988 | 4/1997 | (WO) . |

OTHER PUBLICATIONS

Fox, J., Bio/Technology, vol. 12, Feb. 1994, p. 128.*
Stein et al., Clinical Infectious Diseases, 17, 1993, 749–771.*
Jeffrey L. Fox, Bio/Technology, vol. 12 Feb, p. 28, 1994.*
Stein et al., CID, 1993: Oct. 17, 1993, pp. 749–771.*
Fahey et al, Clin Exp Immunology, 88, 1–5, 1992.*
Akke et al., "Three–Dimensional Solution Structure of Calbindin $D_{9k}$," *Techniques in Protein Chemistry II*, Villafranca, J., San Diego:Academic Press pp. 401–408 (1991).
Atherton et al., "Solid Phase Peptide Synthesis using $N\alpha$–Fluorenylmethoxycarbonylamino Acid Pentafluorophenyl Esters" *J. Chem. Soc., Chem. Commun.* pp. 165–166 (1985).
Aue et al., "Two–dimensional spectroscopy. Application to nuclear magnetic resonance" *J. Chem. Phys.* 64:2229–2246 (1976).
Bax et al., "MLEV–17–Based Two–Dimensional Homonuclear Magnetization Transfer Spectroscopy" *J. Magn. Reson.* 65:355–360 (1985).
Berman et al., "Neutralization of Multiple Laboratory and Clinical Isolates of Human Immunodeficiency Virus Type 1 (HIV–1) by Antisera Raised against gp120 from the MN Isolate of HIV–1" *Journal of Virology* 66:4464–4469 (1992).
Bernstein et al., "The Protein Data Bank: A Computer–based Archival File for Macromolecular Structures" *J. Mol. Biol.* 112:535–542 (1977).
Blacklow et al., "A Trimeric Subdomain of the Simian Immunodeficiency Virus Envelope Glycoprotein" *Biochemistry* 34:14955–14962 (1995).
Bodenhausen et al., "Selection of Coherence–Transfer Pathways in NMR Pulse Experiments" *J. Magn. Reson.* 58:370–388 (1984).
Bothner–By et al., "Structure Determination of a Tetrasaccharide: Transient Nuclear Overhauser Effects in the Rotating Frame" *J. Am. Chem. Soc.* 106:811–813 (1984).
Bracken et al., "Synthesis and nuclear magnetic resonance structure determination of an $\alpha$–helical, bicyclic, lactam–bridged hexapeptide" *J. Am. Chem. Soc.* 116:6431–6432 (1994).
Braunschweiler et al., "Coherence Transfer by Isotropic Mixing: Application of Proton Correlation Spectroscopy" *J. Magn. Reson.* 53:521–528 (1983).
Brown et al., "Helix–Coil Transition of the Isolated Amino Terminus of Ribonuclease" *Biochemistry* 10:470–476 (1971).
Bullough et al., "Structure of influenza haemagglutinin at the pH of membrane fusion" *Nature* 371:37–43 (1994).
Callewaert et al., "The Disulphide Bridges of Apamin" *FEBS Letters* 1:111–113 (1968).

(List continued on next page.)

*Primary Examiner*—Dwayne C. Jones
*Assistant Examiner*—C. Delacroix-Muirheid
(74) *Attorney, Agent, or Firm*—Piper Marbury Rudnick & Wolfe LLP; Steven B. Kelber

(57) ABSTRACT

Provided are cyclized peptides with a constrained region(s) having an $\alpha$-helical conformation. Constrained helical peptides having amino acid sequences from HIV gp41 are provided, as is their use in preparing antibodies that prevent viral membrane fusion. Also provided are methods for making such cyclized peptides.

4 Claims, 34 Drawing Sheets

OTHER PUBLICATIONS

Carr et al., "A Spring–Loaded Mechanism for the Conformational Change of Influenza Hemagglutinin" *Cell* 73:823–832 (1993).

Cavanagh et al., "Suppression of Cross–Relaxation Effects in TOCSY Spectra via a Modified DIPSI–2 Mixing Sequence" *J. Magn. Reson.* 96:670–678 (1992).

Chan et al., "Core Structure of gp41 from the HIV Envelope Glycoprotein" *Cell* 89:263–273 (1997).

Chen et al., "A Molecular Clasp in the Human Immunodeficiency Virus (HIV) Type 1 TM Protein Determines the Anti–HIV Activity of gp41 Derivatives: Implication for Viral Fusion" *Journal of Virology* 69:3771–3777 (1995).

Chorev et al., "Cyclic parathyroid hormone related protein antagonists: Lysine 13 to aspartic acid 17 [i to (i +4(] side chain to side chain lactamization" *Biochemistry* 30:5968–5974 (1991).

Edelhoch, "Spectroscopic Determination of Tryptophan and Tyrosine in Proteins" *Biochemistry* 6:1948–1954 (1967).

Fass et al., "Retrovirus envelope domain at 1.7 angstrom resolution" *Nature* 3:465–468 (1996).

Fields et al., "Solid phase peptide synthesis utilizing 9–fluorenylmethoxycarbonyl amino acids" *Int. J. Peptide Protein Res.* 35:161–214 (1990).

Gao et al., "Molecular Cloning and Analysis of Functional Envelope Genes from Human Immunodeficiency Virus Type 1 Sequence Subtypes A through G" *Journal of Virology* 70:1651–1667 (1996).

Habermann et al. "Zur Biochemie der Bienengiftpeptide Melittin und Apamin" *Biochemische Zeitschrift* 343:192–203 (1965).

Haigwood et al., "Native but Not Denatured Recombinant Human Immunodeficiency Virus Type 1 gp120 Generates Broad–Spectrum Neutralizing Antibodies in Baboons" *Journal of Virology* 66:172–182 (1992).

Harper et al., "Helix Stop Signals in Proteins and Peptides: The Capping Box" *Biochemistry* 32:7605–7609 (1993).

Haynes et al. "Conversion of an immunogenic human immunodeficiency virus (HIV) envelope synthetic peptide to a tolerogen in chimpanzees by the fusogenic domain of HIV gp41 envelope protein" *Journal of Experimental Medicine* 177:717–727 (1993).

Houston Jr. et al., "Lactam bridge stabilization of α–helical peptides: ring size, orientation and positional effects" *J. Peptide Science* 1:274–282 (1995).

Jackson et al., "General approach to the synthesis of short α–helical peptides" *J. Am. Chem. Soc.* 113:9391–9392 (1991).

Jiang et al., "HIV–1 inhibition by a peptide" *Nature* 365:113 (1993).

Jiang et al., "Inhibition of HIV–1 Infection by a Fusion Domain Binding Peptide from the HIV–1 Envelope Glycoprotein GP41" *Biochemical and Biophysical Research Communications* 195:533–538 (1993).

Johnson Jr. et al., "Circular Dichroism of Polypeptide Solutions in the Vacuum Ultraviolet" *J. Am. Chem. Soc.* 94:4389–4390 (1972).

Kaiser et al., "Color Test for Detection of Free Terminal Amino Groups in the Solid–Phase Synthesis of Peptides" *Analytical Biochemistry* 34:595–598 (1970).

Kumar et al., "A Two–Dimensional Nuclear Overhauser Enhancement (2D NOE) Experiment for the Elucidation of Complete Proton–Proton Cross–Relaxation Networks in Biological Macromolecules" *Biochem. & Biophys. Res. Comm.* 95:1–6 (1980).

Lawless et al., "HIV–1 Membrane Fusion Mechanism: Structural Studies of the Interactions between Biologically–Active Peptides from gp41" *Biochemistry* 35:13697–13708 (1996).

Lu et al., "A trimeric structural domain of the HIV–1 transmembrane glycoprotein" *Nature* 2(12):1075–1082 (1995).

Lupas et al., "Predicting Coiled Coils from Protein Sequences" *Science* 252:1162–1164 (1991).

Lyu et al., "α–Helix stabilization by natural and unnatural amino acids with alkyl side chains" *Proc. Natl. Acad. Sci. USA* 88:5317–5320 (1991).

Marion et al., "Application of Phase Sensitive Two–Dimensional Correlated Spectroscopy (COSY) for Measurements of $1_H–1_H$ Spin–Spin Coupling Constants in Proteins" *Biochem. & Biophys. Res. Comm.* 113:967–974 (1983).

Marqusee et al., "Unusually stable helix formation in short alanine–based peptides" *Proc. Natl. Acad. Sci. USA* 86:5286–5290 (1989).

Merrifield, R.B., "Solid Phase Peptide Synthesis. I. The Synthesis of a Tetrapeptide" *J. Am. Chem. Soc.* 85:2149–2154 (1963).

Osapay et al., "Multicyclic polypeptide model compounds. 1. Synthesis of a tricyclic amphiphilic α–helical peptide using an oxime resin, segment–condensation approach" *J. Am. Chem. Soc.* 112:6046–6051 (1990).

Osapay et al., "Multicyclic polypeptide model compounds. 2. Synthesis and conformational properties of a highly α–helical uncosapeptide constrained by three side–chain to side–chain lactam bridges" *J. Am. Chem. Soc.* 114:6966–6973 (1992).

Phelan et al., "A General Method for Constraining Short Peptides to an α–Helical Conformation" *J. Am. Chem. Soc.* 119:455–460 (1997).

Rabenstein et al., "HIV–1 gp41 Tertiary Structure Studied by EPR Spectroscopy" *Biochemistry* 35:13922–13928 (1996).

Rance, "Improved Techniques for Homonuclear Rotating–Frame and Isotropic Mixing Experiments" *J. Magn. Reson.* 74:557–564 (1987).

Ravi et al., "Cyclic peptide disulfides. Solution and Solid–State Conformation of Boc–Cys–Pro–Aib–Cys–NHMe, a Disulfide–Bridged Peptide Helix" *J. Am .Chem. Soc.* 105:105–109 (1983).

Salmon–Ceron et al., "Safety and Immunogenicity of a Recombinant HIV Type 1 Glycoprotein 160 Boosted by a V3 Synthetic Peptide in HIV–Negative Volunteers" *AIDS Res. and Human Retroviruses* 11:1479–1486 (1995).

Schollkopf et al., "Enantioselective Synthesis of (R)–Amino Acids Using L–Valine as Chiral Agent" *Angew. Chem. Int. Ed. Engl.* 20:798–799 (1981).

Shipolini et al., "The Structure fo Apamin" *Chem. Commun.* pp. 679–680 (1967).

Shugars et al., "Biophysical Characterization of Recombinant Proteins Expressing the Leucine Zipper–Like Domain of the Human Immunodeficiency Virus Type 1 Transmembrane Protein gp41" *Journal of Virology* 70:2982–2991 (1996).

Skelton et al. "Determination of the Solution Structure of the Peptide Hormone Guanylin: Observation of a Novel Form of Topological Stereoisomerism" *Biochemistry* 33:13581–13592 (1994).

Weiner et al., "An All Atom Force Field for Simulations of Proteins and Nucleic Acids" *J. Comp. Chem.* 7:230–252 (1986).

Weiner et al., "A New Force Field for Molecular Mechanical Simulation of Nucleic Acids and Proteins" *J. Am. Chem. Soc.* 106:765–784 (1984).

Wild et al., "Peptides corresponding to a predictive α–helical domain of human immunodeficiency virus type 1 gp41 are potent inhibitors of virus infection" *Proc. Natl. Acad. Sci. USA* 91:9770–9774 (1994).

Wild et al., "Propensity for a leucine zipper–like domain of human immunodeficiency virus type 1 gp41 to form oligomers correlates with a role in virus–induced fusion rather than assembly of the glycoprotein complex" *Proc. Natl. Acad. Sci. USA* 91:12676–12680 (1994).

Wild et al., "A synthetic peptide inhibitor of human immunodeficiency virus replication: Correlation between solution structure and viral inhibition" *Proc. Natl. Acad. Sci. USA* 89:10537–10541 (1992).

Zhang et al., "HIV–1 subtype and second–receptor use" *Nature* 383:768 (1996).

Zhang et al., "Synthetic CD4 exocyclics inhibit binding of human immunodeficiency virus type 1 envelope to CD4 and virus replication in T lymphocytes" *Nature Biotechnology* 15(2):150–154 (Feb. 1997).

* cited by examiner

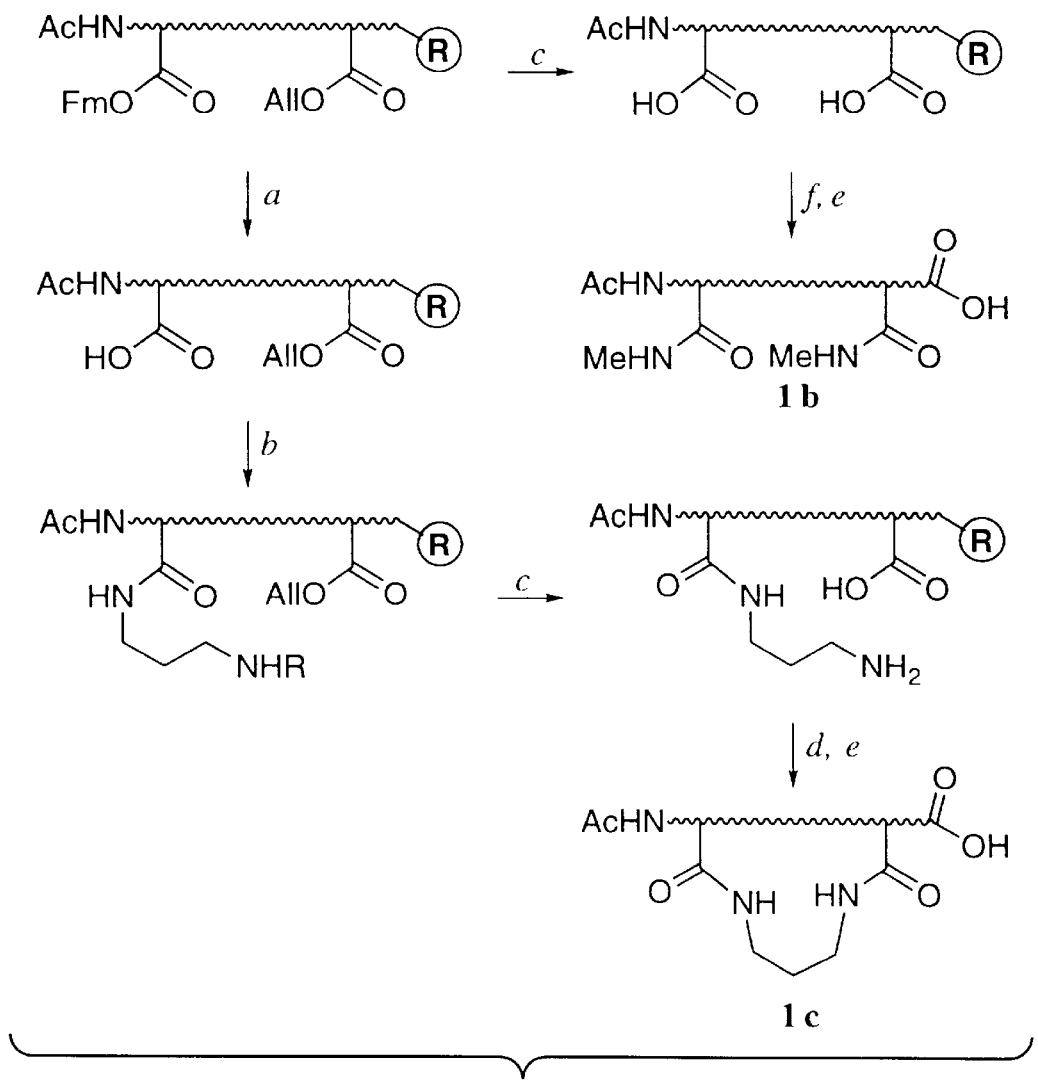
FIG._1

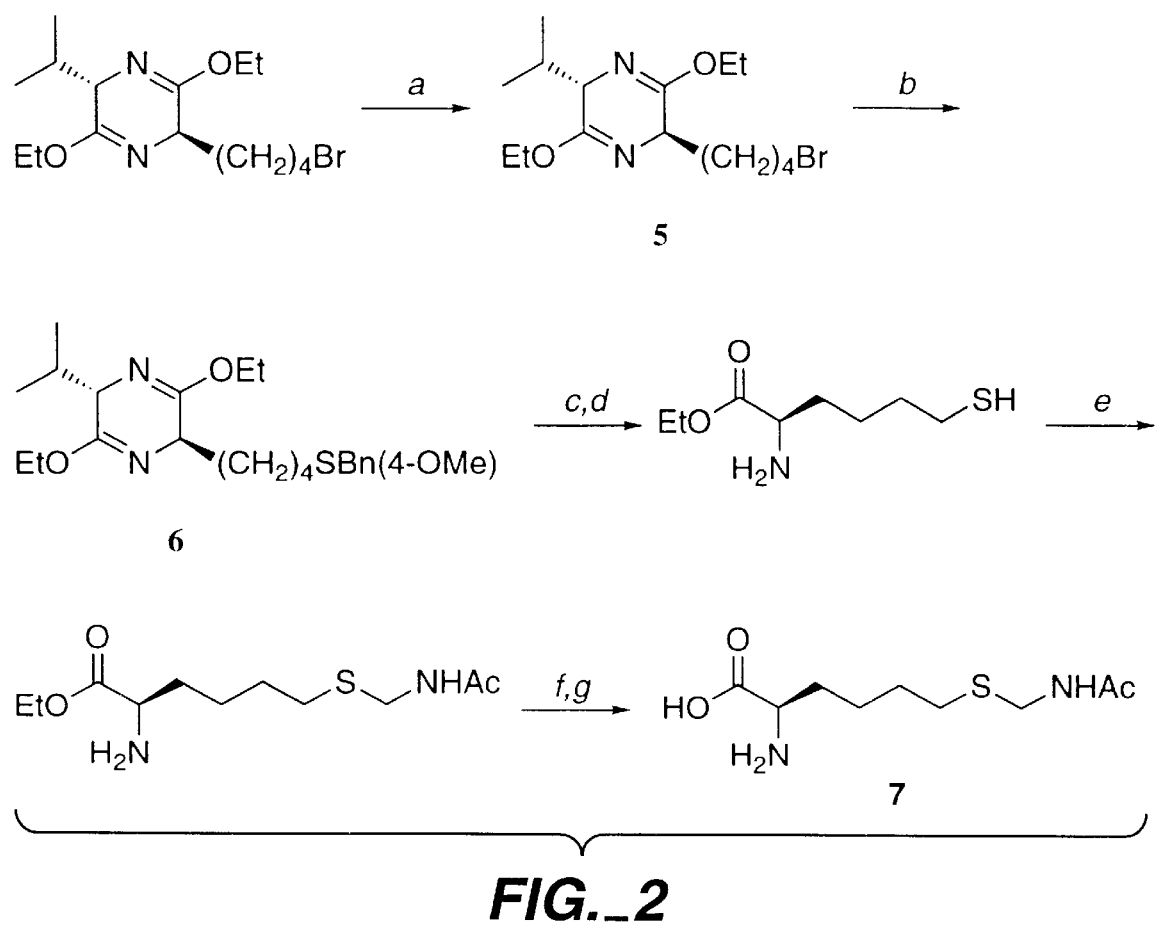
FIG._2

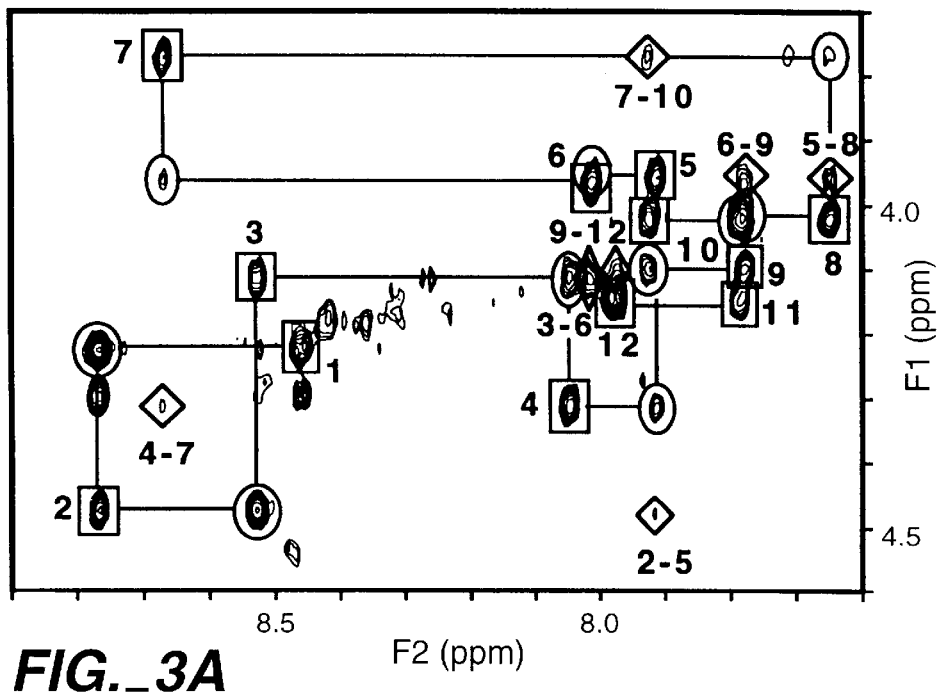
FIG._3A
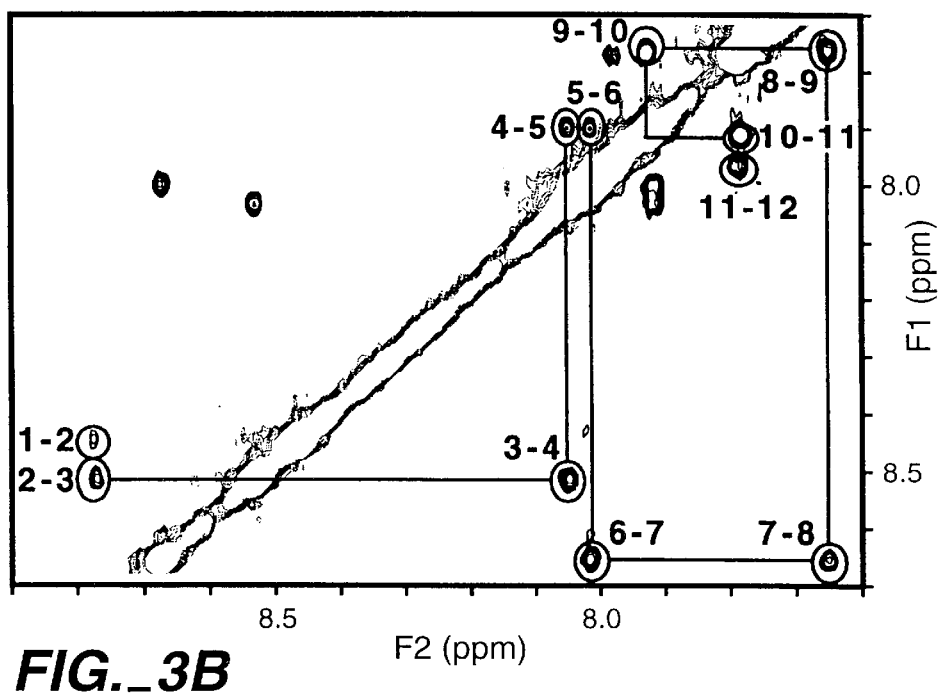
FIG._3B

| | 1        5              10 |
|---|---|
| | T  N  X  D  L  A  A  R  R  X  Q  Q |
| $(CH_2)_3$ LINK | |
| $d_{NN}$ (i,i+1) | |
| $d_{\alpha N}$ (i,i+1) | * * |
| $d_{\alpha N}$ (i,i+3) | |
| $d_{\alpha \beta}$ (i,i+3) | |
| $^3J_{HN-H\alpha}$ | |
| NO LINKER | |
| $d_{NN}$ (i,i+1) | * * |
| $d_{\alpha N}$ (i,i+1) | * |
| $d_{\alpha N}$ (i,i+3) | |
| $d_{\alpha \beta}$ (i,i+3) | |
| $^3J_{HN-H\alpha}$ | |

*FIG._4*

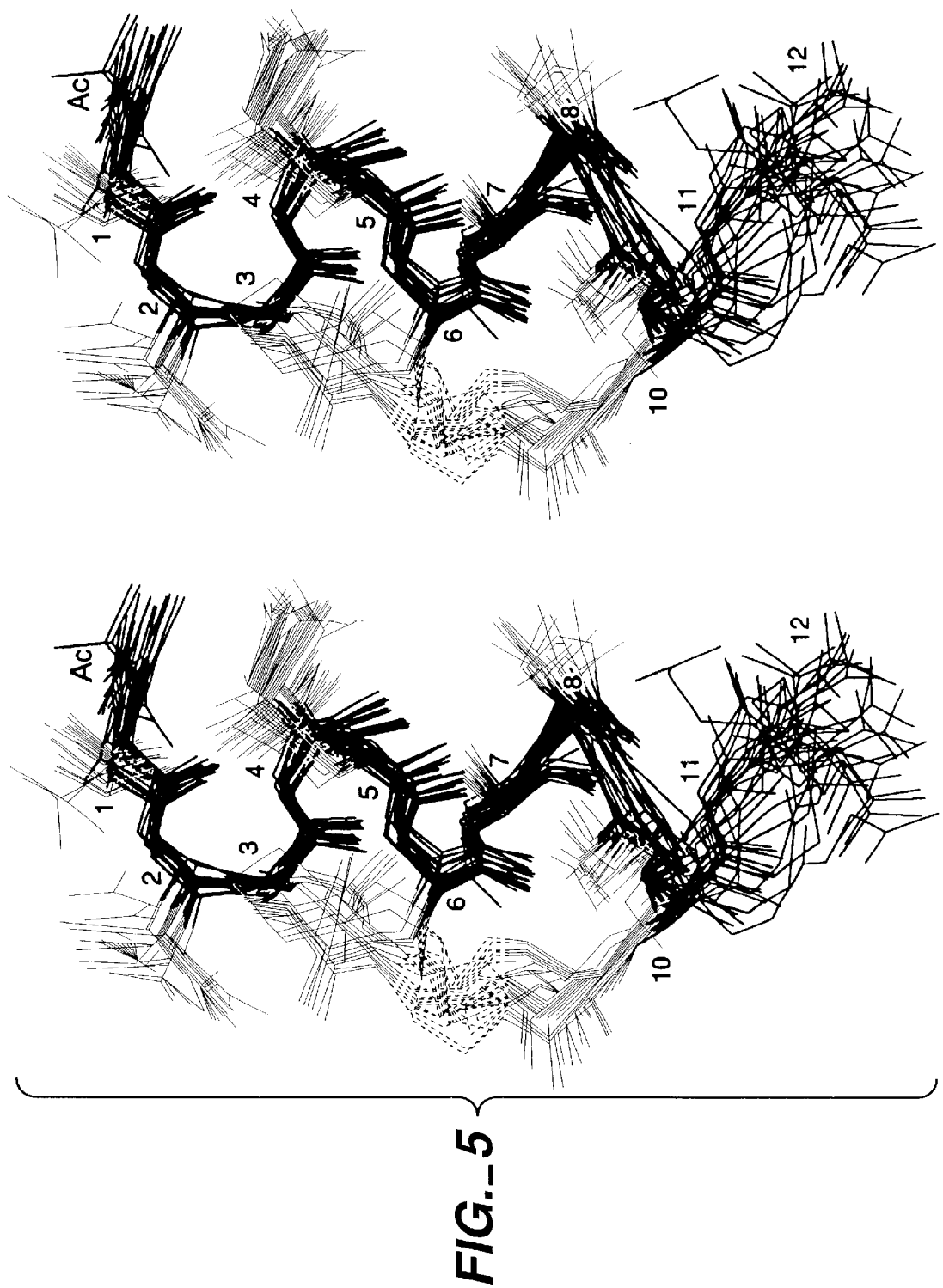
FIG.—5

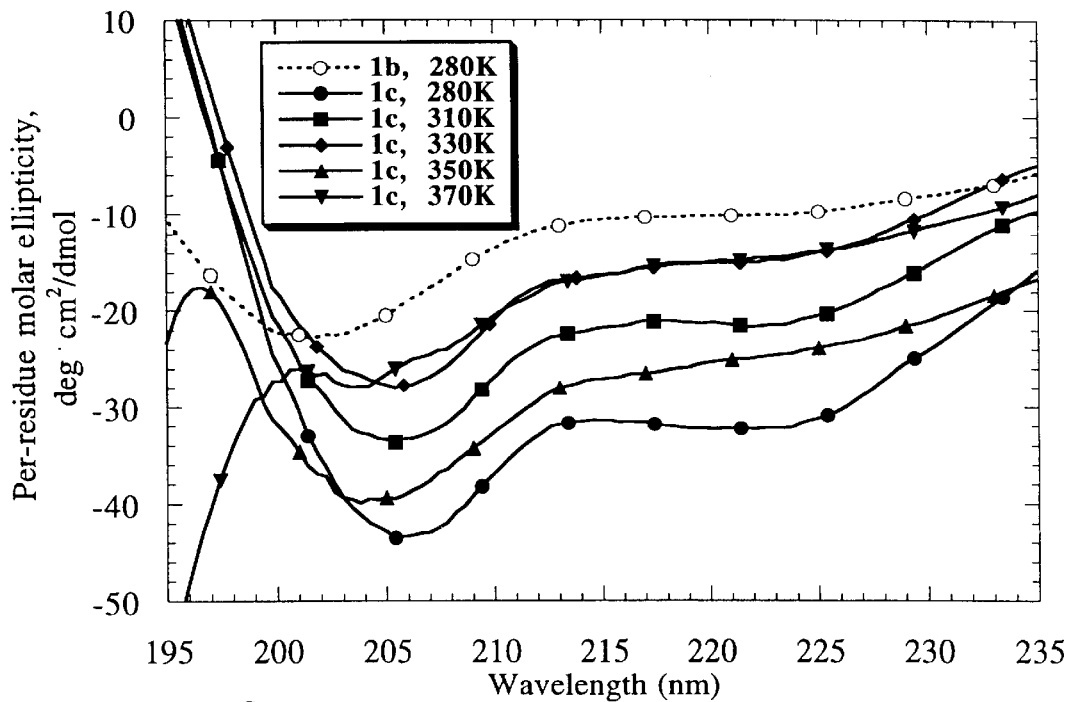
FIG._6
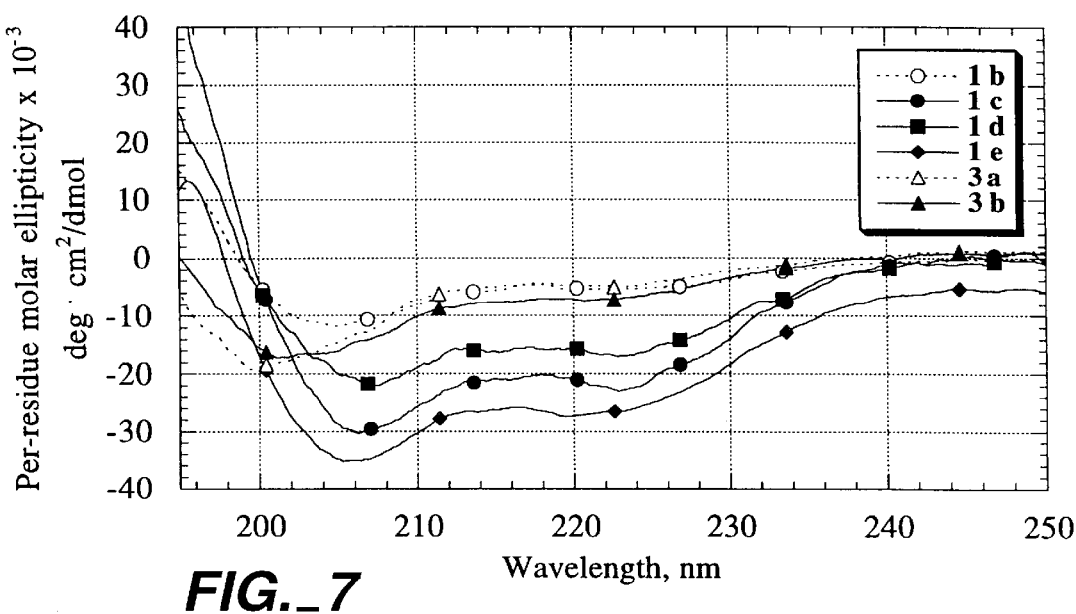
FIG._7

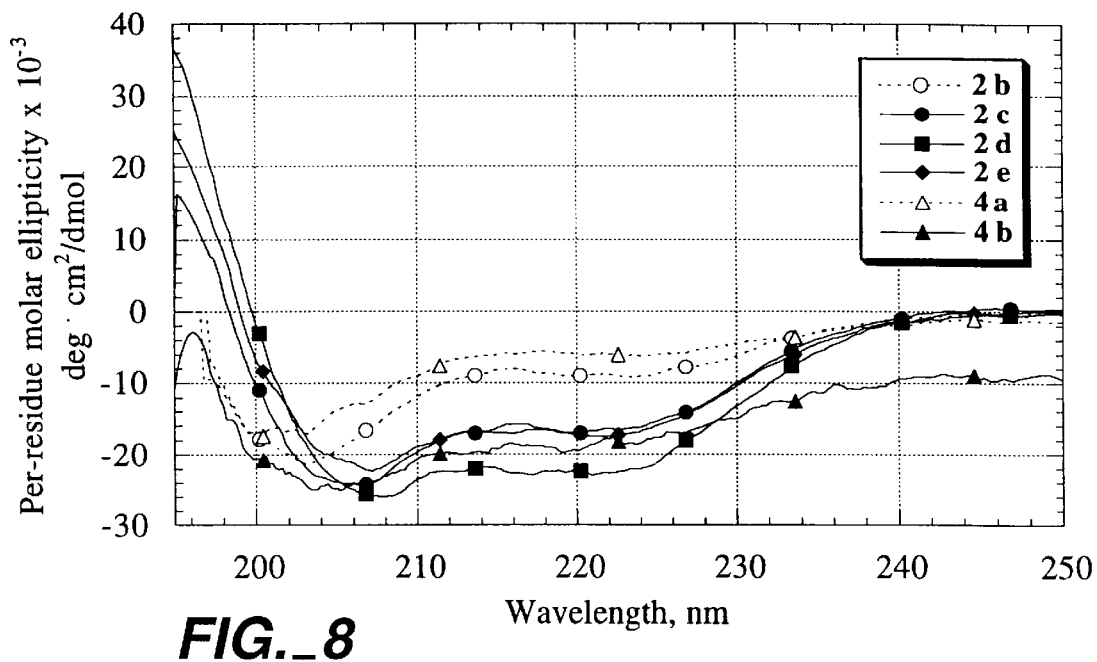
FIG._8
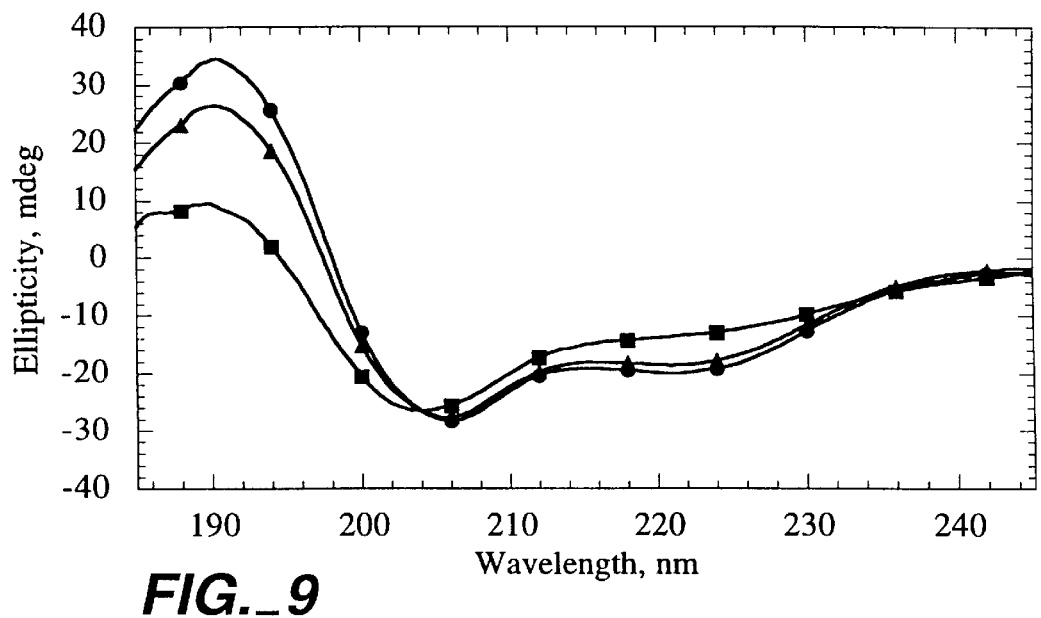
FIG._9

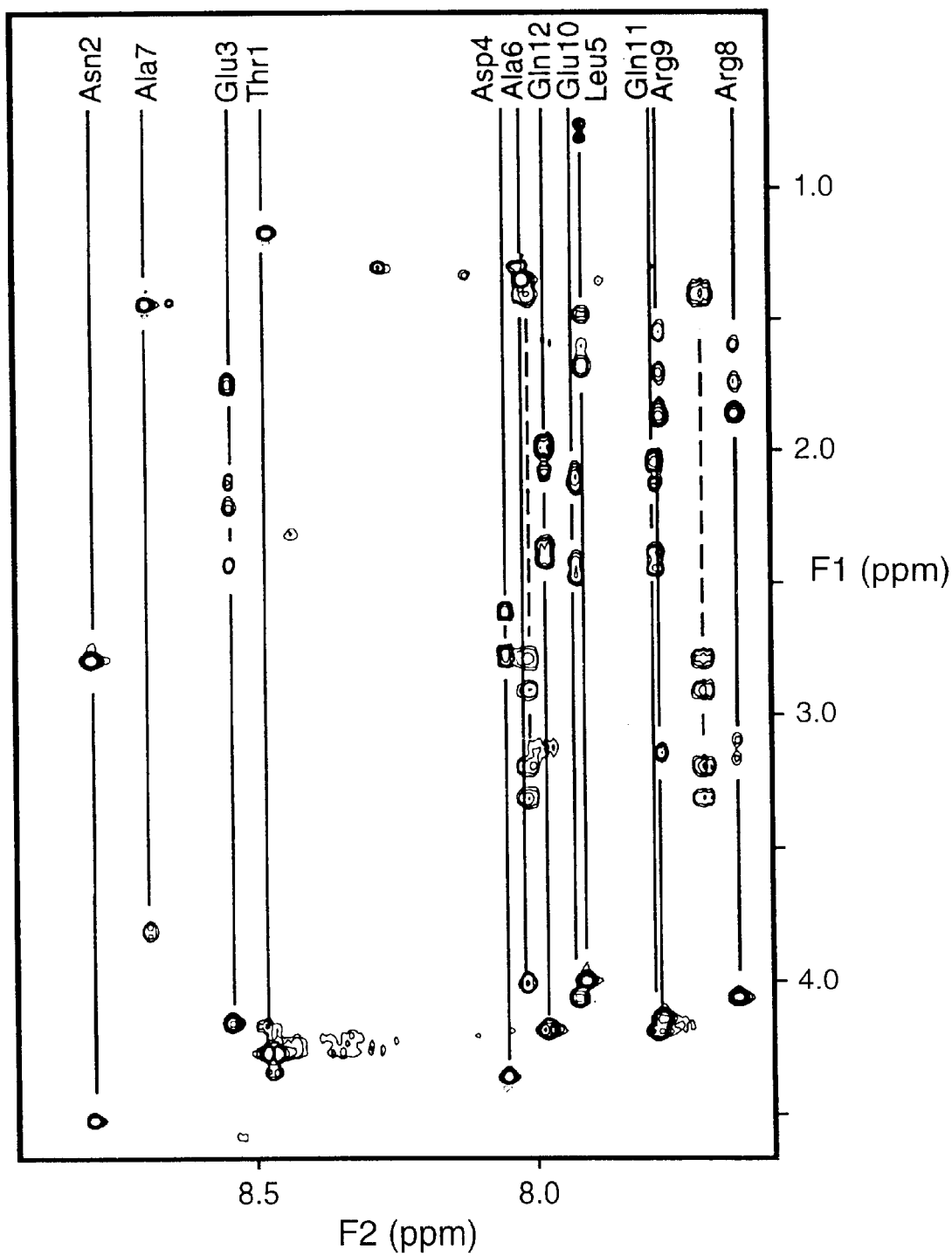
FIG._10

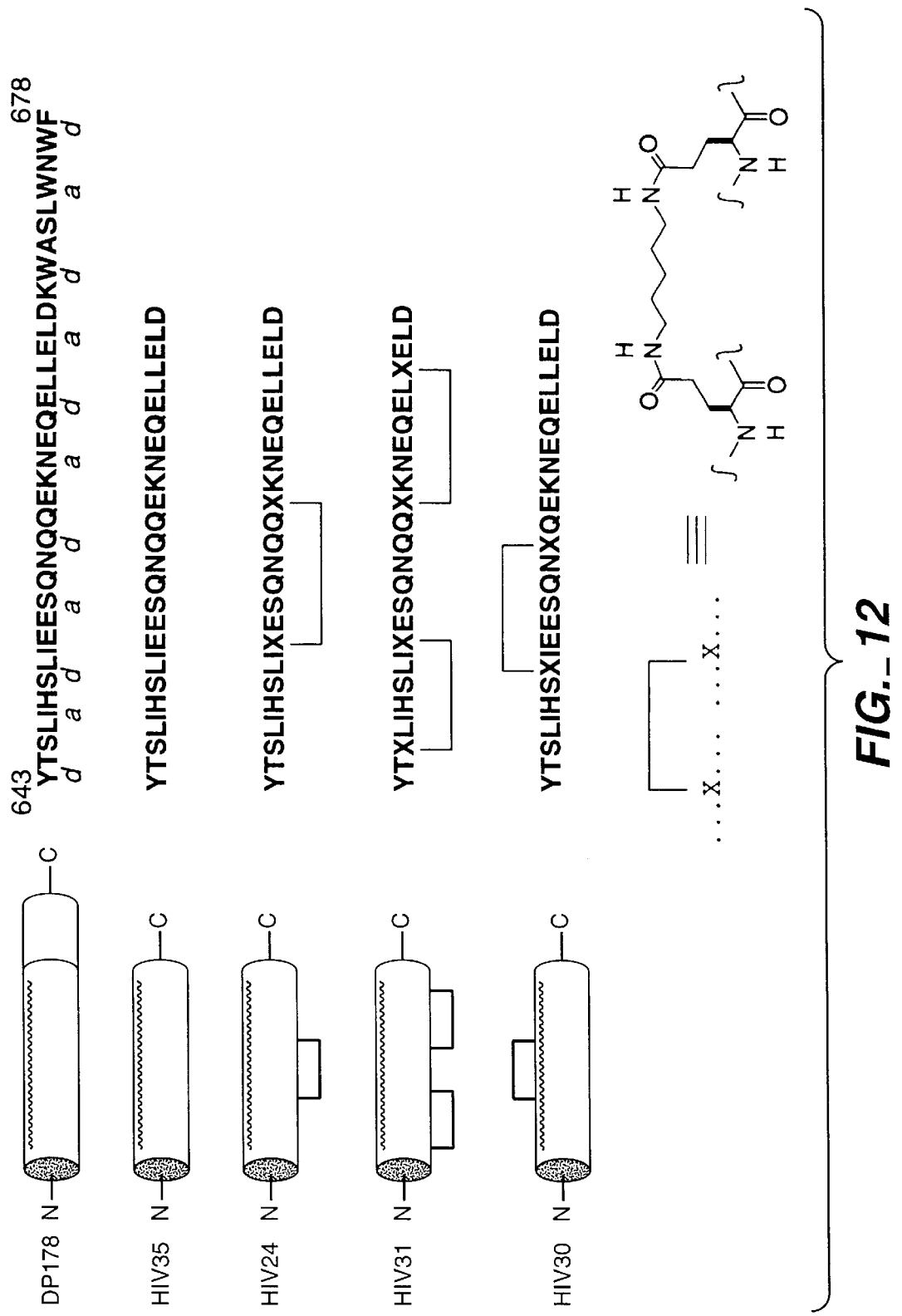
FIG._12

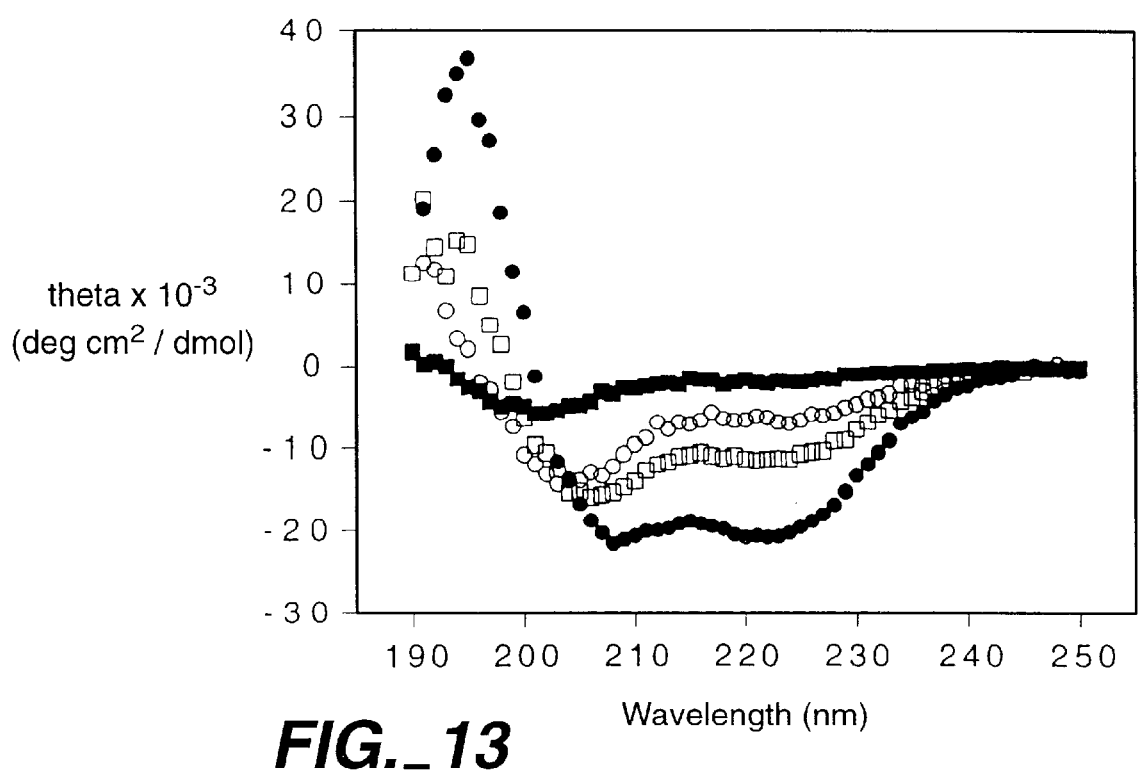
FIG._13

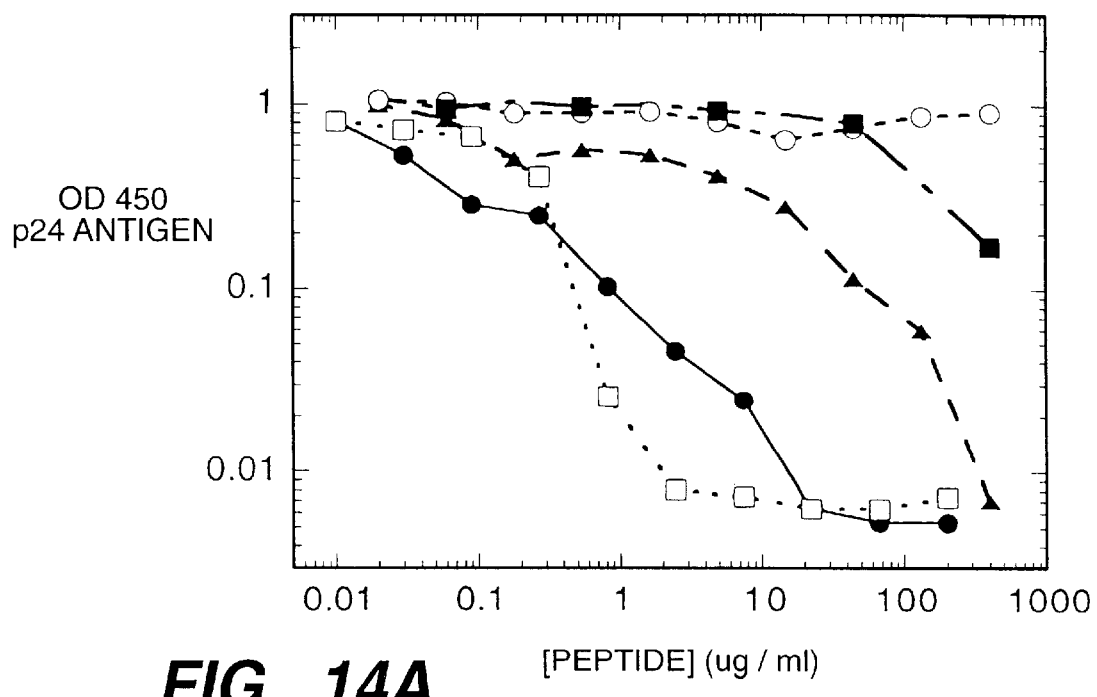
FIG._14A
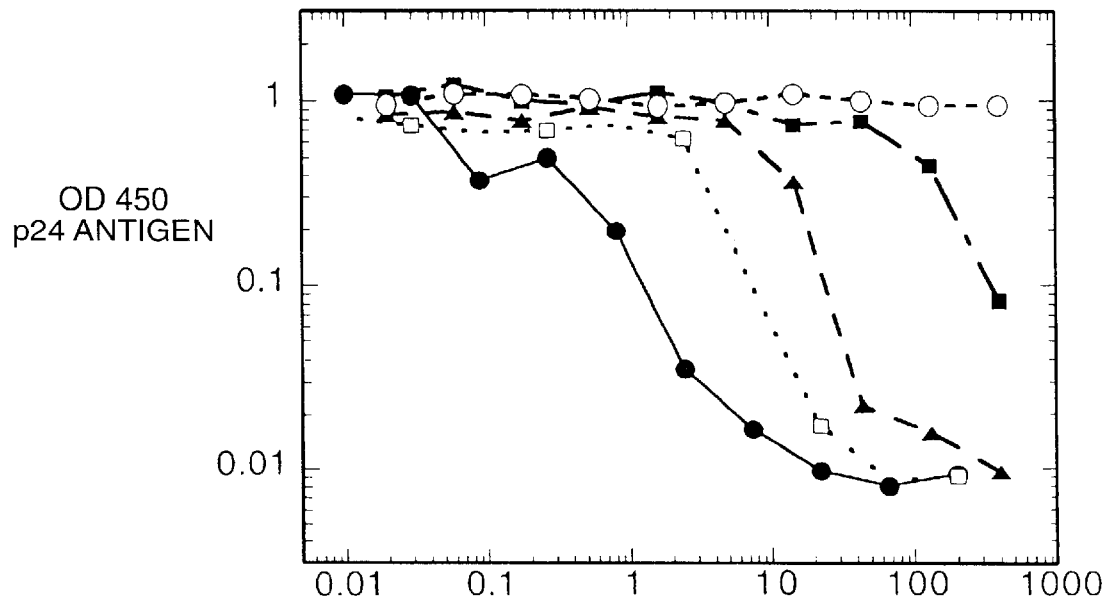
FIG._14B

FIG. 16A

```
                                                                              gp120/gp41
CONSENSUS.B  gGGdMrdNWRseLYKYKVvkIEplGvAPTkakrRvv..QrekRAvg?iGamflGflGaAGSTMgaasm
HIVJRCSF     G--D-RD---SE-------VK--PL-V---KAKR-VV...-REK--VG.I-ALFL-F--A-----GARSM  493
HIVJRFL      G--D-RD---SE-------VK--PL-V---KAKR-VV...-REK--VG.I-AVFL-F--A-----GAASM  527
HIVALA1      G--D-RD---SE-------VK--PL-V---RAKR-VV...-REK--VG.L-ALFL-F--A-----GARSM  526
HIVBRVA      G--N-RD---SE-------VK--PL-V---KAKR-VV...-REK--VG.L-ALFL-F--A-----GAASL  528
HIVJH3       G--N-RD---SE-------VK--LL-V---KAKR-VV...-REK--VG.I-AVFL-F--A-----GA.SM  531
HIVSC        G--D-RD---SE-------VK--PL-V---KAKR-VV...-REK--VGTI-AMFL-F--A-----GATSM  546
HIVBAL1      G--D-RD---SE-------VK--PL-V---KAKR-VV...-REK--VG.I-AVFL-F--A-----GAAAM  535
HIVYU2       G--D-RD---SE-------VK--PL-V---KAKR-VV...-REK--VG.I-AVFL-F--A-----GAASI  533
HIVMN        G--D-RD---SE-------VT--PL-V---KAKR-VV...-REK--VG.L-ALFL-F--A-----GAASV  522
HIVHXB2R     G--D-RD---SE-------VK--PL-V---KAKR-VV...-REK--A..I-ALFL-F--A-----GAASM  536
HIVLAI       G--D-RD---SE-------VK--PL-V---KAKR-VV...-REK--VG.I-ALFL-F--A-----GARSM  535
HIVNL43      G--D-RD---SE-------VK--PL-V---KAKR-VV...-REK--VG.I-ALFL-F--A-----GCTSM  540
HIVMFA       G--D-RD---SE-------VK--TL-V---KAKR-VV...-REK--VG.I-ALFL-F--A-----GAASM  533
HIVCAM1      G--D-RD---SE-------VK--PL-V---KAKR-VV...-REK--VGAI-ALFL-F--A-----GAVAL  533
HIVNY5CG     G--D-RD---SE-------VK--PL-V---KAKR-VV...-REK--VGLL-AVFL-F--A-----GAASM  535
HIVADA       G--D-RD---SE-------VK--PL-V---KAKR-VV...-REK--VGAL-ALFL-F--A-----GARSL  529
HIVJFL       G--N-RD---SK-------VK--PL-V---KAKR-VV...-RKK--VGTI-AMFL-F--A-----GAASI  532
HIVSIMI84    G--D-RD---SE-------VK--PL-V---KAKR-VV...-REK--VGTI-AMFL-F--A-----GAASM  530
HIVD31       G--D-RD---SE-------VK--PL-V---KAKR-VV...-REK--VGLI-ALFL-F--A-----GAASM  535
HIVSF162     G--N-RD---SE-------VK--PL-V---KAKR-VV...-REK--VGLL-AVFL-F--A-----GARSM  529
HIVOYI       A--D-RD---SE-------VK--PL-V---KARR-VV...-REK--V.TL-AMFL-F--A-----GARSL  526
HIVSF33      A--N-KD---SE-------VK--PL-V---KAKR-VV...-REK--VGML-AMFL-F--A-----GARSM  534
HIVCDC4      G--D-RD---SE-------VK--PL-V---KAKR-VV...-REK--VGVI-AMFL-F--A-----GAASI  531
HIVSF2       G--D-RD---SE-------IK--PL-I---KAKR-VV...-REK--VGML-AMFL-F--A-----GATSM  547
HIVSF2B13    G--D-RD---SE-------VK--PL-V---KAKR-VV...-REK--VGIV-AMFL-F--A-----GAVSL  534
HIVHAN       G--D-RD---SE-------VK--PL-V---KAKR-VV...-REK--VGII-AMFL-F--A-----GARSM  532
HIVRF        G--N-RD---NE-------VK--PL-V---KAKR-VV...-REK--VGML-AMFL-F--A-----GARSL  534
HIVWMJ2      G--N-RD---SE-------VR--PL-V---RAKR-VV...-REK--VGTI-AMFL-F--A-----GAGSI  544
HIVTB132     G--N-RD---SE-------VR--PL-V---KAKR-VV...-REK--VGTI-AMFL-F--A-----GAGSL  526
                                                                                        516
             G--N-RD---SE-------VK--PL-V---xAKR-VV...-REK--VG.I-AASP-F--A-----xAAPT
```

| | | | | | | |
|---|---|---|---|---|---|---|
| B2BR020W.01043hED | G--D-RD---SE------ | -VR--PL-I---RAKR-VV...... | -REK- | -VGTL-AMFL-F--A---- | -GAASV | 530 |
| B2TH014W.01123hED | G--D-RD---SE------ | -VK--PL-V---KPKR-VV...... | -REK- | -VGTI-AMFL-F--T---- | -GAASI | 522 |
| B2US711D.01143hED | G--D-RD---SE------ | -VK--PL-I---KAKR-VV...... | -REK- | -VGI.-AVFL-F--A---- | -GAAAM | 526 |
| B2US712D.01043hED | G--D-RE---SE------ | -VK--PL-V---KAKR-VV...... | -REK- | -VGF.-AMFL-F--A---- | -GAASM | 529 |
| B2US715D.01063hED | G--N-KD---SE------ | -VR--PL-I---RAKR-VV...... | -REK- | -AGL.-VMFL-F--A---- | -GAASI | 531 |
| B2US716D.01063hED | G--N-RD---SE------ | -VK--PL-V---RAKR-VV...... | -REK- | -VGI.-AMFL-F--A---- | -GAASL | 522 |
| B2HA593D.01013hED | G--D-RD---SE------ | -VK--PL-V---RAKR-VV...... | -REK- | -VGIV-AMFL-F--A---- | -GAASM | 552 |
| B2HA594D.01103hED | G--D-RD---SE------ | -VK--PL-V---KAKR-VV...... | -REK- | -VGAL-AMFL-F--A---- | -GAASM | 526 |
| B2HA596D.01043hED | G--D-RD---SE------ | -VK--PL-V---KAKR-VV...... | -REK- | -VGVL-AMFL-F--A---- | -GAASM | 533 |
| B2HA599D.01243hED | G--D-RD---SE------ | -VK--PL-V---KAKS-VV...... | -REK- | -VGTL-AMFL-L--A---- | -GAASM | 543 |
| B1HA651D.0113hED | G--D-RD---SE------ | -VK--PL-V---KAKR-VV...... | -REK- | -VGTL-AMFL-F--A---- | -GAASM | 527 |
| HIVRJS | G--D-RD---SE------ | -VK--PL-V---KAKR-VV...... | -REK- | -VGVI-AMFL-F--A---- | -GAASM | 532 |
| HIVGUN | G--D-RD---SE------ | -VK--PL-V---KAKR-VV...... | -REK- | -VGTI-VMFL-F--A---- | -GAASI | 497 |
| HIVSBA | G--D-RD---SE------ | -VR--PL-I---RAKR-VV...... | -REK- | -VG.I-AMFL-F--A---- | -GAASI | 277 |
| HIVSBC | G--D-RD---SE------ | -VK--PL-V---KAKR-VV...... | -REK- | -VG.I-AVFL-F--A---- | -GAASI | 275 |
| HIVSBB | A--D-RD---SE------ | -IQ--PL-V---KAKR-VV...... | -REK- | -VG.I-AVLF-F--A---- | -GAASL | 286 |
| B2BR014W.01012hED | G--D-RD---SE------ | -VK--PL-V---KAKR-VV...... | -RER- | -VGAL-AMFL-F--A---- | -GAASL | 532 |
| B2TH026W.01062hED | G--D-KD---SK------ | -VK--PL-V---RAKR-VV...... | -REK- | -VGTI-AMFL-F--A---- | -GAASI | 519 |
| HIVBR1 | G--D-RD---SE------ | -VK--PL-V---RAKR-VV...... | -RER- | -VGAL-AMFL-F--A---- | -GAASL | 532 |
| HIVTH6 | G--D-KD---SK------ | -VK--PL-V---RAKR-VV...... | -RER- | -VGTI-AMFL-F--A---- | -GAASL | 521 |
| HIVJ61 | G--N-RD---SE------ | -VK--PL-V---RAKR-VV...... | -REK- | -VG.I-AVFL-F--A---- | -GARSM | 262 |
| HIVJB02 | G--N-RD---SE------ | -VK--PL-V---RAKR-VV...... | -REK- | -VG.I-AVFL-F--A---- | -GARSM | 262 |
| B2BR020W.01062rED | G--D-RD---SE------ | -VK--PL-V---RAKR-EV...... | -REK- | -VGTL-AMFL-F--A---- | -GAASV | 532 |
| B2BR021W.01062rED | G--D-RD---SE------ | -VR--PL-I---RAKR-VV...... | -GEK- | -VGTI-AMFL-F--A---- | -GARSI | 535 |
| B2BR021W.01192rED | G--D-RD---SE------ | -VR--PL-V---KAKR-VV...... | -REK- | -VGTI-AMFL-F--A---- | -GAASI | 530 |
| HIVACH9 | G--D-RD---SE------ | -VK--PL-V---RAKR-VV...... | -REK- | -VGTI-AMFL-F------- | | 484 |
| HIVACP1 | G--N-RD---SE------ | -VK--PL-V---RAKR-VV...... | -REK- | -IGTI-ALFL-F------- | | 473 |
| HIVJM | G--N-KD---SE------ | -VK--PL-V---RAKR-VV...... | -REK- | -V.TM-ALFL-F------- | | 513 |
| HIVWM | G--D-RD---SE------ | -VK--PL-V---RAKR-VV...... | -REK- | -VG.L-AMFL-F------- | | 490 |
| HIVMA208 | G--D-RD---SE------ | -VK--PL-V---TAKR-VM...... | -REK- | | | 533 |
| HIVMA1CON | G--D-RD---SE------ | -VK--PL-V---TAKR-...... | | | | 531 |
| HIVFO | | | | | | |

*FIG._16B*

```
                    gGGdMrDNWrSELYKYKvVKIEPLGVAPtrAKRRVV...   gp120/gp41
                                                              eREKRAvg?lGAvFlGFLGAAGSTMGAasI
CONSENSUS.A         gGGdMrDNWrSELYKYKvVKIEPLGVAPtrAKRRVV...   eREKRAvg?lGAvFlGFLGAAGSTMGAasI
HIVSF1703           T--N-----R-------V--------------TP----    .Q-----VG.I--V-I-------A---       483
HIVU455             G--D-----K-------V--------------TR----    .E-----VG.L--I-L-------A---       540
HIVU321             G--D-----R-------V--------------TK----    .A-----IG.M--F-L-------A---       528
A2RW020W.01053hED   G--N-----R-------V--------------SR----    .E-----VG.I--V-L-------A---       535
A2UG031W.01043hED   G--N-----R-------V--------------TR----    .E-----IG.M--V-I-------A---       516
HIVD687             G--D-----R-------D--------------TR----    .E-----VG.L--V-L-------A---       484
A2RW009W.01142hED   G--D-----R-------V--------------TR----    .E-----VG.L--V-I-------A---       415
HIVUG06             G--D-----R-------V--------------SR----    .W-----VVEI--V-L---               530
                                                                                                266

CONSENSUS.C         GGGdMrdNWRsELYKYKVVEIKPLGvAPT?aKRRVV...   eREKRAVG?iGAVfLGFLGaAGSTmgAASi
C3MA959D.01183hED   ---D-RD--S-------V----------V---KA----    ER-----I-----F---A---MG---V       485
C3MA960D.01033hED   ---D-RD--S-------V----------V---EA----    ER-----I-----F---A---MG---I       524
HIVD757             ---D-RN--S-------V----------V---TA----    ER-----I-----F---A---MG---M       520
HIVD747             ---D-RD--S-------V----------V---TA----    ER-----I-----F---A---MG---M       412
HIVD760             ---D-RD--S-------V----------V---TA----    ER-----I-----F---A---MG---I       459
HIVNOF              ---N-KD--N-------I----------I---GS----    ER-----L-----L---A---MA---I       466
HIVD1044            ---D-RN--S-------V----------V---TP----    ER-----I-----F---A---MG---I       403
C2BR025W.01012sCD                                                                               408
C2BR025W.01052sCD

CONSENSUS.D         GGGDMrdNWrsELYKYKVVrIEPlG?APT?aKRRVV...   eREKRAIG.LGA?FLGFLGAAGSTMGAasl
HIVJY1              ----K--WRN------VR---L-I----RAK----       .E--K------V----------VSV         471
HIVNDK              ----R--WRS------VK---I-V----KAR----       .E--K------V----------ASV         542
HIVMAL              ----R--WIS------VR---L-V----KAK----       .E--K------M----------ASL         525
HIVELI              ----R--WRS------VQ---L-V----RAK----       .E--K------M----------RSV         537
HIVZ2Z6             ----R--WRS------VK---L-V----RAK----       .E--K------M----------RSL         532
```

FIG._16C

```
D2UG024W.01__3m_D   ------R--WRS-------IK---L-L---RAK-------------A--K----------V-------ASL   529
D2UG021W.01092hED   ------R--WRN-------VR---L-L---KAR------------.E--K----------L-------ASL   518
D2UG038W.01072rED   ------R--WRS-------VR---L-I---MSK------------.E--K----------L-------ATL   529
D2UG046W.01082rED   ------R--WRS-------VR---L-L---EAK------------.E--K----------M-------ASM   529
HIVUG23             ------R--RRS-------VK---L-V---KTK------------.E--E----------M-------      240
D2UG038W.01012sCD   ------R--WRS-------VR---L-I---MAK------------.E--K------------------      471
D2UG038W.01022sCD   ------R--WRS-------VR---L-I---MAK------------.E--K------------------      470

CONSENSUS.E         GGGNIKDNWRSELYKYKVVQIEPLGIAPTRAKRRVV....EREKRAVG?iGAMIFGFLGAAGSTMGAaSI   516
E3TH966D.01083hED   ---------------------------------------------------I----------A------      527
E3TH975D.01153hED   ---------------------------------------------------I----------A------      525
E2TH022W.01043hED   ---------------------------------------------------I----------A------      525
HIVTN243            ---------------------------------------------------I----------A------      531
E2TH006W.01053hED   ---------------------------------------------------I----------A------      524
E2TH011W.01052rED   ---------------------------------------------------I----------P------      507

CONSENSUS.F         ?ggdmkDiWRteLynYkVVrikP?SVAPTk??Rp?i?????hR?KRavg?lGmlFLGvLsAAGSTMGAAat   431
HIVBRA7944          IGGDMK-I--TE-FN-K--RVK-F-----RIA-PVI.STRTH-E-AVG.L-ML---V-S------AT      537

CONSENSUS.O         VGGDMK-I--TK-YN-K--QIK-F-----KMS-PIINIHTPH-E-AVG.L-ML---V-S------AT      547
HIVANT70
HIVMVP5180
SIVCPZGAB           TGGNMK-I--SE-YK-K--RIE-L-----KAR-HTV.ARQKD-Q--AAFGL-AL---F-G-------AV    525
```

FIG._16D

| | | |
|---|---|---|
| CONSENSUS.B | tLtVgaRqllsgivQQQnNLLrAIeaQQhllqLTVWGIKQLQARvLAvERyLkDqQLlgiwGCSGKliCtT | |
| HIVJRCSF | T-T-QA-QLLSGI----N---R--EA--HMLQ----------------V--V--Y-K-Q---MGI------LI-T- | 564 |
| HIVJRFL | T-T-QA-LLLSGI----N---R--EA--RMLQ----------------V--V--Y-G-Q---LGI------LI-T- | 598 |
| HIVALA1 | T-T-QA-QLLSGI----N---R--EA--HLLQ----------------V--V--Y-R-Q---LEI------LI-T- | 597 |
| HIVBRVA | T-T-QA-LLLSGI----N---M--EA--HMLE----------------V--V--Y-K-Q---LGI------LI-T- | 599 |
| HIVJH3 | T-T-QA-LLLSGI----N---R--EG--HLLQ----------------I--V--Y-K-Q---LGI------LI-T- | 602 |
| HIVSC | T-T-QA-LLLSGI----N---R--EA--HLLQ----------------V--V--Y-R-Q---LGI------LI-T- | 617 |
| HIVBAL1 | T-T-QA-LLLSGI----N---R--EA--HLLQ----------------V--V--Y-R-Q---LGI------LI-T- | 606 |
| HIVYU2 | T-T-QA-QLLSGI----N---R--EA--HLLQ----------------V--V--Y-R-Q---LGI------LI-T- | 604 |
| HIVMN | T-T-QA-LLLSGI----N---R--EA--HMLQ----------------V--V--Y-K-Q---LGF------LI-T- | 593 |
| HIVHXB2R | T-T-QA-QLLSGI----N---R--EA--HLLQ----------------V--V--Y-K-Q---LGI------LI-T- | 607 |
| HIVLAI | T-T-QA-QLLSGI----N---R--EA--HLLQ----------------I--V--Y-K-Q---LGI------LI-T- | 606 |
| HIVNL43 | T-T-QA-QLLSDI----N---R--EA--HLLQ----------------I--V--Y-K-Q---LGI------LI-T- | 611 |
| HIVMFA | T-T-QA-QLLSGI----N---R--EA--HLLQ----------------V--V--Y-R-Q---LRI------LI-T- | 604 |
| HIVCAM1 | T-T-QT-QLLSGI----N---K--EA--HLLQ----------------V--V--Y-K-Q---LGI------LI-T- | 604 |
| HIVNY5CG | A-T-QT-QLMSGI----S---R--EA--HLLQ----------------V--L--Y-R-Q---LGI------LI-T- | 606 |
| HIVADA | T-T-QA-LLLSGI----N---R--EA--HLLQ----------------V--V--Y-Q-Q---LGI------LV-T- | 600 |
| HIVJFL | T-T-QA-QLLSGI----N---R--EA--HLLQ----------------V--V--Y-R-Q---LGI------LI-T- | 603 |
| HIVSIMI84 | A-T-QA-QLLSGI----N---R--EA--HLLQ----------------V--V--Y-K-Q---LGI------LI-T- | 601 |
| HIVD31 | T-T-QA-QLLSGI----N---R--EA--HLLQ----------------V--V--Y-K-Q---LGI------LI-T- | 606 |
| HIVSF162 | T-T-QA-QLLSGI----N---R--EA--HLLQ----------------V--V--Y-R-Q---LGI------LI-T- | 600 |
| HIVOYI | T-T-QA-KLLSGI----N---R--EA--HLLQ----------------V--V--Y-K-Q---LGI------LI-T- | 597 |
| HIVSF33 | A-T-QA-QLLSGI----N---R--KA--HLLQ----------------I--V--Y-R-Q---LGF------LI-T- | 605 |
| HIVCDC4 | T-T-QA-QLLSGI----N---R--EA--HLLQ----------------V--V--Y-K-Q---LGI------LI-T- | 602 |
| HIVSF2 | T-T-QA-QLLSGI----N---R--EA--HLLQ----------------V--V--Y-R-Q---LGI------LI-T- | 618 |
| HIVSF2B13 | T-T-QA-KLLSGI----N---R--EA--HLLQ----------------V--V--Y-R-Q---LGI------LI-T- | 605 |
| HIVHAN | T-T-QA-QLLSGI----N---R--EA--HLLQ----------------V--V--Y-R-Q---LGI------LI-T- | 603 |
| HIVRF | T-T-QA-HLLSGI----N---R--DA--HLLQ----------------V--V--Y-R-Q---LGI------LI-T- | 605 |
| HIVWMJ2 | T-T-QA-QLLSGI----N---R--EA--HLLQ----------------V--V--Y-K-Q---LGI------LI-T- | 615 |
| HIVTB132 | T-T-QP-QLLSGI----N---R--EA--HLLQ----------------V--V--Y-R-Q---LGI------LI-T- | 587 |

FIG._16E

| | | | | | |
|---|---|---|---|---|---|
| B2BR020W.01043hED | A-T-QA-QLLSGI----N---R--EA--HMLQ- | ------------ | ---V--V--Y-G-Q--LGI---- | ----LI-T- | 601 |
| B2TH014W.01123hED | T-T-QA-QLLSGI----R---R--EA--HLLQ- | ------------ | ---V--V--Y-K-Q--LGI---- | ----LI-T- | 593 |
| B2US711D.01143hED | T-T-QA-LLLTGI----N---K--EA--HLLQ- | ------------ | ---V--V--Y-K-Q--LGI---- | ----LI-T- | 597 |
| B2US712D.01043hED | T-T-QA-LLLSGI----S---R--EA--HLLQ- | ------------ | ---V--V--Y-K-Q--LGI---- | ----LI-T- | 600 |
| B2US715D.01063hED | A-T-QA-QLLSGI----N---R--EA--HMLQ- | ------------ | ---V--V--Y-K-Q--LGI---- | ----LI-T- | 602 |
| B2US716D.01063hED | T-T-QA-LLLSGI----N---R--EA--HLLQ- | ------------ | ---V--V--Y-R-Q--LGI---- | ----LI-T- | 593 |
| B2HA593D.01013hED | T-T-QA-LLLSGI----N---R--EA--HLLQ- | ------------ | ---V--V--Y-K-Q--LGI---- | ----LI-T- | 623 |
| B2HA594D.01103hED | T-T-QA-QLLSGI----N---R--EA--HLLQ- | ------------ | ---V--V--Y-K-Q--LGI---- | ----LI-T- | 597 |
| B2HA596D.01043hED | T-T-QA-QLLSGI----N---R--EA--HLLQ- | ------------ | ---I--V--Y-K-Q--LGI---- | ----LI-T- | 604 |
| B2HA599D.01243hED | T-T-QA-QLLSGI----N---R--EA--HLSQ- | ------------ | ---I--M--Y-K-Q--LGI---- | ----LI-P- | 614 |
| B1HA651D.01113hED | A-T-QA-LLLSGI----N---R--EA--HLLQ- | ------------ | ---V--V--Y-K-R--LGI---- | ----PI-T- | 598 |
| HIVRJS | A-T-QA-QLLSGI----N---R--EA--HLLQ- | ------------ | ---V--V--Y-K-Q--LGI---- | ----LI-T- | 603 |
| HIVGUN | T-T-QA-QLLSGI----N---R--KA--HLLQ- | ------------ | ---V--I--F-R-Q--LGI---- | ----LI-T- | 568 |
| HIVSBA | T-T-QA-LLLSGI----N---R--EA--HLLQ- | ------------ | ---V--V--Y-R-Q--LGI---- | ----LI-T- | 348 |
| HIVSBC | T-T-QA-LLLSGI----N---R--EA--HLLQ- | ------------ | ---V--V--Y-R-Q--LGI---- | ----LI-T- | 346 |
| HIVSBB | T-T-QA-QLLSGI----N---R--EA--HLLQ- | ------------ | ---V--V--Y-K-Q--LGI---- | ----LI-T- | 357 |
| B2BR014W.01012hED | T-T-QA-QLLSGI----N---K--EA--HLLQ- | ------------ | ---V--L--Y-K-Q--LGI---- | ----LI-T- | 571 |
| B2TH026W.01062hED | T-M-QA-QLLSGI----R---R--EA--HLLQ- | ------------ | | | 558 |
| HIVBR1 | T-T-QA-QLLSGI----N---K--EA--HLLQ- | ------------ | | | 571 |
| HIVTH6 | T-M-QA-QLLSGI----R---R--EA--HLLQ- | ------------ | | | 560 |
| HIVJ61 | T-T-QA-LLLSGI----N---R--EA- | | | | 290 |
| HIVJB02 | T-T-QA-LLLSGI----N---R--EA--H | | | | 291 |
| B2BR020W.01062rED | A-T-PL-RIRSCx | | | | 545 |
| B2BR021W.01062rED | T-T-PL-RIRSCx | | | | 548 |
| B2BR021W.01192rED | T-T-PV-RIRSCx | | | | 543 |
| HIVACH9 | | | | | |
| HIVACP1 | | | | | |
| HIVJM | | | | | |
| HIVWM | | | | | |
| HIVMA208 | | | | | |
| HIVMA1CON | | | | | |
| HIVFO | | | | | |

FIG._16F

| | | |
|---|---|---|
| CONSENSUS.A | TLtvQARqLlLSGIVQQQsNLLrAIEAQQHlLkKLTVWGIKQLQARvLAVErYLkDQQLLGIWGCSGKlICtT | 554 |
| HIVSF1703 | --TV----Q-------S----R--------------V--V-----K----L--T- | 611 |
| HIVU455 | --TV----Q-------S----R--------------V--V-----Q----L--T- | 599 |
| HIVZ321 | --TV----R-------N----R--------------I--V-----K----I--P- | 606 |
| A2RW020W.01053hED | --TA----Q-------S----R--------------V--V-----K----L--T- | 587 |
| A2UG031W.01043hED | --MV----Q-------S----R--------------V--L-----R----L--T- | 555 |
| HIVD687 | --TV----Q-------S----M--------------V--L-----K----------- | 486 |
| A2RW009W.01142hED | --TV----Q-------S----R--------------V--L-----K----L--T- | 569 |
| | | |
| CONSENSUS.C | tlTvqARQllsGIVQqqSNLLRAIEAqqH?LQLTvWGIKQLQtrVLAIERYLkdQQLLGiWGCSGKLICTT | 555 |
| C3MA959D.01183hED | TL-VQA--L-F---QQ------QH-L----V-------T----------KD-----I--C- | 595 |
| C3MA960D.01033hED | TL-VQA--L-S---QQ------RQ-M----V-------A----------QD--L--C- | 591 |
| HIVD757 | TL-VQA--L-S---QQ------QQ-L----V-------T----------KD-----I--R- | 483 |
| HIVD747 | TV-VQA--L-S---QQ------QQ-L----I-------A----------KE-----I--C- | 530 |
| HIVD760 | TL-VQA--L-S---QQ------QQ-L----V-------T----------KD-----M--C- | 537 |
| HIVNOF | TL-VQA--L-S---QQ------QQ-M----V-------T----------KD------- | 459 |
| HIVD1044 | TL-VPL- | 415 |
| C2BR025W.01012sCD | | |
| C2BR025W.01052sCD | | |
| | | |
| CONSENSUS.D | tLTvqARQLlSGIVqQQNNLLRAIEAQQHlLQLTVWGIKQLQARvLAVErYLkDQqLLGiWGCSGKhICtT | 542 |
| HIVJY1 | A--GQ---L---Q------------M------------V----S-K--Q--I-----KH--T- | 613 |
| HIVNDK | T--VQ---M---H------------L------------V----R-R--Q--I-----RH--T- | 596 |
| HIVMAL | T--VQ---L---Q------------L------------V----R-Q--R--M-----KH--T- | 608 |
| HIVELI | T--VQ---M---Q------------L----------------I--Q--I-----KH--T- | 603 |
| HIVZ2Z6 | T--VQ---L---Q------------L----------------I--R-K--Q--I-----KL--T- | 603 |

*FIG._16G*

| | |
|---|---|
| D2UG024W.01___3m_D | T--VQ-----M---Q---------------------------------L------------------------V-----S--K---Q----I-------RH--P- 600 |
| D2UG021W.01092hED | T--VQ-----L---Q---------------------------------L------------------------------------------------------- 557 |
| D2UG038W.01072rED | T--Vx 534 |
| D2UG046W.01082rED | T--Vx 534 |
| HIVUG23 | |
| D2UG038W.01012sCD | |
| D2UG038W.01022sCD | |
| | |
| CONSENSUS.E | TLTVqARQLlSGIVqQQSNLLRAiEAQQHlLQLTVWGikQLQARVlAVERYLKDQKFlglwgCSGKIICTT 587 |
| E3TH966D.01083hED | ----Q------V------Q------------I-----L-----IK----L----------FLGLWG---- 598 |
| E3TH975D.01153hED | ----Q------L------Q------------I-----L-----IK----L----------FLGLWG---- 596 |
| E2TH022W.01043hED | ----Q------L------Q------------I-----M-----IK----L----------FLGLWG---- 596 |
| HIVTN243 | ----Q------L------Q------------.-----L-----..----.----------L..GLW---- 595 |
| E2TH006W.01053hED | ----Q------L------Q------------I------------IK----L----------FLGLWG---- 595 |
| E2TH011W.01052rED | ----x 512 |
| | |
| CONSENSUS.F | |
| HIVBRA7944 | |
| | |
| CONSENSUS.O | ?Ltvqt??llkGIVQQQdNLLrAI?aQQhLL?LSvWG??QL?ARllA?Et?lq?QQlLsLWGCkgKlvCyT 491 |
| HIVANT70 | T-AVQTHTLLK-----D---R--QA--Q--R-X---IR--R--LL-L-TLLQN--L-S----KG-LV-Y- 608 |
| HIVMVP5180 | A-TVRTHSVLK-----D---R--QA--H--R--V--IR--R--LQ-L-TLIQN--R-N----KG-LI-Y- 618 |
| SIVCPZGAB | T-TVQARQLLS-----N---K--EA--H--Q--I--VK--Q--LL-V-RYLQD--I-G----SG-AV-Y- 596 |

FIG._16H

```
CONSENSUS.B    aVPWNasWS........Nks.l??iw?nmTWmeWerEIdnYT?lIytLieesQnQQekNeqeLLeLdkWas
HIVJRCSF       A-----TS-.........-KS.LDSIWNNM--ME-EK--EN--NT-YT-IEES-I--EK-EQE--E-DK-AS    622
HIVJRFL        A-----AS-.........-KS.LDRIWNNM--ME-ER--DN--SE-YT-IEES-N--EK-EQE--E-DK-AS    660
HIVALA1        T-----AS-.........-KS.LNQIWDNM--ME-ER--DN--SL-YT-IEES-N--EK-EQE--E-DK-AS    659
HIVBRVA        A-----AS-.........-KS.LSDIWDNM--ME-ER--DN--NL-YS-IEDS-I--EK-EKE--E-DK-AS    661
HIVJH3         A-----AS-.........-KS.LEEIWDNM--ME-ER--DN--SL-YT-IEES-N--EK-EQE--G-DK-AS    664
HIVSC          T-----TS-.........-KS.LDKIWGNM--ME-ER--DN--SL-YT-IEES-N--EK-EQE--E-DK-AS    679
HIVBAL1        A-----AS-.........-KS.LNKIWDNM--IE-DR--NN--SI-YS-IEES-N--EK-EQE--E-DK-AS    668
HIVYU2         T-----TS-.........-KS.LNEIWDNM--MK-ER--DN--HI-YS-IEQS-N--EK-EQE--A-DK-AS    666
HIVMN          T-----AS-.........-KS.LDDIWNNM--MQ-ER--DN--SL-YS-LEKS-T--EK-EQE--E-DK-AS    655
HIVHXB2R       A-----AS-.........-KS.LEQIWNHT--ME-ER--NN--SL-HS-IEES-N--EK-EQE--E-DK-AS    669
HIVLAI         A-----AS-.........-KS.LEQIWNNM--ME-ER--DN--SL-HS-IEES-N--EK-EQE--E-DK-AS    668
HIVNL43        A-----AS-.........-KS.LEQIWNNM--ME-DR--NN--SL-HS-IEES-N--EK-EQE--E-DK-AS    673
HIVMFA         A-----AS-.........-KS.LEQFWNNM--ME-DR--NN--SL-HS-IDES-N--EK-EQE--E-DK-AS    666
HIVCAM1        A-----AS-.........-KS.LDKIWNNM--ME-ER--DN--NL-YT-IEES-N--EK-EKD--E-DT-AS    666
HIVNY5CG       T-----AS-.........-KS.LDKIWDNM--ME-ER--DN--GL-YT-IEES-I--EK-EQE--E-DK-AS    668
HIVADA         A-----AS-.........-KT.LDMIWDNM--ME-ER--EN--GL-YT-IEES-N--EK-EQD--A-DK-AS    662
HIVJFL         T-----AS-.........-KS.LDEIXNNM--MQ-ER--SN--SL-YT-IEES-N--EK-ELE--E-DK-AS    665
HIVSIMI84      T-----AS-.........-KS.LNQIWDNM--ME-ER--DN--GL-YR-IEES-N--EQ-EQD--K-DT-AS    663
HIVD31         A-----AS-.........-KS.MDMIWNNM--ME-ER--DN--SL-YT-IEES-N--EK-EQE--E-NK-EN    668
HIVSF162       A-----AS-.........-KS.LDQIWNNM--ME-ER--DN--NL-YT-IEES-N--EK-EQE--E-DK-AS    662
HIVOYI         T-----AS-.........-KS.LNEIWDNM--MQ-ER--DN--HL-YT-LEES-N--EK-EQE--E-DK-AG    659
HIVSF33        T-----TS-.........-KS.LDKIWNNM--ME-ER--DN--SL-YT-IEES-N--EK-EQE--E-DK-AS    667
HIVCDC4        A-----AS-.........-KT.LDQIWNNM--ME-DR--DN--HL-YT-LEES-N--EK-QQE--Q-DK-AS    664
HIVSF2         A-----AS-.........-KS.LEDIWDNM--ME-ER--DN--NT-YT-LEES-N--EK-EQE--E-DK-AS    680
HIVSF2B13      A-----TS-.........-KS.MEDIWDNM--MQ-EK--DN--NT-YT-IEES-N--EK-EQE--E-DK-AS    667
HIVHAN         T-----AS-.........-KS.LDQIWNNM--ME-ER--DN--SL-YT-IEQS-N--EK-EQE--E-DK-AS    665
HIVRF          A-----AS-.........-KT.LDQIWNNM--ME-ER--DN--GI-YN-LEES-N--EK-EQE--E-DK-AS    667
HIVWMJ2        T-----AS-.........-KS.LNMIWNNM--MQ-ER--DN--GI-YN-LEES-N--EK-EQE--E-DK-AN    577
HIVMJ2         T-----AS-.........-KS.MNQIWDNL--ME-ER--DN--SI-YS-IEES-N--GK-EQE--E-DK-AS    659
HIVTB132       T-----AS-.........-KS.LDEIWNNM--ME-ER--NN--GL-YT-IEES-x--EK-ELD--E-DK-AS    649
```

FIG._16I

```
B2BR020W.01043hED  T----TS-........ -KS.LDDIWTNM--ME-KR--DN--SL-YT-IEES-R--EK-EQE--E-DK-DS  663
B2TH014W.01123rED  A----AS-........ -KS.LDKIWNNM--ME-ER--DN--RE-YT-IEES-N--EK-ELE--E-DK-AS  655
B2US711D.01143hED  T----TS-........ -KS.LDKIWGNM--ME-ER--DN--GL-YT-IEES-N--EK-EQE--E-DK-AS  659
B2US712D.01043hED  N----KT-........ -KS.LDQIWQNM--MQ-ER--DK--DV-YT-IGES-N--EK-EQE--E-DK-AS  662
B2US715D.01063hED  T----AS-........ -KS.HDQIWQNM--MQ-EK--DN--SL-YN-IEVS-N--EK-EQE--E-DK-AS  664
B2US716D.01063hED  T----TS-........ -KS.LDQIWGNM--MQ-ER--DN--GL-YT-IEES-N--EK-EQE--E-DK-AS  655
B2HA593D.01013hED  T----TS-........ -KS.LSEIWDNM--MQ-ER--DN--SL-YT-IEES-N--EK-EQE--E-DK-AG  685
B2HA594D.01103hED  A----TS-........ -KS.LEKIWNNM--ME-ER--DN--GL-YS-IEES-N--EK-EQD--E-DK-AS  659
B2HA596D.01043hED  A----TS-........ -KS.LEKIWNNM--ME-ER--DN--GL-YS-IGES-N--EK-EQD--E-DK-AS  566
B2HA599D.01243hED  A----AS-........ -RS.LQYIWNNM--IE-ER--DN--DI-YS-IEKS-N--EK-EQE--E-DQ-AS  676
B1HA651D.01113hED  S----SS-........ -KS.LEQIWNNM--LE-ER--DN--SL-YS-IKES-N--EK-EQE--E-DK-AS  560
HIVRJS             A----TS-........ -KS.LEEIWDNM--ME-ER--NN--GL-YT-IEQS-N--EK-EQE--A-DT-AS  645
HIVGUN             T----TS-........ -KS.LKQIWDNL--ME-ER--DN--GI-FN-IEEA-N--EK-EQD--E-DK-AG  630
HIVSBA             A----AS-........ -KS.LDQIWDNM--MQ-ER--EN--SL-YN-IEES-N--EK-EQD--E-DK-AS  410
HIVSBC             A----SS-........ -KS.LDQIWNNM--MQ-ER--EN--SL-YN-IEES-N--EK-EQE--E-DK-AS  408
HIVSBB             A----AS-........ -KS.LNDIWDNM--MQ-DR--NK--DS-YQ-IEES-N--EK-EQD--K-DE-AS  419
B2BR014W.01012hED
B2TH026W.01062hED
HIVBR1
HIVTH6
HIVJ61
HIVJB02
B2BR020W.01062rED
B2BR021W.01062rED
B2BR021W.01192rED
HIVACH9
HIVACP1
HIVJM
HIVWM
HIVMA208
HIVMA1CON
HIVFO
```

FIG._16J

```
CONSENSUS.A           nVPWNSSWs........nks?qs?IWdnMTWLqWdKEisnYT?ilYnLIEeSqnQQEkNEqdLLALDKWan   614
HIVSF1703             N------S.........NRT.QSE--NN----Q-D--ISN--DI--N----E-QI---K--QE------AN   673
HIVU455               T------S.........NKS.QED--NN----Q-E--ISS--GI--Q----E-QN---K--LD------AN   661
HIVZ321               N------S.........NKS.QSD--DK----E-D--VSN--QV--N----E-QT---I--RD------AN   668
A2RW020W.01053hED     N------S.........NKS.MNE--DN----Q-D--ISN--QI--N----E-QN---K--QD------AS   649
A2UG031W.01043hED     N------S.........NKS.YSE--DN----Q-D--INN--EL--S----D-QN---K--QD------AN   617
HIVD687               T................SNKTYSD--DN----Q-D--ISN--KI--A----E-AN---K--QD------TS   548
A2RW009W.01142hED
HIVUG06

CONSENSUS.C           ?VpWNSSWS........NrS.qtDIWDNMTWmqWDREISNYTdtIYrLLEDSQNQQErNEKDLLALDSWkN   616
C3MA959D.01183hED     A-A-.............-K-.QS----------E-------DI--K----------R---K---------   657
C3MA960D.01033hED     T-P-.............-K-.KT----------Q-------DT--K----------R---N---------   653
HIVD757               N-P-.............-R-.QT----------Q-------DT--R----------R---K---------   545
HIVD747               T-P-.............-R-.QT----------Q-------ET--R----------R---K---------   592
HIVD760               A-P-.............-R-.QT----------Q-------NT--R----------R---K---------   599
HIVNOF
HIVD1044
C2BR025W.01012sCD
C2BR025W.01052sCD

CONSENSUS.D           ?VPWNSSWS........NrS.LdeIWqNMTWmeWErEIdNYTGlIYsLIEeSQiQQEKNEkeLLeLDKWAS   603
HIVJY1                T-...............-K-.-EE--N----IE--R--D----V--S----N--I----QD--Q------   675
HIVNDK                N-...............-R-.-DE--Q----ME--R--D----L--S----E--I----KE--E------   658
HIVMAL                F-...............-R-.-DD--N----MQ--K--S----I--N----E--I----KE--E------   670
HIVELI                N-...............-R-.-NE--Q----ME--R--D----L--S----E--T----KE--E------   665
HIVZ2Z6               T-...............-R-.-ND--Q----ME--R--D----L--R----E--T----QE--E------   665
D2UG024W.01__3m_D     Q-...............-K-.-DT--G----ME--R--S----L--D----E--I----KD--E------   662
```

FIG._16K

```
D2UG021W.01092hED
D2UG038W.01072rED
D2UG046W.01082rED
HIVUG23
D2UG038W.01012sCD
D2UG038W.01022sCD

CONSENSUS.E        AVPWNSTWS........NrS.fEEIwnMtWiEwEReREISNYTNqIYeILTeSQnQQDRNEKDLLeLDKWAS  649
E3TH966D.01083hED  ----------------.---.-R--F----S--T-I--E-------Q--E---E--N----------E-------  660
E3TH975D.01153hED  ----------------.---.-R--F----N--T-T--E-------Q--D---E--N----------G-------  658
E2TH022W.01043hED  ----------------.---.-K--F----N--T-T--E-------Q--E---E--N----------E-------  658
HIVTN243           ----------------.---.-R--F----N----I---.------Q--E---E--N----------E-------  655
E2TH006W.01053hED  ----------------.---.-R--L----N--T-I--E-------R--E---K--D----------E-------  657

CONSENSUS.F
HIVBRA7944

CONSENSUS.O        ?V?WNnsW?????????Nss????IWdnlTWQ?WDrl?sN????Iy?e?q?Aq?QQEkNek?LlELDeWaS        536
HIVANT70           S-K--RT-I........G-ES.....-DTL---E--RQIS-ISST-YEEIQK-QV---Q-EKK-L---E-A-      668
HIVMVP5180         S-K--TS-S......GRY-DD...S--DNL---Q--QHIN-VSSI-YDEIQA-QD---K-VKA-L---E-A-      681
SIVCPZGAB          T-P--NS-P......GS-ST..DD--GNL---Q--KLVS-YTGK-FGLLEE-QS---K-ERD-L---Q-A-       659
```

*FIG._16L*

| | | | |
|---|---|---|---|
| CONSENSUS.B | LwnWf?ItnwLWyIkiFImIvgGLvGLrivFavLSiVNrvRQGYSPlsfQT?lPaprg.pdrPegieeeGg | | 690 |
| HIVJRCSF | -WN-FG-TKW--Y-KI--M-VG--I--RIV-SV--I---RV------L-F--LL-ATRG.PDR-EGIEEE-G | | 730 |
| HIVJRFL | -WN-FD-TKW--Y-KI--M-VG--V--RLV-TV--I---RV------L-F--LL-APRG.PDR-EGIEEE-G | | 729 |
| HIVALA1 | -WN-FN-TNW--Y-KI--M-VG--V--RIV-SV--I---RV------L-F--RL-ARRE.PDR-EGIEEE-G | | 731 |
| HIVBRVA | -WN-FN-TNW--Y-KI--M-VG--I--RIV-AV--I---RV------L-F--RL-GRRG.PDR-EGIEEE-G | | 734 |
| HIVJH3 | -WN-FT-TNW--Y-RI--M-VG--V--RIV-TV--I---RV------L-F--RL-APRG.PDR-EGIEEE-G | | 749 |
| HIVSC | -WN-FN-TNW--Y-KI--M-VG--V--RIV-TV--I---RV------L-F--RL-SQRG.PDR-EGIEEE-G | | 738 |
| HIVBAL1 | -WN-FD-TKW--Y-KI--M-VG--I--RIV-SV--I---RV------L-F--HL-SSRG.PDR-GGIEEE-G | | 736 |
| HIVYU2 | -WN-FD-TKW--Y-KI--M-VG--I--RIV-VV--I---RV------L-F--HL-AQRG.PDR-DGIEEE-G | | 725 |
| HIVMN | -WN-FD-TNW--Y-KI--M-VG--V--RIV-AV--I---RV------L-L--RP-VPRG.PDR-EGIEEE-G | | 739 |
| HIVHXB2R | -WN-FN-TNW--Y-KL--M-VG--V--RIV-AV--I---RV------L-F--HL-TPRG.PDR-EGIEEE-G | | 738 |
| HIVLAI | -WN-FN-TNW--Y-KI--M-VG--V--RIV-AV--I---RV------L-F--HL-TPRG.PDR-EGIEEE-G | | 743 |
| HIVNL43 | -WN-FN-TNW--Y-KL--M-VG--V--RIV-AV--I---RV------L-F--HL-IPRG.PDR-EGIEEE-G | | 736 |
| HIVMFA | -WN-FN-TNW--Y-KI--M-VG--V--RIV-AV--I---RV------L-F--HL-NRGG.PDR-EGIEEE-G | | 736 |
| HIVCAM1 | -WN-FD-TNW--Y-KI--M-IG--I--RIV-TI--L--RV------L-F--RF-VPRG.PDR-EGIEEE-G | | 738 |
| HIVNY5CG | -WN-FD-TKW--Y-KI--M-VG--I--RIV-TV--I---RV------L-F--RL-AQRG.PDR-EGIEEE-G | | 732 |

*FIG._16M*

```
WHO consensus sequences from HIV clades gp120 <------|------> gp41
CONSENSUS.B   gGGdMrdNWRseLYKYKVvkIEplGvAPTkakrRvv......QrekRAvg?iGamflGfLGaAGSTMgaasm   493
CONSENSUS.A   gGGdMRDNWrSELYKYKvvKIEPLGvAPtrAKRRVV......eREKRAvg?lGAVFlGFLGAAGSTMGAaSI    483
CONSENSUS.C   GGGdMrdNWRSELYKYKYKVVEIKPLGvAPT?aKRRVV....erEKRAVG?iGAVflGFLGaAGSTMgAASi    485
CONSENSUS.D   GGGdMrDNwrsELYKYKVvrIEPlG?APT?akRRVV......eREkRAIG.LGA?FLGFLGAAGSTMGAasl    471
CONSENSUS.E   GGGNIKDNWRSELYKYKYKVVQIEPLGIAPTRAKRRVV.....EREkRAVG?iGAMIFGFLGAAGSTMGAaSI    516

CONSENSUS.B   tLtVqaRqllsgiVQQQnNLLrAIeaQQhllqLTVwGIKQLQLTVwGIKQLQaRvLAvERYLkDqQLlgiwGCSGKlictT   564
CONSENSUS.A   TLtvQARqLLSGIVQQQsNLLrAIEAQQHlLKLTVwGIKQLQARvLAvERYLkDQQLLGIWGCSGKLICtT          554
CONSENSUS.C   tlTvqaRQllsGIVQqqSNLLrAIEAqqH?LQLTvwGIKQLQtRvLAIERYLkdQQLLGiwGcSGKLICTT          555
CONSENSUS.D   tlTTvqARQllSGIVqQQNNLLRAiEAQQHlLQLTVwGIKQLQaRvLAvERYLkDQqLLGIWGCSGkhICtT         542
CONSENSUS.E   TLTVqARQLlSGIVQQQSNLLRAiEAQQHlLQLTVwGikQLQlAQRVlAVERYLKDQKFlglwgCSGKIICTT        587

|------> DP178
CONSENSUS.B   aVPWNasWS........Nks.l??iw?nmTWmeWeREIdnYT?llytLieesQnQekNeqeLLeLdkWas         622
CONSENSUS.A   nVPWNSSWS.........nks?qs?IWdnMTWLqWdKEisnYT?ilYnLIEeSqnQQeKNEqdLLALDKWan      614
CONSENSUS.C   ?VpWNSSWS..........NrS.qtDIWDNMTWMqWDREISNYTdtIYrLLEDSQNQQErNEKDLLALDSWkN      616
CONSENSUS.D   ?VPWNSSWS..........NrS.LdeIWqNMTWmeWEREIdNYTGlIYsLIEeSQiQQEKNEkeLLeLDKWAS      603
CONSENSUS.E   AVPWNSTWS..........NrS.fEEIWnNMtWiEWeREISNYTNqIYeILTeSOnQQDRNEKDLLeLDKWAS      649
              <----|

CONSENSUS.B   LwnWf?ItnwLWyIkiFImIvggGLvGLrivgFavLSiVNrvRQGYSPLSfQT?lPaprg.pdrPegieeeGg        690
CONSENSUS.A   LWnWfdIsnWLWYI?iFimIVGGLIGLRIvFaVLsiINRVRQGYSPLSFQtltpnpr?.pdRpgRIeeeGG         682
CONSENSUS.C   LWNWfsIThnWLWYIkIFIMIVGGLIGLIGLriIFAVLsIVNRVrqGYSPLSFQTLTPNPrG.pDRLgRIEeeGG     686
CONSENSUS.D   LWNWfsItkWLWYIkiFimIvGGLIGLRIvFaVLslVNRVRQGYSPLSfQTLLPaPrG?pDRPegiEEEGG         673
CONSENSUS.E   LWnWfDITnWLWYIKIFIMIVGGLIGLRIIFAvLSiVNRVRQGYSPLSfQtp?HhQrE.pDRPERIEEGGG         718
```

FIG._17

```
DP178-related peptides (and locking positions)

Neurath             EWDREINNYTSLI

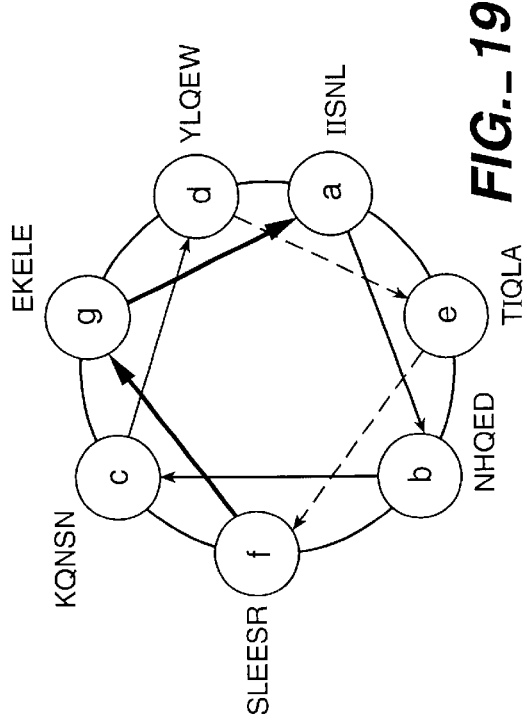

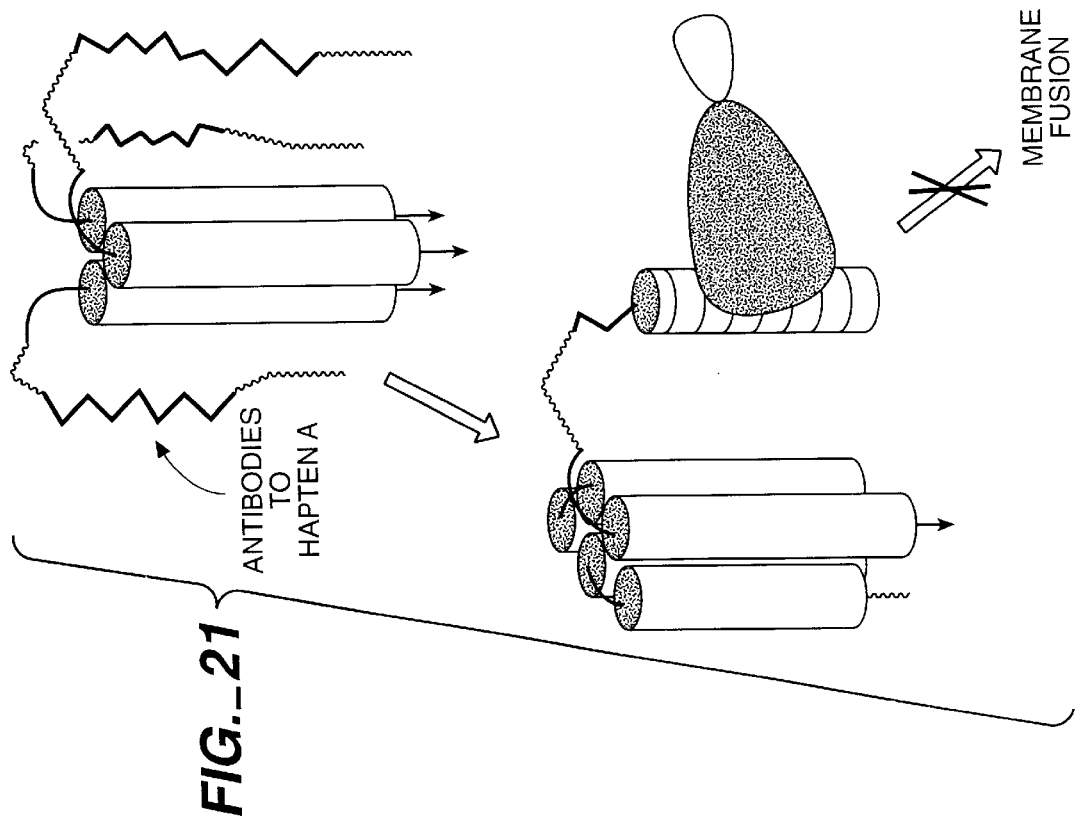
FIG._21
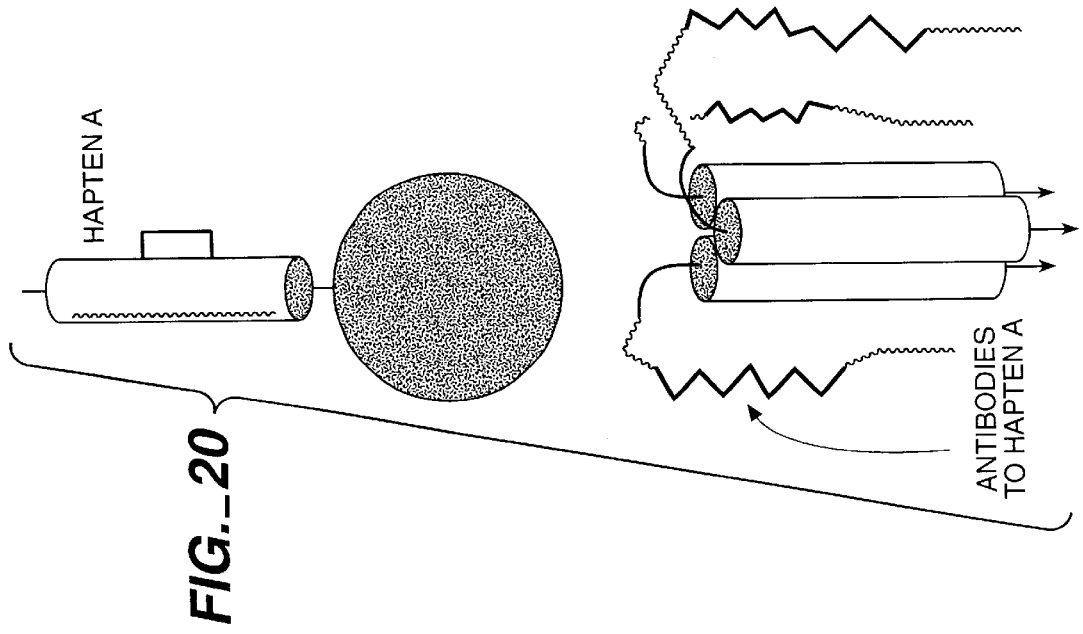
FIG._20

CONSTRAINED HELICAL PEPTIDES AND METHODS OF MAKING SAME

BACKGROUND OF THE INVENTION

This is a non-provisional application filed under 37 CFR 1.53(b), claiming priority under 35 USC 119(e) to provisional Application Ser. No. 60/049,787 filed on Jun. 16, 1997, now abandoned; under 35 USC 120 to non-provisional continuation-in-part Application Ser. No. 08/876,698 filed on Jun. 16, 1997, now abandoned; and under 35 USC 120 to non-provisional Application Ser. No. 08/743,698 filed Nov. 6, 1996, now abandoned.

FIELD OF THE INVENTION

The invention relates to the conformational constraint of peptides. In particular, the invention relates to constraining peptides to an α-helical conformation. This invention also relates to the rational design and preparation of HIV vaccines based on HIV gp41 polypeptide sequences. This invention further relates to improved methods for HIV infection diagnosis and immunogens which induce antibodies useful in the diagnostic methods.

A variety of methods for stabilizing α-helical peptides have been described previously. Addition of trifluoroethanolor hexafluoroisopropanol has frequently been used to stabilize α-helices in aqueous solution. Dimerization of α-helices at hydrophobic interfaces has also provided exogenous stabilization. Short α-helical peptides have been stabilized by incorporating groups at the termini to stabilize the intrinsic helix dipole. Naturally occurring capping motifs as well as organic templates have been used to stabilize α-helices by end-nucleation. Several non-covalent side chain constraints have been investigated for α-helix stabilization, including hydrophobic interactions, salt bridges, and metal ion chelation by both natural and unnatural amino acids.

Finally, α-helices have been stabilized by covalent side chain tethers. Chorev et al., *Biochemistry*, 30: 5968–5974 (1991), Osapay et al., *J. Am. Chem. Soc.,* 112: 6046–6051 (1990), Osapay et al., *J. Am. Chem. Soc.,* 114: 6966–6973 (1990), Bracken et al., *J. Am. Chem. Soc.,* 116: 6431–6432 (1994), and Houston et al., *J. Peptide Science,* 1: 274–282 (1995) described the stabilization of α-helices by side chain to side chain lactamization. Ravi et al., *J. Am. Chem. Soc.,* 105: 105–109 (1983) and Jackson et al., *J. Am. Chem. Soc.,* 113: 9391–9392 (1991) described the constraint of peptides by disulfide bonds between residues. The naturally occurring peptide apamin has been used as a scaffold for the presentation of α-helical peptide sequences constrained in helical conformation by disulfide bonds to scaffold cysteine residues.

Acquired immunodeficiency syndrome (AIDS) is caused by a retrovirus identified as the human immunodeficiency virus (HIV). There have been intense efforts to develop a vaccine that induces a protective immune response based on induction of antibodies or cellular responses. Recent efforts have used subunit vaccines where an HIV protein, rather than attenuated or killed virus, is used as the immunogen in the vaccine for safety reasons. Subunit vaccines generally include gp120, the portion of the HIV envelope protein which is on the surface of the virus.

The HIV envelope protein has been extensively described, and the amino acid and nucleic acid sequences encoding HIV envelope from a number of HIV strains are known (Myers, G. et al., 1992. Human Retroviruses and AIDS. A compilation and analysis of nucleic acid and amino acid sequences. Los Alamos National Laboratory, Los Alamos, N.M.). The HIV envelope protein is a glycoprotein of about 160 kd (gp160) which is anchored in the membrane bilayer at its carboxyl terminal region. The N-terminal segment, gp120, protrudes into the aqueous environment surrounding the virion and the C-terminal segment, gp41, spans the membrane. Via a host-cell mediated process, gp160 is cleaved to form gp120 and the integral membrane protein gp41. As there is no covalent attachment between gp120 and gp41, free gp120 is sometimes released from the surface of virions and infected cells.

gp120 has been the object of intensive investigation as a vaccine candidate for subunit vaccines, as the viral protein which is most likely to be accessible to immune attack. At present, clinical trials using gp120 MN strain are underway.

However, effective vaccines based on gp120 or another HIV protein for protection against additional strains of HIV are still being sought to prevent the spread of this disease.

SUMMARY OF THE INVENTION

The invention provides a method for constructing a constrained helical peptide comprising the steps of: (1) synthesizing a peptide, wherein the peptide comprises a sequence of eight amino acid residues, wherein the sequence of eight amino acid residues has a first terminal residue and a second terminal residue, wherein the first terminal residue and the second terminal residue flank an internal sequence of six amino acid residues, and wherein the first terminal residue has a side chain containing an amide bond-forming substituent and the second terminal residue has a side chain containing an amide bond-forming substituent; (2) providing a difunctional linker having a first functional group capable of forming an amide linkage with the side chain amide bond-forming substituent of the first terminal residue and having a second functional group capable of forming an amide linkage with the side chain amide bond-forming substituent of the second terminal residue; and (3) cyclizing the peptide by reacting the side chain amide bond-forming substituent of the first terminal residue with the first functional group of the difunctional linker to form an amide linkage and reacting the side chain amide bond-forming substituent of the second terminal residue with the second functional group of the difunctional linker to form an amide linkage, yielding a constrained helical peptide.

The invention also provides a method for constructing a constrained helical peptide comprising the steps of: (1) synthesizing a peptide, wherein the peptide comprises a sequence of eight amino acid residues, wherein the sequence of eight amino acid residues has a first terminal residue and a second terminal residue, wherein the first terminal residue and the second terminal residue flank an internal sequence of six amino acid residues, wherein the first terminal residue has a side chain containing an amide bond-forming substituent and the second terminal residue has a side chain containing an amide bond-forming substituent, and wherein the side chain amide bond-forming substituent of the first terminal residue is protected with a first protecting group and the side chain amide bond-forming substituent of the second terminal residue is protected with a second protecting group such that the first protecting group and the second protecting group are differentially removable; (2) removing the first protecting group such that the side chain amide bond-forming substituent of the first terminal residue is deprotected and the side chain amide bond-forming substituent of the second terminal residue is not deprotected; (3) providing a difunctional linker having a first functional group capable of forming an amide linkage with the side chain amide bond-forming substituent of the first terminal residue and having a second functional group capable of forming an amide linkage with the side chain amide bond-forming substituent of the second terminal residue; (4) reacting the peptide with the difunctional linker to form an amide linkage between the first functional group of the difunctional linker and the side chain amide bond-forming substituent of the first terminal residue; (5) removing the second protecting group to deprotect the side chain amide bond-forming substituent of the second terminal residue; and (6) cyclizing the peptide by intramolecularly reacting the side chain amide bond-forming substituent of the second terminal residue with the second functional group of the difunctional linker to form an amide linkage and yield a constrained helical peptide.

The invention further provides a method for constructing a constrained helical peptide, comprising the steps of: (a) synthesizing a peptide, wherein the peptide comprises a sequence of eight amino acid residues, wherein the sequence of eight amino acid residues has a first terminal residue and a second terminal residue, wherein the first terminal residue and the second terminal residue flank an internal sequence of six amino acid residues, wherein the first terminal residue has a side chain containing an amide bond-forming substituent and the second terminal residue has side chain containing an amide bond-forming substituent, wherein the first terminal residue is coupled to a difunctional linker having a first functional group and a second functional group, wherein the first functional group is in an amide linkage with the side chain amide bond-forming substituent of the first terminal residue, and wherein the second functional group of the difunctional linker is capable of forming an amide linkage with the side chain amide bond-forming substituent of the second terminal residue; and (b) cyclizing the peptide by intramolecularly reacting the side chain amide bond-forming substituent of the second terminal residue with the second functional group of the difunctional linker to form an amide linkage and yield a constrained helical peptide.

The invention additionally provides a method for constructing a constrained helical peptide comprising the steps of: (1) synthesizing a peptide, wherein the peptide comprises a sequence of eight amino acid residues, and wherein the sequence of eight amino acid residues has a first terminal residue and a second terminal residue, wherein the first terminal residue and the second terminal residue are independently selected from Asp and Glu; (2) providing a diamine linker having a first amino group capable of forming an amide linkage with the carboxy side chain of the first terminal residue and a second amino group capable of forming an amide linkage with the carboxy side chain of the second terminal residue; and (3) cyclizing the peptide by reacting the first amino group of the diamine linker with the carboxy side chain of the first terminal residue to form an amide linkage and reacting the second amino group of the diamine linker with the carboxy side chain of the second terminal residue to form an amide linkage, yielding a constrained helical peptide.

The invention also encompasses a method for constructing a constrained helical peptide comprising the steps of: (1) synthesizing a peptide, wherein the peptide comprises a sequence of eight amino acid residues, wherein the sequence of eight amino acid residues has a first terminal residue and a second terminal residue, wherein the first terminal residue and the second terminal residue flank an internal sequence of six amino acid residues, wherein the first terminal residue and the second terminal residue are independently selected from Asp and Glu, and wherein the carboxy side chain of the first terminal residue is protected with a first protecting group and the carboxy side chain of the second terminal residue is protected with a second protecting group such that the first protecting group and the second protecting group are differentially removable; (2) removing the first protecting group such that the carboxy side chain of the first terminal residue is deprotected and the carboxy side chain of the second terminal residue is not deprotected; (3) reacting the peptide with a diamine linker having a first amino group and a second amino group to form an amide linkage between the deprotected carboxy side chain of the first terminal residue and the first amino group of the diamine linker; (4) removing the second protecting group to deprotect the carboxy side chain of the second terminal residue; and (5) cyclizing the peptide by intramolecularly reacting the deprotected carboxy side chain of the second terminal residue with the second amino group of the diamine linker to form an amide linkage and yield a constrained helical peptide.

The invention further encompasses a method for constructing a constrained helical peptide comprising the steps of: (1) synthesizing a peptide, wherein the peptide comprises a sequence of eight amino acid residues, wherein the sequence of eight amino acid residues has a first terminal residue and a second terminal residue, wherein the first terminal residue and the second terminal residue flank an internal sequence of six amino acid residues, wherein the first terminal residue and the second terminal residue are independently selected from Asp and Glu, and wherein the carboxy side chain of the first terminal residue is coupled to a diamine linker having a first amino group and a second amino group, such that the carboxy side chain of the first terminal residue is in an amide linkage with the first amino group of the diamine linker; and (2) cyclizing the peptide by intramolecularlyreacting the carboxy side chain of the second terminal residue with the second amino group of the diamine linker to form an amide linkage and yield a constrained helical peptide.

The invention also encompasses a compound selected from the group consisting of:

the compound represented by Formula (1):

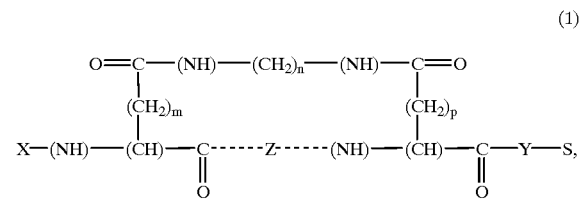

wherein S is absent or is a macromolecule, X is hydrogen or is any amino acid or amino acid sequence, Y is absent, or is hydroxyl if S is absent, or is any amino acid or amino acid sequence, Z is any amino acid sequence consisting of six amino acids; m and p are independently selected from the integers 0 to 6 inclusive, provided that m+p is less than or equal to 6, and n is any integer in the range defined by (7−(m+p)) to (9−(m+p)) inclusive, provided that n is greater than 1;

the compound represented by Formula (6):

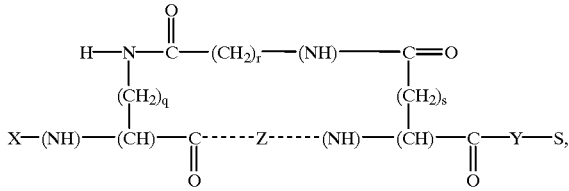

(6)

wherein S is absent or is a macromolecule, X is hydrogen or is any amino acid or amino acid sequence, Y is absent, or is hydroxyl if S is absent, or is any amino acid or amino acid sequence, Z is any amino acid sequence consisting of six amino acids, q is selected from the integers 1 to 7 inclusive, s is selected from the integers 0 to 6 inclusive, provided that q+s is less than or equal to 7, and r is any integer in the range defined by (7−(q+s)) to (9−(q+s)) inclusive, provided that r is greater than 0;

the compound represented by Formula (11):

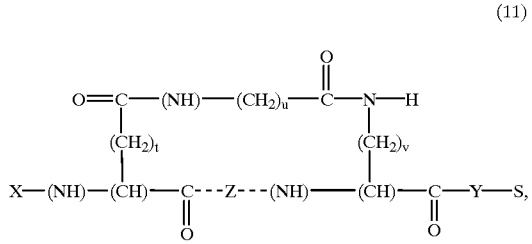

(11)

wherein S is absent or is a macromolecule, X is hydrogen or is any amino acid or amino acid sequence, Y is absent, or is hydroxyl if S is absent, or is any amino acid or amino acid sequence, Z is any amino acid sequence consisting of six amino acids; t is selected from the integers 0 to 6 inclusive, and v is selected from the integers 1 to 7 inclusive, provided that t+v is less than or equal to 7; and u is any integer in the range defined by (7−(t+v)) to (9−(t+v)) inclusive, provided that u is greater than 0; and the compound represented by Formula (16):

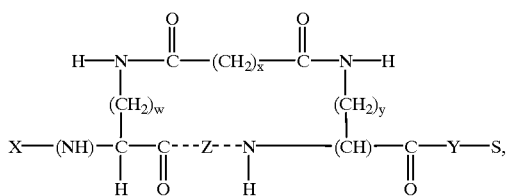

(16)

wherein S is absent or is a macromolecule, X is hydrogen or is any amino acid or amino acid sequence, Y is absent, or is hydroxyl if S is absent, or is any amino acid or amino acid sequence, Z is any amino acid sequence consisting of six amino acids; w and y are independently selected from the integers 1 to 7 inclusive, provided that w+y is less than or equal to 8, and x is any integer in the range defined by (7−(w+y)) to (9−(w+y)) inclusive, provided that x is greater than or equal to 0.

In a preferred embodiment is provided a compound 1 containing a constrained helical peptide that in turn contains a peptide of a sequence of eight amino acid residues, in which the sequence of eight amino acid residues has a first terminal residue and a second terminal residue that flank an internal sequence of six amino acids and that have a side chain that are linked to each other forming a locking moiety to form a constrained helical peptide. The internal sequence of six amino acid; has the form gabcde, defgab, or cdefga and is selected from the group of sequences consisting of a sequence of six contiguous amino acids in HIV-1LAI strain gp41 amino acid sequence 633 to 678, in its homolog sequence from another HIV strain, in a consensus sequence of its homolog sequences from any one HIV clade, or an amino acid substituted variant thereof, in which amino acid 633 or its corresponding amino acid in the homolog, consensus or variant sequence is assigned position a of a repeating abcdefg assignment for the 633–678 sequence (as shown in FIG. 18). In these compounds the locking moiety or tether is between adjacent f positions when the internal sequence is of the form gabcde, adjacent c positions when the internal sequence is of the form defgab, or adjacent b positions when the internal sequence is of the form cdefga. Most preferably the lock is between adjacent f positions. FIG. 18 provides the alignment of the repeating abcdefg assignment to the amino acids in the 633–678 region. In a preferred embodiment the internal sequence of six amino acids has the form gabcde. The compounds preferably have HIV anti-fusogenic or anti-infection activity.

Preferred compounds are those selected from the group consisting of constrained helical peptides of each possible sequence having any one or any combination of amino acid substitutions indicated in the constrained helical peptide series I to XII as shown in FIGS. 23A and 23D in combination with any one or any combination of amino acid truncations indicated in the constrained helical peptide series I to XII as shown in FIGS. 23A and 23D. Peptides HIV24 and HIV31 are particularly preferred compounds of this type.

In another embodiment the compounds of the invention are used as haptens, preferably attached to carriers, for use as an immunogen to raise antibodies that have a diagnostic use or as a vaccine for prophylactic or therapeutic treatment of patients at risk for or infected with HIV. Examples of such prophylactic use of the peptides may include, but are not limited to, prevention of virus transmission from mother to infant and other settings where the likelihood of HIV transmission exists, such as, for example, accidents in health care settings wherein workers are exposed to HIV-containing blood products. The constrained peptides of the invention can serve the role of a prophylactic vaccine, wherein the host raises antibodies against the peptides of the invention, which then serve to neutralize HIV viruses by, for example, inhibiting further HIV infection.

BRIEF DESCRIPTION OF THE DRAWINGS

FIG. 1 is a diagram depicting the synthesis of peptide 1b and 1c. Reagent a represents 20% piperidine/DMA; reagent b represents $H_2NCH_2CH_2CH_2NHR$ (R=H or BOC), BOP, DIPEA, $CH_2Cl_2$; reagent c represents Pd(PPh3)4, 20% piperidine/DMA, (R=BOC) $TFA/CH_2Cl_2$/anisole/1,2-ethanedithiol 45:45:5:5 v/v; reagent d represents BOP, DIPEA, $CH_2Cl_2$; reagent e represents HF/anisole/EtSMe20:2:1 v/v, 0° C.; and reagent f represents $CH_3NH_2$, BOP, $CH_2Cl_2$.

FIG. 2 is a diagram depicting the synthesis of N-Fmoc-S-Acm-D-thiolysine (compound 7). Reagent a represents "BuLi, THF, −78° C.; $Br(CH_2)_4Br$; reagent b represents 4-MeOBnSH, KO$^t$Bu, THF; reagent c represents 0.25 M HCl, THF/$H_2O$; reagent d represents $Hg(OAc)_2$, TFA; $H_2S$; reagent e represents acetamidomethanol, TFA; reagent f represents LiOH, THF/$H_2O$; and reagent g represents Fmoc-OSu, dioxane, $NaHCO_3$.

FIGS. 3a and 3b are graphs depicting the $H^N$—$H^\alpha$ and $H^N$—$H^N$ sections, respectively, of the ROESY spectrum of peptide 1c. The spectrum was collected at 280 K, pH 5.0, 500 MHZ and a peptide concentration of 1.5 mM with a 4.5 kHz spin-lock mixing pulse of 200 ms duration. Lines connect the ROEs by which sequential assignments were made. Rectangular, oval and diamond shaped boxes denote intra residue, sequential and (I, I+3) correlations, respectively.

FIG. 4 is a graph depicting ROE and $^3J_{HN-H\alpha}$ data for peptides 1c and 1b. For the $d_{NN}$ and $d_{\alpha N}$ rows, observation of the sequential ROE is indicated by a bar connecting two residues, the thickness of the bar indicating the relative intensity of the ROE. The downward pointing arrows indicate $^3J_{HN-H\alpha}$ less than 6.0 Hz. Observed medium range ROEs ($H^\alpha$—$H^N$ I, I+3 and $H^\alpha$—$H^\beta$ I, I+3) are indicated by the lines in the lower part of the figure; dotted lines and stars indicate ROEs that could not be unambiguously observed because of chemical shift degeneracy. The coil motif above the primary sequence indicates the region deduced to have helical structure from the NMR data; the dashed coil indicates sections of peptide where only some of the NMR data indicate helical character.

FIG. 5 is a molecular model depicting an ensemble of 20 rMD structures calculated using NMR data for peptide 1c. The structures were overlayed using the N, Cα and C atoms of residue Thr1 to Gln10. Backbone and side-chain heavy atoms are connected by solid and dotted lines, respectively. The side-chains of Arg8 and Arg9 are truncated at C$^\gamma$, and all side-chain atoms of Gln11 and Gln12 are omitted for clarity.

FIG. 6 is a graph depicting the CD spectra of peptide 1c at 280, 310, 330, 350, and 370 K.

FIG. 7 is a graph depicting the CD spectra of peptides 1 and 3 (Apamin-based sequences) at 280 K.

FIG. 8 is a graph depicting the CD spectra of peptides 2 and 4 (C-peptide-based sequences) at 280 K.

FIG. 9 is a graph depicting the thermal denaturation profile of peptide 1c as determined by CD spectra obtained before, during and after heating for 1 day at 87° C. Circles indicate the initial spectrum obtained from a sample before heating; squares indicate the spectrum obtained from a sample at 87° C. during incubation; triangles indicate the spectrum obtained from a sample after recooling to 7° C. at 0.2° C./min.

FIG. 10 is a graph depicting a section of the TOCSY spectrum of peptide 1c. The data were collected at 280 K, pH 5.0, 500 MHZ and a peptide concentration of 1.5 mM with a mixing time of 90 ms. The solid lines connect cross-peaks between backbone amide and side chain protons; assignments are indicated at the top of each line. Dashed lines connect cross-peaks between the side chain amide protons of Gln3 and Gln10 and the methylene linker resonances.

FIG. 12 depicts sequences and schematic representations of the locked-helix peptide embodiments of the invention. The cylinders represent α-helices, with the stippled faces corresponding to the 4, 3 hydrophobic repeat. Covalent restraints linking sidechains at I and I+7 are represented as dark lines.

FIG. 13 is a circular dichroism spectra of peptides HIV24 (open squares), HIV30 (open circles), HIV31 (closed circles), and HIV35 (closed squares). Spectra were acquired at 7° C. in 10 mM Tris-HCl, pH 7.5 (21).

FIGS. 14A and 14B are graphs depicting the effect of inhibitory peptides in primary infectivity assays using PBMCs with virus JRCSF, an NSI strain (FIG. 14A), and BZ167, an SI strain (FIG. 14B) (22). HIV24 (closed triangles); HIV30 (open circles); HIV31 (closed circles); HIV35 (closed squares); DP178, (open squares).

FIGS. 16A to 16M present amino acid sequences of gp41 from known HIV virus strains and their consensus sequences based on statistical amino acid frequency. Amino acids are represented by the standard single letter code. The strains within each HIV clade are presented. A "-" in a sequence represents the amino acid present in the consensus sequence for that clade. A "." represents an amino acid gap. A "?" in a consensus sequence represents any amino acid at that corresponding position found in a viral sequence within that clade. A lower case amino acid represents the most frequent amino acid from among all amino acids at that corresponding position in viral sequences within that clade. An upper case amino acid in a consensus sequence indicates that only that amino acid is found at that corresponding position in viral sequences within that clade. Strain designations with no sequence information indicate that the complete gp41 sequence has not been determined.

FIG. 17 is a summary of consensus sequences from known strains. The peptide sequence of DP178 is delineated. The nomenclature is the same as in FIGS. 16A to 16M.

FIG. 18 is a schematic presenting an alignment of sequences from clades A, B, C, D, and E consensus sequences, peptides DP178, HIV35 and the Neurath peptide, in which the repeating heptad abcdefg assignment as taught herein is provided, and positions of some constraining locks are indicated. For example, amino acids in the sequence ESQNQQ of DP178 are assigned positions g, a, b, c, d, and e, respectively, and thus has the form gabcde, for purposes o the present invention. This sequence is the internal sequence of six amino acids present in peptide HIV24, which is a single-lock form of the HIV35 sequence. Locations of internal sequences of the invention are those found between locking residues, whose positions are indicated by the "|" symbols and each of which, in this example, correspond to assigned position f. Positions for placing either one, two or three locks in the representative presented sequences are shown. The figure delineates five gabcde form helical sections suitable for locking when locks occur at adjacent f positions. Also shown are locations of gabcde form helical sections when one, two or three i to i+7 locks are present in a 633–678 sequence or variant thereof. The two-lock variants are labeled (II), (III), HIV31, (VI) and (VII), and the one-lock variants (VIII), (IX), HIV24, (XI) and (XII). Three-lock variant is labeled (I).

FIG. 19 is a helical wheel representation of the representative gp41 fusion peptide sequence from the HIV-1 LAI strain, showing the "abcdefg" heptad reading fame and the heptad repeat pattern as assigned herein (see FIG. 18) for the purposes of the present invention.

FIG. 20 is a schematic depicting the use of the compounds of the invention as haptens for immunization and shows the gp41 core trimer, its DP178 binding groove and the 633–678 region that binds this grove.

FIG. 21 is a schematic depicting a proposed mechanism for antibody intervention in HIV viral infectivity.

FIG. 22 is presents a consensus sequence of the HIV gp41 sequences from FIG. 17 with all allowed amino acid substitutions in each position listed. For example, at the fifth amino acid position (starting from the N-terminal amino acid (left end)), the amino acids E (glutamic acid), D (aspartic acid) and K (lysine) are allowed without disrupting H-bonding, thus without disrupting helicity or significantly interfering with the peptide's interaction with the core coiled-coil trimer of gp41. "X" indicates positions that can be substituted with any non-helix breaking amino acid. The repeating heptad abcdefg assignment for each amino acid position in the 633 to 678 sequence, for purposes of the present invention, is shown. The "*" indicate b, c, and f positions that, when not used for locking the helix, can be replaced with a non helix-breaking amino acid without significantly disturbing H-bonding, helicity and trimer groove binding.

FIGS. 23A and 23D present a shorthand notation of specific peptides in peptide series I–VII (FIG. 23A) and VIII–XII (FIG. 23B) (as in FIG. 18), indicating locking positions, amino acid substitution variant peptides, and truncation variant peptides of each. The "X" indicates a position that can be substituted with any non helix-breaking amino acid, but preferably with an amino acid present in that position from any one of the known HIV sequences shown in FIG. 16. "B" indicates a position used for the bridging (or tethering or locking) residues. Preferred f positions are presented for locking; however in less preferred embodiments the c and some b positions can be used for locking. As in FIG. 18, locations of internal sequences relevant to the invention are those found between locking residues whose positions are indicated by the "|" symbols and correspond to assigned position f, in this example. Positions for placing either one, two or three locks in the representative presented sequences are shown. The figure delineates five gabcde form helical sections suitable for locking when locks occur at adjacent f positions. The "." indicates positions that can be optionally absent from the final constrained helical peptide compound without substantially effecting the helical properties and groove binding properties of the final constrained helical peptide. For example, a peptide based on peptide 1, having the three locks placed as indicated, can optionally lack any one or all of the five N-terminal amino acids WXXWE, which are marked by a ".". Further, another series of truncated variants is indicated in the figure—C-terminal truncated variants—since the five C-terminal residues (LWNWF) are marked with a "." can be absent. When the lock is placed more centrally in the 633–678 sequence, as shown in peptide series 11, peptides in this series can lack additional amino acids at the C-terminal end as indicated by the "." marked positions.

DETAILED DESCRIPTION OF THE PREFERRED EMBODIMENTS

A. Definitions

Amino acids and amino acid residues described herein may be referred to according to the accepted one or three letter code provided in the table below. Unless otherwise specified, these amino acids or residues are of the naturally occurring L stereoisomer form.

| Common Name | One-Letter Symbol | Three-Letter Symbol |
|---|---|---|
| Alanine | A | Ala |
| Arginine | R | Arg |
| Asparagine | N | Asn |
| Aspartic acid | D | Asp |
| Cysteine | C | Cys |
| Glutamine | Q | Gln |
| Glutamic acid | E | Glu |
| Glycine | G | Gly |
| Histidine | H | His |
| Isoleucine | I | Ile |
| Leucine | L | Leu |
| Lysine | K | Lys |
| Methionine | M | Met |
| Phenylalanine | F | Phe |
| Proline | P | Pro |
| Serine | S | Ser |
| Threonine | T | Thr |
| Tryptophan | W | Trp |
| Tyrosine | Y | Tyr |

In general, unless otherwise specified, the abbreviations used for the designation of amino acids and the protective groups used therefor are based on the recommendations of the IUPAC-IUB Commission of Biochemical Nomenclature (*Biochemistry,* 11: 1726–1732 (1972)).

As used herein, the term $-(CH_2)_n-$ is used to denote a straight chain alkyl substituent of n carbons in length, wherein $-(CH_2)_0-$ is defined as a chemical bond, i.e. indicating that no alkyl substituent is present, $-(CH_2)_1-$ is defined as a methyl substituent, $-(CH_2)_2-$ is defined as an ethyl substituent, etc.

As used herein, the term "$C_1$–$C_6$alkyl" means a saturated aliphatic hydrocarbon substituent having the number of carbon atoms specified. $C_1$–$C_6$alkyl encompasses cyclic and straight chain hydrocarbons, unbranched and branched hydrocarbons, substituted and unsubstituted hydrocarbons, and primary, secondary and tertiary hydrocarbon substituents. Representative examples of these alkyl substituents include methyl, fluorenylmethyl, ethyl, n-propyl, isopropyl, n-butyl, isobutyl, sec-butyl, tert-butyl, n-pentyl, 2-methylbutyl, 2,2-dimethylpropyl, n-hexyl, 2-methylpentyl, 2,2-dimethylbutyl, cyclohexyl, and the like. The terms "lower alkyl", "simple alkyl" and "$C_1$–$C_6$alkyl" are synonymous and used interchangeably.

As used herein, the terms "peptide", "polypeptide", and "protein" are used synonymously and refer to any proteinaceous compound comprising an amino acid sequence of two or more amino acid residues.

As used herein, an "amide bond-forming substituent contained in an amino acid side chain", a "side chain amide bond-forming subsituent", and their grammatical variants, are defined to include (1) any carboxy substituent contained in the side chain ("R" group) of an amino acid wherein the carboxy substituent is capable of forming an amide linkage with an amino group contained in another molecule, i.e. the carboxy substitutent reacts with an amino group contained in another molecule to form an amide linkage; and (2) any amino substituent contained in the side chain ("R" group) of an amino acid wherein the amino substituent is capable of forming an amide linkage with a carboxy group contained in another molecule, i.e. the amino substitutent reacts with a carboxy group contained in another molecule to form an amide linkage.

As used herein, "differentially removable" protecting or protective groups are defined as any pair of protective groups capable of protecting a first amide bond-forming substituent and a second amide bond-forming substituent, wherein it is possible to deprotect the first amide bond-forming substituent protected with one member of the pair under conditions which do not deprotect the second amide bond-forming substituent protected with the other member of the pair. Differentially removable protecting groups are also referred to herein as "orthogonal" protecting groups, and the differentially removable protection conferred by such protective groups is referred to herein as "orthogonal" protection.

Figure 11:
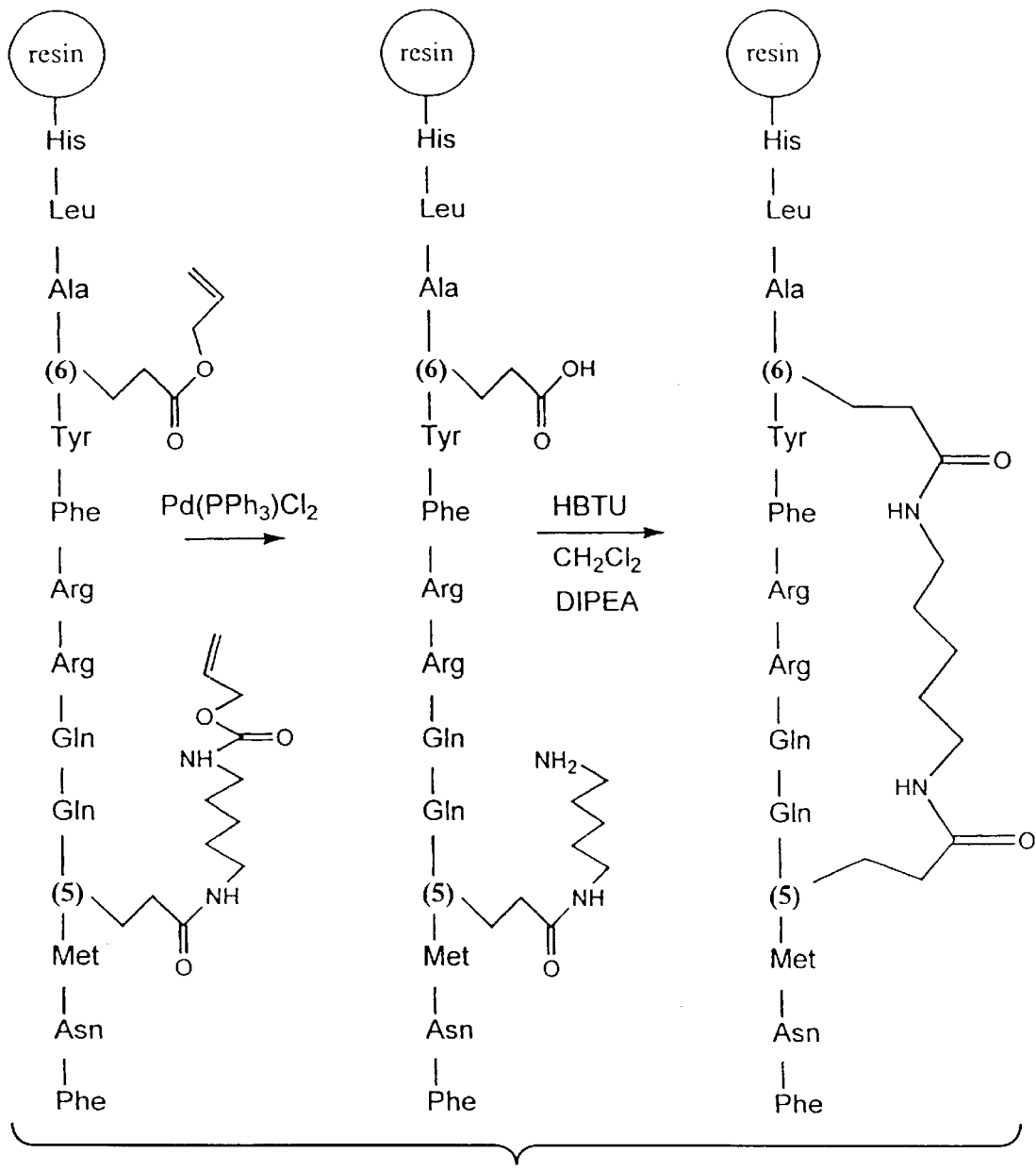
FIG. 11 is a diagram depicting the synthesis of a locked helix species of the peptide Asn-Met-Glu-Gln-Gln-Arg-Arg-Phe-Tyr-Glu-Ala-Leu-His where the carboxy side chains of the Glu residues are covalently linked with a 1,5-pentanediamine linker.

The term "epitope" as used herein, designates the structural component of a molecule that is responsible for specific interactions with corresponding antibody (immunoglobulin) molecules elicited by the same or related antigen. More generally, the term refers to a peptide having the same or similar immunoreactive properties, such as specific antibody binding affinity, as the antigenic protein or peptide used to generate the antibody. Therefore, an epitope that is formed by a specific peptide sequence generally refers to any peptide which is reactive with antibodies directed against the specific sequence.

The term "antigen" as used herein, means a molecule which is used to induce production of antibodies. The term is alternatively used to denote a molecule which is reactive with a specific antibody.

The term "immunogen" as used herein, describes an entity that induces antibody production in a host animal. In some instances the antigen and the immunogen are the same entity, while in other instances the two entities are different.

The term "subunit vaccine" is used herein, as in the art, to refer to a viral vaccine that does not contain virus, but rather contains one or more viral proteins or fragments of viral proteins. As used herein, the term "multivalent", means that the vaccine contains a constrained helical peptide or peptides having a gp41-based sequence from at least two HIV isolates having different amino acid sequences.

The term "break through isolate" or "break through virus" is used herein, as in the art, to refer to a virus isolated from a vaccinee.

B. General Methods

In general, the invention provides a method for removing elements of α-helical secondary structure from the context of a protein without losing the well defined structure found within the protein's α-helix. In one aspect, the method is useful for artificially reconstructing and characterizing the binding determinants that exist within an α-helical binding domain of a protein of interest. The design of molecules which are capable of binding competitively at a protein interface requires the ability to mimic the higher level structure of the natural ligand. If the ligand's structure at the site of protein interface can be mimicked with a short peptide, then the peptide can be used to determine whether it is feasible to design small molecules that competitively bind at the protein interface. A short peptide's ability to compete with the natural ligand for binding at the protein interface would indicate that the ligand's structure at the contact point with the protein interface is such that the short peptide could be used as a model for designing small molecules that compete with the natural ligand for binding at the protein interface.

In another aspect, the methods of the invention are used to stabilize the conformational structure of a protein or peptide. The present methods can be employed to lock in place one (or more) α-helical determinant(s) of interest in a protein or peptide such that the protein (or peptide) retains an α-helical conformation in environments or conditions that would destabilize or deteriorate the α-helical secondary structure of an unconstrained protein or peptide species.

The methods of the invention are also useful for the replication of protein function without an intact protein or intact functional domain. For example, the replication of a protein's binding activity by a constrained helical peptide of the invention would allow the use of affinity purification procedures for the protein's ligand without requiring a supply of intact protein or large fragments thereof. Thus, a constrained helical peptide possessing a particular protein's binding activity could overcome supply or cost problems preventing the use of the protein in affinity purification. In yet another example, a constrained helical peptide possessing the conformational structure at the site of interest in a particular protein could be used to isolate a conformational epitope from the rest of the protein and raise antibodies against the single epitope of interest without interference from the other antigenic sites existing in the intact protein.

Particularly preferred are the use of the compounds of the invention having constrained helical peptides having internal amino acid sequences from the HIV isolate LAI gp41 amino acid sequence 633–678 and homologs thereof, for use as haptens, vaccines, and in diagnostics.

In another aspect, the methods and peptides of the invention can be used to create combinatorial constrained helical peptide libraries that are useful in chemical selection systems.

I. Locked Helix Peptides and Uses Therefor

The invention provides locked helix peptides of formula (1):

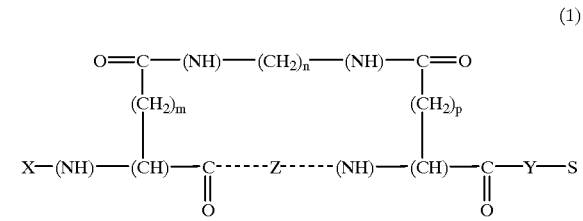

(1)

wherein S is absent or is a macromolecule; X is hydrogen or is any amino acid or amino acid sequence; Y is absent, or is hydroxyl if S is absent, or is any amino acid or amino acid sequence;

Z is any amino acid sequence consisting of six amino acids; m and p are independently selected from the integers 0 to 6 inclusive, provided that m+p is less than or equal to 6; and n is any integer in the range defined by $(7-(m+p))$ to $(9-(m+p))$ inclusive, provided that n is greater than 1.

In another embodiment, the invention provides locked helix peptides of formula (2):

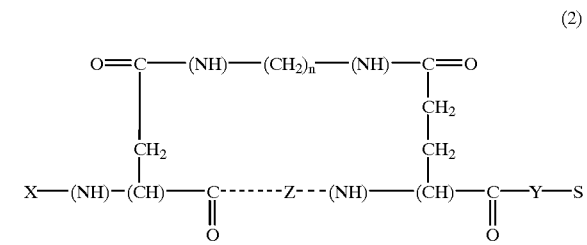

(2)

wherein S is absent or is a macromolecule; X is hydrogen or is any amino acid or amino acid sequence; Y is absent, or is hydroxyl if S is absent, or is any amino acid or amino acid sequence;

Z is any amino acid sequence consisting of six amino acids; and n is any integer from 4 to 6 inclusive.

In yet another embodiment, the invention provides locked helix peptides of formula (3):

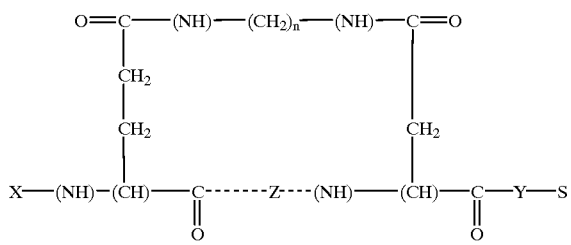

(3)

wherein S is absent or is a macromolecule; X is hydrogen or is any amino acid or amino acid sequence; Y is absent, or is hydroxyl if S is absent, or is any amino acid or amino acid sequence;

Z is any amino acid sequence consisting of six amino acids; and n is any integer from 4 to 6 inclusive.

In still another embodiment, the invention provides locked helix peptides of formula (4):

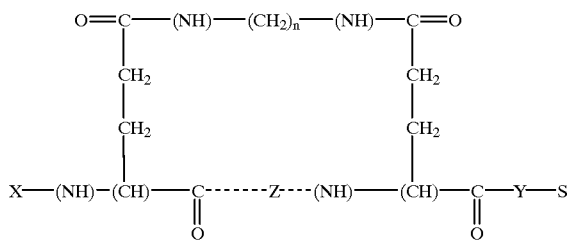

(4)

wherein S is absent or is a macromolecule; X is hydrogen or is any amino acid or amino acid sequence; Y is absent, or is hydroxyl if S is absent, or is any amino acid or amino acid sequence;

Z is any amino acid sequence consisting of six amino acids; and n is any integer from 3 to 5 inclusive.

In still another embodiment, the invention provides locked helix peptides of formula (5):

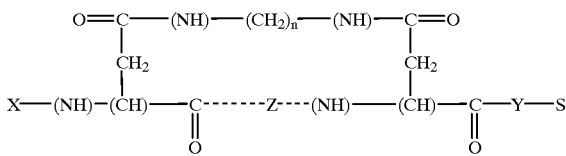

(5)

wherein S is absent or is a macromolecule; X is hydrogen or is any amino acid or amino acid sequence; Y is absent, or is hydroxyl if S is absent, or is any amino acid or amino acid sequence;

Z is any amino acid sequence consisting of six amino acids; and n is any integer from 5 to 7 inclusive.

In still another embodiment, the invention provides locked helix peptides of formula (6):

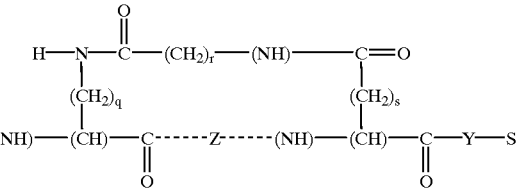

(6)

wherein S is absent or is a macromolecule; X is hydrogen or is any amino acid or amino acid sequence; Y is absent, or is hydroxyl if S is absent, or is any amino acid or amino acid sequence;

Z is any amino acid sequence consisting of six amino acids; q is selected from the integers 1 to 7 inclusive, and s is selected from the integers 0 to 6 inclusive, provided that q+s is less than or equal to 7; and r is any integer in the range defined by (7–(q+s)) to (9–(q+s)) inclusive, provided that r is greater than 0.

In still another embodiment, the invention provides locked helix peptides of formula (7):

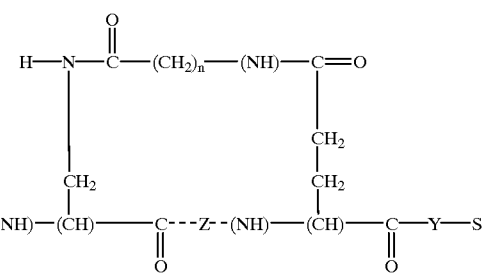

(7)

wherein S is absent or is a macromolecule; X is hydrogen or is any amino acid or amino acid sequence; Y is absent, or is hydroxyl if S is absent, or is any amino acid or amino acid sequence;

Z is any amino acid sequence consisting of six amino acids; and n is any integer from 4 to 6 inclusive.

In still another embodiment, the invention provides locked helix peptides of formula (8):

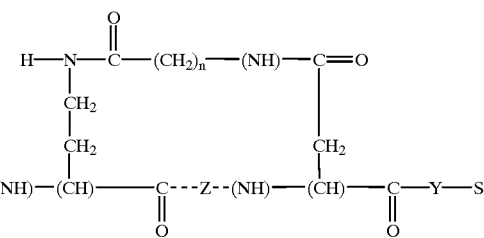

(8)

wherein S is absent or is a macromolecule; X is hydrogen or is any amino acid or amino acid sequence; Y is absent, or is hydroxyl if S is absent, or is any amino acid or amino acid sequence;

Z is any amino acid sequence consisting of six amino acids; and n is any integer from 4 to 6 inclusive.

In still another embodiment, the invention provides locked helix peptides of formula (9):

(9)

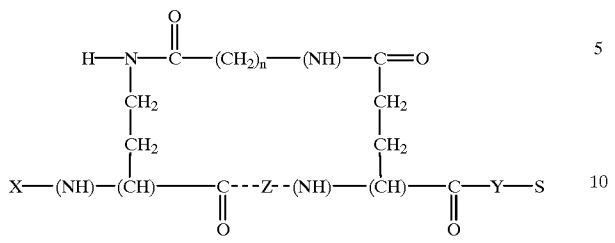

wherein S is absent or is a macromolecule; X is hydrogen or is any amino acid or amino acid sequence; Y is absent, or is hydroxyl if S is absent, or is any amino acid or amino acid sequence;

Z is any amino acid sequence consisting of six amino acids; and n is any integer from 3 to 5 inclusive.

In still another embodiment, the invention provides locked helix peptides of formula (10):

(10)

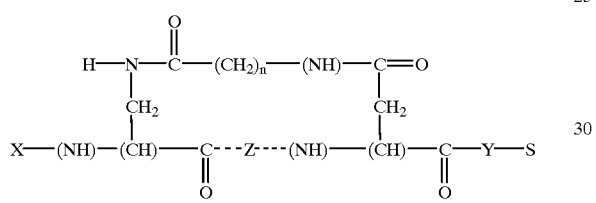

wherein S is absent or is a macromolecule; X is hydrogen or is any amino acid or amino acid sequence; Y is absent, or is hydroxyl if S is absent, or is any amino acid or amino acid sequence;

Z is any amino acid sequence consisting of six amino acids; and n is any integer from 5 to 7 inclusive.

In still another embodiment, the invention provides locked helix peptides of formula (11):

(11)

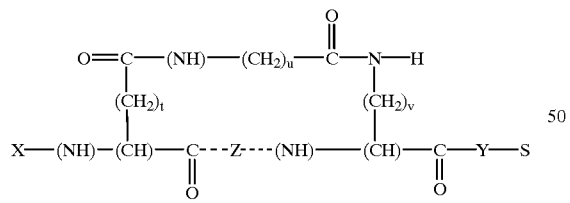

wherein S is absent or is a macromolecule; X is hydrogen or is any amino acid or amino acid sequence; Y is absent, or is hydroxyl if S is absent, or is any amino acid or amino acid sequence;

Z is any amino acid sequence consisting of six amino acids; t is selected from the integers 0 to 6 inclusive, and v is selected from the integers 1 to 7 inclusive, provided that t+v is less than or equal to 7; and u is any integer in the range defined by (7−(t+v)) to (9−(t+v)) inclusive, provided that u is greater than zero.

In still another embodiment, the invention provides locked helix peptides of formula (12):

(12)

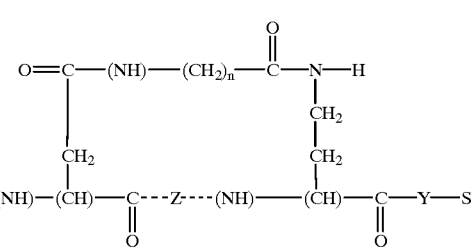

wherein S is absent or is a macromolecule; X is hydrogen or is any amino acid or amino acid sequence; Y is absent, or is hydroxyl if S is absent, or is any amino acid or amino acid sequence;

Z is any amino acid sequence consisting of six amino acids; and n is any integer from 4 to 6 inclusive.

In still another embodiment, the invention provides locked helix peptides of formula (13):

(13)

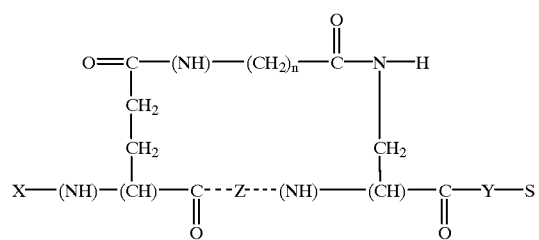

wherein S is absent or is a macromolecule; X is hydrogen or is any amino acid or amino acid sequence; Y is absent, or is hydroxyl if S is absent, or is any amino acid or amino acid sequence;

Z is any amino acid sequence consisting of six amino acids; and n is any integer from 4 to 6 inclusive.

In still another embodiment, the invention provides locked helix peptides of formula (14):

(14)

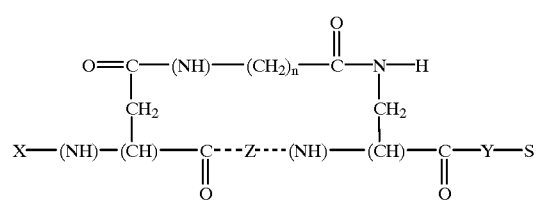

wherein S is absent or is a macromolecule; X is hydrogen or is any amino acid or amino acid sequence; Y is absent, or is hydroxyl if S is absent, or is any amino acid or amino acid sequence;

Z is any amino acid sequence consisting of six amino acids; and n is any integer from 5 to 7 inclusive.

In still another embodiment, the invention provides locked helix peptides of formula (15):

(15)

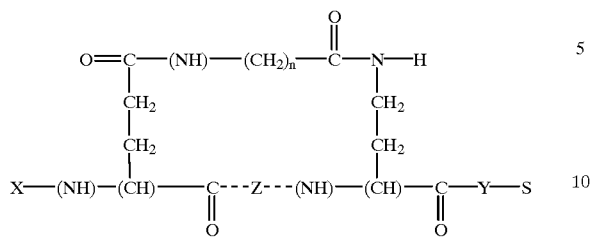

wherein S is absent or is a macromolecule; X is hydrogen or is any amino acid or amino acid sequence; Y is absent, or is hydroxyl if S is absent, or is any amino acid or amino acid sequence;

Z is any amino acid sequence consisting of six amino acids; and n is any integer from 3 to 5 inclusive.

In still another embodiment, the invention provides locked helix peptides of formula (16):

(16)

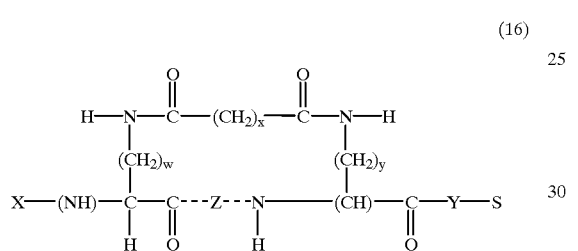

wherein S is absent or is a macromolecule; X is hydrogen or is any amino acid or amino acid sequence; Y is absent, or is hydroxyl if S is absent, or is any amino acid or amino acid sequence;

Z is any amino acid sequence consisting of six amino acids; w and y are independently selected from the integers 1 to 7 inclusive, provided that w+y is less than or equal to 8; and x is any integer in the range defined by (7−(w+y)) to (9−(w+y)) inclusive, provided that x is greater than or equal to 0.

In still another embodiment, the invention provides locked helix peptides of formula (17):

(17)

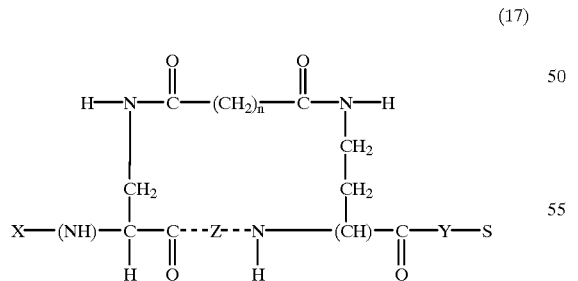

wherein S is absent or is a macromolecule; X is hydrogen or is any amino acid or amino acid sequence; Y is absent, or is hydroxyl if S is absent, or is any amino acid or amino acid sequence;

Z is any amino acid sequence consisting of six amino acids; and n is any integer from 4 to 6 inclusive.

In still another embodiment, the invention provides locked helix peptides of formula (18):

(18)

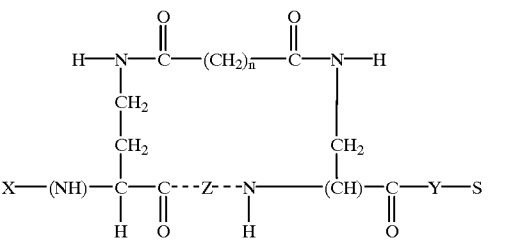

wherein S is absent or is a macromolecule; X is hydrogen or is any amino acid or amino acid sequence; Y is absent, or is hydroxyl if S is absent, or is any amino acid or amino acid sequence;

Z is any amino acid sequence consisting of six amino acids; and n is any integer from 4 to 6 inclusive.

In still another embodiment, the invention provides locked helix peptides of formula (19):

(19)

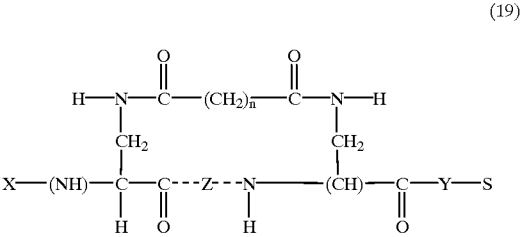

wherein S absent or is a macromolecule; X is hydrogen or is any amino acid or amino acid sequence; Y is absent, or is hydroxyl if S is absent, or is any amino acid or amino acid sequence;

Z is any amino acid sequence consisting of six amino acids; and n is any integer from 5 to 7 inclusive.

In still another embodiment, the invention provides locked helix peptides of formula (20):

(20)

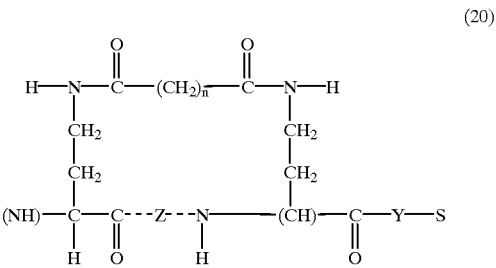

wherein S is absent or is a macromolecule; X is hydrogen or is any amino acid or amino acid sequence; Y is absent, or is hydroxyl if S is absent, or is any amino acid or amino acid sequence;

Z is any amino acid sequence consisting of six amino acids; and n is any integer from 3 to 5 inclusive.

In a further embodiment, the invention provides locked helix peptides of formula (1), formula (2), formula (3), formula (4), formula (5), formula (6), formula (7), formula (8), formula (9), formula (10), formula (11), formula (12), formula (13), formula (14), formula (15), formula (16), formula (17), formula (18), formula (19) and formula (20) wherein X, Y, and Z collectively contain up to or about 35 amino acids (i.e. locked helix peptides of formulas (1), (2), (3), (4), (5), (6), (7), (8), (9), (10), (11), (12), (13), (14), (15), (16), (17), (18), (19) and (20) each of which contains a total of no more than or about 35 amino acid residues).

Also provided herein are locked helix peptides of formula (1), formula (2), formula (3), formula (4), formula (5), formula (6), formula (7), formula (8), formula (9), formula (10), formula (11), formula (12), formula (13), formula (14), formula (15), formula (16), formula (17), formula (18), formula (19) and formula (20) wherein X and/or Y contain(s) up to or about 30 amino acid residues.

Further provided herein are locked helix peptides of formula (1), formula (2), formula (3), formula (4), formula (5), formula (6), formula (7), formula (8), formula (9), formula (10), formula (11), formula (12), formula (13), formula (14), formula (15), formula (16), formula (17), formula (18), formula (19) and formula (20) wherein X and/or Y contain(s) up to or about 25 amino acid residues.

Additionally provided herein are locked helix peptides of formula (1), formula (2), formula (3), formula (4), formula (5), formula (6), formula (7), formula (8), formula (9), formula (10), formula (11), formula (12), formula (13), formula (14), formula (15), formula (16), formula (17), formula (18), formula (19) and formula (20) wherein X and/or Y contain(s) up to or about 20 amino acid residues.

Also encompassed herein are locked helix peptides of formula (1), formula (2), formula (3), formula (4), formula (5), formula (6), formula (7), formula (8), formula (9), formula (10), formula (11), formula (12), formula (13), formula (14), formula (15), formula (16), formula (17), formula (18), formula (19) and formula (20) wherein X and/or Y contain(s) up to or about 15 amino acid residues.

Further encompassed herein are locked helix peptides of formula (1), formula (2), formula (3), formula (4), formula (5), formula (6), formula (7), formula (8), formula (9), formula (10), formula (11), formula (12), formula (13), formula (14), formula (15), formula (16), formula (17), formula (18), formula (19) and formula (20) wherein X and/or Y contain(s) up to or about 10 amino acid residues.

Additionally encompassed herein are locked helix peptides of formula (1), formula (2), formula (3), formula (4), formula (5), formula (6), formula (7), formula (8), formula (9), formula (10), formula (11), formula (12), formula (13), formula (14), formula (15), formula (16), formula (17), formula (18), formula (19) and formula (20) wherein X and/or Y contain(s) up to or about 5 amino acid residues.

Also within the scope of the invention are locked helix peptides of formula (1), formula (2), formula (3), formula (4), formula (5), formula (6), formula (7), formula (8), formula (9), formula (10), formula (11), formula (12), formula (13), formula (14), formula (15), formula (16), formula (17), formula (18), formula (19) and formula (20) wherein X and/or Y contain(s) up to or about 3 amino acid residues.

The invention also provides locked helix peptides of formula (1a):

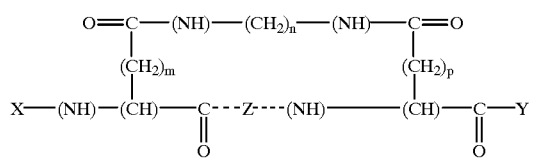

(1a)

wherein X is hydrogen or is any amino acid or amino acid sequence; Y is hydroxyl or is any amino acid or amino acid sequence; Z is any amino acid sequence consisting of six amino acids; m and p are independently selected from the integers 0 to 6 inclusive, provided that m+p is less than or equal to 6; and n is any integer in the range defined by (7−(m+p)) to (9−(m+p)) inclusive, provided that n is greater than 1.

In another embodiment, the invention provides locked helix peptides of formula (2a):

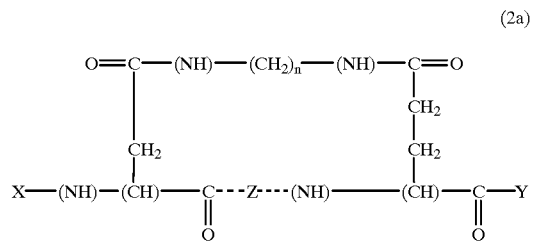

(2a)

wherein X is hydrogen or is any amino acid or amino acid sequence; Y is hydroxyl or is any amino acid or amino acid sequence; Z is any amino acid sequence consisting of six amino acids; and n is any integer from 4 to 6 inclusive.

In yet another embodiment the invention provides locked helix peptides of formula (3a):

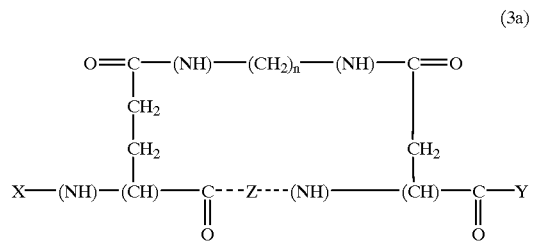

(3a)

wherein X is hydrogen or is any amino acid or amino acid sequence; Y is hydroxyl or is any amino acid or amino acid sequence; Z is any amino acid sequence consisting of six amino acids; and n is any integer from 4 to 6 inclusive.

In still another embodiment, the invention provides locked helix peptides of formula (4a):

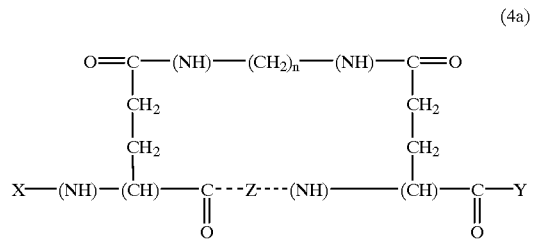

(4a)

wherein X is hydrogen or is any amino acid or amino acid sequence; Y is hydroxyl or is any amino acid or amino acid sequence; Z is any amino acid sequence consisting of six amino acids; and n is any integer from 3 to 5 inclusive.

In still another embodiment, the invention provides locked helix peptides of formula (5a):

(5a)

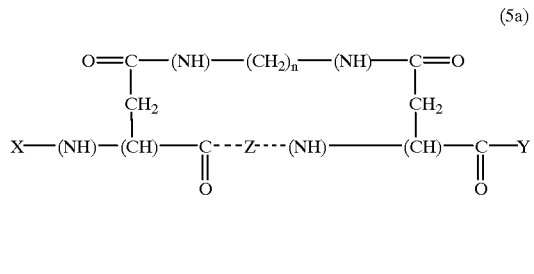

wherein X is hydrogen or is any amino acid or amino acid sequence; Y is hydroxyl or is any amino acid or amino acid sequence; Z is any amino acid sequence consisting of six amino acids; and n is any integer from 5 to 7 inclusive.

In still another embodiment, the invention provides locked helix peptides of formula (6a):

(6a)

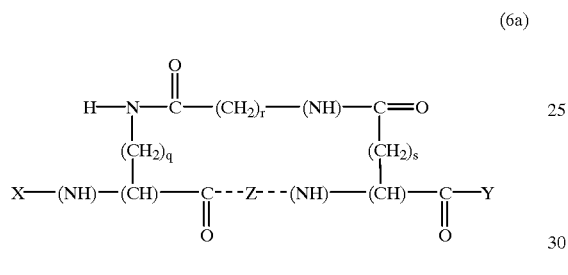

wherein X is hydrogen or is any amino acid or amino acid sequence; Y is hydroxyl or is any amino acid or amino acid sequence; Z is any amino acid sequence consisting of six amino acids; q is selected from the integers 1 to 7 inclusive, and s is selected from the integers 0 to 6 inclusive, provided that q+s is less than or equal to 7; and r is any integer in the range defined by (7−(q+s)) to (9−(q+s)) inclusive, provided that r is greater than 0.

In still another embodiment, the invention provides locked helix peptides of formula (7a):

(7a)

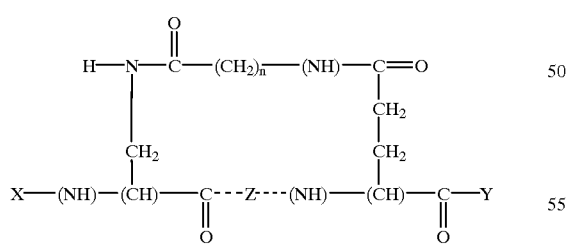

wherein X is hydrogen or is any amino acid or amino acid sequence; Y is hydroxyl or is any amino acid or amino acid sequence; Z is any amino acid sequence consisting of six amino acids; and n is any integer from 4 to 6 inclusive.

In still another embodiment, the invention provides locked helix peptides of formula (8a):

(8a)

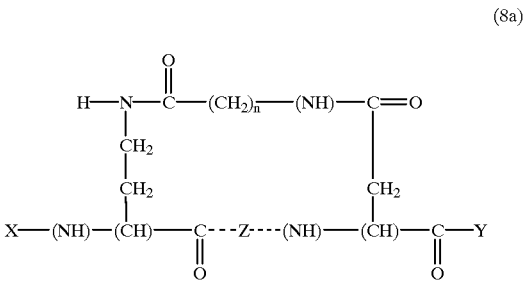

wherein X is hydrogen or is any amino acid or amino acid sequence; Y is hydroxyl or is any amino acid or amino acid sequence; Z is any amino acid sequence consisting of six amino acids; and n is any integer from 4 to 6 inclusive.

In still another embodiment, the invention provides locked helix peptides of formula (9a):

(9a)

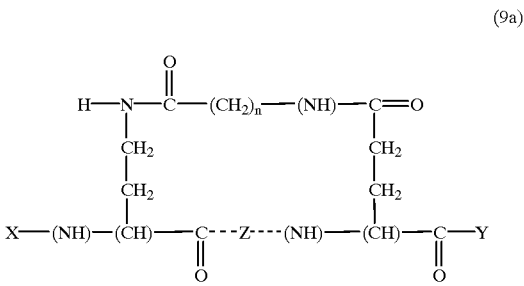

wherein X is hydrogen or is any amino acid or amino acid sequence; Y is hydroxyl or is any amino acid or amino acid sequence; Z is any amino acid sequence consisting of six amino acids; and n is any integer from 3 to 5 inclusive.

In still another embodiment, the invention provides locked helix peptides of formula (10a):

(10a)

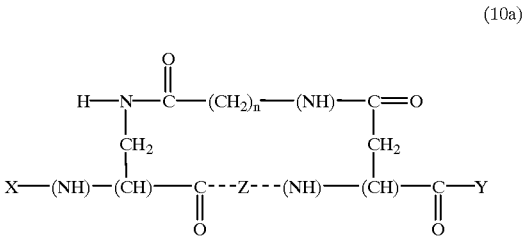

wherein X is hydrogen or is any amino acid or amino acid sequence; Y is hydroxyl or is any amino acid or amino acid sequence; Z is any amino acid sequence consisting of six amino acids; and n is any integer from 5 to 7 inclusive.

In still another embodiment, the invention provides locked helix peptides of formula (11a):

(11a)

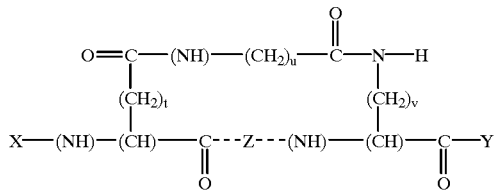

wherein X is hydrogen or is any amino acid or amino acid sequence; Y is hydroxyl or is any amino acid or amino acid sequence; Z is any amino acid sequence consisting of six amino acids; t is selected from the integers 0 to 6 inclusive, and v is selected from the integers 1 to 7 inclusive, provided that t+v is less than or equal to 7; and u is any integer in the range defined by (7−(t+v)) to (9−(t+v)) inclusive, provided that u is greater than 0.

In still another embodiment, the invention provides locked helix peptides of formula (12a):

(12a)

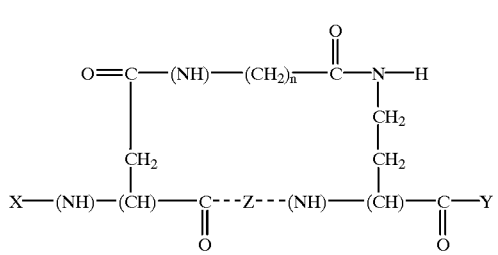

wherein X is hydrogen or is any amino acid or amino acid sequence; Y is hydroxyl or is any amino acid or amino acid sequence; Z is any amino acid sequence consisting of six amino acids; and n is any integer from 4 to 6 inclusive.

In still another embodiment, the invention provides locked helix peptides of formula (13a):

(13a)

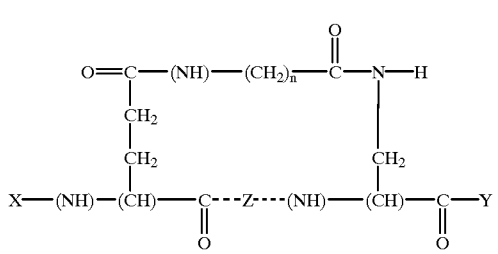

wherein X is hydrogen or is any amino acid or amino acid sequence; Y is hydroxyl or is any amino acid or amino acid sequence; Z is any amino acid sequence consisting of six amino acids; and n is any integer from 4 to 6 inclusive.

In still another embodiment, the invention provides locked helix peptides of formula (14a):

(14a)

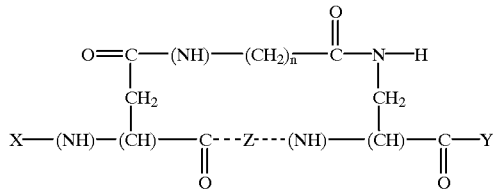

wherein X is hydrogen or is any amino acid or amino acid sequence; Y is hydroxyl or is any amino acid or amino acid sequence; Z is any amino acid sequence consisting of six amino acids; and n is any integer from 5 to 7 inclusive.

In still another embodiment, the invention provides locked helix peptides of formula (15a):

(15a)

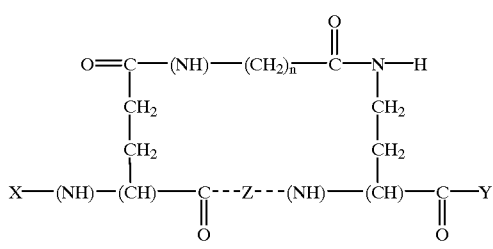

wherein X is hydrogen or is any amino acid or amino acid sequence; Y is hydroxyl or is any amino acid or amino acid sequence; Z is any amino acid sequence consisting of six amino acids; and n is any integer from 3 to 5 inclusive.

In still another embodiment, the invention provides locked helix peptides of formula (16a):

(16a)

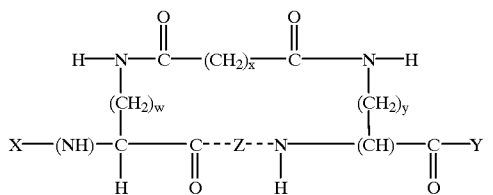

wherein X is hydrogen or is any amino acid or amino acid sequence; Y is hydroxyl or is any amino acid or amino acid sequence; Z is any amino acid sequence consisting of six amino acids; w and y are independently selected from the integers 1 to 7 inclusive, provided that w+y is less than or equal to 8; and x is any integer in the range defined by (7−(w+y)) to (9−(w+y)) inclusive, provided that x is greater than or equal to 0.

In still another embodiment, the invention provides locked helix peptides of formula (17a):

(17a)

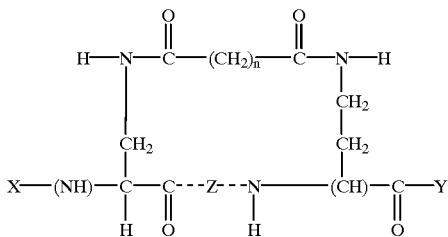

wherein X is hydrogen or is any amino acid or amino acid sequence; Y is hydroxyl or is any amino acid or amino acid sequence; Z is any amino acid sequence consisting of six amino acids; and n is any integer from 4 to 6 inclusive.

In still another embodiment, the invention provides locked helix peptides of formula (18a):

(18a)

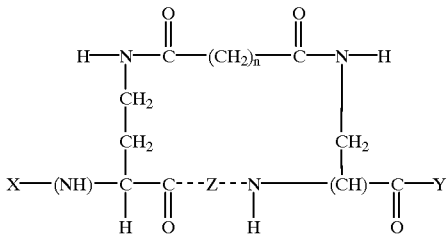

wherein X is hydrogen or is any amino acid or amino acid sequence; Y is hydroxyl or is any amino acid or amino acid sequence; Z is any amino acid sequence consisting of six amino acids; and n is any integer from 4 to 6 inclusive.

In still another embodiment, the invention provides locked helix peptides of formula (19a):

(19a)

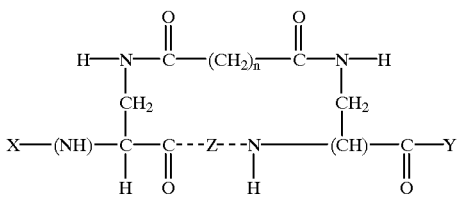

wherein X is hydrogen or is any amino acid or amino acid sequence; Y is hydroxyl or is any amino acid or amino acid sequence; Z is any amino acid sequence consisting of six amino acids; and n is any integer from 5 to 7 inclusive.

In still another embodiment, the invention provides locked helix peptides of formula (20a):

(20a)

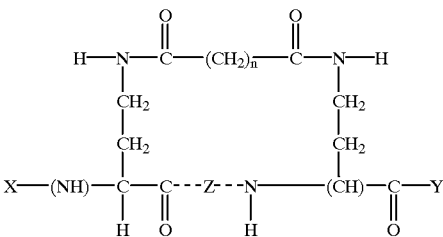

wherein X is hydrogen or is any amino acid or amino acid sequence; Y is hydroxyl or is any amino acid or amino acid sequence; Z is any amino acid sequence consisting of six amino acids; and n is any integer from 3 to 5 inclusive.

In a further embodiment, the invention provides locked helix peptides of formula (1a), formula (2a), formula (3a), formula (4a), formula (5a), formula (6a), formula (7a), formula (8a), formula (9a), formula (10a), formula (11a), formula (12a), formula (13a), formula (14a), formula (15a), formula (16a), formula (17a), formula (18a), formula (19a) and formula (20a) wherein X, Y, and Z collectively contain up to or about 12 amino acids (i.e. locked helix peptides of formulas (1a), (2a), (3a), (4a), (5a), (6a), (7a), (8a), (9a), (10a), (11a), (12a), (13a), (14a), (15a), (16a), (17a), (18a), (19a) and (20a) each of which contains a total of no more than about 12 amino acid residues).

Also provided herein are locked helix peptides of formula (1a), formula (2a), formula (3a), formula (4a), formula (5a), formula (6a), formula (7a), formula (8a), formula (9a), formula (10a), formula (11a), formula (12a), formula (13a), formula (14a), formula (15a), formula (16a), formula (17a), formula (18a), formula (19a) and formula (20a) wherein X and/or Y contain(s) up to or about 30 amino acid residues.

Further provided herein are locked helix peptides of formula (1a), formula (2a), formula (3a), formula (4a), formula (5a), formula (6a), formula (7a), formula (8a), formula (9a), formula (10a), formula (11a), formula (12a), formula (13a), formula (14a), formula (15a), formula (16a), formula (17a), formula (18a), formula (19a) and formula (20a) wherein X and/or Y contain(s) up to or about 25 amino acid residues.

Additionally provided herein are locked helix peptides of formula (1a), formula (2a), formula (3a), formula (4a), formula (5a), formula (6a), formula (7a), formula (8a), formula (9a), formula (10a), formula (11a), formula (12a), formula (13a), formula (14a), formula (15a), formula (16a), formula (17a), formula (18a), formula (19a) and formula (20a) wherein X and/or Y contain(s) up to or about 20 amino acid residues.

Also encompassed herein are locked helix peptides of formula (1a), formula (2a), formula (3a), formula (4a), formula (5a), formula (6a), formula (7a), formula (8a), formula (9a), formula (10a), formula (11a), formula (12a), formula (13a), formula (14a), formula (15a), formula (16a), formula (17a), formula (18a), formula (19a) and formula (20a) wherein X and/or Y contain(s) up to or about 15 amino acid residues.

Further encompassed herein are locked helix peptides of formula (1a), formula (2a), formula (3a), formula (4a), formula (5a), formula (6a), formula (7a), formula (8a), formula (9a), formula (10a), formula (11a), formula (12a), formula (13a), formula (14a), formula (15a), formula (16a), formula (17a), formula 18a), formula (19a) and formula (20a) wherein X and/or Y contain(s) up to or about 10 amino acid residues.

Additionally encompassed herein are locked helix peptides of formula (1a), formula (2a), formula (3a), formula (4a), formula (5a), formula (6a), formula (7a), formula (8a), formula (9a), formula (10a), formula (11a), formula (12a), formula (13a), formula (14a), formula (15a), formula (16a), formula (17a), formula (18a), formula (19a) and formula (20a) wherein X and/or Y contain(s) up to or about 5 amino acid residues.

Also within the scope of the invention are locked helix peptides of formula (1a), formula (2a), formula (3a), formula (4a), formula (5a), formula (6a), formula (7a), formula (8a), formula (9a), formula (10a), formula (11a), formula (12a), formula (13a), formula (14a), formula (15a), formula (16a), formula (17a), formula (18a), formula (19a), formula (20a) wherein X and for Y contain(s) up to or about 3 amino acid residues.

The invention also provides locked helix peptides of formula (1b):

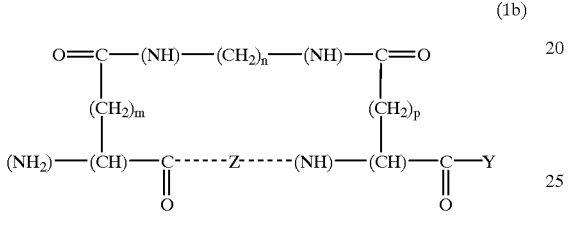

(1b)

wherein Y is hydroxyl or is any amino acid or amino acid sequence; Z is any amino acid sequence consisting of six amino acids; m and p are independently selected from the integers 0 to 6 inclusive, provided that m+p is less than or equal to 6; and n is any integer in the range defined by (7−(m+p)) to (9−(m+p)) inclusive, provided that n is greater than 1.

In another embodiment, the invention provides locked helix peptides of formula (2b):

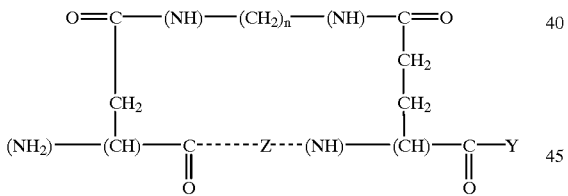

(2b)

wherein Y is hydroxyl or is any amino acid or amino acid sequence; Z is any amino acid sequence consisting of six amino acids; and n is any integer from 4 to 6 inclusive.

In yet another embodiment, the invention provides locked helix peptides of formula (3b):

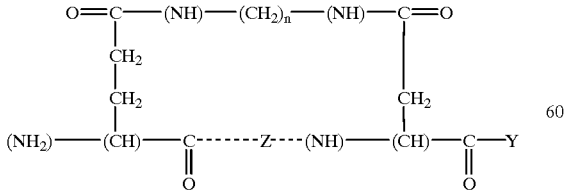

(3b)

wherein Y is hydroxyl or is any amino acid or amino acid sequence; Z is any amino acid sequence consisting of six amino acids; and n is any integer from 4 to 6 inclusive.

In still another embodiment, the invention provides locked helix peptides of formula (4b):

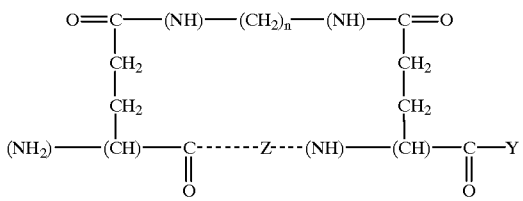

(4b)

wherein Y is hydroxyl or is any amino acid or amino acid sequence; Z is any amino acid sequence consisting of six amino acids; and n is any integer from 3 to 5 inclusive.

In still another embodiment, the invention provides locked helix peptides of formula (5b):

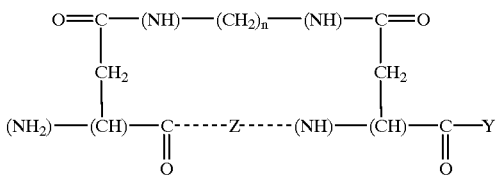

(5b)

wherein Y is hydroxyl or is any amino acid or amino acid sequence; Z is any amino acid sequence consisting of six amino acids; and n is any integer from 5 to 7 inclusive.

In still another embodiment, the invention provides locked helix peptides of formula (6b):

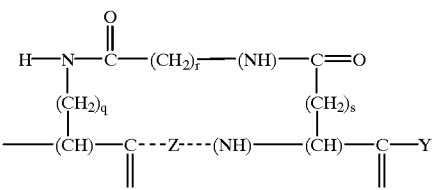

wherein Y is hydroxyl or is any amino acid or amino acid sequence; Z is any amino acid sequence consisting of six amino acids; q is selected from the integers 1 to 7 inclusive, and s is selected from the integers 0 to 6 inclusive, provided that q+s is less than or equal to 7; and r is any integer in the range defined by (7−(q+s)) to (9−(q+s)) inclusive, provided that r is greater than 0.

In still another embodiment, the invention provides locked helix peptides of formula (7b):

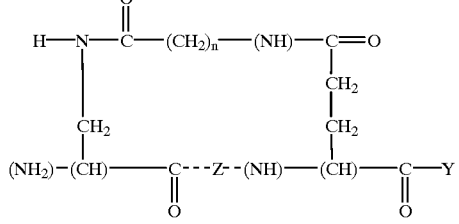

(7b)

wherein Y is hydroxyl or is any amino acid or amino acid sequence; Z is any amino acid sequence consisting of six amino acids; and n is any integer from 4 to 6 inclusive.

In still another embodiment, the invention provides locked helix peptides of formula (8b):

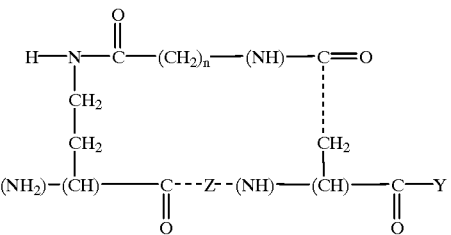

(8b)

wherein Y is hydroxyl or is any amino acid or amino acid sequence; Z is any amino acid sequence consisting of six amino acids; and n is any integer from 4 to 6 inclusive.

In still another embodiment, the invention provides locked helix peptides of formula (9b):

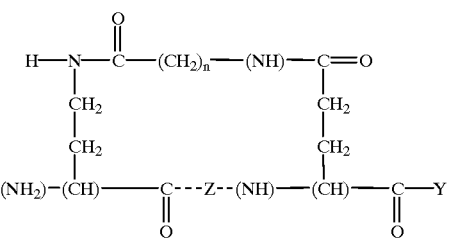

(9b)

wherein Y is hydroxyl or is any amino acid or amino acid sequence; Z is any amino acid sequence consisting of six amino acids; and n is any integer from 3 to 5 inclusive.

In still another embodiment, the invention provides locked helix peptides of formula (10b):

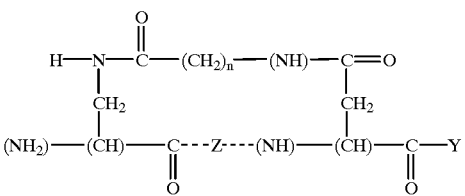

(10b)

wherein Y is hydroxyl or is any amino acid or amino acid sequence; Z is any amino acid sequence consisting of six amino acids; and n is any integer from 5 to 7 inclusive.

In still another embodiment, the invention provides locked helix peptides of formula (11b):

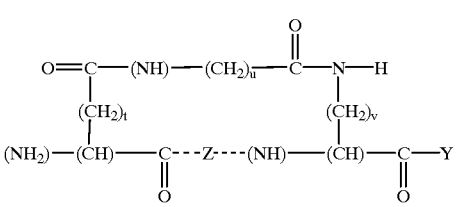

(11b)

wherein Y is hydroxyl or is any amino acid or amino acid sequence; Z is any amino acid sequence consisting of six amino acids; t is selected from the integers 0 to 6 inclusive, and v is selected from the integers 1 to 7 inclusive, provided that t+v is less than or equal to 7; and u is any integer in the range defined by (7−(t+v)) to (9−(t+v)) inclusive, provided that u is greater than 0.

In still another embodiment, the invention provides locked helix peptides of formula (12b):

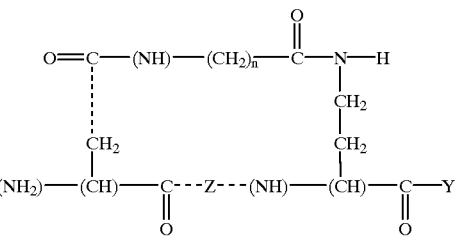

(12b)

wherein Y is hydroxyl or is any amino acid or amino acid sequence; Z is any amino acid sequence consisting of six amino acids; and n is any integer from 4 to 6 inclusive.

In still another embodiment, the invention provides locked helix peptides of formula (13b):

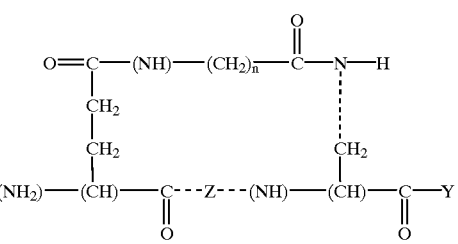

(13b)

wherein Y is hydroxyl or is any amino acid or amino acid sequence; Z is any amino acid sequence consisting of six amino acids; and n is any integer from 4 to 6 inclusive.

In still another embodiment, the invention provides locked helix peptides of formula (14b):

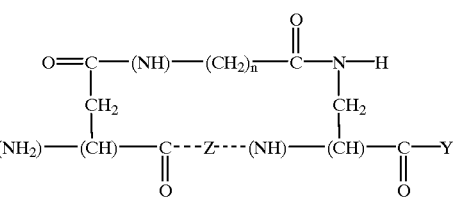

(14b)

wherein Y is hydroxyl or is any amino acid or amino acid sequence; Z is any amino acid sequence consisting of six amino acids; and n is any integer from 5 to 7 inclusive.

In still another embodiment, the invention provides locked helix peptides of formula (15b):

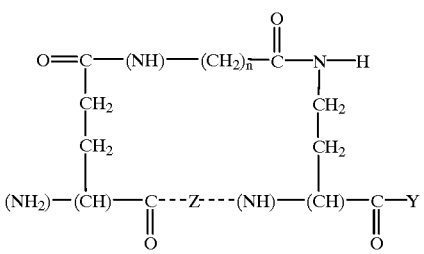
(15b)

wherein Y is hydroxyl or is any amino acid or amino acid sequence; Z is any amino acid sequence consisting of six amino acids; and n is any integer from 3 to 5 inclusive.

In still another embodiment, the invention provides locked helix peptides of formula (16b):

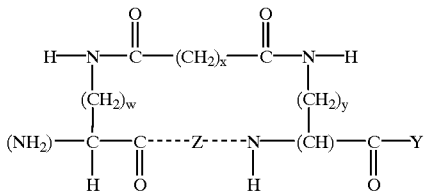
(16b)

wherein Y is hydroxyl or is any amino acid or amino acid sequence; Z is any amino acid sequence consisting of six amino acids; w and y are independently selected from the integers 1 to 7 inclusive, provided that w+y is less than or equal to 8; and x is any integer in the range defined by (7−(w+y)) to (9−(w+y)) inclusive, provided that x is greater than or equal to 0.

In still another embodiment, the invention provides locked helix peptides of formula (17b):

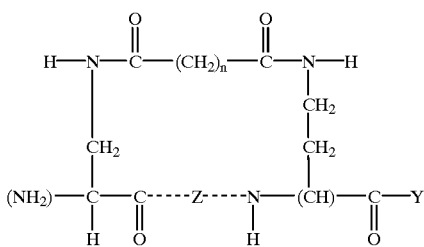
(17b)

wherein Y is hydroxyl or is any amino acid or amino acid sequence; Z is any amino acid sequence consisting of six amino acids; and n is any integer from 4 to 6 inclusive.

In still another embodiment, the invention provides locked helix peptides of formula (18b):

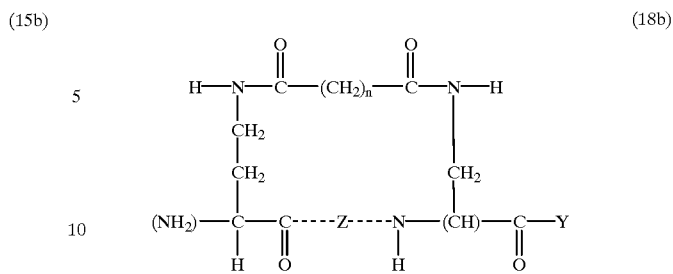
(18b)

wherein Y is hydroxyl or is any amino acid or amino acid sequence; Z is any amino acid sequence consisting of six amino acids; and n is any integer from 4 to 6 inclusive.

In still another embodiment, the invention provides locked helix peptides of formula (19b):

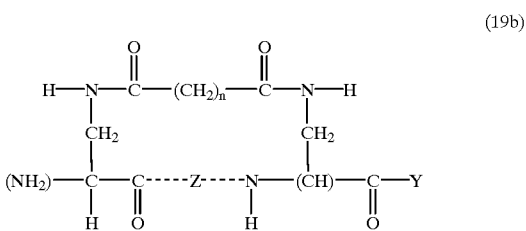
(19b)

wherein Y is hydroxyl or is any amino acid or amino acid sequence; Z is any amino acid sequence consisting of six amino acids; and n is any integer from 5 to 7 inclusive.

In still another embodiment, the invention provides locked helix peptides of formula (20b):

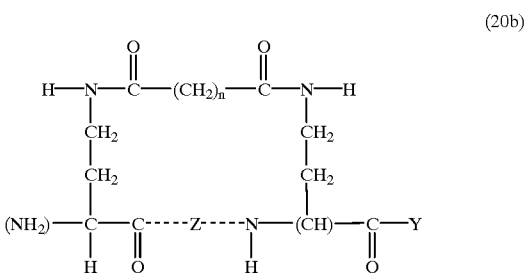
(20b)

wherein Y is hydroxyl or is any amino acid or amino acid sequence; Z is any amino acid sequence consisting of six amino acids; and n is any integer from 3 to 5 inclusive.

Also provided herein are locked helix peptides of formula (1b), formula (2b), formula (3b), formula (4b), formula (5b), formula (6b), formula (7b), formula (8b), formula (9b), formula (10b), formula (11b), formula (12b), formula (13b), formula (14b), formula (15b), formula (16b), formula (17b), formula (18b), formula (19b) and formula (20b) wherein Y contains up to or about 30 amino acid residues.

Further provided herein are locked helix peptides of formula (1b), formula (2b), formula (3b), formula (4b), formula (5b), formula (6b), formula (7b), formula (8b), formula (9b), formula (10b), formula (11b), formula (12b), formula (13b), formula (14b), formula (15b), formula (16b), formula (17b), formula (18b), formula (19b) and formula (20b) wherein Y contains up to or about 25 amino acid residues.

Additionally provided herein are locked helix peptides of formula (1b), formula (2b), formula (3b), formula (4b), formula (5b), formula (6b), formula (7b), formula (8b), formula (9b), formula (10b), formula (11b), formula (12b), formula (13b), formula (14b), formula (15b), formula (16b), formula (17b), formula (18b), formula (19b) and formula (20b) wherein Y contains up to or about 20 amino acid residues.

Also encompassed herein are locked helix peptides of formula (1b), formula (2b), formula (3b), formula (4b), formula (5b), formula (6b), formula (7b), formula (8b), formula (9b), formula (10b), formula (11b), formula (12b), formula (13b), formula (14b), formula (15b), formula (16b), formula (17b), formula (18b), formula (19b) and formula (20b) wherein Y contains up to or about 15 amino acid residues.

Further encompassed herein are locked helix peptides of formula (1b), formula (2b), formula (3b), formula (4b), formula (5b), formula (6b), formula (7b), formula (8b), formula (9b), formula (10b), formula (11b), formula (12b), formula (13b), formula (14b), formula (15b), formula (16b), formula (17b), formula (18b), formula (19b) and formula (20b) wherein Y contains up to or about 10 amino acid residues.

Additionally encompassed herein are locked helix peptides of formula (1b), formula (2b), formula (3b), formula (4b), formula (5b), formula (6b), formula (7b), formula (8b), formula (9b), formula (10b), formula (11b), formula (12b), formula (13b), formula (14b), formula (15b), formula (16b), formula (17b), formula (18b), formula (19b) and formula (20b) wherein Y contains up to or about 5 amino acid residues.

Also within the scope of the invention are locked helix peptides of formula (1b), formula (2b), formula (3b), formula (4b), formula (5b), formula (6b), formula (7b), formula (8b), formula (9b), formula (10b), formula (11b), formula (12b), formula (13b), formula (14b), formula (15b), formula (16b), formula (17b), formula (18b), formula (19b) and formula (20b) wherein Y contains up to or about 3 amino acid residues.

The invention also provides locked helix peptides of formula (1c):

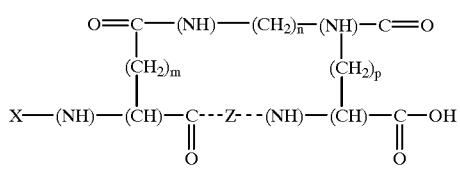

(1c)

wherein X is hydrogen or is any amino acid or amino acid sequence; Z is any amino acid sequence consisting of six amino acids; m and p are independently selected from the integers 0 to 6 inclusive, provided that m+p is less than or equal to 6; and n is any integer in the range defined by (7−(m+p)) to (9−(m+p)) inclusive, provided that n is greater than 1.

In another embodiment, the invention provides locked helix peptides of formula (2c):

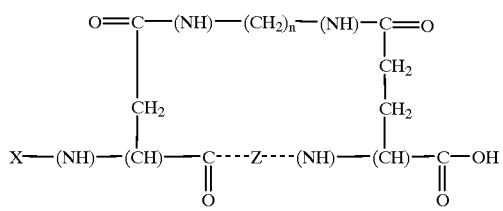

(2c)

wherein X is hydrogen or is any amino acid or amino acid sequence; Z is any amino acid sequence consisting of six amino acids; and n is any integer from 4 to 6 inclusive.

In yet another embodiment, the invention provides locked helix peptides of formula (3c):

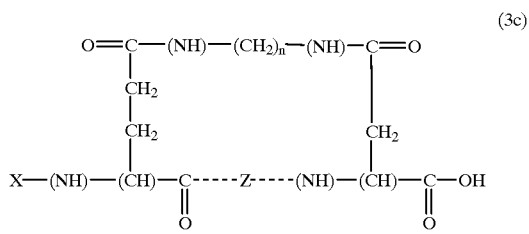

(3c)

wherein X is hydrogen or is any amino acid or amino acid sequence; Z is any amino acid sequence consisting of six amino acids; and n is any integer from 4 to 6 inclusive.

In still another embodiment, the invention provides locked helix peptides of formula (4c):

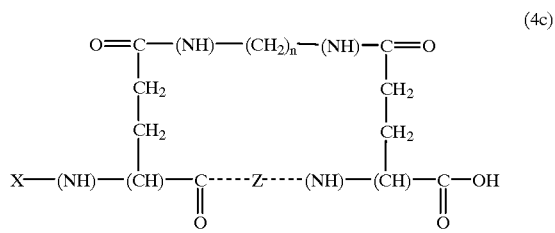

(4c)

wherein X is hydrogen or is any amino acid or amino acid sequence; Z is any amino acid sequence consisting of six amino acids; and n is any integer from 3 to 5 inclusive.

In still another embodiment, the invention provides locked helix peptides of formula (5c):

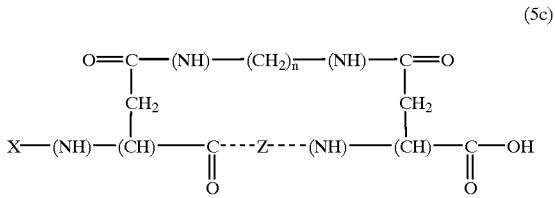

(5c)

wherein X is hydrogen or is any amino acid or amino acid sequence; Z is any amino acid sequence consisting of six amino acids; and n is any integer from 5 to 7 inclusive.

In still another embodiment, the invention provides locked helix peptides of formula (6c):

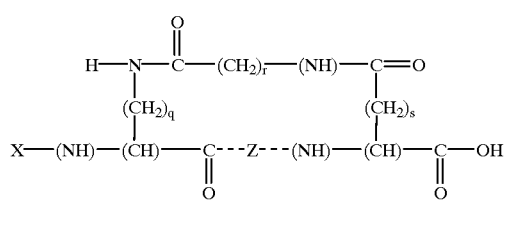

(6c)

wherein X is hydrogen or is any amino acid or amino acid sequence; Z is any amino acid sequence consisting of six amino acids; q is selected from the integers 1 to 7 inclusive, and s is selected from the integers 0 to 6 inclusive, provided that q+s is less than or equal to 7; and r is any integer in the range defined by (7−(q+s)) to (9−(q+s)) inclusive, provided that r is greater than 0.

In still another embodiment, the invention provides locked helix peptides of formula (7c):

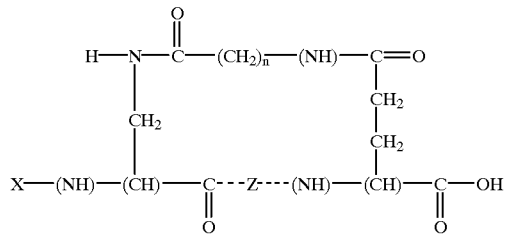

(7c)

wherein X is hydrogen or is any amino acid or amino acid sequence; Z is any amino acid sequence consisting of six amino acids; and n is any integer from 4 to 6 inclusive.

In still another embodiment, the invention provides locked helix peptides of formula (8c):

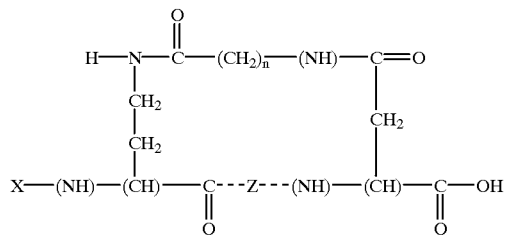

(8c)

wherein X is hydrogen or is any amino acid or amino acid sequence; Z is any amino acid sequence consisting of six amino acids; and n is any integer from 4 to 6 inclusive.

In still another embodiment, the invention provides locked helix peptides of formula (9c):

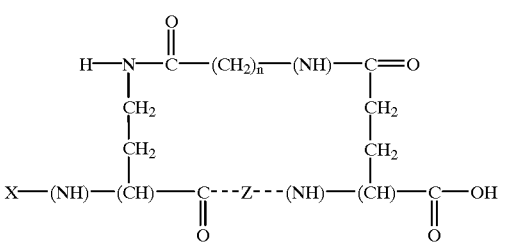

(9c)

wherein X is hydrogen or is any amino acid or amino acid sequence; Z is any amino acid sequence consisting of six amino acids; and n is any integer from 3 to 5 inclusive.

In still another embodiment, the invention provides locked helix peptides of formula (10c):

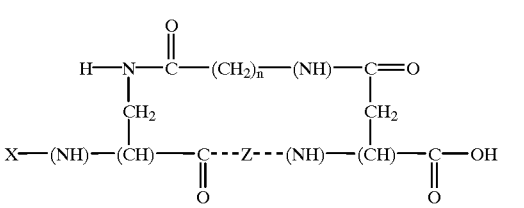

(10c)

wherein X is hydrogen or is any amino acid or amino acid sequence; Z is any amino acid sequence consisting of six amino acids; and n is any integer from 5 to 7 inclusive.

In still another embodiment, the invention provides locked helix peptides of formula (11c):

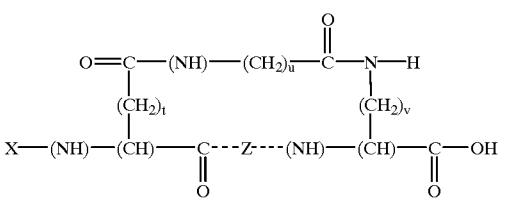

(11c)

wherein X is hydrogen or is any amino acid or amino acid sequence; Z is any amino acid sequence consisting of six amino acids; t is selected from the integers 0 to 6 inclusive, and v is selected from the integers 1 to 7 inclusive, provided that t+v is less than or equal to 7; and u is any integer in the range defined by (7−(t+v)) to (9−(t+v)) inclusive, provided that u is greater than 0.

In still another embodiment, the invention provides locked helix peptides of formula (12c):

(12c)

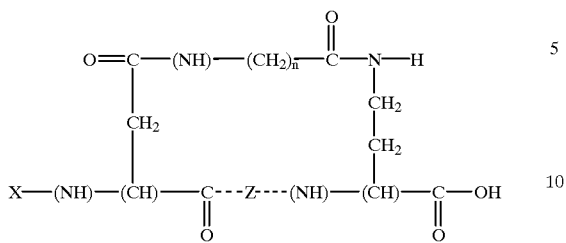

wherein X is hydrogen or is any amino acid or amino acid sequence; Z is any amino acid sequence consisting of six amino acids; and n is any integer from 4 to 6 inclusive.

In still another embodiment, the invention provides locked helix peptides of formula (13c):

(13c)

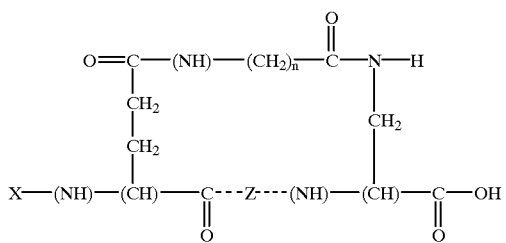

wherein X is hydrogen or is any amino acid or amino acid sequence; Z is any amino acid sequence consisting of six amino acids; and n is any integer from 4 to 6 inclusive.

In still another embodiment, the invention provides locked helix peptides of formula (14c):

(14c)

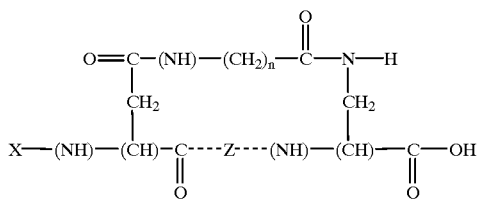

wherein X is hydrogen or is any amino acid or amino acid sequence; Z is any amino acid sequence consisting of six amino acids; and n is any integer from 5 to 7 inclusive.

In still another embodiment, the invention provides locked helix peptides of formula (15c):

(15c)

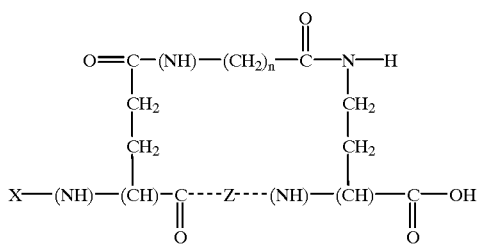

wherein X is hydrogen or is any amino acid or amino acid sequence; Z is any amino acid sequence consisting of six amino acids; and n is any integer from 3 to 5 inclusive.

In still another embodiment, the invention provides locked helix peptides of formula (16c):

(16c)

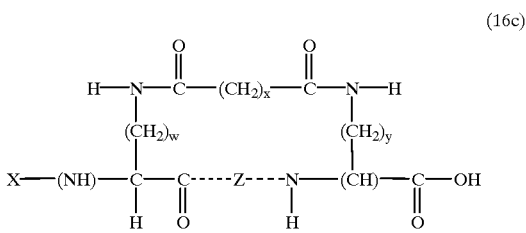

wherein X is hydrogen or is any amino acid or amino acid sequence; Z is any amino acid sequence consisting of six amino acids; w and y are independently selected from the integers 1 to 7 inclusive, provided that w+y is less than or equal to 8; and x is any integer in the range defined by (7−(w+y)) to (9−(w+y)) inclusive, provided that x is greater than or equal to 0.

In still another embodiment, the invention provides locked helix peptides of formula (17c):

(17c)

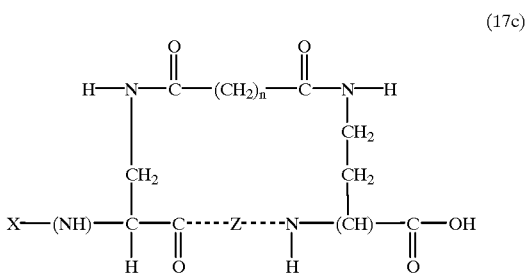

wherein X is hydrogen or is any amino acid or amino acid sequence; Z is any amino acid sequence consisting of six amino acids; and n is any integer from 4 to 6 inclusive.

In still another embodiment, the invention provides locked helix peptides of formula (18c):

(18c)

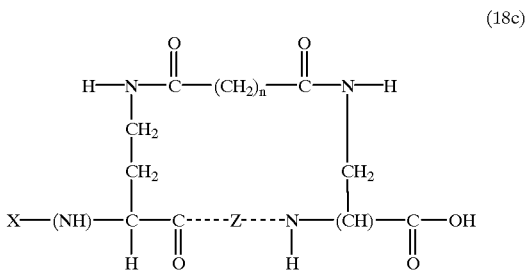

wherein X is hydrogen or is any amino acid or amino acid sequence; Z is any amino acid sequence consisting of six amino acids; and n is any integer from 4 to 6 inclusive.

In still another embodiment, the invention provides locked helix peptides of formula (19c):

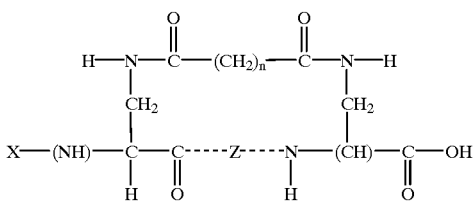

(19c)

wherein X is hydrogen or is any amino acid or amino acid sequence; Z is any amino acid sequence consisting of six amino acids; and n is any integer from 5 to 7 inclusive.

In still another embodiment, the invention provides locked helix peptides of formula (20c):

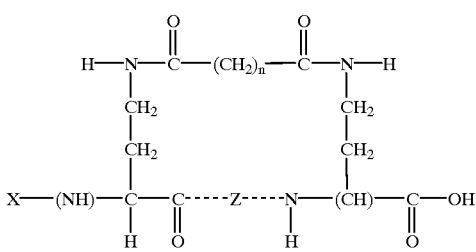

(20c)

wherein X is hydrogen or is any amino acid or amino acid sequence; Z is any amino acid sequence consisting of six amino acids; and n is any integer from 3 to 5 inclusive.

Also provided herein are locked helix peptides of formula (1c), formula (2c), formula (3c), formula (4c), formula (5c), formula (6c), formula (7c), formula (8c), formula (9c), formula (10c), formula (11c), formula (12c), formula (13c), formula (14c), formula (15c), formula (16c), formula (17c), formula (18c), formula (9c) and formula (20c) wherein X contains up to or about 30 amino acid residues.

Further provided herein are locked helix peptides of formula (1c), formula (2c), formula (3c), formula (4c), formula (5c), formula (6c), formula (7c), formula (8c), formula (9c), formula (10c), formula (11c), formula (12c), formula (13c), formula (14c), formula (15c), formula (16c), formula (17c), formula (18c), formula (19c) and formula (20c) wherein X contains up to or about 25 amino acid residues.

Additionally provided herein are locked helix peptides of formula (1c), formula (2c), formula (3c), formula (4c), formula (5c), formula (6c), formula (7c), formula (8c), formula (9c), formula (10c), formula (11c), formula (12c), formula (13c), formula (14c), formula (15c), formula (16c), formula (17c), formula (18c), formula (19c) and formula (20c) wherein X contains up to or about 20 amino acid residues.

Also encompassed herein are locked helix peptides of formula (1c), formula (2c), formula (3c), formula (4c), formula (5c), formula (6c), formula (7c), formula (8c), formula (9c), formula (10c), formula (11c), formula (12c), formula (13c), formula (14c), formula (15c), formula (16c), formula (17c), formula (18c), formula (19c) and formula (20c) wherein X contains up to or about 15 amino acid residues.

Further encompassed herein are locked helix peptides of formula (1c), formula (2c), formula (3c), formula (4c), formula (5c), formula (6c), formula (7c), formula (8c), formula (9c), formula (10c), formula (11c), formula (12c), formula (13c), formula (14c), formula (1 5c), formula (16c), formula (17c), formula (18c), formula (19c) and formula (20c) wherein X contains up to or about 10 amino acid residues.

Additionally encompassed herein are locked helix peptides of formula (1c), formula (2c), formula (3c), formula (4c), formula (5c), formula (6c), formula (7c), formula (8c), formula (9c), formula (10c), formula (11c), formula (12c), formula (13c), formula (14c), formula (15c), formula (16c), formula (17), formula (18c), formula (19c) and formula (20c) wherein X contains up to or about 5 amino acid residues.

Also within the scope of the invention are locked helix peptides of formula (1c), formula (2c), formula (3c), formula (4c), formula (5c), formula (6c), formula (7c), formula (8c), formula (9c), formula (10c), formula (11c), formula (12c), formula (13c), formula (14c), formula (15c), formula (16c), formula (17c), formula (18c), formula (19c) and formula (20c) wherein X contains up to or about 3 amino acid residues.

The invention also provides locked helix peptides of formula (1d):

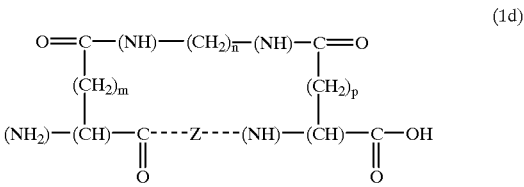

(1d)

wherein Z is any amino acid sequence consisting of six amino acids; m and p are independently selected from the integers 0 to 6 inclusive, provided that m+p is less than or equal to 6; and n is any integer in the range defined by (7−(m+p)) to (9−(m+p)) inclusive, provided that n is greater than 1.

In another embodiment, the invention provides locked helix peptides of formula (2d):

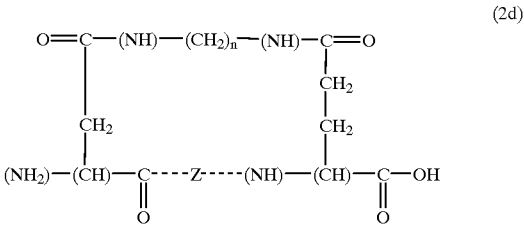

(2d)

wherein Z is any amino acid sequence consisting of six amino acids; and n is any integer from 4 to 6 inclusive.

In yet another embodiment, the invention provides locked helix peptides of formula (3d):

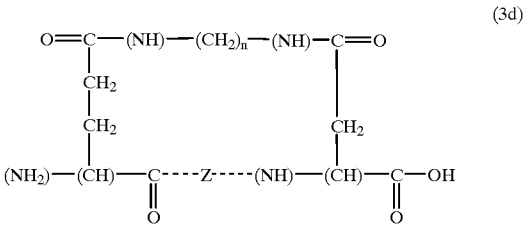

(3d)

wherein Z is any amino acid sequence consisting of six amino acids; and n is any integer from 4 to 6 inclusive.

In still another embodiment, the invention provides locked helix peptides of formula (4d):

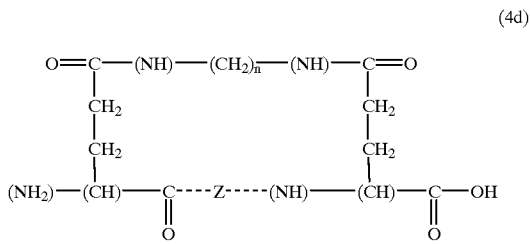
(4d)

wherein Z is any amino acid sequence consisting of six amino acids; and n is any integer from 3 to 5 inclusive.

In still another embodiment, the invention provides locked helix peptides of formula (5d):

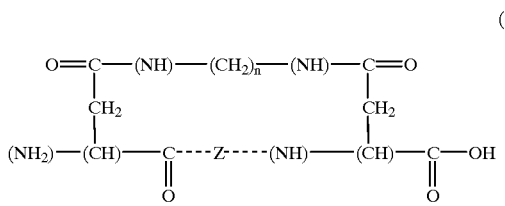
(5d)

wherein Z is any amino acid sequence consisting of six amino acids; and n is any integer from 5 to 7 inclusive.

In still another embodiment, the invention provides locked helix peptides of formula (6d):

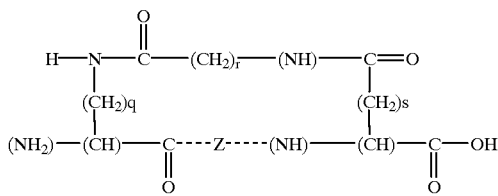
(6d)

wherein Z is any amino acid sequence consisting of six amino acids; q is selected from the integers 1 to 7 inclusive, and s is selected from the integers 0 to 6 inclusive, provided that q+s is less than or equal to 7; and r is any integer in the range defined by (7−(q+s)) to (9−(q+s)) inclusive, provided that r is greater than 0.

In still another embodiment, the invention provides locked helix peptides of formula (7d):

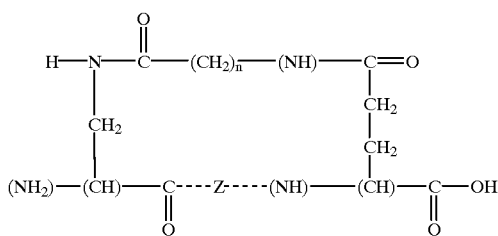
(7d)

wherein Z is any amino acid sequence consisting of six amino acids; and n is any integer from 4 to 6 inclusive.

In still another embodiment, the invention provides locked helix peptides of formula (8d):

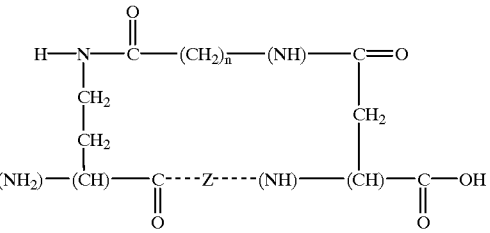
(8d)

wherein Z is any amino acid sequence consisting of six amino acids; and n is any integer from 4 to 6 inclusive.

In still another embodiment, the invention provides locked helix peptides of formula (9d):

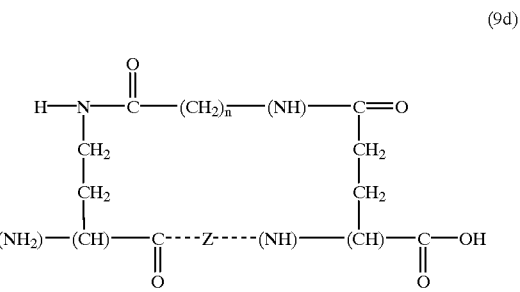
(9d)

wherein Z is any amino acid sequence consisting of six amino acids; and n is any integer from 3 to 5 inclusive.

In still another embodiment, the invention provides locked helix peptides of formula (10d):

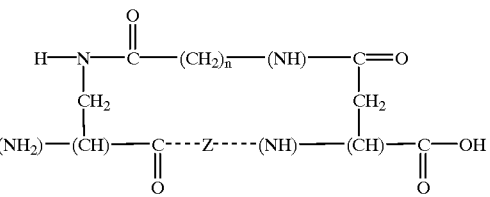
(10d)

wherein Z is any amino acid sequence consisting of six amino acids; and n is any integer from 5 to 7 inclusive.

In still another embodiment, the invention provides locked helix peptides of formula (11d):

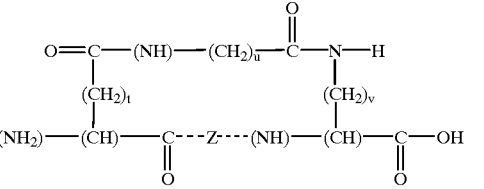
(11d)

wherein Z is any amino acid sequence consisting of six amino acids; t is selected from the integers 0 to 6 inclusive, and v is selected from the integers 1 to 7 inclusive, provided that t+v is less than or equal to 7; and u is any integer in the range defined by (7−(t+v)) to (9−(t+v)) inclusive, provided that u is greater than 0.

In still another embodiment, the invention provides locked helix peptides of formula (12d):

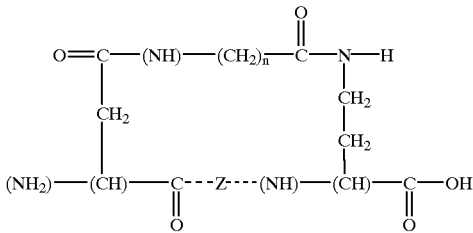

(12d)

wherein Z is any amino acid sequence consisting of six amino acids; and n is any integer from 4 to 6 inclusive.

In still another embodiment, the invention provides locked helix peptides of formula (13d):

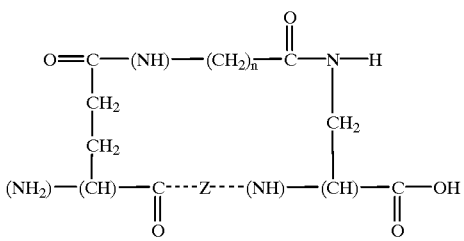

(13d)

wherein Z is any amino acid sequence consisting of six amino acids; and n is any integer from 4 to 6 inclusive.

In still another embodiment, the invention provides locked helix peptides of formula (14d):

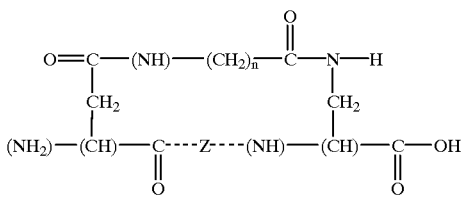

(14d)

wherein Z is any amino acid sequence consisting of six amino acids; and n is any integer from 5 to 7 inclusive.

In still another embodiment, the invention provides locked helix peptides of formula (15d):

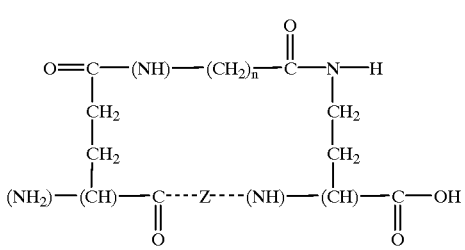

(15d)

wherein is any amino acid sequence consisting of six amino acids; and n is any integer from 3 to 5 inclusive.

In still another embodiment, the invention provides locked helix peptides of formula (16d):

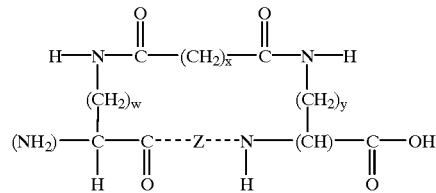

(16d)

wherein Z is any amino acid sequence consisting of six amino acids; w and y are independently selected from the integers 1 to 7 inclusive, provided that w+y is less than or equal to 8; and x is any integer in the range defined by (7−(w+y)) to (9−(w+y)) inclusive, provided that x is greater than or equal to 0.

In still another embodiment, the invention provides locked helix peptides of formula (17d):

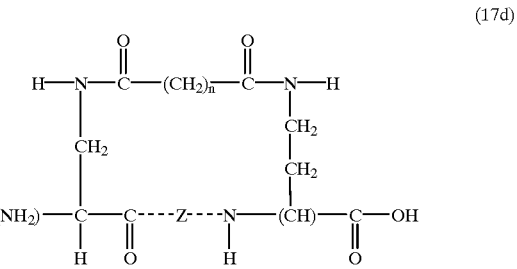

(17d)

wherein Z is any amino acid sequence consisting of six amino acids; and n is any integer from 4 to 6 inclusive.

In still another embodiment, the invention provides locked helix peptides of formula (18d):

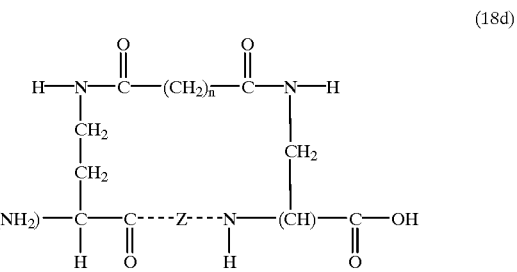

(18d)

wherein Z is any amino acid sequence consisting of six amino acids; and n is any integer from 4 to 6 inclusive.

In still another embodiment, the invention provides locked helix peptides of formula (19d):

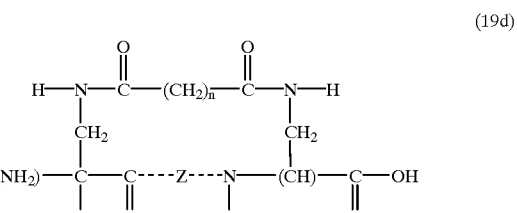

(19d)

wherein Z is any amino acid sequence consisting of six amino acids; and n is any integer from 5 to 7 inclusive.

In still another embodiment, the invention provides locked helix peptides of formula (20d):

(20d)

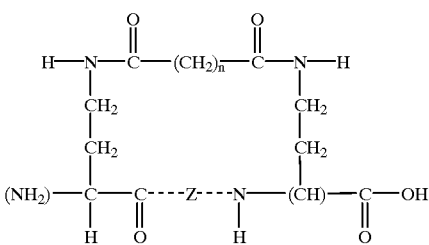

wherein Z is any amino acid sequence consisting of six amino acids; and n is any integer from 3 to 5 inclusive.

The invention also provides locked helix peptides of formula (1e):

(1e)

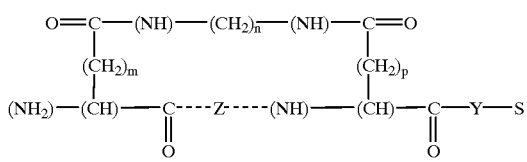

wherein S is absent or is a macromolecule; Y is absent, or is hydroxyl if S is absent, or is any amino acid or amino acid sequence; Z is any amino acid sequence consisting of six amino acids; m and p are independently selected from the integers 0 to 6 inclusive, provided that m+p is less than or equal to 6; and n is any integer in the range defined by (7−(m+p)) to (9−(m+p)) inclusive, provided that n is greater than 1.

In another embodiment, the invention provides locked helix peptides of formula (2e):

(2e)

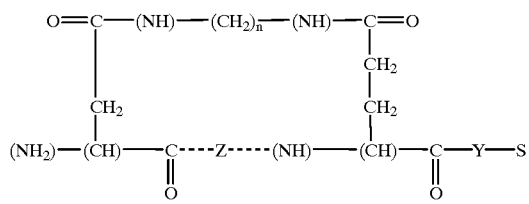

wherein S is absent or is a macromolecule; Y is absent, or is hydroxyl if S is absent, or is any amino acid or amino acid sequence; Z is any amino acid sequence consisting of six amino acids; and n is any integer from 4 to 6 inclusive.

In yet another embodiment, the invention provides locked helix peptides of formula (3e):

(3e)

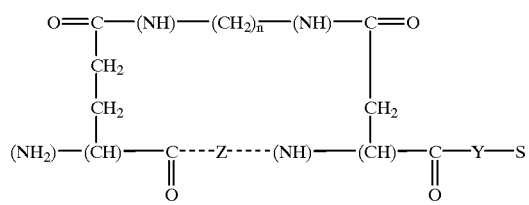

wherein S is absent or is a macromolecule; Y is absent, or is hydroxyl if S is absent, or is any amino acid or amino acid sequence; Z is any amino acid sequence consisting of six amino acids; and n is any integer from 4 to 6 inclusive.

In still another embodiment, the invention provides locked helix peptides of formula (4e):

(4e)

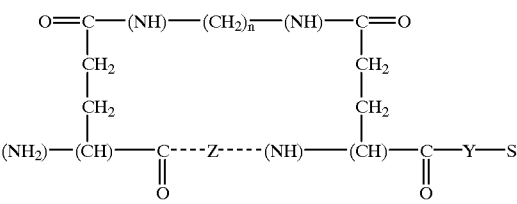

wherein S is absent or is a macromolecule; Y is absent, or is hydroxyl if S is absent, or is any amino acid or amino acid sequence; Z is any amino acid sequence consisting of six amino acids; and n is any integer from 3 to 5 inclusive.

In still another embodiment, the invention provides locked helix peptides of formula (5e):

(5e)

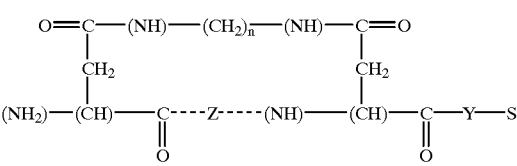

wherein S is absent or is a macromolecule; Y is absent, or is hydroxyl if S is absent, or is any amino acid or amino acid sequence; Z is any amino acid sequence consisting of six amino acids; and n is any integer from 5 to 7 inclusive.

In still another embodiment, the invention provides locked helix peptides of formula (6e):

(6e)

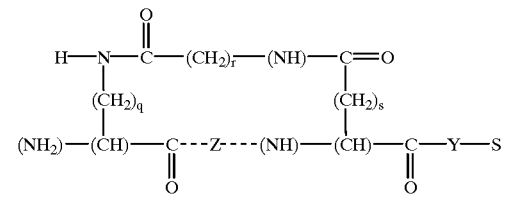

wherein S is absent or is a macromolecule; Y is absent, or is hydroxyl if S is absent, or is any amino acid or amino acid sequence; Z is any amino acid sequence consisting of six amino acids; q is selected from the integers 1 to 7 inclusive, and s is selected from the integers 0 to 6 inclusive, provided that q+s is less than or equal to 7; and r is any integer in the range defined by (7−(q+s)) to (9−(q+s)) inclusive, provided that r is greater than 0.

In still another embodiment, the invention provides locked helix peptides of formula (7e):

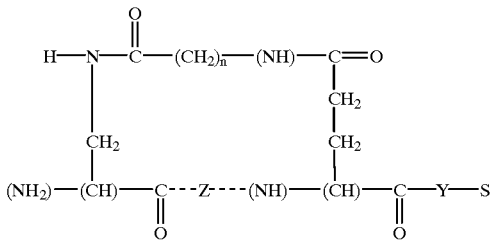

(7e)

wherein S is absent or is a macromolecule; Y is absent, or is hydroxyl if S is absent, or is any amino acid or amino acid sequence; Z is any amino acid sequence consisting of six amino acids; and n is any integer from 4 to 6 inclusive.

In still another embodiment, the invention provides locked helix peptides of formula (8e):

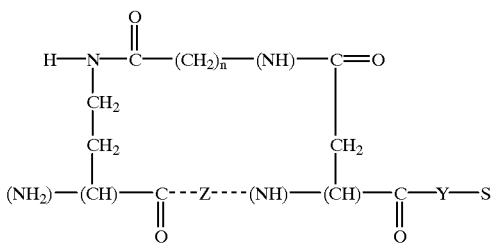

(8e)

wherein S is absent or is a macromolecule; Y is absent, or is hydroxyl if S is absent, or is any amino acid or amino acid sequence; Z is any amino acid sequence consisting of six amino acids; and n is any integer from 4 to 6 inclusive.

In still another embodiment, the invention provides locked helix peptides of formula (9e):

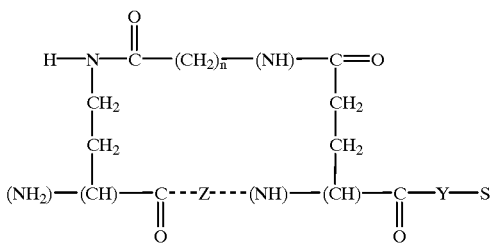

(9e)

wherein S is absent or is a macromolecule; Y is absent, or is hydroxyl if S is absent, or is any amino acid or amino acid sequence; Z is any amino acid sequence consisting of six amino acids; and n is any integer from 3 to 5 inclusive.

In still another embodiment, the invention provides locked helix peptides of formula (10e):

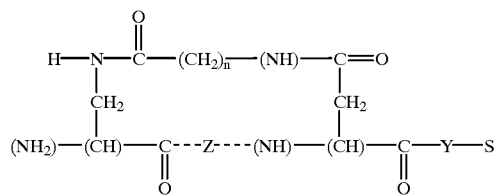

(10e)

wherein S is absent or is a macromolecule; Y is absent, or is hydroxyl if S is absent, or is any amino acid or amino acid sequence; Z is any amino acid sequence consisting of six amino acids; and n is any integer from 5 to 7 inclusive.

In still another embodiment, the invention provides locked helix peptides of formula (11e):

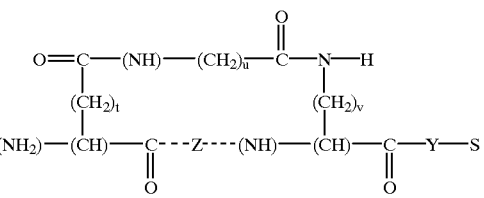

(11e)

wherein S is absent or is a macromolecule; Y is absent, or is hydroxyl if S is absent, or is any amino acid or amino acid sequence; Z is any amino acid sequence consisting of six amino acids; t is selected from the integers 0 to 6 inclusive, and v is selected from the integers 1 to 7 inclusive, provided that t+v is less than or equal to 7; and u is any integer in the range defined by $(7-(t+v))$ to $(9-(t+v))$ inclusive, provided that u is greater than 0.

In still another embodiment, the invention provides locked helix peptides of formula (12e):

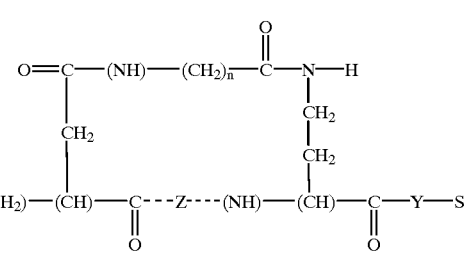

(12e)

wherein S is absent or is a macromolecule; Y is absent, or is hydroxyl if S is absent, or is any amino acid or amino acid sequence; Z is any amino acid sequence consisting of six amino acids; and n is any integer from 4 to 6 inclusive.

In still another embodiment, the invention provides locked helix peptides of formula (13e):

(13e)

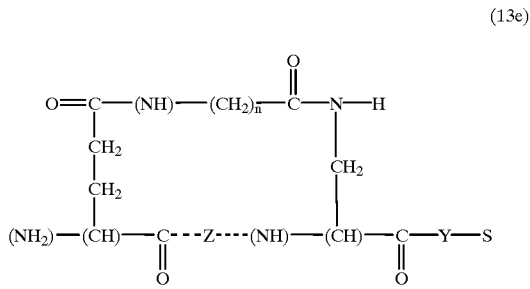

wherein S is absent or is a macromolecule; Y is absent, or is hydroxyl if S is absent, or is any amino acid or amino acid sequence; Z is any amino acid sequence consisting of six amino acids; and n is any integer from 4 to 6 inclusive.

In still another embodiment, the invention provides locked helix peptides of formula (14e):

(14e)

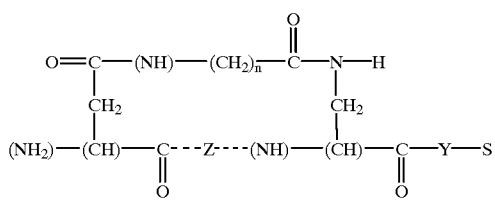

wherein S is absent or is a macromolecule; Y is absent, or is hydroxyl if S is absent, or is any amino acid or amino acid sequence; Z is any amino acid sequence consisting of six amino acids; and n is any integer from 5 to 7 inclusive.

In still another embodiment, the invention provides locked helix peptides of formula (15e):

(15e)

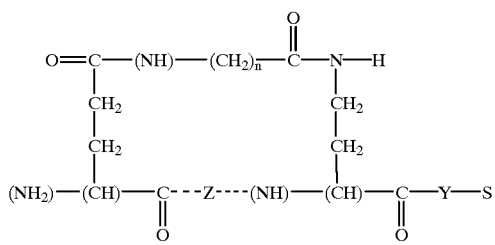

wherein S is absent or is a macromolecule; Y is absent, or is hydroxyl if S is absent, or is any amino acid or amino acid sequence; Z is any amino acid sequence consisting of six amino acids; and n is any integer from 3 to 5 inclusive.

In still another embodiment, the invention provides locked helix peptides of formula (16e):

(16e)

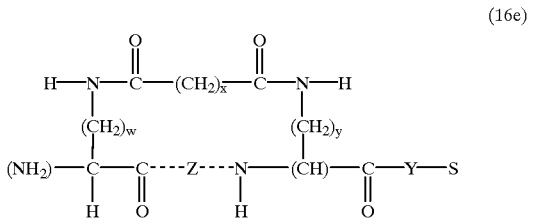

wherein S is absent or is a macromolecule; Y is absent, or is hydroxyl if S is absent, or is any amino acid or amino acid sequence; Z is any amino acid sequence consisting of six amino acids; w and y are independently selected from the integers 1 to 7 inclusive, provided that w+y is less than or equal to 8; and x is any integer in the range defined by (7−(w+y)) to (9−(w+y)) inclusive, provided that x is greater than or equal to 0.

In still another embodiment, the invention provides locked helix peptides of formula (17e):

(17e)

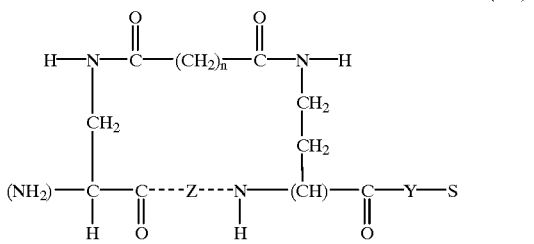

wherein S is absent or is a macromolecule; Y is absent, or is hydroxyl if S is absent, or is any amino acid or amino acid sequence; Z is any amino acid sequence consisting of six amino acids; and n is any integer from 4 to 6 inclusive.

In still another embodiment, the invention provides locked helix peptides of formula (18e):

(18e)

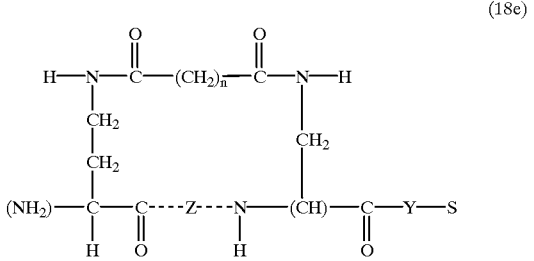

wherein S is absent or is a macromolecule; Y is absent, or is hydroxyl if S is absent, or is any amino acid or amino acid sequence; Z is any amino acid sequence consisting of six amino acids; and n is any integer from 4 to 6 inclusive.

In still another embodiment, the invention provides locked helix peptides of formula (19e):

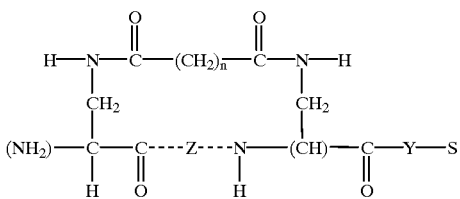

(19e)

wherein S is absent or is a macromolecule; Y is absent, or is hydroxyl if S is absent, or is any amino acid or amino acid sequence; Z is any amino acid sequence consisting of six amino acids; and n is any integer from 5 to 7 inclusive.

In still another embodiment, the invention provides locked helix peptides of formula (20e):

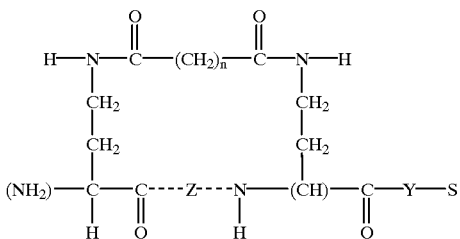

(20e)

wherein S is absent or is a macromolecule; Y is absent, or is hydroxyl if S is absent, or is any amino acid or amino acid sequence; Z is any amino acid sequence consisting of six amino acids; and n is any integer from 3 to 5 inclusive.

Also provided herein are locked helix peptides of formula (1e), formula (2e), formula (3e), formula (4e), formula (5e), formula (6e), formula (7e), formula (8e), formula (9e), formula (10e), formula (11e), formula (12e), formula (13e), formula (14e), formula (15e), formula (16e), formula (17e), formula (18e), formula (19e) and formula (20e) wherein Y contains up to or about 30 amino acid residues.

Further provided herein are locked helix peptides of formula (1e), formula (2e), formula (3e), formula (4e), formula (5e), formula (6e), formula (7e), formula (8e), formula (9e), formula (10e), formula (11e), formula (12e), formula (13e), formula (14e), formula (15e), formula (16e), formula (17e), formula (18e), formula (19e) and formula (20e) wherein Y contains up to or about 25 amino acid residues.

Additionally provided herein are locked helix peptides of formula (1e), formula (2e), formula (3e), formula (4e), formula (5e), formula (6e), formula (7e), formula (8e), formula (9e), formula (10e), formula (11e), formula (12e), formula (13e), formula (14e), formula (15e), formula (16e), formula (17e), formula (18e), formula (19e) and formula (20e) wherein Y contains up to or about 20 amino acid residues.

Also encompassed herein are locked helix peptides of formula (1e), formula (2e), formula (3e), formula (4e), formula (5e), formula (6e), formula (7e), formula (8e), formula (9e), formula (10e), formula (11e), formula (12e), formula (13e), formula (14e), formula (15e), formula (16e), formula (17e), formula (18e), formula (19e) and formula (20e) wherein Y contains up to or about 15 amino acid residues.

Further encompassed herein are locked helix peptides of formula (1e), formula (2e), formula (3e), formula (4e), formula (5e), formula (6e), formula (7e), formula (8e), formula (9e), formula (10e), formula (11e), formula (12e), formula (13e), formula (14e), formula (15e), formula (16e), formula (17e), formula (18e), formula (19e) and formula (20e) wherein Y contains up to or about 10 amino acid residues.

Additionally encompassed herein are locked helix peptides of formula (1e), formula (2e), formula (3e), formula (4e), formula (5e), formula (6e), formula (7e), formula (8e), formula (9e), formula (10e) formula (11e), formula (12e), formula (13e), formula (14e), formula (15e), formula (16e), formula (17e), formula (18e), formula (19e) and formula (20e) wherein Y contains up to or about 5 amino acid residues.

Also within the scope of the invention are locked helix peptides of formula (1e), formula (2e), formula (3e), formula (4e), formula (5e), formula (6e), formula (7e), formula (8e), formula (9e), formula (10e), formula (11e), formula (12e), formula (13e), formula (14e), formula (15e), formula (16e), formula (17e), formula (18e), formula (19e) and formula (20e) wherein Y contains up to or about 3 amino acid residues.

The invention also provides locked helix peptides of formula (1f):

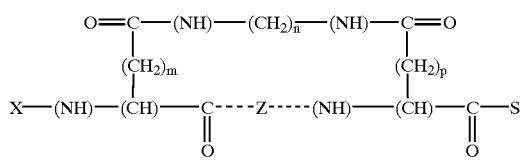

(1f)

wherein S is hydroxyl or is a macromolecule; X is hydrogen or is any amino acid or amino acid sequence; Z is any amino acid sequence consisting of six amino acids; m and p are independently selected from the integers 0 to 6 inclusive, provided that m+p is less than or equal to 6; and n is any integer in the range defined by (7−(m+p)) to (9−(m+p)) inclusive, provided that n is greater than 1.

In another embodiment, the invention provides locked helix peptides of formula (2f):

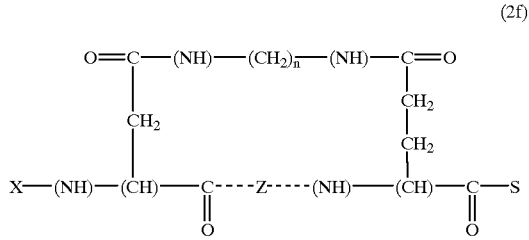

(2f)

wherein S is hydroxyl or is a macromolecule; X is hydrogen or is any amino acid or amino acid sequence; Z is any amino acid sequence consisting of six amino acids; and n is any integer from 4 to 6 inclusive.

In yet another embodiment, the invention provides locked helix peptides of formula (3f):

(3f)

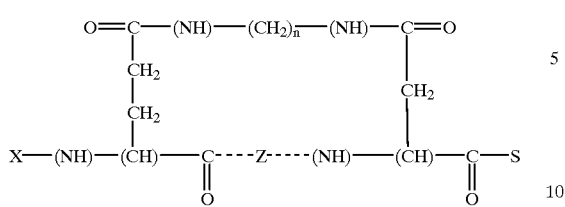

wherein S is hydroxyl or is a macromolecule; X is hydrogen or is any amino acid or amino acid sequence; Z is any amino acid sequence consisting of six amino acids; and n is any integer from 4 to 6 inclusive.

In still another embodiment, the invention provides locked helix peptides of formula (4f):

(4f)

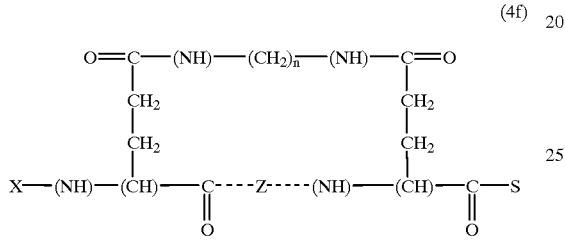

wherein S is hydroxyl or is a macromolecule; X is hydrogen or is any amino acid or amino acid sequence; Z is any amino acid sequence consisting of six amino acids; and n is any integer from 3 to 5 inclusive.

In still another embodiment, the invention provides locked helix peptides of formula (5f):

(5f)

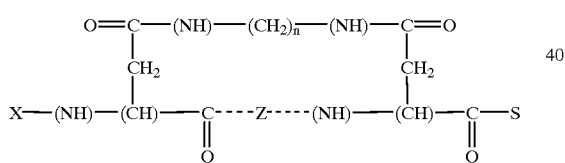

wherein S is hydroxyl or is a macromolecule; X is hydrogen or is any amino acid or amino acid sequence; Z is any amino acid sequence consisting of six amino acids; and n is any integer from 5 to 7 inclusive.

In still another embodiment, the invention provides locked helix peptides of formula (6f):

(6f)

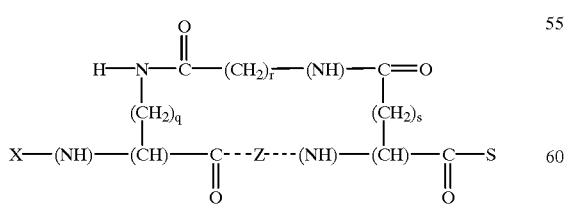

wherein S is hydroxyl or is a macromolecule; X is hydrogen or is any amino acid or amino acid sequence; Z is any amino acid sequence consisting of six amino acids; q is selected from the integers 1 to 7 inclusive, and s is selected from the integers 0 to 6 inclusive, provided that q+s is less than or equal to 7; and r is any integer in the range defined by (7−(q+s)) to (9−(q+s)) inclusive, provided that r is greater than 0.

In still another embodiment, the invention provides locked helix peptides of formula (7f):

(7f)

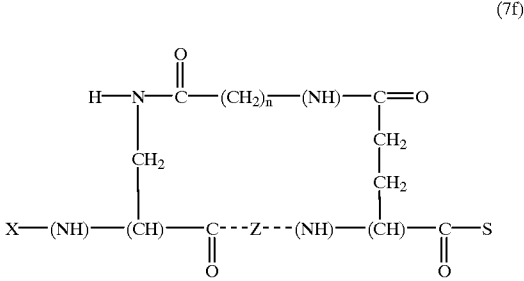

wherein S is hydroxyl or is a macromolecule; X is hydrogen or is any amino acid or amino acid sequence; Z is any amino acid sequence consisting of six amino acids; and n is any integer from 4 to 6 inclusive.

In still another embodiment, the invention provides locked helix peptides of formula (8f):

(8f)

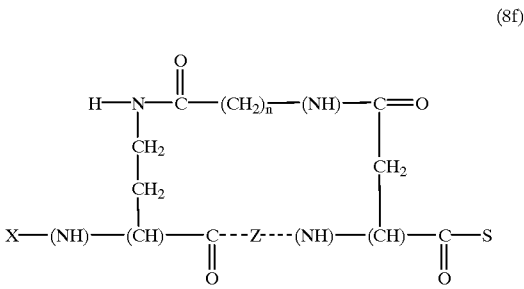

wherein S is hydroxyl or is a macromolecule; X is hydrogen or is any amino acid or amino acid sequence; Z is any amino acid sequence consisting of six amino acids; and n is any integer from 4 to 6 inclusive.

In still another embodiment, the invention provides locked helix peptides of formula (9f):

(9f)

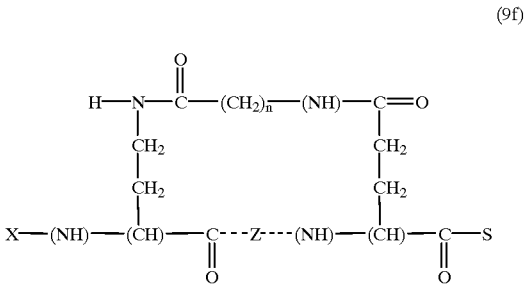

wherein S is hydroxyl or is a macromolecule; X is hydrogen or is any amino acid or amino acid sequence; Z is any amino acid sequence consisting of six amino acids; and n is any integer from 3 to 5 inclusive.

In still another embodiment, the invention provides locked helix peptides of formula (10f):

(10f)

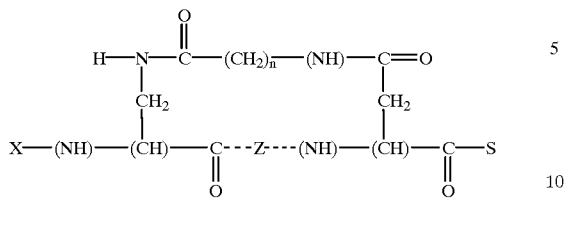

wherein S is hydroxyl or is a macromolecule; X is hydrogen or is any amino acid or amino acid sequence; Z is any amino acid sequence consisting of six amino acids; and n is any integer from 5 to 7 inclusive.

In still another embodiment, the invention provides locked helix peptides of formula (11f):

(11f)

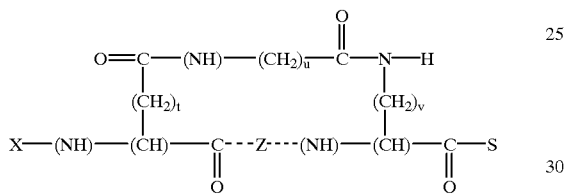

wherein S is hydroxyl or is a macromolecule; X is hydrogen or is any amino acid or amino acid sequence; Z is any amino acid sequence consisting of six amino acids; t is selected from the integers 0 to 6 inclusive, and v is selected from the integers 1 to 7 inclusive, provided that t+v is less than or equal to 7; and u is any integer in the range defined by (7−(t+v)) to (9−(t+v)) inclusive, provided that u is greater than 0.

In still another embodiment, the invention provides locked helix peptides of formula (12f):

(12f)

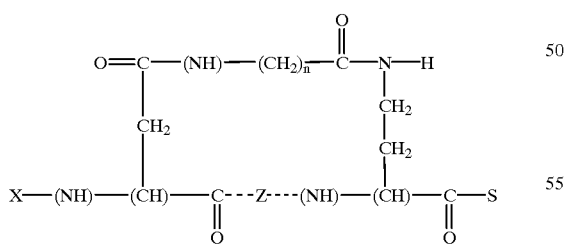

wherein S is hydroxyl or is a macromolecule; X is hydrogen or is any amino acid or amino acid sequence; Z is any amino acid sequence consisting of six amino acids; and n is any integer from 4 to 6 inclusive.

In still another embodiment, the invention provides locked helix peptides of formula (13f):

(13f)

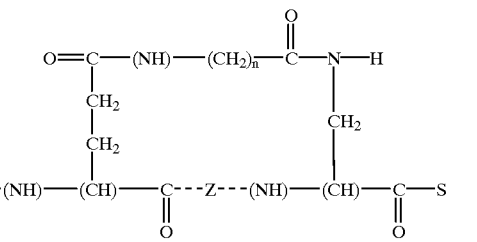

wherein S is hydroxyl or is a macromolecule; X is hydrogen or is any amino acid or amino acid sequence; Z is any amino acid sequence consisting of six amino acids; and n is any integer from 4 to 6 inclusive.

In still another embodiment, the invention provides locked helix peptides of formula (14f):

(14f)

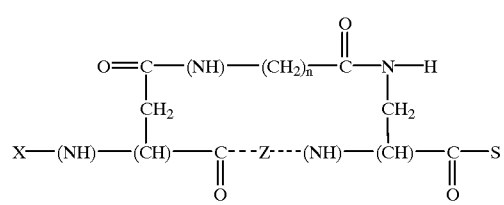

wherein S is hydroxyl or is a macromolecule; X is hydrogen or is any amino acid or amino acid sequence; Z is any amino acid sequence consisting of six amino acids; and n is any integer from 5 to 7 inclusive.

In still another embodiment, the invention provides locked helix peptides of formula (15f):

(15f)

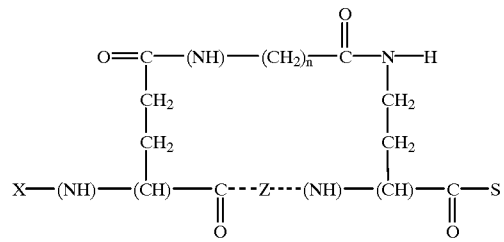

wherein S is hydroxyl or is a macromolecule; X is hydrogen or is any amino acid or amino acid sequence; Z is any amino acid sequence consisting of six amino acids; and n is any integer from 3 to 5 inclusive.

In still another embodiment, the invention provides locked helix peptides of formula (16f):

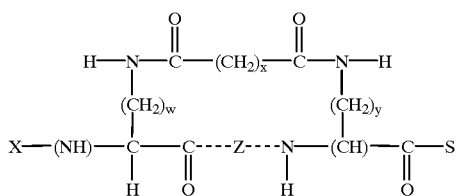

(16f)

wherein S is hydroxyl or is a macromolecule; X is hydrogen or is any amino acid or amino acid sequence; Z is any amino acid sequence consisting of six amino acids; w and y are independently selected from the integers 1 to 7 inclusive, provided that w+y is less than or equal to 8; and x is any integer in the range defined by (7−(w+y)) to (9−(w+y)) inclusive, provided that x is greater than or equal to 0.

In still another embodiment, the invention provides locked helix peptides of formula (17f):

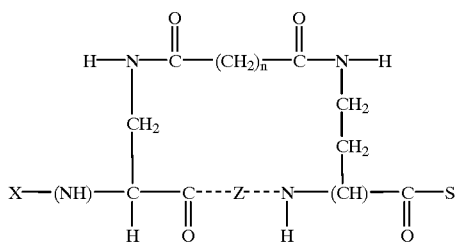

(17f)

wherein S is hydroxyl or is a macromolecule; X is hydrogen or is any amino acid or amino acid sequence; Z is any amino acid sequence consisting of six amino acids; and n is any integer from 4 to 6 inclusive.

In still another embodiment, the invention provides locked helix peptides of formula (18f):

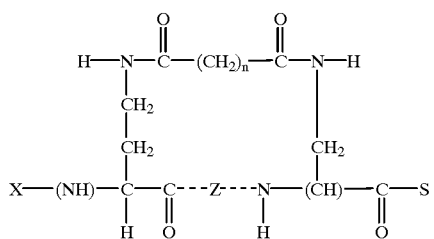

(18f)

wherein S is hydroxyl or is a macromolecule; X is hydrogen or is any amino acid or amino acid sequence; Z is any amino acid sequence consisting of six amino acids; and n is any integer from 4 to 6 inclusive.

In still another embodiment, the invention provides locked helix peptides of formula (19f):

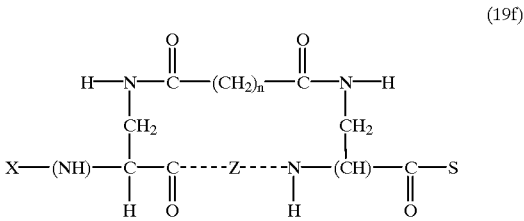

(19f)

wherein S is hydroxyl or is a macromolecule; X is hydrogen or is any amino acid or amino acid sequence; Z is any amino acid sequence consisting of six amino acids; and n is any integer from 5 to 7 inclusive.

In still another embodiment, the invention provides locked helix peptides of formula (20f):

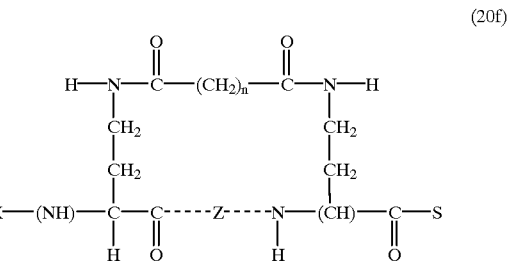

(20f)

wherein S is hydroxyl or is a macromolecule; X is hydrogen or is any amino acid or amino acid sequence; Z is any amino acid sequence consisting of six amino acids; and n is any integer from 3 to 5 inclusive.

Also provided herein are locked helix peptides of formula (1f), formula (2f), formula (3f), formula (4f), formula (5f), formula (6f), formula (7f), formula (8f), formula (9f), formula (10f), formula (11f), formula (12f), formula (13f), formula (14f), formula (15f), formula (16f), formula (17f), formula (18f), formula (19f) and formula (20f) wherein X contains up to or about 30 amino acid residues.

Further provided herein are locked helix peptides of formula (1f), formula (2f), formula (3f), formula (4f), formula (5f), formula (6f), formula (7f), formula (8f), formula (9f), formula (10f), formula (11f), formula (12f), formula (13f), formula (14f), formula (15f), formula (16f), formula (17f), formula (18f), formula (19f) and formula (20f) wherein X contains up to or about 25 amino acid residues.

Additionally provided herein are locked helix peptides of formula (1f), formula (2f), formula (3f), formula (4f), formula (5f), formula (6f), formula (7f), formula (8f), formula (9f), formula (10f), formula (11f), formula (12f), formula (13f), formula (14f), formula (15f), formula (16f), formula (17f), formula (18), formula (19f) and formula (20f) wherein X contains up to or about 20 amino acid residues.

Also encompassed herein are locked helix peptides of formula (1f), formula (2f), formula (3f), formula (4f), formula (5f), formula (6f), formula (7f), formula (8f), formula (9f), formula (10f), formula (11f), formula (12f), formula (13f), formula (14f), formula (15f), formula (16f), formula (17f), formula (18), formula (19f) and formula (20f) wherein X contains up to or about 15 amino acid residues.

Further encompassed herein are locked helix peptides of formula (1f), formula (2f), formula (3f), formula (4f), formula (5f), formula (6f), formula (7f), formula (8f), formula (9f), formula (10f), formula (11f), formula (12f), formula (13f), formula (14f), formula (15f), formula (16f), formula (17f), formula (18f), formula (19f) and formula (20f) wherein X contains up to or about 10 amino acid residues.

Additionally encompassed herein are locked helix peptides of formula (1f), formula (2f), formula (3f), formula (4f), formula (5f), formula (6f), formula (7f), formula (8f), formula (9f), formula (10f), formula (11f), formula (12f), formula (13f), formula (14f), formula (15f), formula (16f), formula (17f), formula (18f), formula (19f) and formula (20f) wherein X contains up to or about 5 amino acid residues.

Also within the scope of the invention are locked helix peptides of formula (1f), formula (2f), formula (3f), formula (4f), formula (5f), formula (6f), formula (7f), formula (8f), formula (9f), formula (10f), formula (11f), formula (12f), formula (13f), formula (14f), formula (15f), formula (16f), formula (17f), formula (18f), formula (19f) and formula (20f) wherein X contains up to or about 3 amino acid residues.

The invention also provides locked helix peptides of formula (1g):

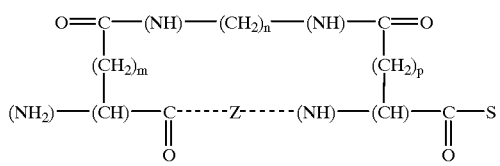

(1g)

wherein S is hydroxyl or is a macromolecule; Z is any amino acid sequence consisting of six amino acids; m and p are independently selected from the integers 0 to 6 inclusive, provided that m+p is less than or equal to 6; and n is any integer in the range defined by (7−(m+p)) to (9−(m+p)) inclusive, provided that n is greater than 1.

In another embodiment, the invention provides locked helix peptides of formula (2g):

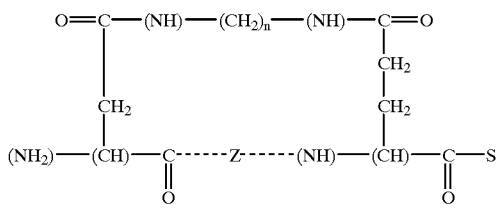

(2g)

wherein S is hydroxyl or is a macromolecule; Z is any amino acid sequence consisting of six amino acids; and n is any integer from 4 to 6 inclusive.

In yet another embodiment, the invention provides locked helix peptides of formula (3g):

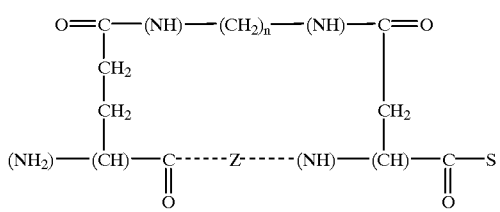

(3g)

wherein S is hydroxyl or is a macromolecule; Z is any amino acid sequence consisting of six amino acids; and n is any integer from 4 to 6 inclusive.

In still another embodiment, the invention provides locked helix peptides of formula (4g):

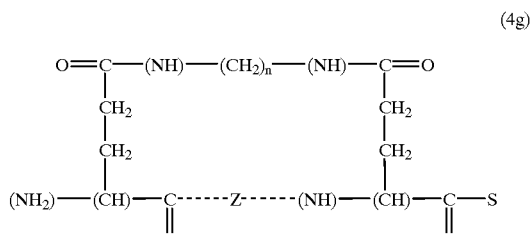

(4g)

wherein S is hydroxyl or is a macromolecule; Z is any amino acid sequence consisting of six amino acids; and n is any integer from 3 to 5 inclusive.

In still another embodiment, the invention provides locked helix peptides of formula (5g):

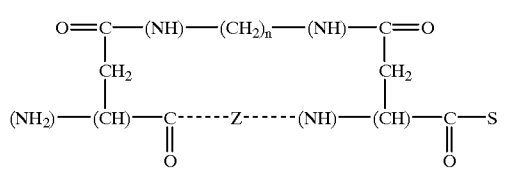

(5g)

wherein S is hydroxyl or is a macromolecule; Z is any amino acid sequence consisting of six amino acids; and n is any integer from 5 to 7 inclusive.

In still another embodiment, the invention provides locked helix peptides of formula (6g):

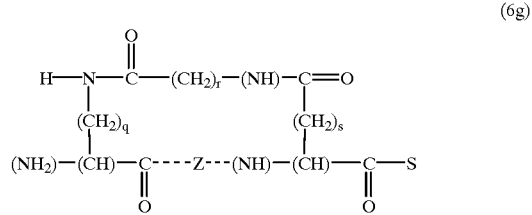

(6g)

wherein S is hydroxyl or is a macromolecule; Z is any amino acid sequence consisting of six amino acids; q is selected from the integers 1 to 7 inclusive, and s is selected from the integers 0 to 6 inclusive, provided that q+s is less than or equal to 7; and r is any integer in the range defined by (7−(q+s)) to (9−(q+s)) inclusive, provided that r is greater than 0.

In still another embodiment, the invention provides locked helix peptides of formula (7g):

(7g)

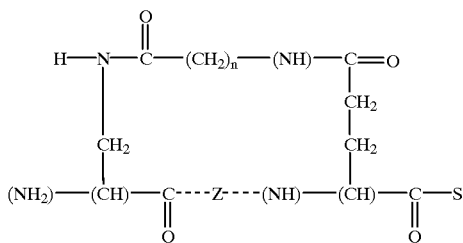

wherein S is hydroxyl or is a macromolecule; Z is any amino acid sequence consisting of six amino acids; and n is any integer from 4 to 6 inclusive.

In still another embodiment, the invention provides locked helix peptides of formula (8g):

(8g)

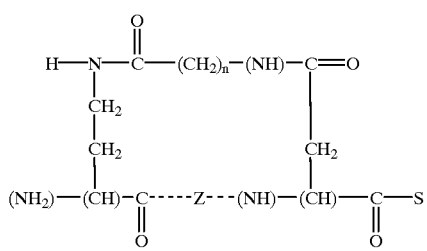

wherein S is hydroxyl or is a macromolecule; Z is any amino acid sequence consisting of six amino acids; and n is any integer from 4 to 6 inclusive.

In still another embodiment, the invention provides locked helix peptides of formula (9g):

(9g)

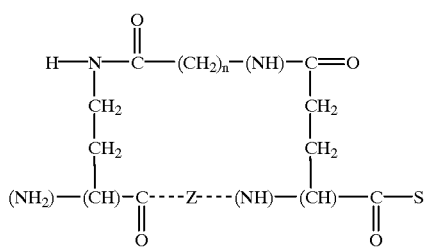

wherein S is hydroxyl or is a macromolecule; Z is any amino acid sequence consisting of six amino acids; and n is any integer from 3 to 5 inclusive.

In still another embodiment, the invention provides locked helix peptides of formula (10g):

(10g)

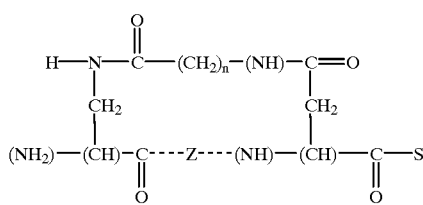

wherein S is hydroxyl or is a macromolecule; Z is any amino acid sequence consisting of six amino acids; and n is any integer from 5 to 7 inclusive.

In still another embodiment, the invention provides locked helix peptides of formula (11g):

(11g)

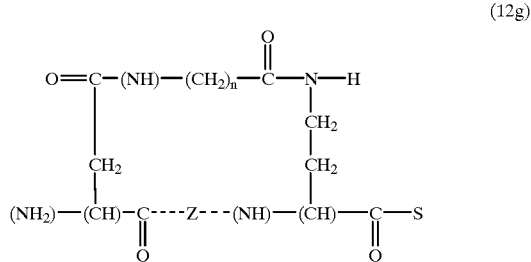

wherein S is hydroxyl or is a macromolecule; Z is any amino acid sequence consisting of six amino acids; t is selected from the integers 0 to 6 inclusive, and v is selected from the integers 1 to 7 inclusive, provided that t+v is less than or equal to 7; and u is any integer in the range defined by (7−(t+v)) to (9−(t+v)) inclusive, provided that u is greater than 0.

In still another embodiment, the invention provides locked helix peptides of formula (12g):

(12g)

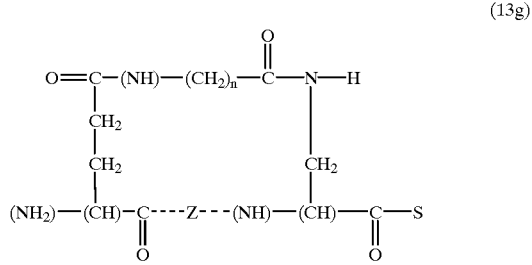

wherein S is hydroxyl or is a macromolecule; Z is any amino acid sequence consisting of six amino acids; and n is any integer from 4 to 6 inclusive.

In still another embodiment, the invention provides locked helix peptides of formula (13g):

(13g)

wherein S is hydroxyl or is a macromolecule; Z is any amino acid sequence consisting of six amino acids; and n is any integer from 4 to 6 inclusive.

In still another embodiment, the invention provides locked helix peptides of formula (14g):

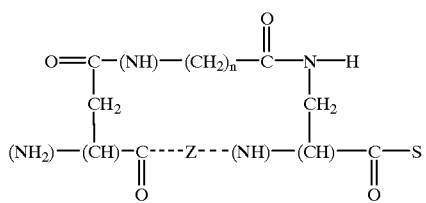

(14g)

wherein S is hydroxyl or is a macromolecule; Z is any amino acid sequence consisting of six amino acids; and is any integer from 5 to 7 inclusive.

In still another embodiment, the invention provides locked helix peptides of formula (15g):

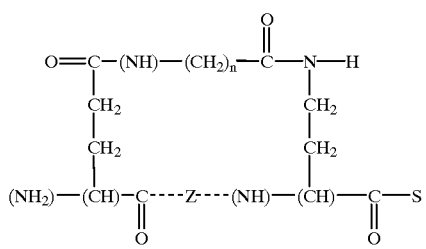

(15g)

wherein S is hydroxyl or is a macromolecule; Z is any amino acid sequence consisting of six amino acids; and is any integer from 3 to 5 inclusive.

In still another embodiment, the invention provides locked helix peptides of formula (16g):

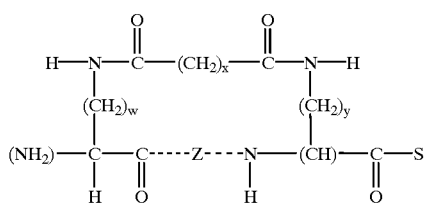

(16g)

wherein S is hydroxyl or is a macromolecule; Z is any amino acid sequence consisting of six amino acids; w and y are independently selected from the integers 1 to 7 inclusive, provided that w+y is less than or equal to 8; and x is any integer in the range defined by (7−(w+y)) to (9−(w+y)) inclusive, provided that x is greater than or equal to 0.

In still another embodiment, the invention provides locked helix peptides of formula (17g):

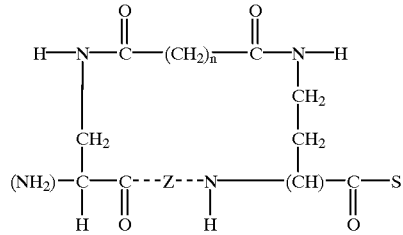

(17g)

wherein S is hydroxyl or is a macromolecule; Z is any amino acid sequence consisting of six amino acids; and n is any integer from 4 to 6 inclusive.

In still another embodiment, the invention provides locked helix peptides of formula (18g):

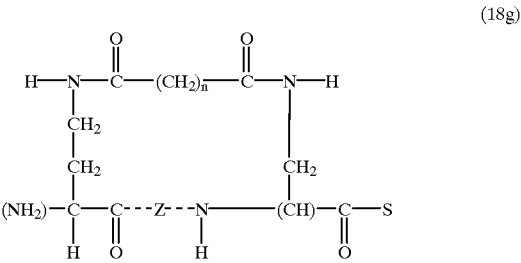

(18g)

wherein S is hydroxyl or is a macromolecule; Z is any amino acid sequence consisting of six amino acids; and n is any integer from 4 to 6 inclusive.

In still another embodiment, the invention provides locked helix peptides of formula (19g):

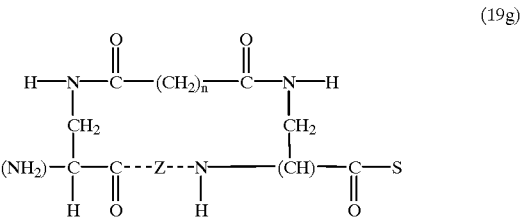

(19g)

wherein S is hydroxyl or is a macromolecule; Z is any amino acid sequence consisting of six amino acids; and n is any integer from 5 to 7 inclusive.

In still another embodiment, the invention provides locked helix peptides of formula (20g):

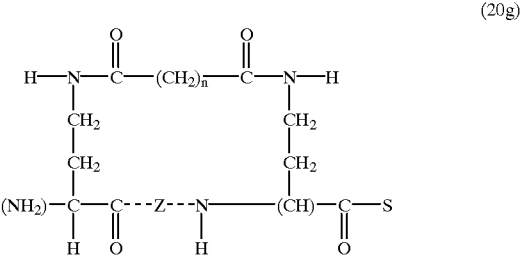

(20g)

wherein S is hydroxyl or is a macromolecule; Z is any amino acid sequence consisting of six amino acids; and n is any integer from 3 to 5 inclusive.

For locked helix peptides of formulas (1), (2), (3), (4), (5), (6), (7), (8), (9), (10), (11), (12), (13), (14), (15), (16), (17), (18), (19), (20), (1e), (2e), (3e), (4e), (5e), (6e), (7e), (8e), (9e), (10e), (11e), (12e), (13e), (14e), (15e), (16e), (17e), (18e), (19e), (20e), (1f), (2f), (3f), (4f), (5f), (6f), (7f), (8f), (9f), (10f), (11f), (12f), (13f), (14f), (15f), (16f), (17f), (18f), (19f), (20f), (1g), (2g), (3g), (4g), (5g), (6g), (7g), (8g), (9g), (10g), (11g), (12g), (13g), (14g), (15g), (16g), (17g), (18g), (19g), or (20g) bound to a macromolecule, the invention encompasses any macromolecule capable of serving as an anchor for the C-terminus of the locked helix peptide. Typically, the macromolecule functions as a solid support. In general, the solid support is an inert matrix, such as a polymeric gel, comprising a three dimensional structure, lattice or network of a material. Almost any macromolecule, synthetic or natural, can form a gel in a suitable liquid when suitably cross-linked with a difunctional reagent. In one embodiment, the macromolecule selected is convenient for use in affinity chromatography. Most chromatographic matrices used for affinity chromatography are xerogels. Such gels shrink on drying to a compact solid comprising only the gel matrix. When the dried xerogel is resuspended in the liquid, the gel matrix imbibes liquid, swells and returns to the gel state. Xerogels suitable for use herein include polymeric gels, such as cellulose, cross-linked dextrans (e.g. Sepharose), agarose, cross-linked agarose, polyacrylamide gels, and polyacrylamide-agarose gels.

The locked helix peptides provided herein can be constructed according to the methods of the invention described in Sections II and III below.

In one embodiment, the peptides of the invention are designed to isolate the binding determinants from α-helical binding domains of known proteins. Such peptides have a number of uses, including the determination of whether a binding determinant in an α-helical binding domain of a known protein can serve as a structural model for the design of peptidomimetics or small molecules capable of mimicking or antagonizing the binding activity of the intact protein. In using the peptides of the invention for this purpose, the practitioner selects a binding protein with a helical domain that interacts with ligand, and then identifies a candidate binding determinant situated within a sequence of six (or more) contiguous amino acids in the helical binding domain. The candidate binding determinant can be identified by using alanine scanning mutagenesis to determine whether the candidate sequence contains one or more amino acid residues that are critical for ligand binding. Next, a constrained peptide containing the candidate sequence is designed by selecting two residues in the candidate sequence (designated I and I+7) which are separated by an intervening sequence of six amino acids and which do not interact with ligand (as determined by alanine scanning mutagenesis in the previous step) for substitution with amino acid residues having a side chain containing an amide bond-forming substitutent. The peptide is synthesized and the side chain amide bond-forming substitutent of the foreign I and I+7 residues are used to tether the peptide in an α-helical conformation according to the methods of the invention described in Section II below. Finally, the locked helix peptide's binding activity with the ligand is assayed, e.g., in a binding competition assay with the intact binding protein, and the results of the assay can be used to determine whether a peptidomimetic or small molecule antagonist could be developed using the binding determinant as a structural model.

In another embodiment, the locked helix peptides of the invention are used to replace intact binding proteins or protein binding domains in the affinity purification of ligand. For example, Protein A is commonly used for affinity chromatographic purification of IgG molecules. The Z-domain of Protein A is a three helix bundle, 59 residues in length, which binds to the Fc portion of IgG. As described in Example 2 below, a locked helix species of the peptide Phe-Asn-Met-(1)-Gln-Gln-Arg-Arg-Phe-Tyr-(2)-Ala-Leu-His (wherein the amino acid residues at the (1) and (2) positions in the corresponding Z-domain sequence are both replaced with glutamic acid residues), corresponding to a binding determinant in helix 1 of the Z-domain can be used to bind IgG. Accordingly,the invention provides constrained helix species containing binding determinants in helix 1 of the Z-domain in Protein A, including molecules of formula (4) above wherein Z is Gln-Gln-Arg-Arg-Phe-Tyr. In one embodiment, the constrained helix species is a molecule of formula (4) wherein Z is Gln-Gln-Arg-Arg-Phe-Tyr, X is Phe-Asn-Met, and Y is Ala-Leu-His. The IgG binding molecules of the invention are conveniently synthesized using the solid phase peptide synthesis methods described in Section II below, such that the molecules are anchored to resin beads suitable for column or batch affinity chromatography.

In still another embodiment, the locked helix peptides of the invention are designed to mimic epitopes in proteins and are used to selectively raise polyclonal or monoclonal antibodies against such individual epitopes. Since the peptides will frequently be too small to generate an immune response, the peptides can be conjugated to carriers known to be immunogenic in the species to be immunized, e.g., keyhole limpet hemocyanin, serum albumin, bovine thyroglobulin, or soybean trypsin inhibitor using a difunctional or derivatizing agent, for example, maleimidobenzoyl sulfosuccinimide ester (conjugation through cysteine residues), N-hydroxysuccinimide (through lysine residues), glutaraldehyde, succinic anhydride, $SOCl_2$, or $R^1N=C=NR$, where R and $R^1$ are different alkyl groups.

The locked helix peptides of the invention are particularly useful in isolating synthetic antibody clones with a selected binding activity from phage display combinatorial libraries. The locked helix peptide provides a significant advantage over the intact protein or protein domain in that using the locked helix peptide allows the isolation of binding activities for the particular conformational epitope of interest. Without the locked helix peptides of the invention, the conformation epitope of interest would likely require structural support from other regions of the protein or protein domain whose presence in the ligand would result in the concomitant isolation of undesired clones. In addition, the synthesis of locked helix peptides anchored to polymeric resins as described in Sections II and III below would provide material that can be conveniently packed into columns for panning phage display libraries.

In another aspect, the locked helix peptides of the invention are used to provide conformationally stable variants of peptides or proteins which exhibit "floppy" or unstable α-helical secondary structure at one or more site(s) in unrestrained form under conditions of interest. In particular, the methods of the invention can solve problems presented by some antigens which relate to the instability of conformational epitopes. A conformational epitope can fail to present the desired antigenic determinant because of "floppy" or unstable α-helical secondary structure element (s) in the epitope. The restraint of such "floppy" α-helical structure(s) according to the methods of the invention would stabilize the conformational epitope and allow presentation of the desired antigenic determinant This application of the present methods and peptides is particularly useful, for example, in vaccine design and in generating polyclonal or monoclonal antibodies from host animals or isolating antibody clones from phage display libraries.

In one embodiment the invention, where the locked helix peptides of the invention are used to provide conformationally stable variants of peptides or proteins which exhibit "floppy" or unstable α-helical secondary structure at one or more sites in unrestrained form under conditions of interest, a compound containing a constrained helical peptide that is useful as an immunogen, vaccine and diagnostic for human immunodeficiency virus (HIV) is provided. Acquired immunodeficiency syndrome (AIDS) is caused by a retrovirus identified as the human immunodeficiency virus (HIV). There have been intense efforts to develop a vaccine that induces a protective immune response based on induction of antibodies or cellular responses. Recent efforts have used subunit vaccines where an HIV protein, rather than attenuated or killed virus, is used as the immunogen in the vaccine for safety reasons.

The human immunodeficiency virus 1 (HIV-1) envelope glycoproteins gp120 and gp41 mediate viral tropism to and subsequent entry into target cells (Freed et al., *The Journal of Biological Chemistry* 270, 23883–23886 (1995)). The role of gp120 is to bind to target cells by interactions with CD4 and one of several co-receptors (D'Souza et al., *Nature Medicine* 2, 1293–1300 (1996)), after which gp41 promotes the fusion of viral and cellular membranes. The mechanism by which gp41 mediates membrane fusion has recently been the subject of intensive study. Evidence suggests that the process may involve the formation of a coiled-coil trimer, which is thought to drive the transition from resting to fusogenic states, as modeled for influenza hemagglutinin (Wilson et al., *Nature* 289, 366–373 (1981); Carr, et al., *Cell* 73, 823–832 (1993); Bullough et al., *Nature* 371, 37–43 (1994)).

Two linear peptides derived from HIV-1 gp41 have been found to inhibit viral fusion. The first of these, DIP107, represents a portion of gp41 near the N-terminal fusion peptide and has been shown to be helical in solution and oligomerize in a manner consistent with coiled-coil formation (Gallaher et al., *AIDS Res. Hum. Retroviruses* 5, 431–440 (1989); Weissenhorn et al., *Nature* 387, 426–430 (1997)). A more potent peptide, DP178, was derived from the C-terminal region of the gp41 ectodomain (Wild, et al., PNAS 91: 9770–9774 (1994); Jiang et al., Nature, 365:113 (1993)). Although this region of gp41 was predicted to be α-helical (Gallaher et al., *AIDS Res. Hum. Retroviruses* 5, 431–440 (1989)), DP178 itself lacks discernable structure in solution (Wild, et al., PNAS 91: 9770–9774(1994). Attempts to explore the mechanism of action of DP178 have been complicated by a lack of understanding of its bioactive conformation. Recently, crystallographic (Chan et al., *Cell* 89, 263–273 (1997); Weissenhorn et al., *Nature* 387, 426–430 (1997)) and solution (Lawless, et al., *Biochemistry* 35, 13697–13708 (1996); Lu et al., *Nature Structural Biology* 2, 1075–1082 (1995); Rabenstein et al., *Biochemistry* 35, 13922–13928 (1996)) studies have shown that disconnected segments of HIV-1 gp41 that overlap DP107 and DP178 associate in a tightly-packed helical bundle. The C-terminal segment, corresponding to DP178, forms an extended helix which packs in an antiparallel fashion against a groove created by an N-terminal (DP107) coiled-coil trimer. While these data suggest one possible conformation for DP178, they do not provide conclusive information about the mechanism of peptide inhibition during viral fusion events.

The present invention provides helical constrained forms of DP178 and homologous sequences and variants, overcoming the limitations in the art concerning DP178 and providing more effective use of DP-178 like sequences. Accordingly, in one embodiment of the invention is provided a constrained helical peptide having at least its internal amino acid sequence (and preferably adjacent amino acid sequences) selected from the C-terminal region of the HIV-1 LAI isolate transmembrane protein gp41 ectodomain amino acids 633 to 678, which overlap with the sequence corresponding to peptide DP-178 (amino acid residues 643 to 673). This region is a 46-amino acid sequence (reading from the amino to carboxy terminus): NH2-WMEWEREIDNYTSLIHSLIEESQNQQEKNEQELLELD KWASLWNWF-COOH.

Peptides in an alpha-helical coiled-coil conformation interact with one another in a characteristic manner that is determined by the primary sequence of each peptide. The tertiary structure of an alpha-helix is such that 7 amino acid residues in the primary sequence correspond to approximately 2 turns of the alpha-helix. Accordingly, a primary amino acid sequence giving rise to an alpha-helical conformation may be broken down into units of 7 residues each, termed heptads (having the form abcdefg). The core polypeptides are comprised of a series of heptads in tandem. When the sequence of a heptad is repeated in a particular core polypeptide, the heptad may be referred to as a "heptad repeat", or simply "repeat".

According to the invention, embodiments are provided as compounds containing a constrained helical peptide that is composed of a peptide which contains a sequence of eight amino acid residues, where the sequence of eight amino acid residues has a fist terminal residue and a second terminal residue, where the first terminal residue and the second terminal residue flank an internal sequence of six amino acids, wherein the first and second terminal residues have a side chain that are linked to each other forming a locking moiety to constrain the peptide to a helical form. The internal sequence of six amino acids has the form gabcde, defgab, or cdefga and has a sequences of six contiguous amino acids found in HIV-1 LAI strain transmembrane protein gp41 amino acid sequence 633 to 678, in its homolog sequence from another HIV strain, in a consensus sequence of its homolog sequences from any one HIV clade, or amino acid substituted variant thereof. According to the invention, each of the amino acids in the aforementioned sequences is assigned a position of a, b, c, d, e, f; or g. The assignment is based on assigning the amino acid 633 of the HIV LAI gp41 633–678 sequence to position a of a repeating abcdefg heptad assignment. Subsequent amino acids in the sequence are assigned positions accordingly. FIG. 18 indicates the heptad positional assignment of each amino acid in the sequence. The assignment can be readily applied to homologs and consensus sequences by aligning their amino acids to the corresponding amino acid in the representative HIV LAI sequence. The 633 amino acid or its corresponding amino acid in a homolog or consensus sequence is assigned position a, which begins the repeating abcdefg assignment pattern.

In these representative compounds and sequences shown in FIGS. 16–18, the locking moiety or tether is between adjacent f positions when the internal sequence is of the form gabcde, adjacent c positions when the internal sequence is of the form defgab, or adjacent b positions when the internal sequence is of the form cdefga. In the most preferred embodiments the locking occurs between adjacent f positions, in which case the f position amino acids are replaced by amino acids suitable for providing a helix locking moiety. FIG. 18 provides the alignment of the repeating abcdefg assignment with the sequences relevant to the invention. In a preferred embodiment the internal sequence of six amino acids has the form gabcde. These "internal sequence" of six amino acids from gp41 can substitute for moiety "Z" in any of the compounds, formulas, and synthetic methods taught herein.

While the internal amino acid sequence is preferably from a sequence of six contiguous amino acids in HIV-1 LAI strain gp41 amino acid sequence 633 to 678, in its homolog sequence from another HIV strain, or in a consensus sequence of its homolog sequences from any one HIV clade, it may be an amino acid substituted variant thereof. The sequences of the invention also include analogs of HIV gp41 l sequence 633–678, truncations which may include, but are not limited to, peptides comprising the 633–678 sequence, containing one or more amino acid substitutions, insertions and/or deletions. The analogs of the sequence will exhibit antiviral activity when in constrained peptides of the invention, and may, further, possess additional advantageous features, such as, for example, increased bioavailability, and/or stability, or generate antibodies with increased HIV strain recognition.

HIV-1 and HIV-2 envelope proteins are structurally distinct, but there exists a striking amino acid conservation within the gp41 633–678 corresponding regions of HIV-1 and HIV-2. Amino acid substitutions may be of a conserved or non-conserved nature. Conserved amino acid substitutions consist of replacing one or more amino acids of the 633–678 peptide sequence with amino acids of similar charge, size, and/or hydrophobicity characteristics, such as, for example, a glutamic acid (E) to aspartic acid (D) amino acid substitution. Non-conserved substitutions consist of replacing one or more amino acids of the 633–678 peptide sequence with amino acids possessing dissimilar charge, size, and/or hydrophobicity characteristics, such as, for example, a glutamic acid (E) to valine (V) substitution.

Deletions of the 633–678 region or its homologs are also within the scope of the invention. Such deletions consist of the removal of one or more amino acids with the lower limit length of the resulting peptide sequence being 6 amino acids for use as an internal sequence of a constrained helical peptide. Preferably the deletions retain sufficient amino acids such that at least two locks may be incorporated as taught herein. Examples of such deletions are the HIV35 peptide and its constrained helix compounds of the invention that have one lock (e.g. HIV 24) and two locks (e.g. HIV 31). Most preferably, the deletions are terminal truncations, but in any event result in peptides which, when constrained along the f-b-c helical face, are still recognized by the coiled coil search algorithms used herein, or alternatively, retain the a-d helical face orientation and spatial arrangement of the parent molecule, or alternatively, can exhibit antifusogenic or antiviral activity.

Most preferred compounds are those that, when used as immunogens, generate antibodies that neutralize HIV viral fusogenic activity or infectivity.

The peptides of the invention may further include homolog sequences of the HIV LAI strain 633–678 sequence which exhibit antiviral activity when in constrained helical form. Most preferably, the constrained peptides, when used as haptens, will generate antibodies that block viral fusion events, leading to an inhibition of viral infectivity. Such homologs are peptides whose amino acid sequences are comprised of the amino acid sequences of peptide regions of other (i.e., other than HIV-1LAI) viruses that correspond to the gp41 peptide region of 633–678. Such viruses may include, but are not limited to, other HIV-1 isolates and HIV-2 isolates. Homologs derived from the corresponding gp41 peptide region of other (i.e., non HIV-1LAI) HIV-1 isolates may include those provide in FIGS. 16A to 16M, or other known corresponding sequences. Particularly preferred are those derived from HIV-1SF2, HIV-1RF, and HIV-1MN, GNE6, GNE8, and Thai strain isolate A244.

In a particularly preferred embodiment, amino acids at positions a and d of the internal sequence of six amino acids are not amino acid substituted in the helical peptide, but are the amino acids in the known isolates or consensus sequences (see FIGS. 16A–16G and 17).

Also most preferred are embodiments where the amino acids at positions g and e of the internal sequence of six amino acids are not amino acid substituted in the helical peptide. An amino acid at any one of positions a, d, g, or e of the internal sequence of six amino acids can be conservatively substituted in the helical peptide in preferred embodiments. The a and d positions, and less directly the g and e positions, are believed to be those that are on the face of the constrained helix that interacts with the gp41 core trimer (see FIG. 19). Since positions f, b and c are believed to not directly participate in binding, but rather serve to allow helix structure, preferred variations at positions b and c of the internal sequence of six amino acids are not amino acid substituted in the helical peptide, when not the locking (tethering) residues. Less preferred are compounds wherein an amino acid at any one of positions b, c, or f of the internal sequence of six amino acids is conservatively substituted or is any non-helix-breaking amino acid in the helical peptide, that does not interfere with the locking moiety. Preferred internal sequence chimeras are those in which an amino acid at any one of positions a, d, g, or e of the internal sequence of six amino acids is substituted in the helical peptide with an amino acid from the corresponding position of a different HIV virus strain.

Preferred compounds of the invention can include sequences from HIV-1 clade consensus sequences:

(clade B consensus) WmeWerEIdnYT?lIytLIeesQnQQekNeqeLLeLdkWasLwn Wf (SEQ ID NO: 109);

(clade A consensus) WLqWdKEIsnYT?IIYnLIEeSqnQQEkNEqdLLALDKWanL wnWF (SEQ ID NO: 110);

(clade C consensus) WMqWDREISNYTdtIYrLLEDSQNQQErNEKDLLALDSWk NLWNWF (SEQ ID NO: 111);

(clade D consensus) WmeWErEIdNYTGIIYsLIEeSQIQQEKNEkeLLeLDKWAS LWNWF (SEQ ID NO: 112); and (clade E consensus) WIEWeREISNYTNqIYeILTeSQnQQDRNEKDLLeLDKWA SLWnWf (SEQ ID NO: 113).

The amino acids in these sequences are represented by a single letter code, wherein a lower case letter is the represented amino acid or is substituted with an amino acid from that corresponding position in a sequence within the same clade, and wherein a ? is any amino acid from that corresponding position in a sequence from within the same clade. Most preferred are homologs or consensus sequences from FIGS. 16A–16G. The internal sequences are preferably found virus sequences in the group of HIV-1 clades consisting of clades A, B, C, D, E, F, G and F/B.

While the locking moiety can be any structure that constrains the internal sequence to a helical peptide form and does not interfere with the a–d face (active face) of the constrained peptide, the preferred compounds use the locking chemistry taught herein. Compounds of the invention can have the first and second terminal residues with a side chain containing an amide bond-forming substituent that are linked to each other forming an amide bond to form a constrained helical peptide. The side chain amide bond-forming substituent of the first terminal residue and the side chain amide bond-forming substituent of the second terminal residue are independently selected from the group consisting of an amino substituent and a carboxy substituent. The side chain amide bond-forming substituent of the first terminal residue is a carboxy substituent, the side chain amide bond-forming substituent of the second terminal residue is a carboxy substituent, and the difunctional linker is a diamine wherein the first and second functional groups are amino groups. In preferred form the first terminal residue and the second terminal residue are independently selected from the group consisting of Asp and Glu, more preferred the first terminal residue and the second terminal residue are both Glu. The first terminal residues can have a D-thiolysine side chain and the second terminal residue a L-thio-lysine that are linked to each other forming a disulfide bonded locking moiety to form a constrained helical peptide.

In another embodiment the constrained peptide is a hapten that is attached to a carrier macromolecule, preferably covalently linked to the constrained helical peptide, as discussed herein. The macromolecule can be linked to the helical peptide at the locking moiety or at amino acids at positions f, b, or c of the constrained helical peptide, and can be any carrier that does not interfere with the a–d face of the constrained helical peptide. A preferred carrier for immunogenic purposes is keyhole limpet hemocyanin, or other carriers discussed herein.

In other embodiments the compounds contain more than one constrained helical peptide. The internal sequences of a first and a second constrained helical peptide in these embodiments are preferably different. The internal sequences of the first and second constrained helical peptides are from the same HIV gp41 sequence or the same HIV clade consensus sequence, or amino acid substituted variant thereof. The internal sequences of the first and second constrained helical peptides are chosen from those that were separated by at least two helical turns (or six residues) in the HIV gp41 sequence or the same HIV clade consensus sequence, or amino acid substituted variant thereof. The compounds can further comprise a third constrained helical peptide. Again, the internal sequences of the first, second, and third constrained helical peptides are preferably different. In one example, the three sequences are present as separate constrained helical segments in a super helix of the polypeptide backbone of a 633–678 sequence as depicted in FIG. 18.

In other embodiments the compounds of the invention contain 1 to 38, 1 to 35, or more preferably, 1 to 19 amino acids flanking either or both terminal residues of the helical peptide. The flanking amino acids preferably are the flanking amino acids for the internal sequence as found in a sequence from an HIV gp41 sequence.

In yet other embodiments the compounds further comprising a blocking group attached at either or both of the terminal residues of the helical peptide to prevent proteolytic degradation. The blocking group can contain a D-amino acid or a non-amide bond between adjacent flanking amino acids.

Particularly preferred compounds include those in which a single lock is placed within sequence YTSLIH-SLIEESQNQQEKNEQELLELD (SEQ ID NO: 2) sequence or a homolog sequence thereof, within EWDREINNYTS-LIHSLIEESQNQQEKNEQE (SEQ ID NO: 107) sequence or a homolog sequence thereof, within YTSLIHSLIEESQN-QQEKNEQELLELDKWASLWNF (SEQ ID NO: 108) sequence or a homolog sequence thereof, to yield a constrained helical peptide. More than one constraint, preferably two, can be placed in these sequences, with examples shown in FIG. 18. Shown in FIG. 18 are locations of gabcde form helical sections when one, two or three i to i+7 locks are present in a 633–678 sequence or variant (truncated or sequence variant) thereof. The two-lock variants (II), (III), and HIV31, and the one-lock variants HIV24, (IX) and (XI) (FIG. 18) are preferred compounds demonstrating preferred locking positions. Less preferred are the three-lock variant, the two-lock (VI) and (VII) variants, and the one lock VIII and XII variants. Particularly preferred are the truncated variants HIV24 and HIV31 and their homologs from other HIV strains or consensus sequences or substitution variants thereof. Much less preferred are i to i+4 lock to constrain a "floppy" helical segment.

In a preferred embodiment the re are at least two constrained helical peptides in the compound, for example attached as different and independent haptens to KHL or a synthetic TASP or lysine network, or as two or more locked helical segments within a longer polypeptide sequence, preferably one that has a tendency to form an extended or super helical structure. The internal sequences of the first and second constrained helical peptides are preferably different, for example as multiple haptens on a single hapten carrier or two or more locked helical segments within a longer super helix polypeptide sequence. In the latter case, the internal sequences of the first and second constrained helical peptides are preferably from the same HIV gp41 sequence, the same HIV clade consensus sequence, or the same amino acid substituted variant thereof. The two helical peptides are attached to each other by a separating amino acid sequence, which can comprises from 5 to 7, 12 to 14, or 19 to 21 non helix-breaking natural or unnatural amino acids, and where preferably, the internal sequences of the first and second constrained helical peptides are from the same HIV gp41 sequence, the same HIV clade consensus sequence, or the same amino acid substituted variant thereof. The separating sequence can be a contiguous amino acid sequence selected from an intervening sequence that is located between the two internal sequences present in the same HIV gp41 sequence, the same HIV clade consensus sequence, or the same amino acid substituted variant thereof, and that excludes the two amino acids that correspond to the helical peptide locking positions immediately flanking the intervening sequence. An example is HIV31, in which the two constrained segments (internal amino acid sequences) are separated in the parent sequence (HIV35) by an eight amino acid sequence of which the amino acids at adjacent f positions used in locking are not considered part of the intervening sequence, such that the intervening sequence is a six amino acid sequence which is synthesized into the final peptide as a six amino acid separating sequence. The separating sequence is most preferably 6, 13, or 20 amino acids, in order to maintain alignment of a–d faces in between to constrained helical peptides.

The amino acids in the separating sequence retain abcdefg assignment positions of the intervening sequence, wherein preferably the amino acids in positions a and d in the separating sequence are identical to their corresponding intervening sequence amino acids. In addition, in preferred embodiments the amino acids in the separating sequence positions g and e also are identical to their corresponding intervening sequence amino acids. Less preferably, an amino acid at any one of positions a, d, g, or e is conservatively substituted in the separating sequence (with a sequence other than that represented in the clade at that position). Most preferably, the amino acids in the separating sequence retain abcdefg assignment positions of the intervening sequence and an amino acid at any one of positions a, d, g, or e is substituted in the separating sequence with a corresponding amino acid from its homolog sequence from another HIV strain, from a consensus sequence of its homolog sequence s from any one HIV clade, or from an amino acid substituted variant thereof. The amino acids in the separating sequence positions b, c, or f can be any non-helix-breaking amino acid, with the preferences given in FIGS. 22 and 23A and B. Chimeras can be formed where an amino acid at any one of positions a, d, g, or e of the internal sequence of six amino acids is substituted in the helical peptide with an amino acid from the corresponding position of a different HIV virus strain. Likewise substitutions of the same nature can be made in flanking or in separating sequences. Preferred are compounds wherein the internal amino acid sequence is from any one of the peptide sequences from FIG. 23A and 23D. More preferably, the compound of the invention is selected from the group consisting of constrained helical peptides of each possible sequence having any one or any combination of amino acid substitutions indicated in the constrained helical peptide series I to XII as shown in FIGS. 23A and 23D. In other embodiments, the compound is selected from the group consisting of constrained helical peptides of each possible sequence having any one or any combination of amino acid truncations indicated in the constrained helical peptide series I to XII as shown in FIGS. 23A and 23D. In yet other embodiments, the compound is selected from the group consisting of constrained helical peptides of each possible sequence having any one or any combination of amino acid substitutions indicated in the constrained helical peptide series I to XII as shown in FIGS. 23A and 23B in combination with any one or any combination of amino acid truncations indicated in the constrained helical peptide series I to XII as shown in FIGS. 23A and 23D. X in these sequences can be any non helix-breaking amino acid.

In yet another embodiment of the invention, peptides comprising the sequences described herein can be synthesized with additional chemical groups present at their amino and/or carboxy termini, such that, for example, the stability, bioavailability, and/or inhibitory activity of the peptides is enhanced. For example, hydrophobic groups such as carbobenzoxyl, dansyl, or t-butyloxycarbonyl groups, may be added to the amino termini. An acetyl group or a 9-fluorenylmethoxy-carbonyl group may be placed at the amino termini. A hydrophobic group, t-butyloxycarbonyl, or an amido group may be added to carboxy termini. Furthermore, the peptides of the invention can be synthesized such that their steric configuration is altered. For example, the D-isomer of one or more of the amino acid residues of the peptide can be used, rather than the usual L-isomer. The compounds can contain at least one bond linking adjacent amino acids that is a non-peptide bond, and is preferably not helix breaking. Non-peptide bonds for use in flanking sequences include an imino, ester, hydrazine, semicarbazide, oxime, or azo bond. Still further, at least one of the amino acid residues of the peptides of the invention can be substituted by one of the well known non-naturally occurring amino acid residues, that is preferably not helix breaking. Most preferably the non-natural amino acid or non-amide bond linking adjacent amino acids, when present, is present outside of the internal sequence, and is, more preferably, not helix breaking. Still further, at least one of the amino acid residues of the peptides of the invention can be substituted by one of the well known non-naturally occurring amino acid residues. Alterations such as these can serve to increase the stability, bioavailability, immunogenicity, and/or inhibitory action of the peptides of the invention.

While not wishing to be limited by any one theory, the constrained helical peptides are believed to derive their activity by interaction of the a–d face of the helix. The potent anti-HIV activity of the compounds of the invention derive from the gp41 633–678 region which corresponds to a putative alpha-helix region located in the C-terminal end of the gp41 ectodomain, and which appears to associate with a distal site on gp41 whose interactive structure is influenced by the leucine zipper motif, a coiled-coil structure, referred to as DP-107. The association of these two domains may reflect a molecular linkage or "molecular clasp" intimately involved in the fusion process (see FIGS. 18 and 19). The DP107 region forms a core trimer complex with a groove that recognizes and binds the a–d face of the helical peptides of the invention.

When synthesized as peptides both DP-107 and DP-178 are potent inhibitors of HIV infection and fusion, probably by virtue of their ability to form complexes with viral gp41 and interfere with its fusogenic process; e.g., during the structural transition of the viral protein from the native structure to the fusogenic state, the DP-107 and DP-178 peptides may gain access to their respective binding sites on the viral gp41, and exert a disruptive influence.

Consequently, when more than one constrained helical peptide is present, as part of a super helix or extended helix polypeptide backbone, the positions a and d of a first constrained helical peptide are in the same plane as positions a and d of the second constrained helical peptide. In other words, the a–d face of the two helices are aligned in the same plane. To achieve this orientation when the helices are in a polypeptide super helix, the first and second constrained helical peptides are separated by either 5 to 7, 12 to 14 or 19 to 21 natural or unnatural helix-forming amino acids. Preferably, the first and second constrained helical peptides are separated by either 6, 13, or 20 natural or unnatural helix-forming amino acids. A most preferred spatial alignment of the first, second, and any additional constrained helical peptides is that found in DP107, wherein the a–d faces are aligned in the same plane to allow interaction with the grove in the core trimer.

When the particularly preferred tethering chemistry as taught herein is used, the compounds of the invention are selected from the group consisting of: the compound represented by Formula (1):

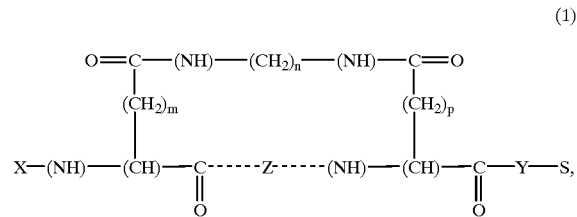

wherein

S is absent or is a macromolecule,

X is hydrogen or is any amino acid or amino acid sequence,

Y is absent, or is hydroxyl if S is absent, or is any amino acid or amino acid sequence, Z is an amino acid sequence consisting of six amino acids, wherein the internal sequence of six amino acids has the form gabcde, defgab, or cdefga and is selected from the group of sequences consisting of a sequence of six contiguous amino acids in HIV-1LAI strain gp41 amino acid sequence 633 to 678, in its homolog sequence from another HIV strain, in a consensus sequence of its homolog sequences from any one HIV clade, or amino acid substituted variant thereof, in which amino acid 633 or its corresponding amino acid in the homolog, consensus or variant sequence is assigned position a of a repeating abcdefg assignment;

m and p are independently selected from the integers 0 to 6 inclusive, provided that m+p is less than or equal to 6, and n is any integer in the range defined by (7−(m+p)) to (9−(m+p)) inclusive, provided that n is greater than 1;

the compound represented by Formula (6):

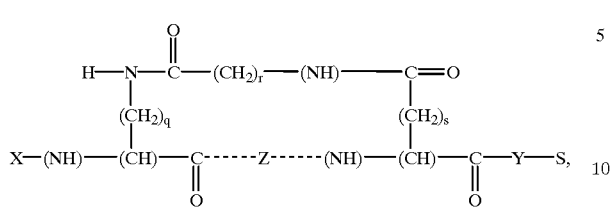

(6)

wherein S is absent or is a macromolecule, X is hydrogen or is any amino acid or amino acid sequence, Y is absent, or is hydroxyl if S is absent, or is any amino acid or amino acid sequence, Z is an amino acid sequence consisting of six amino acids, wherein the internal sequence of six amino acids has the form gabcde, defgab, or cdefga and is selected from the group of sequences consisting of a sequence of six contiguous amino acids in HIV-1LAI strain gp41 amino acid sequence 633 to 678, in its homolog sequence from another HIV strain, in a consensus sequence of its homolog sequences from any one HIV clade, or amino acid substituted variant thereof, in which amino acid 633 or its corresponding amino acid in the homolog, consensus or variant sequence is assigned position a of a repeating abcdefg; q is selected from the integers 1 to 7 inclusive, s is selected from the integers 0 to 6 inclusive, provided that q+s is less than or equal to 7, and r is any integer in the range defined by (7−(q+s)) to (9−(q+s)) inclusive, provided that r is greater than 0;

the compound represented by Formula (11):

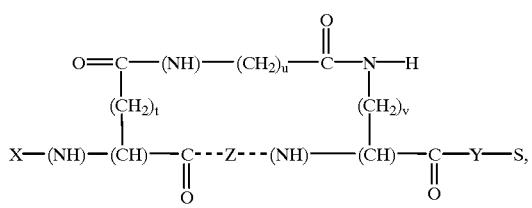

(11)

wherein S is absent or is a macromolecule, X is hydrogen or is any amino acid or amino acid sequence, Y is absent, or is hydroxyl if S is absent, or is any amino acid or amino acid sequence, Z is an amino acid sequence consisting of six amino acids, wherein the internal sequence of six amino acids has the form gabcde, defgab, or cdefga and is selected from the group of sequences consisting of a sequence of six contiguous amino acids in HIV-1LAI strain gp41 amino acid sequence 633 to 678, in its homolog sequence from another HIV strain, in a consensus sequence of its homolog sequences from any one HIV clade, or amino acid substituted variant thereof, in which amino acid 633 or its corresponding amino acid in the homolog, consensus or variant sequence is assigned position a of a repeating abcdefg assignment; t is selected from the integers 0 to 6 inclusive, and v is selected from the integers 1 to 7 inclusive, provided that t+v is less than or equal to 7; and u is any integer in the range defined by (7−(t+v))to (9−(t+v)) inclusive, provided that u is greater than 0; and the compound represented by Formula (16):

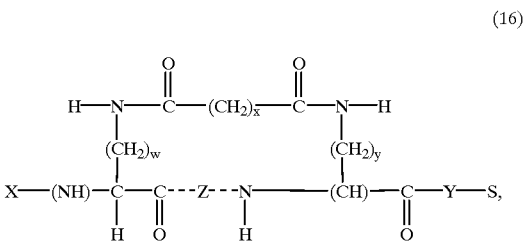

(16)

wherein S is absent or is a macromolecule, X is hydrogen or is any amino acid or amino acid sequence, Y is absent, or is hydroxyl if S is absent, or is any amino acid or amino acid sequence, Z is an amino acid sequence consisting of six amino acids, wherein the internal sequence of six amino acids has the form gabcde, defgab, or cdefga and is selected from the group of sequences consisting of a sequence of six contiguous amino acids in HIV-1LAI strain gp41 amino acid sequence 633 to 678, in its homolog sequence from another HIV strain, in a consensus sequence of its homolog sequences from any one HIV clade, or amino acid substituted variant thereof, in which amino acid 633 or its corresponding amino acid in the homolog, consensus or variant sequence is assigned position a of a repeating abedefg assignment; w and y are independently selected from the integers 1 to 7 inclusive, provided that w+y is less than or equal to 8, and x is any integer in the range defined by (7−(w+y)) to (9−(w+y)) inclusive, provided that x is greater than or equal to 0.

These compounds can further contain S' when S is absent and X is any amino acid or amino acid sequence, wherein S' is a macromolecule attached to X. The X or Y can contain a blocking group that prevents enzymatic degradation. Standard terminal blacking groups as known in the art are suitable. X or Y can also contain a D-amino acid or a non-amide bond between adjacent amino acids to prevent enzymatic degradation.

The compounds can be formulated with a carrier as taught herein. When the helical peptide is to be used as a hapten the carrier can be an adjuvant Typically, compositions of the invention are sterile. Compositions can contain at least two compounds of the invention, ether free or covalently or ionically attached to one another. The peptides of the invention that have a virus fusion inhibitor activity, can be used in combination with other the therapeutic agents, preferably in combination with another antiviral agent, to enhance its antiviral effect. Such antiviral agents include but are not limited to those which function on a different target molecule involved in viral replication, e.g., reverse transcriptase inhibitors, viral protease inhibitors, glycosylation inhibitors; those which act on a different target molecule involved in viral transmission; those which act on a different loci of the same molecule; and those which prevent or reduce the occurrence of viral resistance.

In treating mammals, including humans, having a viral infection, a the therapeutically effective amount of the compounds of the invention, or a pharmaceutically acceptable derivative, is administered is a dose sufficient to inhibit viral replication, either alone or in combination with other virus inhibiting drugs. For example HIV31 or HIV 24 can be administered as an infusion at about 0.1 mg/kg to 1.0 mg/kg per day for about 12 weeks. A preferable dose is from 20 mg to 35 mg. Doses can be administered in intervals of from about once per day to 4 times per day and preferably from about once every two days to once per day. A preferred dose is administered to achieve peak plasma concentrations of compound of from about 1 mg/ml to 10 mg/ml. This may be achieved by the sterile injection of about a 2.0% solution of the administered ingredients in buffered saline (any suitable saline solutions known to those skilled in the art of chemistry may be used). Desirable blood levels may be maintained by a continuous infusion as ascertained by plasma levels measured by HPLC. Pharmaceutical compositions containing the compounds of the invention can be administered to a human patient, by itself, or in pharmaceutical compositions where it is mixed with suitable carriers or excipient(s), as taught herein, at doses to treat a viral infection, in particular HIV infection. Suitable routes of administration include oral, rectal, transmucosal, or intestinal administration; parenteral delivery, including intramuscular, subcutaneous, intramedullary injections, as well as intrathecal, direct intraventricular, intravenous, intraperitoneal, intranasal, or intraocular injections; transdermal, topical, vaginal and the like. Dosage forms include but are not limited to tablets, troches, dispersions, suspensions, suppositories, solutions, capsules, creams, patches, minipumps and the like.

As discussed herein the compounds of the invention are particularly suited as haptens to raise an antibody that binds to the compound, preferably the antibody specifically binds an epitope comprising an amino acid at position a, d, e, or g in the helical peptide. Preferred antibodies are monoclonal. Antibodies of the invention, not only recognize the peptides of the invention, but preferably recognize the corresponding sequence when present in the virus. They may also bind unconstrained DP178. More preferably, the antibody neutralize HIV viral infectivity and/or neutralizes HIV virus membrane fusion. Thus the antibodies can recognize and bind gp41 sequence.

In another embodiment is provided a method to immunize an animal, comprising administering to the animal an immunogenic amount of a compound of the invention.

In yet another embodiment is provided a method to prophylactically or therapeutically treat a mammal at risk for or infected with HIV, comprising administering a composition comprising a prophylacticall y or therapeutically effective amount of a compound of the invention and a carrier. While antibodies of the invention are expected to have broad viral activity, preferably, the composition comprises internal six amino acid sequences from different HIV strains or HIV clades. The compositions include a vaccine formulation. The formulations can contain one or more (multivalent) constrained helical peptides form different HIV strains, for use as a vaccine or immunogen. The composition can be administered, prophylactically or therapeutically, to a patient at risk of infection or in need of such treatment using the dosages and routes and means of administration that are readily determined. However, chronic administration may be preferred and dosages can be adjusted accordingly.

Administration of the compounds containing the constrained helical peptides of the invention as a prophylactic vaccine (or therapeutic vaccine), can comprise administering to a host a concentration of peptides effective in raising an immune response which is sufficient to neutralize HIV, by, for example, inhibiting HIV ability to infect cells. The exact concentration will depend upon the specific peptide to be administered, but may be determined by using standard techniques for assaying the development of an immune response which are well known to those of ordinary skill in the art. The peptides to be used as vaccines are usually administered intramuscularly. The peptides may be formulated with a suitable adjuvant in order to enhance the immunological response. Such adjuvants may include, but are not limited to, mineral gels such as aluminum hydroxide; surface active substances such as lysolecithin, pluronic polyols, polyanions; other peptides; oil emulsions; and potentially useful human adjuvants such as BCG and Corynebacterium parvum. Many methods may be used to introduce the vaccine formulations described here. These methods include but are not limited to oral, intradermal, intramuscular, intraperitoneal, intravenous, subcutaneous, and intranasal routes.

A compound of this invention in a suitable carrier or excipient is used to make a vaccine. The polypeptide can be used alone, but is preferably administered in a multivalent subunit vaccine that includes internal sequences from MN strain. The vaccine usually includes constrained helices representing 3 to about 5 different strains, but 30 or more different gp41-based constrained helical polypeptides can be used to provide a more effective vaccine. Of particular interest are gp41 sequences from breakthrough isolates of HIV vaccine trials. Use of a homolog gp41 sequence from one or more of breakthrough isolates in a subunit vaccine, usually together a sequence from a commonly present isolate like the MN sequence, can provide protection against HIV strains that are sufficiently different from the common strain (e.g., MN) that the typical single subunit vaccine does not confer protection against those strains.

Preparation of polypeptides for use in a vaccine is well known. The compound with the desired degree of purity and at a sufficient concentration to induce antibody formation is mixed with a physiologically acceptable carrier. A physiologically acceptable carrier is nontoxic to a recipient at the dosage and concentration employed in the vaccine. Generally, the vaccine is formulated for injection, usually intramuscular or subcutaneous injection. Suitable carriers for injection include sterile water, but preferably are physiologic salt solutions, such as normal saline or buffered salt solutions such as phosphate-buffered saline or ringer's lactate. The vaccine generally contains an adjuvant. Useful adjuvants include QS21 (Quillaja saponaria, commercially available from Cambridge Biotech, Worcester, Mass.), which stimulates cytotoxic T-cells, and alum (aluminum hydroxide adjuvant). Formulations with different adjuvants which enhance cellular a local immunity can also be used.

Additional excipients that can be present in the vaccine include low molecular weight polypeptides (less than about 10 residues), proteins, amino acids, carbohydrates including glucose or dextrans, chelating agents such as EDTA, and other excipients that stabilize the protein or inhibit growth of microorganisms.

The vaccine can also contain other HIV proteins. In particular, gp120, or the extracellular portion of gp41 or HIV-1 core proteins such as P24, P17, and P55 can be present in the vaccine. Preferably, any gp120 present in the vaccine is from an HIV isolate sequence represented in a constrained helical peptide present in the vaccine.

Vaccine formulations generally include a total of about 10 to 5,000 ug of compound, more preferably about 10 to 1000 ug, even more preferably about 300 to 600 $\mu$g, conveniently in about 1.0 ml to 1.5 ml of carrier. The amount of compound representing any one isolate or clade present in the vaccine will vary depending on the immunogenicity of the compound. For example, a constrained helical peptide with sequence from some strains of HIV may be less immunogenic than those from the MN strain. If peptides representing two strains having different immunogenicity are used in combination, empirical titration of the amount each virus would be performed to determine the percent of the peptide of each strain in the vaccine. For isolates having similar immunogenicity, approximately equal amounts of each isolate's peptide would be present in the vaccine. Methods of determining the relative amount of an immunogenic protein in multivalent vaccines are well known and have been used, for example, to determine relative proportions of various isolates in multivalent polio vaccines.

The vaccines are generally administered at 0, 1, and at 6, 8 or 12 months, depending on the protocol. A preferred protocol includes administration at 0, 1, 6, and 12 months. Following the immunization procedure, annual or bi-annual boosts can be administered. However, during the immunization process and thereafter, neutralizing antibody levels can be assayed and the protocol adjusted accordingly.

The vaccine is administered to uninfected individuals. In addition, the vaccine can be administered to seropositive individuals to augment immune response to the virus.

Although the compounds described herein can be used as a vaccine as described above, the compound can also be used alone or in combinations in the same type of formulation, for use as an immunogen, to induce antibodies that recognize the isolate(s) present in the immunogen. Immunogens are formulated in the same manner as vaccines and can include the same excipients, etc. Antibodies induced by the immunogens can be used in a diagnostic to detect the HIV strain in patient sera or body fluid samples, or to affinity purify the particular gp41 molecule or virus. The compounds also find use in diagnostic assays to detect the presence of antibodies in HIV in sera from individuals suspected of being infected.

In a further embodiment, the locked helix peptides of the invention are used to create constrained combinatorial peptide libraries. Combinatorial peptide libraries are uniquely suited to incorporate constrained peptides. The libraries are constructed with a "split synthesis" method in which a solid support (e.g. beads) is aliquoted equally and a different amino acid is coupled separately to each portion. The portions are pooled, resplit and the process is repeated. In the "peptides-on-beads" technique, this process yields a mixture of beads, each of which is coupled to a peptide of unique sequence. The bead mixture can be used directly in a binding selection, with binding detected colorimetrically and positive beads physically removed from the mixture for microsequencing (Clackson and Wells, *Tibtech*, 2: 173–184 (1994)). To produce a library of peptides containing a random sequence of six (or more) amino acids locked into a helical conformation by I and I+7 residues according to the invention, the split synthesis technique is modified to place I and I+7 residues in set positions separated by six residues in each random amino acid sequence, and the peptides are cyclized by linking the side chain amide bond-forming substituents of the I and I+7 residues in each peptide using any of the methods described in Section II below.

Combinatorial libraries containing the constrained peptides of the invention are a particularly powerful tool for identification of high affinity ligands in drug design. Given the prevalence of the α-helical motif in active sites of binding proteins, including DNA binding proteins, and the absence of amino acid sequence constraints in the invention's tethering system, the locked helix peptides of the invention greatly increase the utility of combinatorial peptide libraries in screening methods for specific binding activities, such as the methods of U.S. Pat. No. 5,306,619 used to screen for DNA sequence-specific binding molecules.

II. Methods for Constructing Synthetic Locked Helix Peptides

According to the present method, an element of α-helical structure is removed from its context in a native protein by constructing a peptide with an amino acid sequence spanning the α-helical secondary structure of interest in the native protein, and constraining the short peptide into an α-helical conformation that mimics the α-helical secondary structure of interest. The present methods enable the practitioner to lock into a helical conformation any peptide that is six amino acids in length by placing an amino acid with a side chain amide bond-forming substitutent at the N-terminus of the peptide and placing another amino acid with a side chain amide bond-forming substitutent at the C-terminus of the peptide, and then joining the side chain amide bond-forming substituents of the N-terminal and C-terminal residues to form a cyclized structure which mimics the conformation of an α-helix. The present methods also enable the practitioner to lock into a helical conformation any sequence of six amino acid residues in a larger peptide by importing two residues with side chain amide bond-forming substituents into the N-terminal amino acid position and the C-terminal position amino acid position flanking the sequence (of six amino acid residues) of interest within a larger peptide, and then joining the side chain amide bond-forming substituents of the N-terminal and C-terminal flanking residues to form a cyclized structure which mimics the conformation of an α-helix.

There are at least two general methods for constructing the constrained helix peptides of the invention: (1) synthesis of a linear peptide comprising a pair of residues that flank an amino acid sequence that is six residues in length, wherein the two flanking residues are independently selected from the group consisting of amino acid residues with side chain amide bond-forming substituents, followed by bridging the side chain amide bond-forming substituents of the flanking residues with a difunctional linker to cyclize the peptide; and (2) synthesis of a linear peptide comprising a pair of residues that flank an amino acid sequence that is six residues in length, wherein the two flanking residues are independently selected from the group consisting of amino acid residues with side chain amide bond-forming substituents, and wherein one of the flanking residues is added to the peptide chain carrying a difunctional linker such that one functional group of the linker is coupled to the residue's side chain amide bond-forming substituent, followed by coupling of the linker's free functional group to the side chain amide bond-forming substitutent on the other flanking residue to cyclize the peptide.

Any amino acid that has a side chain containing a substitutent capable of forming an amide bond can be used as a flanking residue herein. Suitable flanking amino acid residues include amino acids with side chains carrying a free carboxy group, such as aminopropanedioic acid, Asp, Glu, 2-amninohexanedioic acid, and 2-aminoheptanedioic acid, and amino acids with side chains carrying a free amino group, such as 2,3-diaminopropanoicacid (2,3-diaminopropionicacid), 2,4-diaminobutanoicacid (2,4-diaminobutyricacid), 2,5-diaminopentanoic acid, and Lys.

(1) Synthesis of Linear Peptide without Difunctional Linker-Coupled Flanking Amino Acid a. Peptide Synthesis The desired peptide sequence is designed such that the sequence of six amino acid residues to be helicized extends between two flanking residues independently selected from the group consisting of amino acid residues with side chain amide bond-forming substituents. In one embodiment, the side chain amide bond-forming substituents of the N-terminal and C-terminal flanking residues are independently selected from the group consisting of a carboxy substitutent and an amino substitutent. In another embodiment, the side chain amide bond-forming substituents of the N-terminal and C-terminal flanking residues are both carboxy substituents. In yet another embodiment, the side chain amide bond-forming substitutent of one of the flanking residues is a carboxy substitutent and the side chain amide bond-forming substitutent of the other flanking residue is an amino substitutent. In still another embodiment, the side chain amide bond-forming substituents of the flanking residues are both amino substituents. In yet another embodiment, the flanking residues are independently selected from the group consisting of aminopropanedioic acid, Asp, Glu, 2-aminohexanedioicacid, 2-aminoheptanedioic acid, 2-aminooctanedioic acid, 2-aminononanedioic acid, 2,3-diaminopropanoic acid, 2,4-diaminobutanoicacid, 2,5-diaminopentanoicacid, Lys, 2,7-diaminoheptanoicacid, 2,8-diaminooctanoic acid, and 2,9-diaminononanoic acid.

In some embodiments, the desired peptide contains an additional amino acid or amino acids extending from the C-terminal flanking residue and/or N-terminal flanking residue.

Once the desired peptide sequence is selected, chemical synthesis can be employed to construct the constrained helix peptide of the invention. This can be accomplished by modifying any one of a number of methodolgies well known in the art (see Kelley, R. F. & Winkler, M. E. in *Genetic Engineering Principles and Methods*, Setlow, J. K, ed., Plenum Press, N.Y., vol. 12, pp 1–19 (1990), Stewart, J. M. Young, J. D., *Solid Phase Peptide Synthesis*, Pierce Chemical Co., Rockford, Ill. (1984); see also U.S. Pat. Nos. 4,105,603; 3,972,859; 3,842,067; and 3,862,925) to produce a the desired peptide.

Peptides of the invention can be conveniently prepared using solid phase peptide synthesis (Merrifield *J. Am. Chem. Soc.*, 85: 2149 (1964); Houghten, *Proc. Natl. Acad. Sci. USA*, 82: 5132 (1985). Solid phase synthesis begins at the carboxy terminus of the putative peptide by coupling a protected amino acid to an inert solid support. The inert solid support can be any macromolecule capable of serving as an anchor for the C-terminus of the initial amino acid. Typically, the macromolecular support is a cross-linked polymeric resin (e.g. a polyamide or polystyrene resin) as shown in FIGS. 1-1 and 1-2, on pages 2 and 4 of Stewart and Young, supra. In one embodiment, the C-terminal amino acid is coupled to a polystyrene resin to form a benzyl ester. A macromolecular support is selected such that the peptide anchor link is stable under the conditions used to deprotect the α-amino group of the blocked amino acids in peptide synthesis. If an base-labile α-protecting group is used, then it is desirable to use an acid-labile link between the peptide and the solid support. For example, an acid-labile ether resin is effective for base-labile Fmoc-amino acid peptide synthesis as described on page 16 of Stewart and Young, supra. Alternatively, a peptide anchor link and α-protecting group that are differentially labile to acidolysis can be used. For example, an aminomethyl resin such as the phenylacetamidomethyl (Pam) resin works well in conjunction with Boc-amino acid peptide synthesis as described on pages 11–12 of Stewart and Young, supra.

After the initial amino acid is coupled to an inert solid support, the α-amino protecting group of the initial amino acid is removed with, for example, trifluoroacetic acid (TFA) in methylene chloride and neutralizing in, for example, triethylamine (TEA). Following deprotection of the initial amino acid's α-amino group, the next α-amino and side chain protected amino acid in the synthesis is added. The remaining α-amino protected and, if necessary, side chain protected amino acids are then coupled sequentially in the desired order by condensation to obtain an intermediate compound connected to the solid support. Alternatively, some amino acids may be coupled to one another to form a fragment of the desired peptide followed by addition of the peptide fragment to the growing solid phase peptide chain.

The condensation reaction between two amino acids, or an amino acid and a peptide, or a peptide and a peptide an be carried out according to the usual condensation methods such as the axide method, mixed acid anhydride method, DCC (N,N'-dicyclohexylcarbodiimide) or DIC (N,N'-diisopropylcarbodiimide) methods, active ester method, p-nitrophenyl ester method, BOP (benzotriazole-1-yl-oxy-tris[dimethylamino] phosphonium hexafluorophosphate) method, N-hydroxysuccinicacid imido ester method, etc, and Woodward reagent K method.

It is common in the chemical syntheses of peptides to protect any reactive side-chain groups of the amino acid with suitable protecting groups. Ultimately, these protecting groups are removed after the desired polypeptide chain has been sequentially assembled. Also common is the protection of the α-amino group on an amino acid or a fragment while that entity reacts at the carboxy group followed by the selective removal of the α-amino protecting group to allow subsequent reaction to take place at that location. Accordingly, it is common in polypeptide synthesis that an intermediate compound is produced which contains each of the amino acid residues located in the desired sequence in the peptide chain with various of these residues having side chain protecting groups attached. These protecting groups are then commonly removed at substantially the same time so as to produce the desired product following cleavage from the resin. Protecting groups and procedure for their use in peptide synthesis are reviewed in *Protective Groups in Organic Synthesis*, 2d ed., Greene, T. W. and Wuts, P. G. M., Wiley & Sons (New York: 1991).

Suitable protecting groups for α-amino and side chain amino groups are exemplified by benzyloxycarbonyl (abbreviated Z), isonicotinyloxycarbonyl (iNOC), o-chlorobenzyloxycarbonyl [Z(2Cl)], p-nitrobezyloxycarbonyl [Z(NO$_2$)], p-methoxybenzyloxycarbonyl [Z(OMe)], t-butoxycarbonyl (Boc), t-amyloxycarbonyl(Aoc), isobornyloxycarbonyl, adamantyloxycarbonyl, 2-(4-biphenyl)-2-propyloxycarbonyl (Bpoc), 9-fluorenylmethoxycarbonyl (Fmoc), methylsulfonyethoxycarbonyl (Msc), trifluoroacetyl, phthalyl, formyl, 2-nitrophenylsulfenyl (NPS), diphenylphosphinothioyl (Ppt), and dimethylphosphinothioyl (Mpt) groups, and the like.

Protective groups for the carboxy functional group are exemplified by benzyl ester, (Obz), cyclohexyl ester (Chx), 4-nitrobenzyl ester (Onb), t-butyl ester (Obut), 4-pyridylmethyl ester (Opic), and the like. It is often desirable that amino acids such as arginine, cysteine, and serine possessing a functional group other than amino an carboxy groups be protected by a suitable protecting group. For example, the guanidino group of arginine may be protected with nitro, p-toluenesulfonyl, benzyloxycarbonyl, adamantyloxycarbonyl, p-methoxybenzenesulfonyl, 4-methoxy-2, 6-dimethylbenzenesulfonyl (Nds), 1,3,5-trimethylphenysulfonyl (Mts), and the like. The thiol group of cysteine can be protected with p-methoxybenzyl, trityl, and the like.

In one embodiment, the peptides of the invention are synthesized with the help of blocking groups that protect the side chain amide bond-forming substituents of the N-terminal and C-terminal flanking residues. The protecting group or groups used for the side chain amide bond-forming substituents of the N-terminal and C-terminal flanking residues can be the same or different than the protecting group or groups used to block the side chain functional groups of other residues in the peptide. In a preferred embodiment, the protecting group or groups used to block the side chain amide bond-forming substituents is (are) differentially removable with respect to the protecting groups used for other side chain functional groups in the peptide, i.e. the side chain amide bond-forming substituents can be deprotected without deprotecting the other side chain functional groups in the peptide, in addition to being differentially removable with respect to the α-amino protecting group used in peptide synthesis. In another preferred embodiment, the side chain amide bond-forming substituents of the flanking residues are orthogonally protected with respect to each other such that the side chain amide bond-forming substituent of one flanking residue can be deprotected without deprotecting the side chain amide bond-forming substituent of the other flanking residue.

Suitable protecting groups for use in orthogonally protecting the side chain amide bond-forming substituents of the flanking residues with respect to other functional groups and/or with respect to each other include pairs of differentially removable carboxy protective groups, such as a reduction-labile carboxy protective group, e.g. allyl or benzyl esters, paired with a base-labile carboxy protective group, e.g. fluorenylmethylesters, methyl or other primary alkyl esters. Fluorenylmethyl, methyl or other primary alkyl groups or other base-labile carboxy protective groups can be removed from their corresponding esters to yield a free carboxy group (without deprotecting allyl or benzyl esters or other reduction-labile esters) by saponification of the esters with a suitable base such as piperidine and sodium hydroxide in a suitable solvent such as dimethylacetamide, or methanol and water, for a period of 10 to 120 minutes, and preferably 20 minutes, 0 to 50° C. The allyl or benzyl or other reduction-labile esters can be removed when desired by reduction in the presence of a suitable transition metal catalyst, such as $Pd(PPh_3)_4$, $Pd(PPh_3)_2Cl_2$, $Pd(OAc)_2$ or Pd on carbon with a source of hydrogen, e.g. $H_2$ gas, in a suitable solvent such as dimethylacetamide, dimethylformamide, N-methylpyrrolidinoneor methanol for a period of 10 to 500 minutes, and preferably 100 minutes, at 0 to 50° C. For the sake of simplicity and convenience, all carboxy protective groups that are removable by Pd-catalyzed methods which result in the reduction of the protected carboxy substitutent are included n the term "reduction-labile protective groups" as used herein, even though such Pd-catalyzed deprotection methods may not result in the reduction of the protective group in question.

In embodiments wherein Pd catalysis involves the formation of intermediates of Pd derivatized with reduction-labile protecting groups, e.g. Pd-allyl derivatives, the Pd catalyst can be restored by reaction with a suitable nucleophile, such as piperidine or tributyltin hydride. When such reduction-labile groups are used to provide orthogonal protection in combination with base-labile protecting groups, it is preferable to either (1) utilize a synthetic scheme that calls for the removal of the base-labile protecting groups before the removal of the reduction-labile protecting groups or (2) restore the Pd catalyst with a nucleophile that does not deprotect the base-labile protecting groups.

Alternatively, the carboxy substituents of the flanking residues can be orthogonally protected with respect the other functional groups and/or with respect to each other by using an acid-labile protecting group, such as a tertiary alkyl ester, e.g. t-butyl ester, in combination with a reduction-labile protecting group, such as the allyl or benzyl esters described above. The tertiary alkyl or other acid-labile ester group can be removed by acidolysis, e.g. with trifluoroacetic acid in methylene chloride, and the allyl or benzyl or other reduction-labile esters can be removed by reduction in the presence of a transition metal catalyst as described above.

In another embodiment, the carboxy substituents of the flanking residues can be orthogonally protected with respect to other functional groups and/or with respect to each other by using a fluoride ion-labile protecting group, such as 2-(trimethylsilyl)ethyl and silyl esters, in combination with a reduction-labile protecting group, such as the allyl or benzyl esters described above, or in combination with a base-labile protecting group, such as the fluorenylmethyl, methyl or other primary alkyl esters described above, without deprotecing the reduction-labile or base-labile esters. The 2-(trimethylsilyl)ethyl, silyl or other fluoride-labile ester group can be removed by reaction with a suitable fluoride ion source, such as tetrabutylammonium fluoride in the presence of a suitable solvent, such as dimethylacetamide(DMA), dimethylformamide (DMF), tetrahydrofuran (THF), or acetonitrile.

Suitable protecting groups for use in orthogonally protecting the side chain amide bond-forming substituents of the flanking residues with respect to other functional groups and/or with respect to each other also include pairs of differentially removable amino protective groups, such as an allyloxycarbonyl or other reduction-labile amino protective group paired with a t-butoxycarbonyl (Boc) or other acid-labile amino protective group, and a reduction-labile amino protective group paired with a fluorenylmethoxycarbonyl (Fmoc) or other base-labile amino protective group. An allyloxycarbonyl (or other reduction-labile blocking group) protected amino group can be deprotected by reduction using a transition metal catalyst as in the procedure for removing reduction-labile carboxy protective groups described above, without deprotecting a Boc or Fmoc protected amino group. Likewise, an acid-labile amino protective group and a base-labile amino protective group can be removed by acidolysis and base saponification, respectively, without removing a reduction-labile amino protective group. For the sake of simplicity and convenience, all amino protective groups that it are removable by Pd-catalyzed methods which result in the reduction of the protected amino substitutent are included in the term "reduction-labile protective groups" as used herein, even though such Pd-catalyzed deprotection methods may not result in the reduction of the protective group in question.

In another embodiment, the amino substituents of the flanking residues can be orthogonally protected with respect to other functional groups and/or with respect to each other by using a fluoride-labile protecting group, such as 2-trimethylsilylethylcarbamate(Teoc), in combination with a reduction-labile protecting group, such as allyloxylcarbonyl, or in combination with a base-labile protecting group, such as fluorenylmethoxycarbonyl, as described above. The Teoc or other fluoride-labile group can be removed by reaction a with a suitable fluoride ion source, such as tetrabutylammonium fluoride, as in the procedures for removal of fluoride-labile carboxy protective groups described above, without deprotecting an allyloxycarbonyl or fluorenylmethoxycarbonyl protected amino group. Likewise, a reduction-labile amino protective group and a base-labile amino protective group can be removed by reduction and base saponification, respectively, without removing a fluoride-labile amino protective group.

In embodiments that use a carboxy substituent as the side chain amide bond-forming substituent of one flanking residue and that use an amino substituent as the side chain amide bond-forming substituent of the other flanking residue, the carboxy substituent and the amino substituent can be orthogonally protected with respect to each other by using a reduction-labile protecting group to block one substituent, e.g. allyl ester or allyloxycarbonyl, and a fluoride-labile, acid-labile or base-labile protecting group to block other substituent, e.g. silyl ester, t-butyl ester, fluorenylmethyl ester, Teoc, Boc, or Fmoc.

In a preferred embodiment, a reduction-labile protecting group is used to block the side chain amide bond-forming substituent of one flanking residue and the protecting group for the side chain amide bond-forming substituent of the other flanking residue is selected such that it provides orthogonal protection with respect to both the reduction-labile protecting group and the α-amino protecting group used in peptide synthesis. For example, in an embodiment using Fmoc chemistry for peptide synthesis, orthogonal protection of the side chain amide bond-forming substituents would be provided by a reduction-labile protecting group and an acid-labile protecting group. Likewise, in an embodiment using Boc chemistry for peptide synthesis, orthogonal protection of the side chain amide bond-forming substituents would be provided by a reduction-labile protecting group and a base-labile protecting group.

In yet another preferred embodiment, the side chain amide bond-forming substituents of the flanking residues are orthogonally protected with respect to each other, with respect to α-amino protecting group used in peptide synthesis, and with respect to the protecting groups used to block other side chain functional groups in the peptide chain.

In still another preferred embodiment, the side chain amide bond-forming substituents of the flanking residues are orthogonally protected with respect to each other, and with respect to α-amino protecting group used in peptide synthesis, but only one of the side chain amide bond-forming substituents is orthogonally protected with respect to the protecting groups used to block other side chain functional groups in the peptide chain. In this embodiment, it is preferable to use the side chain amide bond-forming substituent with fully orthogonal protection as the target for initial coupling of the peptide to the difunctional linker. Since the side chain amide bond-forming substituent with fully orthogonal protection can be deprotected without deprotecting other functional groups, the coupling reaction will be specific to the desired side chain amide bond-forming substituent, and will reduce the production of unwanted peptide/difunctional linker derivatives. Although cyclization will require the deprotection of the side chain amide bond-forming substituent of the other flanking residue, and may cause concomitant deprotection of other side chain functional groups, unwanted derivatives are less likely to form given that the peptide chains are anchored to a solid support and that the linker length will regioselectively favor a coupling reaction between the unbound functional group of the linker and the side chain amide bond-forming substituent of the other flanking residue. If further peptide chain synthesis is desired after cyclization, any side chain functional groups on other amino acid residues left unprotected by the cyclization reactions can be reprotected before chain synthesis is resumed.

Many of the blocked amino acids described above can be obtained from commercial sources such as Novabiochem (San Diego, Calif.), Bachem Calif. (Torrence, Calif.) or Peninsula Labs (Belmont, Calif.).

In addition, the methods of the invention can be practiced in conjunction with solution phase peptide synthesis, for example, the solution phase peptide synthesis methods described in *Principles of Peptide Synthesis,* 2d ed, M. Bodanszky, Springer-Verlag (1993) or in *The Practice of Peptide Synthesis,* 2d ed, M. Bodanszky and A. Bodanszky, Springer-Verlag (1994). It will be appreciated that solution phase peptide synthesis methods can be easily modified to incorporate the desired flanking residues, with or without orthogonally-protected side chain amide bond-forming substituents, into the peptide chain of interest, using procedures similar to those used in the solid phase peptide synthesis methods described herein. It will be further appreciated that all references to peptide synthesis herein encompass both solid phase and solution (or liquid) phase peptide synthesis methods, unless otherwise indicated.

b. Peptide Cyclization

After the desired amino acid sequence has been completed, the linear peptide is cyclized in order to constrain the peptide in a helical conformation. Any method of bridging the side chain amide bond-forming substituents of the flanking residues with a difunctional linker is suitable for producing the constrained helical peptides of the invention.

(i) Selection of Difunctional Linker

Typically, the difunctional linker suitable for use herein is capable of presenting two functional groups separated by a distance of or about 5 Å to or about 30 Å, and preferably of or about 8 Å to or about 14 Å, and more preferably of or about 10 Å, such that the side chain amide bond-forming substituent of one of the flanking residues can form an amide linkage with one or either of the functional groups of the linker and the side chain amide bond-forming substituent of the other flanking residue can form an amide linkage with the remaining functional group of the linker. It will be appreciated that the nature of the molecular scaffold used to present the desired functional groups in the proper spatial relationship is not critical to the practice of the invention. Although straight chain and branched alkyl scaffolds are suitable for use herein, the invention is not so limited. For example, alkenyl, alkynyl, cycloalkyl, or other aliphatic hydrocarbon species, with or without heteroatoms, and monophenyl, biphenyl, naphthyl, and other aromatic hydrocarbon species, with or without heteroatoms, that are substituted with the desired functional groups in the proper spatial relationship (e.g. para- or meta-substitutions in ring structures such as monophenyl, biphenyl, naphthyl and the like) can be used to link the side chain amide bond-forming substituents of the flanking residues.

The functional groups used in the difunctional linker are selected such that they are capable of forming amide linkages with the side chain amide bond-forming substituents of the flanking residues used in the peptide to be cyclized. In embodiments wherein the side chain amide bond-forming substituent of each flanking residue is a carboxy substituent, the peptide can be conveniently cyclized with a diamine linker. In one example, the flanking residues and the diamine linker are selected according to Table 1 below. It will be appreciated that each of the flanking residues and linker molecules listed in Table 1 below is considered to represent not only the particular molecule corresponding to the given chemical name under IUPAC rules, but also any variant of the molecule containing additional substituents or modified substituents which do not prevent or substantially alter the functioning of the amino and/or carboxy groups contained in the molecule, which functioning is necessary for use of the molecule in the methods of the invention. Accordingly, each molecule listed will be understood to encompasses variant molecules containing alkenyl, alkynyl and other unsaturated bonds, heteroatoms, cycloalkyl substituents, aromatic substituents, or other substituents in the carbon backbone of the molecule, and/or variants containing the foregoing or other substituents or groups in place of hydrogen atoms on the carbon backbone of the molecule.

TABLE 1

| Item No. | Flanking Residue #1 | Flanking Residue #2 | Diamine Linker |
|---|---|---|---|
| 1 | ammopropanedioic acid | aminopropanedioic acid | 1,7-diaminoheptane; 1,8-diaminooctane; 1,9-diaminononane |
| 2 | aminopropanedioic acid | aspartic acid | 1,6-diaminohexane; 1,7-diaminoheptane; 1,8-diaminooctane |
| 3 | aminopropanedioic acid | glutamic acid | 1,5-diaminopentane; 1,6-diaminohexane; 1,7-diaminoheptane, |
| 4 | aminopropanedioic acid | 2-aminohexanedioic acid | 1,4-diaminobutane; 1,5-diaminopentane; 1,6-diaminohexane |
| 5 | aminopropanedioic acid | 2-aminoheptanedioic acid | 1,3-diaminopropane; 1,4-diaminobutane; 1,5-diaminopentane |
| 6 | aminopropanedioic acid | 2-aminooctanedioic acid | 1,2-diaminoethane; 1,3-diaminopropane; 1,4-diaminobutane |
| 7 | aminopropanedioic acid | 2-aminononanedioic acid | 1,2-diaminoethane; 1,3-diaminopropane |
| 8 | aspartic acid | aspartic acid | 1,5-diaminopentane; 1,6-diaminohexane; 1,7-diaminoheptane |
| 9 | aspartic acid | glutamic acid | 1,4-diaminobutane; 1,5-diaminopentane; 1,6-diaminohexane |
| 10 | aspartic acid | 2-aminohexanedioic acid | 1,3-diaminopropane; 1,4-diaminobutane; 1,5-diaminopentane |
| 11 | aspartic acid | 2-aminoheptanedioic acid | 1,2-diaminoethane; 1,3-diaminopropane; 1,4-diaminobutane |
| 12 | aspartic acid | 2-aminooctanedioic acid | 1,2-diaminoethane; 1,3-diaminopropane; |
| 13 | glutamic acid | glutamic acid | 1,3-diaminopropane; 1,4-diaminobutane; 1,5-diaminopentane |
| 14 | glutamic acid | 2-aminohexanedioic acid | 1,2-diaminoethane; 1,3-diaminopropane; 1,4-diaminobutane |
| 15 | glutamic acid | 2-aminoheptanedioic acid | 1,2-diaminoethane; 1,3-diaminopropane |
| 16 | 2-aminohexanedioic acid | 2-aminohexanedioic acid | 1,2-diaminoethane; 1,3-diaminopropane |

In embodiments wherein the side chain amide bond-forming substituent of each flanking residue is an amino substituent, the peptide can be conveniently cyclized with a dicarboxylic acid linker. In one example, the flanking residues and the dicarboxylic acid linker are selected according to Table 2 below. It will be appreciated that each of the flanking residues and linker molecules listed in Table 2 below is considered to represent not only the particular molecule corresponding to the given chemical name under IUPAC rules, but also any variant of the molecule containing additional substituents or modified substituents which do not prevent or substantially alter the functioning of the amino and/or carboxy groups contained in the molecule, which functioning is necessary for use of the molecule in the methods of the invention. Accordingly, each molecule listed will be understood to encompasses variant molecules containing alkenyl, alkynyl and other unsaturated bonds, heteroatoms, cycloalkyl substituents, aromatic substituents, or other substituents in the carbon backbone of the molecule, and/or variants containing the foregoing or other substituents or groups in place of hydrogen atoms on the carbon backbone of the molecule.

TABLE 2

| Item No | Flanking Residue #1 | Flanking Residue #2 | Dicarboxylic acid Linker |
|---|---|---|---|
| 1 | 2,3-diaminopropanoic acid | 2,3-diaminopropanoic acid | heptanedioic acid; octanedioic acid; nonanedioic acid |
| 2 | 2,3-diaminopropanoic acid | 2,4-diaminobutanoic acid | hexanedioic acid; heptanedioic acid; octanedioic acid |
| 3 | 2,3-diaminopropanoic acid | 2,5-diaminopentanoic acid | pentanedioic acid; hexanedioic acid; heptanedioic acid |
| 4 | 2,3-diaminopropanoic acid | lysine | butanedioic acid; pentanedioic acid; hexanedioic acid |
| 5 | 2,3-diaminopropanoic acid | 2,7-diaminoheptanoic acid | propanedioic acid; butanedioic acid; pentanedioic acid |
| 6 | 2,3-diaminopropanoic acid | 2,8-diaminooctanoic acid | ethanedioic acid; propanedioic acid; butanedioic acid |
| 7 | 2,3-diaminopropanoic acid | 2,9-diaminononanoic acid | ethanedioic acid; propanedioic acid |
| 8 | 2,4-diaminobutanoic acid | 2,4-diaminobutanoic acid | pentanedioic acid; hexanedioic acid; heptanedioic acid |
| 9 | 2,4-diaminobutanoic acid | 2,5-diaminopentanoic acid | butanedioic acid; pentanedioic acid; hexanedioic acid |
| 10 | 2,4-diaminobutanoic acid | lysine | propanedioic acid; butanedioic acid; pentanedioic acid |
| 11 | 2,4-diaminobutanoic acid | 2,7-diaminoheptanoic acid | ethanedioic acid; propanedioic acid; butanedioic acid |
| 12 | 2,4-diaminobutanoic acid | 2,8-diaminooctanoic acid | ethanedioic acid; propanedioic acid |
| 13 | 2,5-diaminopentanoic acid | 2,5-diaminopentanoic acid | propanedioic acid; butanedioic acid; pentanedioic acid |
| 14 | 2,5-diaminopentanoic acid | lysine | ethanedioic acid; propanedioic acid; butanedioic acid; |
| 15 | 2,5-diaminopentanoic acid | 2,7-diaminoheptanoic acid | ethanedioic acid; propanedioic acid; |
| 16 | lysine | lysine | ethanedioic acid; propanedioic acid |

In embodiments using an amino substituents the side chain amide bond-forming substituent of one flanking residue and a carboxy substituent as the side chain amide bond-forming substituent of the other flanking residue, the peptide can be conveniently cyclized with an amino-substituted carboxylic acid (aminocarboxylicacid) linker. In one example, the flanking residues and the aminocarboxylic acid linker are selected according to Table 3 below. It will be appreciated that each of the flanking residues and linker molecules listed in Table 3 below is considered to represent not only the particular molecule corresponding to the given chemical name under IUPAC rules, but also any variant of the molecule containing additional substituents or modified substituents which do not prevent or substantially alter the functioning of the amino and/or carboxy groups contained in the molecule, which functioning is necessary for use of the molecule in the methods of the invention. Accordingly, each molecule listed will be understood to encompasses variant molecules containing alkenyl, alkynyl and other unsaturated bonds, heteroatoms, cycloalkyl substituents, aromatic substituents, or other substituents in the carbon backbone of the molecule, and/or variants containing the foregoing or other substituents or groups in place of hydrogen atoms on the carbon backbone of the molecule.

TABLE 3

| Item No | Flanking Residue #1 | Flanking Residue #2 | Aminocarboxylic acid Linker |
|---|---|---|---|
| 1 | aminopropanedioic acid | 2,3-diaminopropanoic acid | 7-aminoheptanoic acid; 8-aminooctanoic acid; 9-aminononanoic acid |
| 2 | aminopropanedioic acid | 2,4-diaminobutanoic acid | 6-aminohexanoic acid; 7-aminoheptanoic acid; 8-aminooctanoic acid |
| 3 | aminopropanedioic acid | 2,5-diaminopentanoic acid | 5-aminopentanoic acid; 6-aminohexanoic acid; 7-aminoheptanoic acid |
| 4 | aminopropanedioic acid | 2,6-diaminohexanoic acid | 4-aminobutanoic acid; 5-aminopentanoic acid; 6-aminohexanoic acid |
| 5 | aminopropanedioic acid | 2,7-diaminoheptanoic acid | 3-aminopropanoic acid; 4-aminobutanoic acid; 5-aminopentanoic acid |
| 6 | aminopropanedioic acid | 2,8-diaminooctanoic acid | aminoethanoic acid; 3-aminopropanoic acid; 4-aminobutanoic acid |
| 7 | aminopropanedioic acid | 2,9-diaminononanoic acid | aminoethanoic acid; 3-aminopropanoic acid |
| 8 | aspartic acid | 2,3-diaminopropanoic acid | 6-aminohexanoic acid; 7-aminoheptanoic acid; 8-aminooctanoic acid |
| 9 | aspartic acid | 2,4-diaminobutanoic acid | 5-aminopentanoic acid; 6-aminohexanoic acid; 7-aminoheptanoic acid |
| 10 | aspartic acid | 2,5-diaminopentanoic acid | 4-aminobutanoic acid; 5-aminopentanoic acid; 6-aminohexanoic acid |
| 11 | aspartic acid | 2,6-diaminohexanoic acid | 3-aminopropanoic acid; 4-aminobutanoic acid; 5-aminopentanoic acid |
| 12 | aspartic acid | 2,7-diaminoheptanoic acid | aminoethanoic acid; 3-aminopropanoic acid; 4-aminobutanoic acid |
| 13 | aspartic acid | 2,8-diaminooctanoic acid | aminoethanoic acid; 3-aminopropanoic acid |
| 14 | glutamic acid | 2,3-diaminopropanoic acid | 5-aminoheptanoic acid; 6-aminohexanoic acid; 7-aminoheptanoic acid |
| 15 | glutamic acid | 2,4-diaminobutanoic acid | 4-aminobutanoic acid; 5-aminoheptanoic acid; 6-aminohexanoic acid |
| 16 | glutamic acid | 2,5-diaminopentanoic acid | 3-aminopropanoic acid; 4-aminobutanoic acid; 5-aminoheptanoic acid |
| 17 | glutamic acid | 2,6-diaminohexanoic acid | aminoethanoic acid; 3-aminopropanoic acid; 4-aminobutanoic acid |
| 18 | glutamic acid | 2,7-diaminoheptanoic acid | aminoethanoic acid; 3-aminopropanoic acid |
| 19 | 2-aminohexanedioic acid | 2,3-diaminopropanoic acid | 4-aminobutanoic acid; 5-aminoheptanoic acid; 6-aminohexanoic acid |
| 20 | 2-aminohexanedioic acid | 2,4-diaminobutanoic acid | 3-aminopropanoic acid; 4-aminobutanoic acid; 5-aminoheptanoic acid |
| 21 | 2-aminohexanedioic acid | 2,5-diaminopentanoic acid | aminoethanoic acid; 3-aminopropanoic acid; 4-aminobutanoic acid |
| 22 | 2-aminohexanedioic acid | lysine | aminoethanoic acid; 3-aminopropanoic acid |
| 23 | 2-aminoheptanedioic acid | 2,3-diaminopropanoic acid | 3-aminopropanoic acid; 4-aminobutanoic acid; 5-aminoheptanoic acid |
| 24 | 2-aminoheptanedioic acid | 2,4-diaminobutanoic acid | aminoethanoic acid; 3-aminopropanoic acid; 4-aminobutanoic acid |
| 25 | 2-aminoheptanedioic acid | 2,5-diaminopentanoic acid | aminoethanoic acid; 3-aminopropanoic acid; |
| 26 | 2-aminooctanedioic acid | 2,3-diaminopropanoic acid | aminoethanoic acid; 3-aminopropanoic |

TABLE 3-continued

| Item No | Flanking Residue #1 | Flanking Residue #2 | Aminocarboxylic acid Linker |
|---|---|---|---|
| | | | acid; 4-aminobutanoic acid |
| 27 | 2-aminooctanedioic acid | 2,4-diaminobutanoic acid | aminoethanoic acid; 3-aminopropanoic acid |
| 28 | 2-aminononanedioic acid | 2,3-diaminopropanoic acid | aminoethanoic acid; 3-aminopropanoic acid |

(ii) Cyclization Methods

Once the flanking residues and difunctional linker have been selected and the peptide chain spanning the flanking residues has been synthesized on solid phase, the difunctional linker can be used to cyclize the solid phase-bound peptide by any convenient method. It will be appreciated that the invention encompasses methods of cyclizing a peptide after the finished peptide chain is fully synthesized, and methods of cyclizing the peptide at any point during peptide synthesis in which the peptide chain contains the flanking residues that are to be cross linked by the difunctional linker. Methods for cyclizing the peptide include (1) deprotecting the side chain amide bond-forming substituents of the flanking residues and reacting the solid phase peptide with the difunctional linker to simultaneously form amide linkages between the two functional groups of the linker and the side chain amide bond-forming substituents of both flanking residues; (2) deprotecting the side chain amide bond-forming substituent of only one of the flanking residues (without deprotecting the side chain amide bond-forming substituent of the other flanking residue), reacting the difunctional linker with the solid phase peptide to form an amide linkage between one functional group on the linker and the side chain amide bond-forming substituent of the deprotected flanking residue, deprotecting the side chain amide bond-forming substituent of the other flanking residue, and then intramolecularly reacting the free functional group on the linker and the side chain amide bond-forming substituent of the other flanking residue, thereby cyclizing the peptide; and (3) deprotecting the side chain amide bond-forming substituents of both of the flanking residues, obtaining a monoprotected difunctional linker wherein only one of the linker's two amide bond-forming functional groups is capable of reacting with a counterpart side chain amide bond-forming substituent in a flanking residue, reacting the monoprotected, difunctional linker with the solid phase peptide to form an amide linkage between the free functional group on the linker and the side chain amide bond-forming substituent of one of the deprotected flanking residues, deprotecting the blocked functional group on the linker, and then intramolecularly reacting the free functional group on the linker and the side chain amide bond-forming substituent of the other flanking residue, thereby cyclizing the peptide. The orthogonal deprotection reactions, non-orthogonal deprotection reactions, and amide bond formation reactions can be performed as described in Section (B)(II)(1)(a) above.

In implementing the methods of the invention generally described as methods (2) and (3) above, it is desirable to use synthesis schemes that exploit the advantages of orthogonal protection and deprotection of functional groups to avoid formation of unwanted derivatives. It will be evident to the practitioner from the following representative synthetic schemes that the protecting groups for the side chain amide bond-forming substituents of the flanking residues, the method of peptide synthesis used, and the sequence of peptide cyclization reactions can be selected such that each of these components of the synthetic scheme increases the specificity of the reactions and improves yield of the desired product.

(iii) Cyclization Using Diamine Linkers

In an example using carboxy substituents for the side chain amide bond-forming substituents of both flanking residues, a diamine linker for cyclization, and Fmoc chemistry for peptide synthesis, the carboxy substituents are orthogonally protected with respect to each other and with respect to the Fmoc-protected α-amino group of the N-terminal residue in the peptide chain by using an allyl group to protect the carboxy substituent of one flanking residue and a t-butyl ester to protect the carboxy substituent of the other flanking residue. In this example, the peptide can be cyclized by (1) using reduction to deprotect the allyl-protected carboxy substituent of one flanking residue (without deprotecting the t-butyl ester-protected carboxy substituent of the other flanking residue); (2) reacting an unprotected or monoprotected (e.g. allyloxycarbonyl- or Boc-monoprotected) diamine linker with the solid phase peptide to form an amide linkage between one of the linker's amino groups and the deprotected carboxy substituent;(3) using acidolysis to deprotect the t-butyl ester-protected carboxy substituent of the other flanking residue and deprotect the Boc-protected amino group of the linker if a Boc-monoprotected diamine linker is used as the linker; (4) using reduction to deprotect the allyloxycarbonyl-protected amino group of the linker if an allyloxycarbonyl-monoprotected diamine linker is used as the linker; and (5) intramolecularly reacting the free carboxy substituent of the other flanking residue with the free amino group of the linker to form an amide linkage that cyclizes the peptide.

Alternatively, the peptide can be cyclized by (1) using acidolysis to deprotect the t-butyl ester-protected carboxy substituent of one flanking residue (without deprotecting the allyl-protected carboxy substituent of the other flanking residue); (2) reacting an unprotected or monoprotected (e.g. allyloxycarbonyl- or Boc-monoprotected) diamine linker with the solid phase peptide to form an amide linkage between one of the linker's amino groups and the deprotected carboxy substituent; (3) using reduction to deprotect the allyl-protected carboxy substituent of the other flanking residue and deprotect the allyloxycarbonyl-protected amino group of the linker if an allyloxycarbonyl-monoprotected diamine linker is used as the linker, (4) using acidolysis to deprotect the Boc-protected amino group of the linker if a Boc-monoprotected diamine linker is used as the linker; and (5) intramolecularly reacting the free carboxy substituent of the other flanking residue with the free amino group of the linker to form an amide linkage that cyclizes the peptide.

In an example using carboxy substituents for the side chain amide bond-forming substituents of both flanking residues, a diamine linker for cyclization, and Boc chemistry for peptide synthesis, the carboxy substituents are orthogonally protected with respect to each other and with respect to the Boc-protected α-amino group of the N-terminal residue in the peptide chain by using an allyl group to protect the carboxy substituent of one flanking residue and a fluorenylmethyl (Fm) ester to protect the carboxy substituent of the other flanking residue. In this example, the peptide can be cyclized by (1) using reduction to deprotect the allyl-protected carboxy substituent of one flanking residue (without deprotecting the Fm ester-protected carboxy substituent of the other flanking residue); (2) reacting an unprotected or monoprotected (e.g. allyloxycarbonyl- or Fmoc-monoprotected) diamine linker with the solid phase peptide to form an amide linkage between one of the linker's amino groups and the deprotected carboxy substituent; (3) using base saponification to deprotect the Fm ester-protected carboxy substituent of the other flanking residue and deprotect the Fmoc-protected amino group of the linker if a Fmoc-monoprotected diamine linker is used as the linker; (4) using reduction to deprotect the allyloxycarbonyl-protected amino group of the linker if an allyloxycarbonyl-monoprotected diamine linker is used as the linker; and (5) intramolecularly reacting the free carboxy substituent of the other flanking residue with the free amino group of the linker to form an amide linkage that cyclizes the peptide.

Alternatively, the peptide can be cyclized by (1) using base saponification to deprotect the Fm ester-protected carboxy substituent of one flanking residue (without deprotecting the allyl-protected carboxy substituent of the other flanking residue); (2) reacting an unprotected or monoprotected (e.g. allyloxycarbonyl- or Fmoc-monoprotected) diamine linker with the solid phase peptide to form an amide linkage between one of the linker's amino groups and the deprotected carboxy substituent; (3) using reduction to deprotect the allyl-protected carboxy substituent of the other flanking residue and deprotect the allyloxycarbonyl-protected amino group of the linker if an allyloxycarbonyl-monoprotected diamine linker is used as the linker; (4) using base saponification to deprotect the Fmoc-protected amino group of the linker if a Fmoc-monoprotected diamine linker is used as the linker; and (5) intramolecularly reacting the free carboxy substituent of the other flanking residue with the free amino group of the linker to form an amide linkage that cyclizes the peptide.

(iv) Cyclization Using Dicarboxylic Acid Linkers

In an example using amino substituents for the side chain amide bond-forming substituents of both flanking residues, a dicarboxylic acid linker for cyclization, and Fmoc chemistry for peptide synthesis, the amino substituents are orthogonally protected with respect to each other and with respect to the Fmoc-protected α-amino group of the N-terminal residue in the peptide chain by using an allyloxycarbonyl group to protect the amino substituent of one flanking residue and a Boc group to protect the amino substituent of the other flanking residue. In this example, the peptide can be cyclized by (1) using reduction to deprotect the allyloxycarbonyl-protected amino substituent of one flanking residue (without deprotecting the Boc-protected amino substituent of the other flanking residue); (2) reacting an unprotected or monoprotected (e.g. allyl- or t-butyl ester-monoprotected) dicarboxylic acid linker with the solid phase peptide to form an amide linkage between one of the linker's carboxy groups and the deprotected amino substituent; (3) using acidolysis to deprotect the Boc-protected amino substituent of the other flanking residue, and to deprotect the t-butyl ester-protected carboxy group of the linker if a t-butyl ester-monoprotected dicarboxylic acid linker is used as the linker; (4) using reduction to deprotect the allyl-protected carboxy group of the linker if an allyl-monoprotected dicarboxylic acid linker is used as the linker; and (5) intramolecularly reacting the free amino substituent of the other flanking residue with the free carboxy group of the linker to form an amide linkage that cyclizes the peptide.

Alternatively, the peptide can be cyclized by (1) using acidolysis to deprotect the Boc-protected amino substituent of one flanking residue (without deprotecting the allyloxycarbonyl-protected amino substituent of the other flanking residue); (2) reacting an unprotected or monoprotected (e.g. allyl- or t-butyl ester-monoprotected) dicarboxylic acid linker with the solid phase peptide to form an amide linkage between one of the linker's carboxy groups and the deprotected amino substituent; (3) using reduction to deprotect the allyloxycarbonyl-protected amino substituent of the other flanking residue, and to deprotect the allyl-protected carboxy group of the linker if an allyl-monoprotected dicarboxylic acid linker is used as the linker; (4) using acidolysis to deprotect the t-butyl ester-protected carboxy group of the linker if a t-butyl ester-monoprotected dicarboxylic acid linker is used as the linker; and (5) intramolecularly reacting the free amino substituent of the other flanking residue with the free carboxy group of the linker to form an amide linkage that cyclizes the peptide.

In an example using amino substituents for the side chain amide bond-forming substituents of both flanking residues, a dicarboxylic acid linker for cyclization, and Boc chemistry for peptide synthesis, the amino substituents are orthogonally protected with respect to each other and with respect to the Boc-protected α-amino group of the N-terminal residue in the peptide chain by using an allyloxycarbonyl group to protect the amino substituent of one flanking residue and a Fmoc group to protect the amino substituent of the other flanking residue. In this example, the peptide can be cyclized by (1) using reduction to deprotect the allyloxycarbonyl-protected amino substituent of one flanking residue (without deprotecting the Fmoc-protected amino substituent of the other flanking residue); (2) reacting an unprotected or monoprotected (e.g. allyl- or Fm ester-monoprotected) dicarboxylic acid linker with the solid phase peptide to form an amide linkage between one of the linker's carboxy groups and the deprotected amino substituent; (3) using base saponification to deprotect the Fmoc-protected amino substituent of the other flanking residue, and to deprotect the Fm ester-protected carboxy group of the linker if a Fm ester-monoprotected dicarboxylic acid linker is used as the linker; (4) using reduction to deprotect the allyl-protected carboxy group of the linker if an allyl-monoprotected dicarboxylic acid linker is used as the linker; and (5) intramolecularly reacting the free amino substituent of the other flanking residue with the free carboxy group of the linker to form an amide linkage that cyclizes the peptide.

Alternatively, the peptide can be cyclized by (1) using base saponification to deprotect the Fmoc-protected amino substituent of one flanking residue (without deprotecting the allyloxycarbonyl-protected amino substituent of the other flanking residue); (2) reacting an unprotected or monoprotected (e.g. allyl- or Fm ester-monoprotected) dicarboxylic acid linker with the solid phase peptide to form an amide linkage between one of the linker's carboxy groups and the deprotected amino substituent; (3) using reduction to deprotect the allyloxycarbonyl-protected amino substituent of the other flanking residue, and to deprotect the allyl-protected carboxy group of the linker if an allyl-monoprotected dicarboxylic acid linker is used as the linker, (4) using base saponification to deprotect the Fm ester-protected carboxy group of the linker if a Fmoc-monoprotected dicarboxylic acid linker is used as the linker; and (5) intramolecularly reacting the free amino substituent of the other flanking residue with the free carboxy group of the linker to form an amide linkage that cyclizes the peptide.

(v) Cyclization Using Aminocarboxylic Acid Linkers

In an example using an amino substituent for the side chain amide bond-forming substituent of one flanking residue, a carboxy substituent for the side chain amide bond-forming substituent of the other flanking residue, an aminocarboxylic acid linker for cyclization, and Fmoc chemistry for peptide synthesis, the side chain amide bond-forming substituents of the flanking residues are orthogonally protected with respect to each other and with respect to the Fmoc-protected α-amino group of the N-terminal residue in the peptide chain by using an allyloxycarbonyl group to protect the amino substituent of one flanking residue and a t-butyl ester to protect the carboxy substituent of the other flanking residue. In this example, the peptide can be cyclized by (1) using reduction to deprotect the allyloxycarbonyl-protected amino substituent of one flanking residue (without deprotecting the t-butyl ester-protected carboxy substituent of the other flanking residue); (2) reacting an unprotected or amino-protected (e.g. allyloxycarbonyl-protected amino or Boc-protected amino) aminocarboxylic acid linker with the solid phase peptide to form an amide linkage between the linker's carboxy group and the deprotected amino substituent; (3) using acidolysis to deprotect the t-butyl ester-protected carboxy substituent of the other flanking residue, and to deprotect the Boc-protected amino group of the linker if an aminocarboxylic acid with a Boc-protected amino group is used as the linker; (4) using reduction to deprotect the allyloxycarbonyl-protected amino group of the linker if an aminocarboxylic acid with an allyloxycarbonyl-protected amino group is used as the linker, and (5) intramolecularly reacting the free carboxy substituent of the other flanking residue and the free amino group of the aminocarboxylic acid linker to cyclize the peptide.

Alternatively, the peptide can be cyclized by (1) using acidolysis to deprotect the t-butyl ester-protected carboxy substituent of one flanking residue (without deprotecting the allyloxycarbonyl-protected amino substituent of the other flanking residue); (2) reacting an unprotected or carboxy-protected (e.g. allyl- or t-butyl ester-protected carboxy) aminocarboxylic acid linker with the solid phase peptide to form an amide linkage between the linker's amino group and the deprotected carboxy substituent; (3) using reduction to deprotect the allyloxycarbonyl-protected amino substituent of the other flanking residue, and to deprotect the allyl-protected carboxy group of the linker if an aminocarboxylic acid with an allyl-protected carboxy group is used as the linker; (4) using acidolysis to deprotect the t-butyl ester-protected carboxy group of the linker if an aminocarboxylic acid with a t-butyl ester-protected carboxy group is used as the linker; and (5) intramolecularly reacting the free amino substituent of the other flanking residue and the free carboxy group of the aminocarboxylic acid linker to cyclize the peptide.

In another example using an amino substituent for the side chain amide bond-forming substituent of one flanking residue, a carboxy substituent for the side chain amide bond-forming substituent of the other flanking residue, an aminocarboxylic acid linker for cyclization, and Fmoc chemistry for peptide synthesis, the side chain amide bond-forming substituents of the flanking residues are orthogonally protected with respect to each other and with respect to the Fmoc-protected α-amino group of the N-terminal residue in the peptide chain by using a Boc group to protect the amino substituent of one flanking residue and an allyl group to protect the carboxy substituent of the other flanking residue. In this example, the peptide can be cyclized by (1) using acidolysis to deprotect the Boc-protected amino substituent of one flanking residue (without deprotecting the allyl-protected carboxy substituent of the other flanking residue); (2) reacting an unprotected or amino-protected (e.g. allyloxycarbonyl-protected amino or Boc-protected amino) aminocarboxylic acid linker with the solid phase peptide to form an amide linkage between the linker's carboxy group and the deprotected amino substituent;(3) using reduction to deprotect the allyl-protected carboxy substituent of the other flanking residue, and to deprotect the allyloxycarbonyl-protected amino group of the linker if an aminocarboxylic acid with a allyloxycarbonyl-protected amino group is used; (4) using acidolysis to deprotect the Boc-protected amino group of the linker if an aminocarboxylic acid with an Boc-protected amino group is used as the linker; and (5) intramolecularly reacting the free carboxy substituent of the other flanking residue and the free amino group of the aminocarboxylic acid linker to cyclize the peptide.

Alternatively, the peptide can be cyclized by (1) using acidolysis to deprotect the Boc-protected amino substituent of one flanking residue (without deprotecting the allyl-protected carboxy substituent of the other flanking residue); (2) reacting an unprotected or amino-protected (e.g. allyloxycarbonyl-protected or Boc-protected amino) aminocarboxylic acid linker with the solid phase peptide to form an amide linkage between the linker's carboxy group and the deprotected amino substituent; (3) using reduction to deprotect the allyl-protected carboxy substituent of the other flanking residue, and to deprotect the allyloxycarbonyl-protected amino group of the linker if an aminocarboxylic acid with an allyloxycarbonyl-protected amino group is used as the linker; (4) using acidolysis to deprotect the Boc-protected amino group of the linker if an aminocarboxylic acid with a Boc-protected amino group is used as the linker; and (5) intramolecularly reacting the free carboxy substituent of the other flanking residue and the free amino group of the aminocarboxylic acid linker to cyclize the peptide.

In an example using an amino substituent for the side chain amide bond-forming substituent of one flanking residue, a carboxy substituent for the side chain amide bond-forming substituent of the other flanking residue, an aminocarboxylic acid linker for cyclization, and Boc chemistry for peptide synthesis, the side chain amide bond-forming substituents of the flanking residues are orthogonally protected with respect to each other and with respect to the Boc-protected α-amino group of the N-terminal residue in the peptide chain by using an allyloxycarbonyl group to protect the amino substituent of one flanking residue and a Fm ester to protect the carboxy substituent of the other flanking residue. In this example, the peptide can be cyclized by (1) using reduction to deprotect the allyloxycarbonyl-protected amino substituent of one flanking residue (without deprotecting the Fm ester-protected carboxy substituent of the other flanking residue); (2) reacting an unprotected or amino-protected (e.g. allyloxycarbonyl-protected amino or Fmoc-protected amino) aminocarboxylic acid linker with the solid phase peptide to form an amide linkage between the linker's carboxy group and the deprotected amino substituent;(3) using base saponification to deprotect the Fm ester-protected carboxy substituent of the other flanking residue, and to deprotect the Fmoc-protected amino group of the linker if an aminocarboxylic acid with a Fmoc-protected amino group is used as the linker; (4) using reduction to deprotect the allyloxycarbonyl-protected amino group of the linker if an aminocarboxylic acid with an allyloxycarbonyl-protected amino group is used as the linker; and (5) intramolecularly reacting the free carboxy substituent of the other flanking residue and the free amino group of the aminocarboxylic acid linker to cyclize the peptide.

Alternatively, the peptide can be cyclized by (1) using base saponification to deprotect the Fm ester-protected carboxy substituent of one flanking residue (without deprotecting the allyloxycarbonyl-protected amino substituent of the other flanking residue); (2) reacting an unprotected or carboxy-protected (e.g. allyl- or Fm ester-protected carboxy) aminocarboxylic acid linker with the solid phase peptide to form an amide linkage between the linker's amino group and the deprotected carboxy substituent; (3) using reduction to deprotect the allyloxycarbonyl-protected amino substituent of the other flanking residue, and to deprotect the allyl-protected carboxy group of the linker if an aminocarboxylic acid with an allyl-protected carboxy group is used as the linker; (4) using base saponification to deprotect the Fm ester-protected carboxy group of the linker if an aminocarboxylic acid with a Fm ester-protected carboxy group is used as the linker; and (5) intramolecularly reacting the free amino substituent of the other flanking residue and the free carboxy group of the aminocarboxylic acid linker to cyclize the peptide.

In another example using an amino substituent for the side chain amide bond-forming substituent of one flanking residue, a carboxy substituent for the side chain amide bond-forming substituent of the other flanking residue, an aminocarboxylic acid linker for cyclization, and Boc chemistry for peptide synthesis, the side chain amide bond-forming substituents of the flanking residues are orthogonally protected with respect to each other and with respect to the Boc-protected α-amino group of the N-terminal residue in the peptide chain by using a Fmoc group to protect the amino substituent of one flanking residue and an allyl group to protect the carboxy substituent of the other flanking residue. In this example, the peptide can be cyclized by (1) using base saponification to deprotect the Fmoc-protected amino substituent of one flanking residue (without deprotecting the allyl-protected carboxy substituent of the other flanking residue); (2) reacting an unprotected or amino-protected (e.g. allyloxycarbonyl-protected amino or Fmoc-protected amino) aminocarboxylic acid linker with the solid phase peptide to form an amide linkage between the linker's carboxy group and the deprotected amino substituent; (3) using reduction to deprotect the allyl-protected carboxy substituent of the other flanking residue, and to deprotect the allyloxycarbonyl-protected amino group of the linker if an aminocarboxylic acid with a allyloxycarbonyl-protected amino group is used; (4) using base saponification to deprotect the Fmoc-protected amino group of the linker if an aminocarboxylic acid with an Fmoc-protected amino group is used as the linker; and (5) intramolecularly reacting the free carboxy substituent of the other flanking residue and the free amino group of the aminocarboxylic acid linker to cyclize the peptide.

Alternatively, the peptide can be cyclized by (1) using reduction to deprotect the allyl-protected carboxy substituent of one flanking residue (without deprotecting the Fmoc-protected amino substituent of the other flanking residue); (2) reacting an unprotected or carboxy-protected (e.g. allyl-protected or Fm ester-protected carboxy) aminocarboxylic acid linker with the solid phase peptide to form an amide linkage between the linker's amino group and the deprotected carboxy substituent; (3) using base saponification to deprotect the Fmoc-protected amino substituent of the other flanking residue, and to deprotect the Fm ester-protected carboxy group of the linker if an aminocarboxylic acid with a Fm ester-protected carboxy group is used as the linker; (4) using reduction to deprotect the allyl-protected carboxy group of the linker if an aminocarboxylic acid with an allyl-protected carboxy group is used as the linker; and (5) intramolecularly reacting the free amino substituent of the other flanking residue and the free carboxy group of the aminocarboxylic acid linker to cyclize the peptide.

In yet another embodiment using an amino substituent for the side chain amide bond-forming substituent of one flanking residue, a carboxy substituent for the side chain amide bond-forming substituent of the other flanking residue, an aminocarboxylic acid linker for cyclization, and Fmoc chemistry for peptide synthesis, the regioselectivity of the cyclization procedure is provided by orthogonally protecting the side chain amide bond-forming substituents of the flanking residues with respect to the Fmoc-protected α-amino group of the N-terminal residue in the peptide chain but not with respect to each other, and orthogonally protecting one of the aminocarboxylic acid linker's functional groups with respect to the Fmoc-protected α-amino group of the N-terminal residue in the peptide chain.

In an example of the foregoing embodiment using an allyloxycarbonyl-protected amino substituent as the side chain amide bond-forming substituent of one flanking residue, an allyl-protected carboxy substituent as the side chain amide-bond forming substituent of the other flanking residue, a monoprotected aminocarboxylic acid liner, and Fmoc chemistry for peptide synthesis, the peptide can be cyclized by (1) using reduction to orthogonally deprotect the side chain amide bond-forming substituents of the flanking residues (without deprotecting the Fmoc-protected α-amino group of the N-terminal residue in the peptide chain); (2) reacting a carboxy-protected (e.g. allyl- or t-butyl ester protected carboxy) or amino-protected (e.g. allyloxycarbonyl- or Boc-protected amino) aminocarboxylic acid linker with the solid phase peptide to form an amide linkage between the unprotected functional group of the linker and the corresponding side chain amide bond-forming substituent on one of the flanking residues; (3) using reduction or acidolysis, as appropriate, to deprotect the protected functional group of the linker; and (4) intramolecularly reacting the free side chain amide bond-forming substituent of the other flanking residue and the free functional group of the linker to cyclize the peptide.

In an example of the foregoing embodiment using a Boc-protected amino substituent as the side chain amide bond-forming substituent of one flanking residue, a t-butyl ester-protected carboxy substituent as the side chain amide-bond forming substituent of the other flanking residue, a monoprotected aminocarboxylic acid linker, and Fmoc chemistry for peptide synthesis, the peptide can be cyclized by (1) using acidolysis to orthogonally deprotect the side chain amide bond-forming substituents of the flanking residues (without deprotecting the Fmoc-protected α-amino group of the N-terminal residue in the peptide chain); (2) reacting a carboxy-protected (e.g. allyl or t-butyl ester-protected carboxy) or amino-protected (e.g. allyloxycarbonyl- or Boc-protected amino) aminocarboxylic acid linker with the solid phase peptide to form an amide linkage between the unprotected functional group of the linker and the corresponding side chain amide bond-forming substituent on one of the flanking residues; (3) using reduction or acidolysis, as appropriate, to deprotect the protected functional group of the linker; and (4) intramolecularly reacting the free side chain amide bond-forming substituent of the other flanking residue and the free functional group of the linker to cyclize the peptide.

In still another embodiment using an amino substituent for the side chain amide bond-forming substituent of one flanking residue, a carboxy substituent for the side chain amide bond-forming substituent of the other flanking residue, an aminocarboxylic acid linker for cyclization, and Boc chemistry for peptide synthesis, the regioselectivity of the cyclization procedure is provided by orthogonally protecting the side chain amide bond-forming substituents of the flanking residues with respect to the Boc-protected α-amino group of the N-terminal residue in the peptide chain but not with respect to each other, and orthogonally protecting one of the aminocarboxylic acid linker's functional groups with respect to the Boc-protected α-amino group of the N-terminal residue in the peptide chain.

In an example of the foregoing embodiment using an allyloxycarbonyl-protected amino substituent as the side chain amide bond-forming substituent of one flanking residue, an allyl-protected carboxy substituent as the side chain amide-bond forming substituent of the other flanking residue, an aminocarboxylic acid linker, and Boc chemistry for peptide synthesis, the peptide can be cyclized by (1) using reduction to orthogonally deprotect the side chain amide bond-forming substituents of the flanking residues (without deprotecting the Boc-protected α-amino group of the N-terminal residue in the peptide chain); (2) reacting a carboxy-protected (e.g. allyl- or Fm ester-protected carboxy) or amino-protected (e.g. allyloxycarbonyl- or Fmoc-protected amino) aminocarboxylic acid linker with the solid phase peptide to form an amide linkage between the unprotected functional group of the linker and the corresponding side chain amide bond-forming substituent on one of the flanking residues; (3) using reduction or base saponification, as appropriate, to deprotect the protected functional group of the linker; and (4) intramolecularly reacting the free side chain amide bond-forming substituent of the other flanking residue and the free functional group of the linker to cyclize the peptide.

In an example of the foregoing embodiment using a Fmoc-protected amino substituent as the side chain amide bond-forming substituent of one flanking residue, a Fm ester-protected carboxy substituent as the side chain amide-bond forming substituent of the other flanking residue, an aminocarboxylic acid linker, and Boc chemistry for peptide synthesis, the peptide can be cyclized by (1) using base saponification to orthogonally deprotect the side chain amide bond-forming substituents of the flanking residues (without deprotecting the Boc-protected α-amino group of the N-terminal residue in the peptide chain); (2) reacting a carboxy-protected (e.g. allyl- or Fm ester-protected carboxy) or amino-protected (e.g. allyloxycarbonyl- or Fmoc-protected amino) aminocarboxylic acid linker with the solid phase peptide to form an amide linkage between the unprotected functional group of the linker and the corresponding side chain amide bond-forming substituent on one of the flanking residues; (3) using reduction or base saponification, as appropriate, to deprotect the protected functional group of the linker, and (4) intramolecularly reacting the free side chain amide bond-forming substituent of the other flanking residue and the free functional group of the linker to cyclize the peptide.

Following cyclization, the helix-constrained peptide is optionally cleaved away from the solid support, recovered and purified. The peptide can be removed from the solid support by a reagent capable of disrupting the peptide-solid phase link, and optionally deprotecting blocked side chain functional groups on the peptide. In one embodiment, the peptide is cleaved away from the solid phase by acidolysis with liquid hydrofluoric acid (HF), which also removes any remaining side chain protective groups. Preferably, in order to avoid alkylation of residues in the peptide (for example, alkylation of methionine, cysteine, and tyrosine residues), the acidolysis reaction mixture contains thio-cresol and cresol scavengers. Following HF cleavage, the resin is washed with ether, and the free peptide is extracted from the resin with sequential washes of acetic acid solutions. The combined washes are lyophilized, and the residue is purified.

c. Liquid Phase Cyclization

Alternatively, the peptide can be cleaved away from the solid support prior to the cyclization step. In one embodiment, after the difunctional linker is coupled to the side chain amide bond-forming substituent of the first flanking residue in the peptide, the peptide is cleaved away from the solid support. The peptide is recovered, deblocked at the side chain amide bond-forming substituent of the second flanking residue (if necessary), and then cyclized at low concentration in a reaction mixture to maximize intramolecular amide bond formation. Typically, a maximum level of intramolecular amide bond formation can be achieved under conditions in which the concentration of the peptide provides an intramolecular concentration of free carboxy and amino groups that exceeds the intermolecular concentration of free carboxy and amino groups in the reaction mixture. In one embodiment, a peptide concentration of 1 nM to 1 M, and preferably 1 μM to 1 mM, and more preferably 1 μM to 100 μM, is used to maximize cyclization. The cyclization of free peptide can be conducted with any of the amino acid coupling reactions used to helicize peptide bound to a solid support described above.

d. Synthetic Schemes

In one embodiment, any helix constrained compound of formulas (1), (1a), (1b), (1c), (1d), (1e), (1f), and (1g) is made by utilizing (in peptide synthesis as described in Section (B)(II)(1)(a) above) the particular combination of flanking residues and diamine linker shown in Table 1 above that provides the values of n, m and p characterizing the compound of interest, and cyclizing the resulting peptide according to the methods described in Section (B)(II)(1)(b) (ii) or (iii) above. For example, any compound of formulas (1), (1a), (1b), (1c), (1d), (1e), (1f), and (1g) characterized by m=0, p=0, and n=7, 8, or 9 can be made by utilizing (in peptide synthesis as described in Section (B)(II)(1)(a) above) the flanking residues and any diamine linker listed in Item No. 1 in Table 1 above, and cyclizing the resulting peptide according to the methods described in Section (B)(II)(1)(b)(ii)or (iii) above. In another example, any compound of formulas (11), (1a), (1b), (1c), (1d), (1e), (1f), and (1g) characterized by m=0, p=6, and n=2 or 3, or characterized by m=6, p=0, and n=2 or 3, can be made by utilizing (in peptide synthesis as described in Section (B)(II)(1)(a) above) the flanking residues and any diamine linker listed in Item No. 7 in Table 1 above, and cyclizing the resulting peptide according to the methods described in Section (B)(II)(1)(b)(ii) or (iii) above. In yet another example, any compound of formulas (1), (1a), (1b), (1c), (1d), (1e), (1f), and (1g) characterized by m=3, p=3, and n=2 or 3, can be made by utilizing (in peptide synthesis as described in Section (B)(II)(1)(a) above) the flanking residues and any diamine linker listed in Item No. 16 in Table 1 above, and cyclizing the resulting peptide according to the methods described in Section (B)(II)(1)(b)(ii) or (iii) above.

In another embodiment, any helix constrained compound of formulas (2), (2a), (2b), (2c), (2d), (2e), (2f), (2g), (3), (3a), (3b), (3c), (3d), (3e), (3f), and (3g) is made by utilizing in Section (B)(II)(1)(a) above) the flanking residues and any diamine linker listed in Item No. 9 in Table 1 above, and cyclizing the resulting peptide according to the methods described in Section (B)(II)(1)(b)(ii) or (iii) above.

In another embodiment, any helix constrained compound of formulas (4), (4a), (4b), (4c), (4d), (4e), (4f), and (4g) is made by utilizing (in peptide synthesis as described in Section (B)(II)(1)(a) above) the flanking residues and any diamine linker listed in Item No. 13 in Table 1 above, and cyclizing the resulting peptide according to the methods described in Section (B)(II)(1)(b)(ii) or (iii) above.

In another embodiment, any helix constrained compound of formulas (5), (5a), (5b), (5c), (5d), (5e), and (5g) is made by utilizing (in peptide synthesis as described in Section (B)(II)(1)(a) above) the flanking residues and any diamine linker listed in Item No. 8 in Table 1 above, and cyclizing the resulting peptide according to the methods described in Section (B)(II)(1)(b)(ii) or (iii) above.

In another embodiment, any helix constrained compound of formulas (6), (6a), (6b), (6c), (6d), (6e), (6f), (6g), (11), (11a), (11b), (11c), (11d), (11e), (11f), and (11g) is made by utilizing (in peptide synthesis as described in Section (B)(II)(1)(a) above) the particular combination of flanking residues and aminocarboxylic acid linker shown in Table 3 above that provides the values of q, r and s characterizing the compound of interest, or the values of t, u and v characterizing the compound of interest, as appropriate, and cyclizing the resulting peptide according to the methods described in Section (B)(II)(1)(b)(ii) or (v) above. For example, any compound of formulas (6), (6a), (6b), (6c), (6d), (6e), (6f), (6g), (11), (11a), (11b), (11c), (11d), (11e), (11f), and (11g) characterized by $q=1$, $s=0$, and $r=6, 7,$ or $8$, or characterized by $t=0$, $v=1$, and $u=6, 7,$ or $8$, as appropriate, can be made by utilizing (in peptide synthesis as described in Section (B)(II)(1)(a) above) the flanking residues and any aminocarboxylic acid linker listed in Item No. 1 in Table 3 above, and cyclizing the resulting peptide according to the methods described in Section (B)(II)(1)(b)(ii) or (v) above.

In another example, any compound of formulas (6), (6a), (6b), (6c), (6d), (6e), (6f), (6g), 11), (11a), (11b), (11c), (11d), (11e), (11f), and (11g) characterized by $q=1$, $s=6$, and $r=1$ or $2$, or characterized by $t=6$, $v=1$, and $u=1$ or $2$, as appropriate, can be made by utilizing (in peptide synthesis as described in Section (B)(II)(1)(a) above) the flanking residues and any aminocarboxylic acid linker listed in Item No. 28 in Table 3 above, and cyclizing the resulting peptide according to the methods described in Section (B)(II)(1)(b)(ii) or (v) above.

In another example, any compound of formulas (6), (6a), (6b), (6c), (6d), (6e), (6f), (6g), (11), (11a), (11b), (11c), (11d), (11e), (11f), and (11g) characterized by $q=7$, $s=0$, and $r=1$ or $2$, or characterized by $t=0$, $v=7$, and $u=1$ or $2$, as appropriate, can be made by utilizing (in peptide synthesis as described in Section (B)(II)(1)(a) above) the flanking residues and any aminocarboxylic acid linker listed in Item No. 7 in Table 3 above, and cyclizing the resulting peptide according to the methods described in Section (B)(II)(1)(b)(ii) or (v) above.

In another example, any compound of formulas (6), (6a), (6b), (6c), (6d), (6e), (6f), (6g), (11), (11a), (11b), (11c), (11d), (11e), (11f), and (11g) characterized by $q=3$, $s=4$, and $r=1$ or $2$, or characterized by $t=4$, $v=3$, and $u=1$ or $2$, as appropriate, can be made by utilizing (in peptide synthesis as described in Section (B)(II)1)(a) above) the flanking residues and any aminocarboxylic acid linker listed in Item No. 25 in Table 3 above, and cyclizing the resulting peptide according to the methods described in Section (B)(II)(1)(b)(ii) or (v) above.

In another embodiment, any helix constrained compound of formulas (7), (7a), (7b), (7c), (7d), (7e), (7f), (7g), (13), (13a), (13b), (13c), (13d), (13e), (13f), and (13g) is made by utilizing (in peptide synthesis as described in Section (B)(II)(1)(a) above) the flanking residues and any aminocarboxylic acid linker listed in Item No. 14 in Table 3 above, and cyclizing the resulting peptide according to the methods described in Section (B)(II)(1)(b)(ii) or (v) above.

In another embodiment, any helix constrained compound of formulas (8), (8a), (8b), (8c), (8d), (8e), (8f), (8g), (12), (12a), (12b), (12c), (12d), (12e), (12f), and (12g) is made by utilizing (in peptide synthesis as described in Section (B) (II)(1)(a) above) the flanking residues and any aminocarboxylic acid linker listed in Item No.9 in Table 3 above, and cyclizing the resulting peptide according to the methods described in Section (B)(II)(1)(b)(ii) or (v) above.

In another embodiment, any helix constrained compound of formulas (9), (9a), (9b), (9c), (9d), (9e), (9f), (9g), (15), (15a), (15b), (15c), (15d), (15e), (15f), and (15g) is made by utilizing (in peptide synthesis as described in Section (B) (II)(1)(a) above) the flanking residues and any aminocarboxylic acid linker listed in Item No. 15 in Table 3 above, and cyclizing the resulting peptide according to the methods described in Section (B)(II)(1)(b)(ii) or (v) above.

In another embodiment, any helix constrained compound of formulas (10), (10a), (10b), (10c), (10d), (10e), (10f), (10g), (14), (14a), (14b), (14c), (14d), (14e), (14f), and (14g) is made by utilizing (in peptide synthesis as described in Section (B)(II)(1)(a) above) the flanking residues and any aminocarboxylic acid linker listed in Item No. 8 in Table 3 above, and cyclizing the resulting peptide according to the methods described in Section (B)(II)(1)(ii) or (v) above.

In one embodiment, any helix constrained compound of formulas (16), (16a), (16b), (16c), (16d), (16e), (16f), and (16g) is made by utilizing (in peptide synthesis as described in Section (B)(II)(1)(a) above) the particular combination of flanking residues and dicarboxylic acid linker shown in Table 2 above that provides the values of w, x and y characterizing the compound of interest, and cyclizing the resulting peptide according to the methods described in Section (B)(II)(1)(b)(ii) or (iv) above. For example, any compound of formulas (16), (16a), (16b), (16c), (16d), (16e), (16f), and (16g) characterized by $w=1$, $y=1$, and $x=5, 6,$ or $7$ can be made by utilizing (in peptide synthesis as described in Section (B)(II)(1)(a) above) the flanking residues and any dicarboxylic acid linker listed in Item No. 1 in Table 2 above, and cyclizing the resulting peptide according to the methods described in Section (B)(II)(1)(ii) or (iv) above. In another example, any compound of formulas (16), (16a), (16b), (16c), (16d), (16e), (16f), and (16g) characterized by $w=1$, $y=7$, and $x=0$ or $1$, or characterized by $w=7$, $y=1$, and $x=0$ or $1$, can be made by utilizing (in peptide synthesis as described in Section (B)(II)(1)(a) above) the flanking residues and any dicarboxylic acid linker listed in Item No. 7 in Table 2 above, and cyclizing the resulting peptide according to the methods described in Section (B)(II)(1)(b)(ii) or (iv) above. In yet another example, any compound of formulas (16), (16a), (16b), (16c), (16d), (16e), (16f), and (16g) characterized by $w=4$, $y=4$, and $x=0$ or $1$, can be made by utilizing (in peptide synthesis as described in Section (B)(II)(1)(a) above) the flanking residues and any dicarboxylic acid linker listed in Item No. 16 in Table 2 above, and cyclizing the resulting peptide according to the methods described in Section (B)(II)(1)(b)(ii) or (iv) above.

In another embodiment, any helix constrained compound of formulas (17), (17a), (17b), (17c), (17d), (17e), (17f), (17g), (18), (18a), (18b), (18c), (18d), (18e), (18f), and (18g) is made by utilizing (in peptide synthesis as described in Section (B)(II)(1)(a) above) the flanking residues and any dicarboxylic acid linker listed in Item No. 2 in Table 2 above, and cyclizing the resulting peptide according to the methods described in Section (B)(II)(1)(b)(ii) or (iv) above.

In another embodiment, any helix constrained compound of formulas (19), (19a), (19b), (19c), (19d), (19e), (19f), and (19g) is made by utilizing (in peptide synthesis as described in Section (B)(II)(1)(a) above) the flanking residues and any dicarboxylic acid linker listed in Item No. 1 in Table 2 above, and cyclizing the resulting peptide according to the methods described in Section (B)(II)(1)(b)(ii) or (iv) above.

In another embodiment, any helix constrained compound of formulas (20), (20a), (20b), (20c), (20d), (20e), (20f), and (20g) is made by utilizing (in peptide synthesis as described in Section (B)(II)(1)(a) above) the flanking residues and any dicarboxylic acid linker listed in Item No. 8 in Table 2 above, and cyclizing the resulting peptide according to the methods described in Section (B)(II)(1)(b)(ii) or (iv) above.

(2) Synthesis of Linear Peptide with Difunctional Linker-Coupled Flanking Amino Acid The peptide is designed such that the sequence to be helicized comprises an amino acid sequence that is six residues in length that extends between flanking residues as described in Section (B)(II)(1)(a) above. The peptide can be constructed using a modification of the solid phase synthesis methods described in Section (B)(II)(1)(a) above wherein one of the flanking residues is coupled to a difunctional linker before addition to the peptide chain. This allows the linker to be incorporated into the peptide as part of a standard amino acid.

The flanking residue can be coupled to the difunctional linker by any convenient means. Typically, the side chain amide bond-forming substituent of the flanking residue is used to form an amide linkage with one of the functional groups on the linker. In one embodiment designed for use in conjunction with Fmoc chemistry, the linker-derivatized flanking residue is created by obtaining from a commercial source an amino acid residue with an Fmoc-protected α-amino substituent, a t-butyl ester-protected α-carboxy substituent, and an unprotected side chain amino substituent, and then reacting the α-substituent protected amino acid with a difunctional linker having a free carboxy group to form an amide linkage between the linker's free carboxy group and the unprotected side chain amino substituent of the amino acid using any of the condensation methods described in Section (B)(II)(1)(a) above. The t-butyl ester-protected α-carboxy substituent of the derivatized amino acid residue is then removed by acidolysis to permit incorporation of the derivatized amino acid into the peptide chain.

In another embodiment designed for use in conjunction with Fmoc chemistry, the linker-derivatized flanking residue is created by obtaining from a commercial source an amino acid residue with an Fmoc-protected α-amino substituent, an allyl-protected α-carboxy substituent, and an unprotected side chain amino substituent, and then reacting the α-substituent protected amino acid with a difunctional linker having a free carboxy group to form an amide linkage between the linker's free carboxy group and the unprotected side chain amino substituent of the amino acid using any of the condensation methods described in Section (B)(II)1)(a) above. The allyl-protected α-carboxy substituent of the derivatized amino acid residue is then removed by reduction to permit incorporation of the derivatized amino acid into the peptide chain.

In one embodiment designed for use in conjunction with Boc chemistry, the linker-derivatized flanking residue is created by obtaining from a commercial source an amino acid residue with an Boc-protected α-amino substituent, a Fm ester-protected α-carboxy substituent, and an unprotected side chain amino substituent, and then reacting the α-substituent protected amino acid with a difunctional linker having a free carboxy group to form an amide linkage between the linker's free carboxy group and the unprotected side chain amino substituent of the amino acid using any of the condensation methods described in Section (B)(II)(1)(a) above. The Fm ester-protected α-carboxy substituent of the derivatized amino acid residue is then removed by base saponification to permit incorporation of the derivatized amino acid into the peptide chain.

In another embodiment designed for use in conjunction with Boc chemistry, the linker-derivatized flanking residue is created by obtaining from a commercial source an amino acid residue with an Boc-protected α-amino substituent, an allyl-protected α-carboxy substituent, and an unprotected side chain amino substituent, and then reacting the α-substituent protected amino acid with a difunctional linker having a free carboxy group to form an amide linkage between the linker's free carboxy group and the unprotected side chain amino substituent of the amino acid using any of the condensation methods described in Section (B)(II)1)(a) above. The allyl-protected α-carboxy substituent of the derivatized amino acid residue is then removed by reduction to permit incorporation of the derivatized amino acid into the peptide chain.

In one embodiment designed for use in conjunction with Fmoc chemistry, the linker-derivatized flanking residue is created by obtaining from a commercial source an amino acid residue with an Fmoc-protected α-amino substituent, a t-butyl ester-protected α-carboxy substituent, and an unprotected side chain carboxy substituent, and then reacting the α-substituent protected amino acid with a difunctional linker having a free amino group to form an amide linkage between the linker's free amino group and the unprotected side chain carboxy substituent of the amino acid using any of the condensation methods described in Section (B)(II)(1)(a) above. The t-butyl ester-protected α-carboxy substituent of the derivatized amino acid residue is then removed by acidolysis to permit incorporation of the derivatized amino acid into the peptide chain.

In another embodiment designed for use in conjunction with Fmoc chemistry, the liner-derivatized flanking residue is created by obtaining from a commercial source an amino acid residue with an Fmoc-protected α-amino substituent, an allyl-protected α-carboxy substituent, and an unprotected side chain carboxy substituent, and then reacting the α-substituent protected amino acid with a difunctional linker having a free amino group to form an amide linkage between the linkers free amino group and the unprotected side chain carboxy substituent of the amino acid using any of the condensation methods described in Section (B)(II)(1)(a) above. The allyl-protected α-carboxy substituent of the derivatized amino acid residue is then removed by reduction to permit incorporation of the derivatized amino acid into the peptide chain.

In one embodiment designed for use in conjunction with Boc chemistry, the linker-derivatized flanking residue is created by obtaining from a commercial source an amino acid residue with an Boc-protected α-amino substituent, a Fm ester-protected α-carboxy substituent, and an unprotected side chain carboxy substituent, and then reacting the α-substituent protected amino acid with a difunctional linker having a free amino group to form an amide linkage between the linker's free amino group and the unprotected side chain carboxy substituent of the amino acid using any of the condensation methods described in Section (B)(II)(1)(a)

above. The Fm ester-protected α-carboxy substituent of the derivatized amino acid residue is then removed by base saponification to permit incorporation of the derivatized amino acid into the peptide chain.

In another embodiment designed for use in conjunction with Boc chemistry, the liner-derivatized flanking residue is created by obtaining from a commercial source an amino acid residue with an Boc-protected α-amino substituent, an allyl-protected α-carboxy substituent, and an unprotected side chain carboxy substituent, and then reacting the α-substituent protected amino acid with a difunctional liner having a free amino group to form an amide linkage between the linker's free amino group and the unprotected side chain carboxy substituent of the amino acid using any of the condensation methods described in Section (B)(II)(1)(a) above. The allyl-protected α-carboxy substituent of the derivatized amino acid residue is then removed by reduction to permit incorporation of the derivatized amino acid into the peptide chain.

It is desirable to protect one of the functional groups on the difunctional linker either before the linker is coupled to the flanking residue that is selected to carry the linker or after the coupling but before the addition of the linker-coupled flanking residue to the peptide chain. This improves yield by avoiding unwanted reaction of the free functional group on the flanking residue-coupled linker during peptide synthesis. The free functional group on the linker can be blocked with any of the amino or carboxy protective groups described in Section (B)(II)1)(a) above. In one embodiment, the free functional group on the linker and the α-amino groups are orthogonally protected such that the α-amino groups can be deprotected in peptide synthesis without deprotecting the free functional group on the linker. It will be appreciated that any of the foregoing procedures for coupling difunctional linkers to flanking residues can be easily modified to derivatize a particular flanking residue with a selected orthogonally monoprotected difunctional linker.

In one embodiment designed for use in conjunction with Fmoc chemistry, an orthogonally monoprotected difunctional linker-derivatized flanking residue is created by obtaining from a commercial source an amino acid residue with an Fmoc-protected α-amino substituent, a t-butyl ester-protected α-carboxy substituent, and an unprotected side chain amino substituent, and then reacting the α-substituent protected amino acid with a difunctional linker carrying a free carboxy group and either an allyl-protected carboxy group or an allyloxycarbonyl-protected amino group to form an amide linkage between the linker's free carboxy group and the unprotected side chain amino substituent of the amino acid using any of the condensation methods described in Section (B)(II)(1)(a) above. The t-butyl ester-protected α-carboxy substituent of the derivatized amino acid residue is then removed by acidolysis to permit incorporation of the derivatized amino acid into the peptide chain.

In another embodiment designed for use in conjunction with Fmoc chemistry, an orthogonally monoprotected difunctional linker-derivatized flanking residue is created by obtaining from a commercial source an amino acid residue with an Fmoc-protected α-amino substituent, an allyl-protected α-carboxy substituent, and an unprotected side chain amino substituent, and then reacting the α-substituent protected amino acid with a difunctional linker carrying a free carboxy group and either a Boc-protected amino group or a t-butyl ester-protected carboxy group to form an amide linkage between the linker's free carboxy group and the unprotected side chain amino substituent of the amino acid using any of the condensation methods described in Section (B)(II)(1)(a) above. The allyl-protected α-carboxy substituent of the derivatized amino acid residue is then removed by reduction to permit incorporation of the derivatized amino acid into the peptide chain.

In one embodiment designed for use in conjunction with Boc chemistry, an orthogonally monoprotected difunctional linker-derivatized flanking residue is created by obtaining from a commercial source an amino acid residue with an Boc-protected α-amino substituent, a Fm ester-protected α-carboxy substituent, and an unprotected side chain amino substituent, and then reacting the α-substituent protected amino acid with a difunctional linker carrying a free carboxy group and either an allyloxycarbonyl-protected amino group or an allyl-protected carboxy group to form an amide linkage between the linker's free carboxy group and the unprotected side chain amino substituent of the amino acid using any of the condensation methods described in Section (B)(II)(1)(a) above. The Fm ester-protected α-carboxy substituent of the derivatized amino acid residue is then removed by base saponification to permit incorporation of the derivatized amino acid into the peptide chain.

In another embodiment designed for use in conjunction with Boc chemistry, an orthogonally monoprotected difunctional linker-derivatized flanking residue is created by obtaining from a commercial source an amino acid residue with an Boc-protected α-amino substituent, an allyl-protected α-carboxy substituent, and an unprotected side chain amino substituent, and then reacting the α-substituent protected amino acid with a difunctional linker carrying a free carboxy group and either a Fmoc-protected amino group or a Fm ester-protected carboxy group to form an amide linkage between the linker's free carboxy group and the unprotected side chain amino substituent of the amino acid using any of the condensation methods described in Section (B)(II)(1)(a) above. The allyl-protected α-carboxy substituent of the derivatized amino acid residue is then removed by reduction to permit incorporation of the derivatized amino acid into the peptide chain.

In one embodiment designed for use in conjunction with Fmoc chemistry, an orthogonally monoprotected difunctional linker-derivatized flanking residue is created by obtaining from a commercial source an amino acid residue with an Fmoc-protected α-amino substituent, a t-butyl ester-protected α-carboxy substituent, and an unprotected side chain carboxy substituent, and then reacting the α-substituent protected amino acid with a difunctional linker carrying a free amino group and either an allyloxycarbonyl-protected amino group or an allyl-protected carboxy group to form an amide linkage between the linker's free amino group and the unprotected side chain carboxy substituent of the amino acid using any of the condensation methods described in Section (B)(II)(1)(a) above. The t-butyl ester-protected α-carboxy substituent of the derivatized amino acid residue is then removed by acidolysis to permit incorporation of the derivatized amino acid into the peptide chain.

In another embodiment designed for use in conjunction with Fmoc chemistry, an orthogonally monoprotected difunctional linker-derivatized flanking residue is created by obtaining from a commercial source an amino acid residue with an Fmoc-protected α-amino substituent, an allyl-protected α-carboxy substituent, and an unprotected side chain carboxy substituent, and then reacting the α-substituent protected amino acid with a difunctional linker carrying a free amino group and either a Boc-protected amino group or a t-butyl ester-protected carboxy group to form an amide linkage between the linker's free amino group and the unprotected side chain carboxy substituent of the amino acid using any of the condensation methods described in Section (B)(II)(1)(a) above. The allyl-protected α-carboxy substituent of the derivatized amino acid residue is then removed by reduction to permit incorporation of the derivatized amino acid into the peptide chain.

In one embodiment designed for use in conjunction with Boc chemistry, an orthogonally monoprotected difunctional linker-derivatized flanking residue is created by obtaining from a commercial source an amino acid residue with an Boc-protected α-amino substituent, a Fm ester-protected α-carboxy substituent, and an unprotected side chain carboxy substituent, and then reacting the α-substituent protected amino acid with a difunctional linker carrying a free amino group and either an allyloxycarbonyl-protected amino group or an allyl-protected carboxy group to form an amide linkage between the linker's free amino group and the unprotected side chain carboxy substituent of the amino acid using any of the condensation methods described in Section (B)(II)(1)(a) above. The Fm ester-protected α-carboxy substituent of the derivatized amino acid residue is then removed by base saponification to permit incorporation of the derivatized amino acid into the peptide chain.

In another embodiment designed for use in conjunction with Boc chemistry, an orthogonally monoprotected difunctional linker-derivatized flanking residue is created by obtaining from a commercial source an amino acid residue with an Boc-protected α-amino substituent, an allyl-protected α-carboxy substituent, and an unprotected side chain carboxy substituent, and then reacting the α-substituent protected amino acid with a difunctional linker carrying a free amino group and either a Fmoc-protected amino group or a Fm ester-protected carboxy group to form an amide linkage between the linker's free amino group and the unprotected side chain carboxy substituent of the amino acid using any of the condensation methods described in Section (B)(II)1)(a) above. The allyl-protected α-carboxy substituent of the derivatized amino acid residue is then removed by reduction to permit incorporation of the derivatized amino acid into the peptide chain.

In another aspect, the foregoing embodiments utilizing a difunctional linker-derivatized flanking residue can be modified by orthogonally protecting the side chain amide bond-forming substituent of the underivatized (not pre-coupled to difunctional linker) flanking residue with respect to the α-amino protection chemistry used in peptide synthesis and with respect to any or all of the amide bond-forming substituents found in the side chains of other amino acid residues in the peptide. In this aspect, the side chain amide bond-forming substituent of the underivatized, flanking residue can be selectively deblocked, yielding a peptide that can be cyclized by a condensation reaction that is specifically targeted to be between the deprotected side chain amide bond-forming substituent of the underivatized, flanking residue and the free functional group of the difunctional linker. Suitable methods for orthogonal protection of side chain amide bond-forming substituents are described in Section (B)(II)(1)(a) above.

Following completion of solid phase peptide synthesis, the peptide can be cyclized by a coupling reaction between the free functional group of the difunctional linker and the side chain amide bond-forming substituent of the underivatized, flanking residue as described in Section (B)(II)(1)(b) above. Any blocking group(s) protecting the underivatized, flanking residue's side chain amide bond-forming substituent and/or the free functional group of the difunctional linker is (are) removed, and the deprotected groups are coupled to form an amide linkage using any of the condensation methods described in Section (B)(II)(1)(a) above. Optionally, the resulting cyclized (constrained helix) peptide is cleaved away from the solid support, recovered and purified.

Alternatively, the peptide can be cleaved away from the solid support prior to the cyclization step. In one embodiment, after synthesis of the linear peptide chain is complete, the peptide is cleaved away from the solid support. The peptide is recovered, deblocked at the side chain amide bond-forming substituent of the underivatized, flanking residue and/or the free functional group of the difunctional linker, and then cyclized at low concentration in a reaction mixture in order to maximize intramolecular amide bond formation. Typically, a maximum level of intramolecular amide bond formation can be achieved under conditions in which the concentration of the peptide provides an intramolecular concentration of free amide bond-forming substituents or groups that exceeds the intermolecular concentration of free amide bond-forming substituents or groups in the reaction mixture. In one embodiment, a peptide concentration of 1 nM to 1 M, and preferably 1 $\mu$M to 1 mM, and more preferably 1 $\mu$M to 100 $\mu$M, is used to maximize cyclization. The cyclization of free peptide can be conducted with any of the condensation reactions used to helicize solid phase peptide described above.

III. Methods for Constructing Semisynthetic Locked Helix Proteins

Also provided herein are semisynthetic proteins comprising locked helix peptides attached onto or incorporated in between one or more larger, recombinantly synthesized protein molecules. The semisynthetic, locked helix peptides of the invention can be made by any convenient method, including ligation of the locked helix peptides synthesized as described in Section (B)(II) above to one or more recombinantly synthesized protein sequences. For example, protein ligases such as the "subtiligases" can be used to concatenate the locked helix peptides made as described herein to larger, recombinantly synthesized protein fragments.

In one embodiment, the methods of the invention are modified in order to produce a locked helix peptide that functions as "first ligation substrate" in the subtiligase catalyzed peptide ligation methods described in International Patent Application No. PCT/US91/05480 (WO 92/02615 published Feb. 20, 1992) or as "donor ester", "donor peptide", and "$P_n$ . . . $P_4$-$P_3$-$P_2$-$P_1$-glc-F-amide ester", respectively, in the subtiligase catalyzed peptide ligation methods described in Abrahmsen et al., *Biochem.*, 30: 4151–4159(1991), Jackson et al., *Science*, 266: 243–247 (1994), and Chang et al., *Proc. Natl. Acad. Sci. USA*, 91: 12544–12548 (1994). The locked helix peptide can be synthesized such that the C-terminal amino acid residue of the cyclized peptide is in an ester linkage with the 2-hydroxyl group of a 2-hydroxycarboxylic acid, such as glycolic acid or lactic acid, to form a leaving group favored by the particular subtiligase of interest, i.e. such that the 2-hydroxycarboxylic acid ester, shown as the X residue of the "first ligation substrate" in FIG. 2B of WO 92/02615, resembles the first residue positioned on the N-terminal side of the hydrolyzable amide bond in the normal peptide substrate of subtilisin, shown as residue $P_1'$ of the "hydrolysis substrate" in FIG. 2B.

In another embodiment, the leaving group comprises a 2-hydroxycarboxylic acid and another amino acid residue, shown as the $R_2"$ residue of the first ligation substrate in FIG. 2B of WO 92/02615, wherein the carboxy group of the 2-hydroxycarboxylic acid residue is in an amide linkage with the α-amino group of the additional amino acid residue. In such embodiments, the amino acid residue in the leaving group can be selected to resemble the second residue positioned on the N-terminal side of the hydrolyzable amide bond in the normal peptide substrate of subtilisin, shown as residue $P_2'$ of the "hydrolysis substrate" in FIG. 2B of WO 92/02615. In a preferred embodiment, the leaving group is a glycolate-phenylalanyl (glc-F) moiety such as the glycolate-phenylalanyl-amide (glc-F-$NH_2$) moiety described in Example 2 of WO 92/02615.

In one aspect, the glc-F leaving group is placed in its proper position at the C-terminus of the locked helix peptide by obtaining a Boc- or Fmoc-α-amino protected phenylalanine, linking the α-amino protected phenylalanine to solid phase resin with an α-carboxy ester or amide linkage, deprotecting the protected α-amino group, adding a glycolic acid residue in the form of a t-butyl ether to form an amide linkage between the carboxy group of the glycolic acid and the free α-amino group of the solid phase phenylalanine, removing the t-butyl ether group from the glycolic acid residue with acid and forming an ester linkage between the free hydroxyl of the glycolic acid residue and the α-carboxy of the next amino acid residue in the C-terminal sequence desired for the locked helix peptide. Subsequent amino acids can be added and the resulting peptide can be helicized according to any of the above described methods which utilize standard Boc or Fmoc chemistry for peptide synthesis. In one embodiment, a glc-F-$NH_2$ leaving group is incorporated into the desired peptide chain essentially as described in Example 2 of WO 92/02615 or as described in Jackson et al., *Science,* 266: 243–247 (1994).

In yet another embodiment, the "donor peptide" includes a flexible linker sequence between the C-terminal residue of the locked helix peptide sequence and the leaving group sequence, such as a di- or tri-glycine linker, to promote flexibility and accessibility of the donor peptide's leaving group to subtiligase.

After the donor peptide (with the helix locking tether in place) is obtained, a subtiligase can be used to ligate a peptide or protein fragment (produced by recombinant or other synthetic methods), designated the "second ligation substrate" in FIG. 2C of WO 92/02615, the "acceptor peptide" in FIG. 1 on page 244 of Jackson et al., *Science,* 266: 243–247 (1994), and the "Nucleophile" peptide in the synthetic scheme on page 12545 of Chang et al., *Proc. Natl. Acad. Sci. USA,* 91: 12544–12548 (1994), to the C-terminus of the donor peptide by displacement of the leaving group according to any of the subtiligase-catalyzed peptide ligation methods described above. In embodiments using acceptor peptides or proteins having a relatively inaccessible N-terminus due to higher order protein structure, ligation efficiency can be improved by altering the design of the acceptor peptide to incorporate a flexible linker sequence, such as a di- or tri-glycine sequence, at the N-terminus to promote flexibility and accessibility of the acceptor peptide N-tenninus in the peptide ligation reaction. Alternatively, the accessibility of the acceptor peptide N-terminus and/or donor peptide C-terminus to subtiligase can be improved by conducting the ligation reaction under denaturing conditions which eliminates unfavorable structural conformations that may be assumed by the peptide substrates. In such embodiments, it is preferable to use a denaturation-stable subtiligase, such as the "stabiligase" described in Chang et al., supra (capable of retaining nearly 50% of catalytic activity in 4 M guanidine hydrochloride).

It will be appreciated that additional peptides can be synthesized with a suitable leaving group at the C-terminus and successively ligated to the N-terminus of the semisynthetic peptide containing the locked helix moiety by repeating the foregoing procedures until a completed peptide with the desired N-terminus is obtained.

In the event that the completed, semisynthetic, locked helix protein is obtained in a denatured, incorrectly folded, or otherwise inactive form as a result of the synthetic procedures used, the inactive species can be refolded into the native or active conformation by renaturation techniques that are well known in the art. Typical renaturation procedures use a chaotrope, such as urea at high pH or guanidine hydrochloride, to unfold inactive material followed by dilution of the denaturant to permit refolding to occur, while preventing the formation of random disulfide bonds prior to the assumption of the biologically active conformation through non-covalent, intramolecular interactions (see, U.S. Pat. Nos. 4,512,922; 4,518,256; 4,511,502; and 4,511,503). Reversed micelles or ion exchange chromatography are used to assist refolding of denatured proteins by enclosing a single protein molecule within micelles or isolating proteins on a resin and then removing the denaturant (Hagen et al., *Biotechnol Bioeng.,* 35: 966–975 (1990); Creighton in *Protein Structure Folding and Design,* Oxender, D. L., ed., Alan R. Liss, Inc. (New York: 1985), pp. 249–251. In addition, conformation-specific refolding can be performed with ligands and antibodies to the native structure of the protein (Cleland and Wang in *Biotechnology,* Rehm, H.-J., and Reed, G., eds, VCH (New York), pp. 528–555. Since they are more likely to interact with the protein in its native conformation, these binding molecules can be used to guide the folding reactions towards native state protein. The foregoing recovery methods are regarded as being universally applicable, with minor modifications, to the recovery of biologically active recombinant proteins from inclusion bodies, and are equally applicable to the recovery of biologically active proteins from the semisynthetic methods of the invention.

IV. Methods for Constructing Macromolecule-Bound Locked Helix Peptides

In one embodiment, the constrained, helical peptides of the invention bound to a macromolecular solid support can be obtained by constructing the locked helix peptides with the solid phase synthesis techniques described in Section (II) above and recovering the intact, solid support-peptide conjugate. Alternatively, the cyclized peptide can be cleaved away from solid phase following synthesis and then attached to the macrom olecule of choice by any convenient method known in the art. For example, a commonly employed technique for attaching peptide ligands to polysaccharidematrices, e.g. agarose, dextran or cellulose, involves activation of the carrier with cyanogen halides and subsequent coupling of the peptide's primary aliphatic or aromatic amines to the activated matrix. The activation of polysaccharides with cyanogen bromide (CNBr) at alkaline pH was introduced to affinity chromatography by Axen et al., *Nature,* 214: 1302 (1967). In one aspect of the invention, the activation of polysaccharide matrices, particularly agarose matrices, is performed according to the titration-activation method. In this procedure, for example, 20 g of exhaustively washed moist agarose cake is added to 20 ml of water in a 100 ml beaker equipped with a 0–100° C. thermometer, a pH meter and a 25 mm magnetic stirring bar. The suspension is stirred slowly,the temperature lowered to about 10–15° C. by the addition of crushed ice and the pH adjusted to 10.8±0.1 by the addition of 1–2 drops of 4 N NaOH. The activation procedure is initiated by the addition of the CNBr and the pH of the reaction maintained at 10.8±0.1 by manual titration with the 4 N NaOH. The CNBr (100 g/mg moist weight gel) can be added as a crystalline solid, a crushed solid, an aqueous solution or by adding an aliquot of a stock solution. The latter can be prepared by dissolving CNBr in acetonitrile (1 g/ml) and storing in a tightly stoppered vial at −20° C. The temperature is subsequently allowed to rise to 18–20° C.

Despite the relative simplicity of the titration method, it may be preferable to use the faster and technically simplified method of March et al., *Anal. Biochem.*, 60: 149 (1974). The activation procedure is performed in concentrated carbonate buffer. The required amount of washed gel is suspended in an equal volume of 2 M $NaHCO_3$—$NaCO_3$ buffer (pH 10.9) in a beaker equipped with a thermometer and magnetic stirring bar. The slurry is cooled to approximately 4–5° C., the activated gel is transferred to a sintered funnel and washed.

The concentration of CNBr recommended in the procedures described above is satisfactory for moderate levels of peptide substitution. When lower or higher levels of activation are required, 50 mg and 200–300 mg CNBr/g moist weight gel respectively can be employed together with 2 M and 8 M NaOH for the titration.

It is generally recognized that the CNBr-activated intermediate functional groups of polysaccharide gels display limited stability and therefore it is preferable that the gel be washed as rapidly as possible prior to transferring the gel to the coupling-reaction medium. At the end of the activation step, the gel is rapidly cooled by the addition of crushed ice and poured into a large sintered glass funnel which has been pre-cooled with crushed ice. The suspension is rapidly filtered into a Buchner flask (2 liter) containing solid ferrous sulfate to remove unreacted CNBr and cyanides as harmless ferrocyanide. The gel is subsequently washed under suction with 1 liter ice-cold distilled water and 1 liter of the buffer to be used in the coupling stage, typically ice-cold 0.1 M $NaHCO_3$—$NaCO_3$ buffer (pH 8.5–9.5).

CNBr-activated Sepharose 4B is available commercially from Pharmacia and obviates the hazardous manipulation of CNBr. The activated gel is freeze dried in the presence of dextran and lactose to preserve the beaded form and supplied in 15 g air-tight packs. The required amount of freeze-dried powder is swollen in 1 mM HCl on a glass filter and washed with at least 200 ml of the same solution per gram of powder. 1 g of freeze-dried material is roughly equivalent to 3.5 ml final gel volume. The peptide ligand-binding capacity of the gel is conserved more effectively by washing with solutions of low pH than with solutions of pH greater than 7. The gel is then ready to couple peptide ligand as soon as the washing is completed.

Pharmacia also markets CNBr-activated Sepharose 6 MB for use in cell biology and immunology for the separation of "functionally homogeneous cell populations". It is produced by activation of Sepharose6MB macrobeads (diameter 200–300 μm) with cyanogen bromide and is handled in a manner analogous to CNBr-activated Sepharose 4B.

The peptide to be coupled is suspended in a volume of the cold buffer equal to the volume of the packed gel, added to the moist, washed gel and then the suspension is immediately mixed (in a Buchner funnel) with a glass stirring rod. The entire procedure of washing, adding the peptide solution, and mixing preferably consumes less than 90 seconds. The suspension is transferred from the Buchner funnel to a beaker containing a magnetic mixing bar and is gently stirred at 4° C. Although the reaction is essentially complete in 2 to 3 hours, the mixture is allowed to stand at 4° C. for 16 to 20 hours to insure complete loss of reactive polysaccharide groups. The peptide-linked gel is then washed with large volumes of water until it is established that peptide is no longer being removed.

The quantity of peptide coupled to the polysaccharide gel can in part be controlled by the amount of peptide added to the activated matrix. When highly substituted polysaccharide gel derivatives are desired, the amount of peptide added should be 20 to 30 times greater than that which is desired in the final product. For ordinary procedures, 100 to 150 mg of cyanogen bromide are used per ml of packed polysaccharide gel, but much higher coupling yields can be obtained if this amount is increased to 250 to 300 mg. The pH at which the coupling reaction is performed also affects the degree of coupling, since it is only the unprotonated form of a peptide's amino groups that reacts with CNBr-activated polysaccharides. Preferably, the N-terminal α-amino group of the peptide ligand is used for coupling with the activated polysaccharide matrix. α-amino groups will couple optimally at a pH of about 9.5 to 10.0. If coupling at the ∈-amino group(s) of the selected peptide ligand (such as the ∈-amino groups of the lysinyl residues) is desired, the coupling reaction should be conducted at a pH value of about 10.0, and a large excess of peptide should be added. If coupling at the aromatic amino groups in the histidyl or tryptophanyl residues of the selected peptide is desired, very high coupling efficiency can be obtained at pH values between 8 and 9.

Further details of the invention can be found in the following examples, which further define the scope of the invention. All references cited throughout the specification, and the references cited therein, are hereby expressly incorporated herein by reference in their entirety.

EXAMPLES

Example 1

Experimental Section

Computational Methods

All calculations were performed with the DISCOVER program (Biosym Technologies, San Diego) using the all-atom AMBER force field (Weiner, S. J.; Kollman, P. A.; Case, D. A.; Singh, U. C.; Ghio, C.; Alagona, G.; Profeta, S., Jr.; Weiner, P. *J. Am. Chem. Soc.* 1984, 106, 765–784; Weiner, S. J.; Kollman, P. A.; Nguyen, D. T.; Case, D. A. *J. Comp. Chem.* 1986, 7, 230–252) with a distance dependent dielectric constant ($\in=4r$).

Synthesis

Materials and Methods

Peptides were synthesized using standard solid phase synthesis techniques (Merrifield, R. B. *J. Am. Chem. Soc.* 1963, 85, 2149–2154; Kaiser, E.; Colescot, R. L.; Bossinger, C. D.; Cook, P. I. *Anal. Biochem.* 1970, 34, 595–598). Organic chemicals were purchased from Aldrich (Milwaukee Wis.) or Fluka (Ronkonkoma, N.Y.). Protected amino acids were purchased from Bachem Calif. (Torrance Calif.) or Peninsula Labs (Belmont Calif.). BOP (benzotriazole-1-yl-oxy-tris [dimethylamnino] phosphonium hexafluorophosphate) was purchased from Richelieu Biotechnologies (Montreal). Solvents were purchased from Baxter (McGaw Park Ill.), Baker (Phillipsburg N.J.), or Mallinckrodt (Paris Ky.). Polystyrene supports were purchased from Advanced ChemTech (Louisville Ky.).

Mono-t-butyloxycarbonyl (BOC) 1,3-propanediamine was prepared as follows. 2-(tert-butoxycarbonyloxyimino)-2-phenylacetonitrile (18 g, 73 mmol) was added portionwise over 10 minutes to a solution of 1,3-diaminopropane (12.5 g, 184 mmol) in 100 mL of tetrahydrofiran cooled to 0° C. After four hours at 0° C. the reaction was allowed to warm to 25° C. for two hours. The reaction was diluted with 150 mL of ethyl acetate and washed twice with 100 mL of saturated aqueous sodium chloride. The organic phase was extracted with three 100 mL volumes of 10% aqueous citric acid, the combined aqueous portions were then washed twice with 100 mL of ethyl acetate. The aqueous phase was cooled in an ice bath and the pH was adjusted to approximately 13 with 50% sodium hydroxide. The basic aqueous phase was then extracted with three 100 mL volumes of dichloromethane. The organic portion was then dried with potassium carbonate and filtered. Solvent was removed by rotary evaporation to yield mono-tert-butyloxycarbonyl-1, 3-diaminopropane.

Peptides were purified by reverse-phase HPLC on a Vydac C-18 column, eluted with acetonitrile-water gradients containing 0.1% v/v trifluoroacetic acid (TFA). Peptides were characterized by electrospray MS on a PE SCIEX API III+triple quadrupole mass spectrometer and by quantitative amino acid analysis on a Beckmann 6300 automated amino acid analyzer. Organic intermediates were analyzed by $^1$H and $^{13}$C nuclear magnetic resonance (NMR) on a Varian VXR-300S and by high-resolution mass spectrometry (MS) on a JEOL JMS-HX110HF/HX110 HF tandem mass spectrometer.

AcTNE(OFm)DLAARRE(OAllyl)QQnh-MBHA-polystyrene (1a)

Linear peptide 1a with the sequence shown was synthesized on p-MBHA resin (4.25 grams (g), 0.57 milliequivalents/gram (meq/g), 2.42 millimoles (mmol)) using standard coupling cycles with three molar equivalents of BOC-amino acid, 3.3 molar equivalents of BOP and 3.3 molar equivalents of N-methylmorpholine in dichloromethane ($CH_2Cl_2$) and dimethyl acetamide (DMA) if needed for solubility, for one hour at room temperature. The N-acetyl cap was attached by treatment with 5 milliliters (mL) of acetic anhydride in 3% triethylamine(TEA) in $CH_2Cl_2$ for 20 minutes at room temperature. The resin was dried and weighed (4.41 g, estimated at 0.22 meq/g).

AcTNE(OFm)DLAARRE(OFm)QQnh-MBHA-polystyrene (1f)

AcAEE(OFm)AAAKFLE(OAllyl)AHAnh-MBHA-polystyrene (2a)

Linear peptides 1f and 2a as shown were synthesized as described above for 1a.

AcTNQ(γ-NHCH$_3$)DLAARRQ(γ-NHCH$_3$)QQnh$_2$ (1b)

Linear resin-bound peptide 1f (0.60 g, 0.17 mmol) was doubly deprotected with 20% piperidine/DMA for 20 minutes. The free carboxylic acids were coupled to methylamine ($CH_3NH_3Cl$, 0.26 g, 3.85 mmol) with BOP (1.57 g, 3.55 mmol) and N-methyhmorpholine (0.90 mL, 8.2 mmol) in $CH_2Cl_2$/DMA for 1.5 hours. The resin was washed and dried, and the peptide-resin bond was cleaved with anhydrous hydrofluoric acid (HF) (10 mL) at 0° C. for one hour with anisole (1 mL) and ethylmethylsulfide (EtSMe)(0.5 mL) as scavengers. The resin was washed twice with ether, once with ethyl acetate, and again with ether. The free peptide was then extracted from the resin with sequential washes of 10% acetic acid, glacial acetic acid, acetonitrile, 10% acetic acid, and water. The combined solutions were lyophilized and the residue was purified.

cyclo-AcTNQ(γ-NH)DLAARRQ(γ-NH)QQnh$_2$ (1c)

1. Using Unprotected Propanediamine

Linear peptide 1a on the resin (0.51 g, 0.11 mmol) was deprotected at the fluorenylmethyl ester with 20% piperidine/DMA for 20 minutes and the resulting piperidine salt was neutralized by washing twice with 1% TFA in $CH_2Cl_2$. The free carboxylic acid was coupled to 1,3-propanediamine (0.12 mL, 1.44 mmol) with BOP (0.40 g, 0.90 mmol) and diisopropylethylamine(DIPEA) (0.17 mL, 0.98 mmol) in $CH_2Cl_2$ for one hour, followed by addition of DMA and continued coupling for an additional 45 minutes. The glutamic acid allyl ester was deprotected with tetrakis (triphenylphosphine)palladium(0)(Pd(PPh$_3$)$_4$)(0.21 g, 0.18 mmol) in 20% piperidine/DMA for 1.5 hours and the piperidine was removed by washing twice with 1% TFA in $CH_2Cl_2$. The resulting amino acid was cyclized with BOP (0.32 g, 0.72 mmol) and DIPEA (0.13 mL, 0.75 mmol) in $CH_2Cl_2$ for 3.5 hours. A Kaiser test gave a noticeable purple color, so the cyclization was repeated with BOP (0.44 g, 0.99 mmol) and DIPEA (0.19 mL, 1.09 mmol) in $CH_2Cl_2$ for three days. The peptide was cleaved from the resin as described above for 1b.

2. Using Mono-BOC Propanediamine

Linear peptide 1a on the resin (0.57 g, 0.13 mmol) was deprotected at the fluorenylmethyl ester with 20% piperidine/DMA for 0.5 hour and the resulting piperidine salt was neutralized by washing twice with 1% TFA in $CH_2Cl_2$. The free carboxylic acid was coupled to mono-tert-butyloxycarbonyl-1,3-propanediamine (0.23 g, 1.32 mmol) with BOP (0.52 g, 1.18 mmol) and DIPEA (0.25 mL, 1.44 mmol) in $CH_2Cl_2$/DMA for one hour. The glutamic acid allyl ester was deprotected with Pd(PPh$_3$)$_4$ (0.21 g, 0.18 mmol) in 20% piperidine/DMA for 1.5 hours and the piperidine was removed by washing twice with 1% TFA in $CH_2Cl_2$; the Kaiser test was negative at this point. The BOC group was removed with TFA/$CH_2Cl_2$/anisole/1,2-ethanedithiol (45:45:5:5 vol/vol); the free amine then gave a positive Kaiser test. The resulting amino acid was cyclized with BOP (0.58 g, 1.31 mmol) and DIPEA (0.30 mL, 1.72 mmol) in $CH_2Cl_2$ for two hours, whereupon the Kaiser test gave only a faint blue-green color. The peptide was cleaved from the resin as described above for 1b.

AcAEQ(γ-NHCH$_3$)AAAKFLQ(γ-NHCH$_3$)AHAnh$_2$ (2b)

Linear peptide 2a on the resin (0.60 g, 0.19 mmol) was deprotected at both the allyl and the fluorenylmethyl esters with Pd(PPh$_3$)$_4$ (0.1 g, 0.09 mmol) in 20% piperidine/DMA for 30 minutes and the resulting piperidine salt was neutralized by washing with 50% TFA in $CH_2Cl_2$ containing anisole and 1,2-ethanedithiol. The free carboxylic acids were coupled to methylamine (40% aqueous, 0.16 mL, 1.86 mmol) with BOP (0.32 g, 0.72 mmol) and DIPEA (0.35 mL, 2.01 mmol) in $CH_2Cl_2$/DMA for 1 hour. The peptide was cleaved from the resin as described above for 1b.

1d, 1e, 2c, 2d, 2e 1d and 1e were prepared from 1a and 2c–2e were prepared from 2a by the same procedures as described above for 1c using unprotected 1,3-propanediamine, coupling with 1,4-butanediamine for 1d and 2d and with 1,5-pentanediamine for 1e and 2e.

AcTNk(S-Acm)DLAARRK(S-Acm)QQnh$_2$ (3a)

AcAEk(S-Acm)AAAKFLK(S-Acm)AHAnh$_2$ (4a)

Linear peptides 3a and 4a were synthesized by standard Merrifield techniques using FMOC chemistry (Atherton, E.;

Sheppard, R. C. J. Chem. Soc., Chem. Commun. 1985, 165–166). Fmoc-D-Thiolys(Acm)-OH (7, k(S-Acm)) and Fmoc-L-Thiolys(Acm)-OH (10, k(S-Acm)) were prepared as described below.

AcTNk(S)DLAARRK(S)QQnh$_2$ (3b)

AcAEk(S)AAAKFLK(S)AHAnh$_2$ (4b)

Cyclic peptides 3b and 4b were prepared from 3a and 4a respectively by simultaneous deprotection and oxidation. Approximately 16 mg of Acm-protected peptide was dissolved in 1.5 mL of water containing 10% acetic acid and then diluted to 50 mL total volume with trifluoroethanol to give a final concentration of approximately 200 micromoles/liter ($\mu$M). A total of 12 mL of a 6 millimoles/liter (mM) solution of iodine (80 milligrams (mg) dissolved in 3 mL of acetic acid and diluted to 50 mL with trifluoroethanol) was added in 1 mL portions over the course of 10 hours while the reaction progress was monitored by HPLC. When the starting material had been consumed, the reaction was diluted with water and lyophilized and the crude oxidized material was purified.

(2S,5R)-2,5-dihydro-3,6-diethoxy-2-isopropyl-5-(4-bromobutyl)pyrazine (5)

n-butyllithium (13.3 mL of a 1.6 M solution in hexanes, 21.3 mmol) was added to a solution of (2S)-2,5-dihydro-3,6-diethoxy-2-isopropyl pyrazine (Schöllkopf reagent)(4.30 g, 20.3 mmol) in tetrahydrofuran (THF) over the course of five minutes. The solution was maintained at −78° C. for 15 minutes after which 1,4-dibromobutane (9.75 mL, 81.2 mmol) was added in a single portion. After 2.5 hours at −78° C. the reaction was allowed to warm to room temperature and diluted with diethyl ether (100 mL). The organic phase was washed with water (100 mL), brine (100 mL) and then dried with magnesium sulfate (MgSO$_4$). Following filtration and concentration most of the residual 1,4-dibromobutane was removed under high vacuum. The remaining oil was purified by silica gel chromatography (2% ethyl acetate in hexanes) to provide 5 (3.7 g, 57%) as a colorless liquid;[$\alpha$]$^{25}_D$−1.13° (c=4.5, CHCl$_3$); IR (thin film) 2957, 1689, 1456, 1364, 1304, 1230, 1144, 1038 cm$^{-1}$; $^1$H NMR(300 MHz, CDCl$_3$) $\delta$4.04–4.18 (m, 4H) 3.94–4.02 (m, 1H) 3.90 (t, J=3.9, 1H) 3.39 (t, J=6.9, 2H) 2.21–2.32 (m, 1H) 1.68–1.92 (m, 4H) 1.33–1.47 (m, 2H) 1.274 (t, J=7.2, 3H) 1.268 (t, J=7.2, 3H) 1.03 (d, J=6.9, 3H) 0.70 (d, J=6.9, 3H); $^{13}$C NMR (100.6 MHz, CDCl$_3$) d 163.12, 163.05, 60.72, 60.48, 55.09, 33.60, 33.11, 32.66, 31.80, 23.22, 19.03, 16.6, 14.34, 14.31; Mass Spectrum (FAB+) 347.1 (MH+).

(2S,5R)-2,5-dihydro-3,6-diethoxy-2-isopropyl-5-(4-4-methoxybenzyl)-thiobutyl) pyrazine (6)

Potassium tert-butoxide (11.8 mL of a 1 M solution in THF) was added over five minutes to a solution of 4-methoxy-$\alpha$-toluenethiol (1.85 mL of 90%, 11.8 mmol) in THF (20 mL) at 25° C., generating a thick white precipitate which was stirred for 25 minutes. A solution of 5 (3.7 g, 10.7 mmol) in THF (20 mL) was added and stirring continued for three hours. The reaction was concentrated by rotary evaporation and then partitioned between water (50 mL) and diethyl ether (100 mL). The organic portion was washed with brine, dried (MgSO$_4$), and concentrated. The residue was purified by silica gel chromatography (1% increasing to 2.5% ethyl acetate in hexanes) to provide 6 (2.90 g, 91%) as a colorless oil; [$\alpha$]$^{25}_D$−3.77° (c=3.5, CHCl$_3$); IR (thin film) 2957, 1689, 1510, 1238, 1038 cm$^{-1}$; $^1$H NMR (300 MHz, CDCl$_3$) $\delta$7.21 (d, J=8.7, 2H) 6.84 (d, J=8.4, 2H) 4.02–4.20 (m, 4H) 3.93–3.99 (m, 1H) 3.88 (t, J=3.3, 1H) 3.80 (s, 3H) 3.65 (s, 2H) 2.39 (t, J=7.5, 2H) 2.20–2.32 (m, 1H) 1.64–1.82 (m, 2H) 1.50–1.62 (m, 2H) 1.22–1.38 (m, 2H) 1.27 (t, J=7.2, 6H) 1.03 (d, J=6.9, 3H) 0.70 (d, J=6.9, 3H); $^{13}$C NMR (100.6 MHz CDCl$_3$) $\delta$163.20, 163.00, 158.50, 130.57, 129.80, 113.80, 60.67, 60.45, 60.40, 55.24, 55.20, 35.57, 33.68, 31.74, 31.14, 29.19, 23.92, 19.05, 16.60, 14.36, 14.32; Mass Spectrum (FAB+) 421.2 (MH+).

(2R) 2-(9-Fluorenylmethoxycarbonyl)amino-6-acetamidomethylthiohexanoic acid (D-Thio(Acm) lysine) (7)

Water (30 mL) and 3N HCl (6.5 mL) was added to a solution of 6 (2.90 g, 9.32 mmol) in THF (50 mL). The mixture was stirred at 25° C. for 12 hours and then the THF was removed by rotary evaporation. The solution was adjusted to pH 10 with aqueous potassium carbonate (K$_2$CO$_3$) and then extracted twice with ethyl acetate (75 mL). The organic extracts were dried (MgSO$_4$), concentrated and the residue was purified by silica gel chromatography (1:1 increasing to 2:1 ethyl acetate/hexanes with 0.5% triethylamine) to yield crude S-methoxybenzylthiolysineethyl ester (2.65 g, 91%) as a colorless oil which was carried on directly to the next step. This ester (3.02 g, 9.71 mmol) was dissolved in a mixture of trifluoroacetic acid (50 mL) and anisole (1 mL) at 0° C., and mercuric acetate (3.09 g, 9.71 mmol) was added to give a clear solution. After 15 minutes the trifluoroacetic acid was removed by rotary evaporation and the residue was first diluted with water (75 mL), then washed with diethyl ether (75 mL). The aqueous portion was treated with hydrogen sulfide (H$_2$S) (bubbled through the solution) for 30 minutes and the resulting black precipitate was removed by filtration through a bed of celite. The filtrate was concentrated by rotary evaporation, redissolved in water (20 mL) and filtered through a 0.45 micrometer ($\mu$m) nylon filter. The solution was again concentrated and the residual foam was dried under high vacuum overnight. The residue was dissolved in trifluoroacetic acid (15 mL) and acetamidomethanol (Fluka, 0.95 g, 10.7 mmol) was added. After 45 minutes the reaction was concentrated by rotary evaporation and then dried under high vacuum overnight. The residue was dissolved in THF (20 mL) and cooled to 0° C. A solution of lithium hydroxide (1.22 g, 29.1 mmol) in water (20 mL) was added in two portions at 15 minute intervals. After two hours the reaction was allowed to warm to room temperature and the pH was adjusted to 7.0 with 1 mole/liter (M) aqueous citric acid. The solvent was removed by rotary evaporation, the residue was dissolved in dioxane (80 mL), and Fmoc N-hydroxy succinimide (3.3 g, 9.71 mmol) was added followed by saturated aqueous sodium bicarbonate (NaHCO$_3$) (15 mL). After one hour, the solvent was removed by rotary evaporation and the residue was partitioned between water (50 mL) and ethyl acetate (50 mL). The aqueous portion was adjusted to pH 2.5 with 1 M aqueous citric acid and then extracted three times with ethyl acetate (75 mL each). The combined organic phases were dried (MgSO$_4$) and concentrated. The residue was purified by silica gel chromatography (first with 2:1 ethyl acetate/hexanes with 0.5% acetic acid, then ethyl acetate with 0.5% acetic acid, then 5% methanol in ethyl acetate with 0.5% acetic acid), product containing fractions were concentrated from toluene (150 mL, three times) prior to dissolution in water with acetonitrile and lyophilization to provide 7 (3.16 g, 71% over four steps) as a white powder; [$\alpha$]$^{25}_D$−1.8° (c=2, EtOH); IR (thin film)2800–3400, 1709, 1536, 1260, 759, 740 cm$^{-1}$; $^1$H NMR (300 MHZ, DMSO-d6) δ8.42 (t, J=6.0, 1H) 7.88 (d, J=7.3, 2H) 7.72 (d, J=7.5, 2H) 7.58 (d, J=8.1, 1H) 7.407 (t, J=7.5, 2H) 7.32 (t, J=7.5, 2H) 4.16–4.30 (m, 5H) 3.91 (m, 1H) 2.53 (t, J=7.2, 2H) 1.82 (s, 3H) 1.33–1.76 (m, 6H); $^{13}$C NMR (100.6 MHZ, DMSO-d6) δ174.00, 169.16, 156.08, 143.86, 143.80, 140.71, 127.61, 127.05, 125.28, 120.08, 65.57, 53.90, 46.68, 30.54, 30.01, 28.79, 24.91, 22.54; High Resolution Mass Spectrum (FAB+) 457.1785, Err[ppm/mmu] −2.7/−1.2.

(2R,5S)-2,5-dihydro-3,6-dimethoxy-2-isopropyl-5-(4-bromobutane) pyrazine (8)

$[\alpha]^{25}{}_D$+1.73° (c=4.4, CHCl$_3$); IR (thin film) 2959, 1696, 1458, 1434, 1237, 1196, 1007 cm$^{-1}$; $^1$H NMR (300 MHZ, CDCl$_3$) δ3.98–4.07 (m, 1H) 3.95 (t, J=3.6, 1H) 3.70 (s, 3H) 3.68 (s, 3H) 3.40 (t, J=6.9, 2H) 2.19–2.32(m, 1H) 1.66–1.94 (m, 4H) 1.34–1.48 (m, 2H) 1.05 (d, J=6.9, 3H) 0.69 (d, J=6.9, 3H); $^{13}$C NMR (100.6 MHZ, CDCl$_3$) δ163.62, 163.60, 60.77, 55.11, 52.31, 33.54, 33.10, 32.61, 31.73, 23.26, 19.02, 16.56; Mass Spectrum (FAB+) 319.1 (MH+).

(2R,5S)-2,5-dihydro-3,6-dimethoxy-2-isopropyl-5-(4-(4-methoxybenzyl)-thiobutyl) pyrazine (9)

$[\alpha]^{25}{}_D$+3.96° (c=3.63, CHCl$_3$); IR (thin film) 2944, 1696, 1510, 1238 cm$^{-1}$; $^1$H NMR (300 MHZ, CDCl$_3$) δ7.21 (d, J=8.7, 2H) 6.83 (d, J=8.4, 2H) 3.97–4.25 (m, 1H) 3.93 (t, J=3.3, 1H) 3.79 (s, 3H) 3.68 (s, 3H) 3.67 (s, 3H) 3.65 (s, 2H) 2.39 (t, J=7.5, 2H) 2.18–2.30 (m, 1H) 1.60–1.84 (m, 2H) 1.49–1.62 (m, 2H) 1.23–1.38 (m, 2H) 1.27 (t, J=7.2, 6H) 1.04 (d, J=6.9, 3H) 0.68 (d, J=6.9, 3H); $^{13}$C NMR (100.6 MHZ, CDCl$_3$) δ163.72, 163.47, 158.48, 130.55, 129.78, 113.78, 60.68, 55.22, 55.18, 52.27, 35.58, 33.63, 31.64, 31.12, 29.13, 23.88, 19.02, 16.51; Mass Spectrum (FAB+) 393.2 (MH+).

(2S) 2-(9-Fluorenylmethoxycarbonyl)amino-6-acetamidomethylthiohexanoicacid: (L-Thio(Acm) lysine) (10)

$[\alpha]^{25}{}_D$+1.3° (c=2, EtOH); IR (thin film) 2800–3400, 1709, 1536, 1260, 759, 740 cm$^{-1}$; $^1$H NMR (300 MHZ, DMSO-d6) δ8.42 (t, J=6.0, 1H) 7.88 (d, J=7.3, 2H) 7.72 (d, J=7.5, 2H) 7.58 (d, J=8.1, 1H) 7.407 (t, J=7.5, 2H) 7.32 (t, J=7.5, 2H) 4.16–4.30 (m, 5H) 3.91 (m, 1H) 2.53 (t, J=7.2, 2H) 1.82 (s, 3H) 1.33–1.76 (m, 6H); $^{13}$C NMR (100.6 MHZ, DMSO-d6) δ174.00, 169.16, 156.08, 143.86, 143.80, 140.71, 127.61, 127.05, 125.28, 120.08, 65.57, 53.90, 46.68, 30.54, 30.01, 28.79, 24.91, 22.54; High Resolution Mass Spectrum (FAB+) 457.1776, Err[ppm/mmu] −4.6/−2.1.

These materials were prepared in the same manner as 5, 6, and 7 starting from (2R)-2,5-dihydro-3,6-dimethoxy-2-isopropyl pyrazine (Merck).

NMR Spectroscopy

For each peptide, 2–4 mg of purified material was dissolved in 440 microliters (μl) of 25 mM d$_3$-sodium acetate containing 5% deuterium oxide (D$_2$O) and 0.1 millimoles/liter (mM) sodium azide yielding a total peptide concentration of 1–6 mM; the pH was adjusted to 4.5 by microliter additions of 1M sodium hydroxide (NaOH). All spectra were acquired at 5° C. or 10° C. on a Bruker AMX-500 spectrometer. Two dimensional COSY (Aue, W. P., Bartholdi, E. & Ernst, R. R. *J. Chem. Phys.* 1976, 64, 2229–2246), ROESY (Bothner-By, A. A., Stephens, R. L., Lee, J.-m., Warren, C. D. & Jeanloz, R. W. *J. Am. Chem. Soc.* 1984, 106, 811–813; Rance, M. *J. Magn. Reson.* 1987, 74, 557–564) and TOCSY (Braunschweiler, L. & Ernst, R. R. *J. Magn. Reson.* 1983, 53, 521–528; Bax, A. & Davis, D. G. *J. Magn. Reson.* 1985, 65, 355–360) spectra were acquired with phase discrimination in ω$_1$ achieved with TPPI (Marion, D. & Wüthrich, K. *Biochem. Biophys. Res. Commun.* 1983, 113, 967–974). Total acquisition times were approximately 2, 4, and 12 hours for COSY, TOCSY and ROESY spectra, respectively. Water suppression was achieved by coherent low power irradiation of the water resonance for the 1.5 second(s) recycle delay. ROESY and TOCSY spectra were acquired as described by Akke, M., Skelton, N. J., Kördel, J. & Chazin, W. J. In *Techniques in Protein Chemistry II; Villafranca, J. J., Ed.; Academic Press, Inc.: Boca Raton, Fla.*, 1991; pp. 401–408; in addition, first-order phase corrections were avoided by acquisition in a sine-modulated fashion in ω$_1$. TOCSY mixing was achieved with a clean DIPSI-2rc sequence applied for 90 milliseconds(ms) (Cavanagh, J. & Rance, M. *J. Magn. Reson.* 1992, 96, 670–678). The ROESY spectra were collected with a 4.0 kilohertz(kHz) spin-lock pulse of 200 ms duration. The spectra were processed and analyzed using the Felix software package (Biosym Technologies, San Diego, Calif.). $^3J_{HN-H\alpha}$ were obtained by fitting an antiphase pair of Lorentzian lines to ω$_2$ slices of high digital resolution COSY spectra.

Amide proton exchange rates with solvent were measured for 1b and 1c by lyophilizing the peptide from H$_2$O and acquiring a series of one dimensional (1D) NMR spectra immediately after dissolving the peptide in D$_2$O. Exchange rate constants were determined by performing a three parameter exponential fit to the decaying amide signals. Protection factors were calculated as the ratio of exchange rate in the cross-linked and uncross-linked peptide.

Structure Calculation

NOESY (Kumar, A., Ernst, R. R. & Wüthrich, K. *Biochem. Biophys. Res. Commun.* 1980, 95, 1–6; Bodenhausen, G., Kogler, H. & Ernst, R. R. *J. Magn. Reson.* 1984, 58, 370–388) and ROESY data were collected with mixing times of 300 ms and 200 ms, respectively, from water (H$_2$O) and D$_2$O using a sample of 1c (approximately 8 mM). Total acquisition times were 24 hours per experiment. Distance restraints were generated from these data by categorizing cross-peaks as strong, medium, weak or very weak according to the integrated peak volume, and assigning an upper bound of 2.9, 3.5, 4.6, or 5.6 angstroms (Å), respectively, to the corresponding interproton distance. The dihedral angle φ was restrained between −90° and −40° for residues in which $^3J_{HN-H\alpha}$ less than 6.0 hertz (Hz). Values of $^3J_{H\alpha-H\beta}$ were determined from a COSY spectrum acquired in D$_2$O solution with a 35° mixing pulse. χ$_1$ restraints and H$_\beta$ stereospecific assignments were obtained for four side-chains on the basis of these coupling constants and the results of initial structure calculations (Skelton, N. J., Garcia, K. C., Goeddel, D. V., Quan, C. & Burnier, J. P. *Biochemistry* 1994, 33, 13581–13592).

Structures were calculated using the program DGII using the CVFF force field parameters (Biosym Technologies, San Diego, Calif.). Input restraints consisted of 141 interproton distances, 9 φ dihedral angle restraints and 5χ$_1$ dihedral angle restraints. Explicit hydrogen bonds were not included. Structures were generated with triangle and tetrangle smoothing prior to perspective embedding of all atoms. The embedded structures were annealed for 10,000 steps in four-dimensional space while cooling from 200 degrees kelvin (K) with all atom masses set to 1000. The DG structures were refined by rMD using the AMBER force field within the DISCOVER program (Biosym Technologies). Structures were annealed at 600 K for 3 picoseconds (ps), cooled to 0 K over 1.8 ps and finally subjected to 200 cycles of rEM. Charges on Glu, Asp, Arg, C-terminal and N-terminal residues were reduced to 0.2 e and a distance dependent dielectric pf 1/4r was employed. Restraints were employed as square well potentials with force constraints of 25 kilocalories/mole/angstrom$^2$ (kcal·mol$^{-1}$Å$^{-2}$) and 100 kilocalories/mole/radian$^2$ (kcal·mol$^{-1}$rad$^{-2}$) for distances and dihedral angles, respectively. In the final round of calculation, 60 structures were embedded in DGII and refined by rMD.

Circular Dichroism

CD spectra were acquired on an Aviv 62 spectrometer with a 0.1 centimeter(cm) path length temperature-controlled cell. Solutions for analytical spectra were prepared by dilution of NMR samples to approximately 100 micromoles/liter ($\mu$M) with additional NMR buffer. Points were taken every 0.2 nanometers(nm) with 0.2 nm bandwidth and 2 seconds(s) averaging time. The shortest wavelength attainable was limited by absorption of the acetate buffer. Curves shown are smoothed with standard parameters (10-point smoothing).

Results and Discussion

Design Considerations

Given synthetic and geometric considerations, it was determined that amide chemistry should be used to link the I and I+7 side-chains. Disulfide bonds, while synthetically feasible, introduced an unwanted 90° twist into the linkage. In order to exploit the ability of simple alkyl chain linkers to avoid steric crowding in the region near the I+3 and I+4 residues, linkage methods for bridging either Gln or Asn at I and I+7 with an alkanediyl chain were considered. Gln was chosen because its greater length allows use of the minimum size tether to link these side-chains. A representative set of protein crystal structures from the Brookhaven Database (Bernstein, F. C.; Koetzle, T. F.; Williams, G. J. B.; Meyer, E. F.; Brice, M. D.; Rodgers, J. R.; Kennard, O.; Shimanouchi, T.; Tasumi, M. *J. Mol. Biol.* 1977, 112, 535–542) was searched for all occurrences of glutamine in an $\alpha$ helical context (with $\phi=-60°\pm30°$ and $\psi=-45°\pm30°$). The resulting data set was used to determine the side-chain rotamer distributions of naturally occurring helical glutamine residues. In general, amino acid residues in an $\alpha$ helical context have $\chi_1 \approx -60°$, a conformation suitable for the I+7 position of aside chain linker. Glutamine has a relatively high population (14.6%) of the $\chi_1=180°$ rotamer, representing a significant natural conformation that points the side chain towards the C terminal end of the helix. Rotamer combinations were identified that minimized the N$\in$2—N$\in$2 distance between the I and I+7 side-chains in a model helical peptide. Depending on $\chi_3$ values, distances ranging from 5.3 Å to 7 Å were found if the I glutamine assumes $\chi_1$ and $\chi_2$ angles of 180° and 60° and the I+7 glutamine assumes $\chi_1$ and $\chi_2$ values of −60° and 180°, respectively.

Model building indicated that a 4-methylene "bridge" could efficiently link these two glutamine side-chains without incurring unfavorable torsional interactions. Models of 3-, 4-, and 5-methylene-bridgedhelical peptides were constructed using distance geometry methods (Quantum Chemistry Program Exchange, Program #590, entitled DGEOM by Blaney et al.) followed by energy minimization. All residues except the linked glutamines were alanine. The conformational stabilities of helical peptides were assessed using 1 nanosecond (ns) of unconstrained molecular dynamics at 298 K following an initial 100 picoseconds (ps) equilibration period during which harmonic restraints (25 kilocalories/mole/angstrom (kcal·mol$^{-1}$Å$^{-1}$)) were applied to maintain helicity. As a control, a polyalanine helix was calculated for 1 ns in the presence of identical restraints.

Peptides containing a 3-methylene bridge maintained a consistent helical conformation but showed significant "bending" of the helix axis. Peptides containing a 4-methylene bridge maintained helicity with little distortion, having comparable backbone dihedral angles to the control peptide; $\chi_1$ and $\chi_2$ angles of the tethered glutamines did not change during the simulation. Peptides based on a 5-methylene bridge transiently escaped out of a helical conformation into nested turns centered around the I+5 residue. Multiple side-chain rotamers were also observed in the I+7 residue. Based on these observations, it was determined that the 4-methylene bridge would provide the preferred tether length.

Synthesis and Characterization

Amino acid sequences for trial peptides were based on the C-terminal helix of apamin (Habermann, E. and Reiz, K. G., *Biochem. Z.* 1965, 343, 192–203; Callewaert, G. L., Shipolini, R., and Vernon, C. A., *FEBS Lett.* 1968, 1, 111–113; Shipolini, R., Bradbury, A. F., Callewaert, G. L., and Vernon, C. A., *Chem. Commun.* 1967, 679–680) and on S peptide derived from the C-peptide from RNAse A (Brown, J. E.; Klee, W. A. *Biochemistry* 1971, 10, 470–476). The sequences of these peptides are shown in Table 1 below.

TABLE 1

Structures of peptides 1–4

| Peptide | Sequence | Side Chain Protection |
|---|---|---|
| 1 | Ac T N X D L A A R R Z Q Q NH$_2$ | a: protected, on resin, X = Glu(OAll), Z = Glu(OFm) |
|   |   | b: X = Z = Gln(NMe) |
| 2 | Ac A E X A A A K F L Z A H A NH$_2$ | c: X - Z = Gln(N(CH$_2$)$_3$N)Gln |
|   |   | d: X - Z = Gln(N(CH$_2$)$_4$N)Gln |
|   |   | e: X - Z = Gln(N(CH$_2$)$_5$N)Gln |
|   |   | f: protected, on resin, X = Z = Glu(OFm) |
| 3 | Ac T N X D L A A R R Z Q Q NH$_2$ | a: X = D-Thiolys(Acm), Z = L-Thiolys(Acm) |
|   |   | b: X - Z = D-Thiolys-S-S-L-Thiolys |
| 4 | Ac A E X A A A K F L Z A H A NH$_2$ | |

Linear protected peptides 1a, 1f, and 2a were synthesized by standard Merrifield methods using t-butyloxycarbonyl (BOC) chemistry. Control peptides 1b and 2b were elaborated from 1f and 2a by simultaneous deprotection of both glutamate residues followed by coupling with methylamine (FIG. 1). Synthesis of 1d from 1f by double deprotection and coupling with 1,4-butanediamine was achieved in low yield/purity. Constrained peptides 1c–e and 2c–e were elaborated from 1a and 2a by removal of the fluorenylmethylester from Glu3, coupling with the appropriate alkanediamine, removal of the allyl ester from Glu 10, and cyclization (FIG. 1). Yields were improved by the use of mono-BOC protected alkanediamine in the first coupling step and by the use of a polystyrene resin with 2% divinylbenzene (DVB) crosslinker. The completed peptides were cleaved from the resin with hydrofluoric acid (HF) and purified by preparative high performance liquid chromatography (HPLC). Installation of the tether on the solid phase allowed the completion of the synthesis with only a single purification.

Thiolysine based peptides 3a and 4a were synthesized in the linear acetamidomethyl-protected form using standard Merrifield methods and FMOC chemistry, followed by cleavage from the resin with trifluoroacetic acid/ triethylsilane(9:1 v/v) and purification by preparative HPLC. These were converted into the disulfide forms 3b and 4b in solution by simultaneous deprotection and oxidation with acetic acid and molecular iodine in trifluoroethanol.

Peptides 1–4 were characterized by mass spectrometry and by quantitative amino acid analysis. All peptides gave results consistent with the intended structures.

Protected D-(7) and L-Thiolysine(10) were prepared as shown in FIG. 2. The Schollkopf reagent (Schöllkpf, U.; Groth, U.; Deng, C. *Angew. Chem. Int. Ed. Engl.* 1981, 20, 798–799) was treated with n-butyllithium followed by 1,4-dibromobutane to give the known bromobutyl pyrazine 5. The bromide was displaced with the potassium salt of methoxytoluenethiol to give 6. The pyrazine was hydrolyzed with aqueous hydrochloric acid (HCl) and the thiol was deprotected with mercuric acetate ($Hg(OAc)_2$) in TFA followed by $H_2S$. The crude thiolysine ethyl ester was then reprotected with acetamidomethanolin TFA. The ester was hydrolyzed with lithium hydroxide(LiOH) and the free S-protected amino acid was N-protected with Fmoc N-hydroxysuccinimide in dioxane to give 7. The same procedures were used for the synthesis of 10.

Proton NMR

Peptides 1–4 were studied by 2D $^1H$ NMR. Resonance positions were obtained by standard sequential assignment methods (Wüthrich, K. (1986) *NMR of Proteins and Nucleic Acids.*, Wiley, New York), and are listed in Table 2 below.

TABLE 2

Chemical Shifts[a] (backbone coupling constants[b]) of the apamin-sequence peptides 1 and 3

| Residue | 1b | 1C | 1d | 1e | 3a | 3b |
|---|---|---|---|---|---|---|
| Acetyl | | | | | | |
| $CH_3$ | 2.02 | 2.01 | 2.02 | 2.02 | 2.02 | 2.02 |
| Thr1 | | | | | | |
| $H^N$ | 8.34 | 8.47 | 8.46 | 8.46 | 8.33 | 8.34 |
| $H^\alpha(^3J_{HN-H\alpha})$ | 4.22 | 4.22 | 4.21 | 4.22 | 4.22 | 4.22 |
| | (7.2) | (6.9) | (6.9) | (6.9) | (7.5) | (7.3) |
| $H^\beta$ | 4.17 | 4.30 | 4.28 | 4.30 | 4.15 | 4.16 |
| $H^\gamma$ | 1.13 | 1.18 | 1.17 | 1.19 | 1.12 | 1.14 |
| Asn2 | | | | | | |
| $H^N$ | 8.69 | 8.78 | 8.78 | 8.79 | 8.55 | 8.6 |
| $H^\alpha(^3J_{HN-H\alpha})$ | 4.54 | 4.47 | 4.49 | 4.47 | 4.60 | 4.54 |
| | (6.6) | (5.0) | (5.4) | (5.0) | (6.9) | (6.3) |
| $H^\beta$ | 2.75* | 2.77* | 2.77* | 2.78* | 2.73* | 2.73* |
| Gln3 (D-Thiolysine) | | | | | | |
| $H^N$ | 8.49 | 8.53 | 8.56 | 8.46 | 8.28 | 8.42 |
| $H^\alpha(^3J_{HN-H\alpha})$ | 4.12 | 4.11 | 3.93 | 4.03 | 4.11 | 4.01 |
| | (6.5) | (4.9) | (4.7) | (4.9) | (6.5) | (6.4) |
| $H^\beta$ | 2.01, 1.87 | 2.11, 1.75 | 2.11, 1.81 | 2.09, 1.83 | 1.72, 1.64 | 1.84* |
| $H^\gamma$ | 2.22* | 2.42, 2.21 | 2.33, 2.26 | 2.33, 2.24 | 1.32* | 1.29* |
| $H^{\delta 7}$ | n.a. | n.a. | n.a. | n.a. | 1.52* | 1.63, 1.47 |
| $H^{\delta 8}$ | ??? | 8.01 | ??? | 7.99 | 2.52* | 2.53, 2.59 |
| Asp4 | | | | | | |
| $H^N$ | 8.32 | 8.05 | 8.09 | 8.03 | 8.29 | 8.07 |
| $H^\alpha(^3J_{HN-H\alpha})$ | 4.46 | 4.31 | 4.32 | 4.32 | 4.50 | 4.37 |
| | (6.6) | (4.8) | (4.7) | (4.8) | (6.7) | (5.5) |
| $H^\beta$ | 2.65* | 2.77, 2.61 | 2.76, 2.60 | 2.76, 2.61 | 2.71, 2.60 | 2.67* |
| Leu5 | | | | | | |
| $H^N$ | 8.20 | 7.92 | 7.93 | 8.03 | 8.24 | 8.15 |
| $H^\alpha(^3J_{HN-H\alpha})$ | 4.05 | 3.95 | 3.97 | 3.94 | 4.07 | 4.06 |
| | (5.7) | (5.3) | (5.1) | (4.8) | (5.5) | (5.5) |
| $H^\beta$ | 1.60* | 1.69, 1.50 | 1.67, 1.50 | 1.66, 1.50 | 1.61, 1.51 | 1.64, 1.51 |
| $H^\gamma$ | 1.50 | 1.61 | 1.60 | 1.59 | 1.58 | 1.61 |
| $H^\delta$ | 0.84, 0.76 | 0.83, 0.79 | 0.83, 0.79 | 0.83, 0.79 | 0.85, 0.77 | 0.85, 0.79 |
| Ala6 | | | | | | |
| $H^N$ | 8.14 | 8.01 | 7.93 | 8.02 | 8.18 | 8.12 |
| $H^\alpha(^3J_{HN-H\alpha})$ | 4.07 | 3.96 | 3.97 | 3.96 | 4.07 | 4.1 |
| | (5.1) | (4.6) | (nd) | (5.0) | (5.2) | (5.8) |
| $H^{\delta 2}$ | 1.33 | 1.37 | 1.33 | 1.36 | 1.33 | 1.38 |
| Ala7 | | | | | | |
| $H^N$ | 7.94 | 8.67 | 8.59 | 8.35 | 8.00 | 8.21 |
| $H^\alpha(^3J_{HN-H\alpha})$ | 4.13 | 3.77 | 3.94 | 3.87 | 4.11 | 4.09 |
| | (5.4) | (4.4) | (4.8) | (4.5) | (5.2) | (5.5) |
| $H^{\delta 2}$ | 1.34 | 1.46 | 1.47 | 1.46 | 1.33 | 1.40 |
| Arg8 | | | | | | |
| $H^N$ | 8.01 | 7.65 | 7.91 | 7.82 | 8.08 | 7.89 |
| $H^\alpha(^3J_{HN-H\alpha})$ | 4.14 | 4.01 | 4.03 | 4.02 | 4.14 | 4.17 |
| | (6.3) | (4.9) | (4.6) | (4.9) | (6.3) | (6.1) |
| $H^{\delta 2}$ | 1.77* | 1.86* | 1.85* | 1.86* | 1.75* | 1.83, 1.75 |
| $H^\gamma$ | 1.64, 1.56 | 1.76, 1.60 | 1.73, 1.59 | 1.77, 1.59 | 1.62, 1.55 | 1.54, 1.49 |
| $H^\delta$ | 3.11* | 3.15, 3.08 | 3.14, 3.05 | 3.15, 3.06 | 3.11* | 3.10* |
| $H^\epsilon$ | ??? | 7.21 | 7.23 | 7.23 | ??? | ??? |
| Arg9 | | | | | | |
| $H^N$ | 8.17 | 7.78 | 7.89 | 7.94 | 8.19 | 7.97 |
| $H^\alpha(^3J_{HN-H\alpha})$ | 4.17 | 4.10 | 4.11 | 4.08 | 4.18 | 4.21 |
| | (6.1) | (5.5) | (5.2) | (5.1) | (6.3) | (6.6) |
| $H^{\delta 2}$ | 1.75* | 1.87* | 1.83* | 1.83* | 1.74* | 1.85, 1.77 |
| $H^\gamma$ | 1.61, 1.54 | 1.71, 1.56 | 1.71, 1.57 | 1.72, 1.56 | 1.61, 1.54 | 1.64, 1.56 |
| $H^\delta$ | 3.11* | 3.13* | 3.12* | 3.11* | 3.11* | 3.11* |
| $H^\epsilon$ | ??? | 7.24 | 7.23 | 7.23 | ??? | ??? |
| Glu10 (L-Thiolysine) | | | | | | |
| $H^N$ | 8.30 | 7.92 | 7.71 | 7.73 | 8.18 | 8.09 |
| $H^\alpha(^3J_{HN-H\alpha})$ | 4.14 | 4.02 | 4.17 | 4.07 | 4.14 | 4.16 |
| | (6.3) | (5.4) | (6.3) | (5.6) | (6.4) | (6.3) |
| $H^{\delta 2}$ | 2.03, 1.95 | 2.11* | 2.08* | 2.12, 2.06 | 1.71* | 1.75, 1.65 |
| $H^\gamma$ | 2.26* | 2.47, 2.41 | 2.49, 2.36 | 2.40, 2.27 | 1.34* | 1.32* |
| $H^\delta$ | n.a. | n.a. | n.a. | n.a. | 1.64* | 1.54, 1.49 |
| $H^\epsilon$ | ??? | 7.71 | ??? | 7.85 | 2.53* | ??? |
| Gln11 | | | | | | |
| $H^N$ | 8.36 | 7.79 | 7.82 | 7.87 | 8.39 | 8.19 |
| $H^\alpha(^3J_{HN-H\alpha})$ | 4.18 | 4.15 | 4.17 | 4.15 | 4.19 | 4.20 |
| | (6.9) | (6.1) | (6.3) | (6.2) | (6.6) | (6.6) |
| $H^{\delta 2}$ | 2.04, 1.95 | 2.13, 2.04 | 2.09, 2.04 | 2.12, 2.05 | 2.04, 1.95 | 2.05, 1.96 |
| $H^\gamma$ | 2.32* | 2.44, 2.38 | 2.38* | 2.39* | 2.32* | 2.31* |

TABLE 2-continued

Chemical Shifts[a] (backbone coupling constants[b]) of the apamin-sequence peptides 1 and 3

| Residue | 1b | 1C | 1d | 1e | 3a | 3b |
|---|---|---|---|---|---|---|
| Gln12 | | | | | | |
| $H^N$ | 8.40 | 7.97 | 8.11 | 7.87 | 8.34 | 8.31 |
| $H^\alpha(^3J_{HN-H\alpha})$ | 4.16 | 4.15 | 4.17 | 4.15 | 4.18 | 4.18 |
| | (7.0) | (6.7) | (6.7) | (6.7) | (7.0) | (6.9) |
| $H^{\beta 2}$ | 2.04, | 2.08, | 2.07, | 2.08, | 2.05, | 2.06, |
| | 1.93 | 1.99 | 1.96 | 1.98 | 1.94 | 1.93 |
| $H^\gamma$ | 2.32* | 2.41, | 2.36* | 2.39, | 2.31* | 2.32* |
| | | 2.37 | | 2.35 | | |

[a] Chemical shifts obtained at pH 4.5 and 5° C. Shifts are relative to the internal HO resonance at 4.96 parts per million (p.p.m.), and are accurate to ± 0.02 p.p.m.
[b] $^3J_{HN-H\alpha}$ are listed in parentheses in units of hertz (Hz).

Representative TOCSY and ROESY spectra of a diamide-constrained peptide (1c) are shown in FIGS. 10 and 3. A summary of the $H^N$—$H^N$ and $H^\alpha$—$H^N$ ROEs between neighboring residues used to make these assignments are depicted in FIG. 4 for 1b and 1c. The degree of helicity of each peptide was judged from these spectra by the presence of intense sequential $H^N$—$H^N$ ROE cross-peaks, the presence of I, I+3 $H^\alpha$—$H^N$ or $H^\alpha$—$H^\beta$ ROE cross-peaks and $^3J_{HN-H\alpha}$ less than 6.0 Hz. The data summarized in FIG. 4 indicate that peptide 1c is helical between residues Asn2 and Gln10. Beyond Gln10, $^3J_{HN-H\alpha}$ rises above 6.0 Hz but some medium range ROEs are still present, indicating partial or transient helical character. Such fraying at helix termini is commonly observed in NMR studies of peptides and proteins. The $^1H$ chemical shifts of 1c change by less than 0.02 ppm over the concentration range 8.0–0.06 mM; this indicated that the helical conformation was not stabilized by a self-association event.

The incorporation of the diamide cross-link in peptides 1 and 2 clearly reduced the mean value of $^3J_{HN-H\alpha}$ in the restrained region, increased the number of observable (I, I+3) ROEs and increased the percent helicity observed by circular dichroism (CD) as shown in Table 3 below. Thus, peptides 1c–1e and 2c–2e were significantly more helical than the control peptides 1b and 2b. The results for peptide 4 indicated that formation of the disulfide bond constrained the peptide to be helical. However, a number of medium-range ROEs could not be observed and $^3J_{HN-H\alpha}$ values were greater than 6.0 Hz for the two thiolysine residues and Leu9 in 4b; this indicated a distortion from an ideal helical structure in the region of the D-thiolysine residue, as expected from simple structural considerations. The data in Table 3 below indicated that incorporation of the disulfide bond in peptide 3b did not impart helical character, suggesting that the thiolysine method may have a dependence on primary sequence and is therefore not generally applicable.

TABLE 3

Evaluation of peptide helicity.

| Peptide | Description | Mean $^3J_{NH-N\alpha}$ in constrained region | Fraction of medium-range ROEs obs. | Percent Helicity by CD |
|---|---|---|---|---|
| 1b | Apamin, N-methyl Gln Control | 6.00 | 0.14 | 20 |
| 1c | Apamin, 3 carbon linker | 4.98 | 0.69 | 84 |
| 1d | Apamin, 4 carbon linker | 5.18 | 0.56 | 63 |
| 1e | Apamin, 5 carbon linker | 4.96 | 0.69 | 100 |
| 2b | C-tide, N-methyl Gln Control | 5.89 | 0.08 | 32 |
| 2c | C-tide, 3 carbon linker | 4.81 | 0.75 | 60 |
| 2d | C-tide, 4 carbon linker | 4.83 | 0.43 | 82 |
| 2e | C-tide, 5 carbon linker | 4.90 | 0.80 | 63 |
| 3a | Apamin, S-Acm thiolys control | 6.01 | 0.03 | 10 |
| 3b | Apamin, thiolys disulfide | 5.96 | 0.08 | 35 |
| 4a | C-tide S-Acm thiolys control | 5.96 | 0.05 | 19 |
| 4b | C-tide, thiolys disulfide | 5.65 | 0.48 | 27 |

Values below 6 for the mean 3-bond NH—Na coupling constant indicate helicity. Medium range I–I+3 ROEs are expressed as the observed fraction of the total number of such ROEs possible, with very weak ROEs counted as one half. Percent helicity as determined by CD is derived as by Lyu et al.,; Sherman, J. C.; Chen, A.; Kallenbach, N. R., *Proc. Natl. Acad. Sci. U.S.A.* 88: 5317–5320 (1991), and Johnson, W. C.; Tinoco Jr., I., *J. Am. Chem. Soc.*, 94: 4389–4390 (1972).

Peptide 1c was chosen for a more detailed analysis by NMR. ROESY spectra with higher sensitivity (increased total acquisition time and peptide concentration) and NOESY spectra were acquired and analyzed to provide input restraints to structure calculations. In addition to the ROEs described above, $H^\alpha$—$H^N$ (I,I+4) interactions were observed, indicating that the helical conformation adopted is not of the $3_{10}$ type, but rather is of the regular a helical variety (Wüthrich, K. (1986) *NMR of Proteins and Nucleic Acids.*, Wiley, New York). Interproton distance restraints were generated from the ROESY and NOESY data, and used as a basis for calculating a structure for 1c using distance geometry (DG) and restrained molecular dynamics (rMD). Nearly half (66) of the 141 restraints were between amino acids two to four residues apart in the primary sequence, as expected for a helical conformation. Dihedral angle restraints, based on observed $^3J_{HN-H\alpha}$ and $^3J_{H\alpha-H\beta}$, were also used in these calculations, but explicit hydrogen bond restraints were not utilized.

The final ensemble of 20 structures is depicted in FIG. 5. The structures agreed with the input data very well, with no distance restraint violations above 0.1 angstroms (Å), no dihedral angle violations above 1.0°, and a mean restraint violation energy term of 0.10±0.09 kilocalories/mole (kcal·mol$^{-1}$). The available NMR data define well the backbone atoms of residues Thr1 to Gln10 (average root mean squared deviation from the mean structure=0.38±0.08 Å), but the two C-terminal glutamine residues are not well defined. The side chains of Thr1, Gln3, Asp4, Leu6 and Gln10 have well defined $\chi_1$ values, but only Gln110 has a consistent value of $\chi_2$ in all structures.

$H^N(I)$—O(I-4) hydrogen bonds are were to the amide protons of Leu5, Ala6, and Gln10 in greater than 90% of the structures, indicating that these residues adopted a predominantly α-helical conformation. Although (i,i-4) hydrogen bonds were observed to the amide protons of Ala7, Arg8 and Arg9 in approximately 50% of the structures, $H^N(I)$—O(I-3)

hydrogen bonds were present in 25–35% of the structures, indicating that there was a slight distortion of the helix in this region. The data presented in Table 4 below indicated that the amide hydrogens of Leu5 to Gln10 were all protected from exchange with solvent in peptide 1c compared to the control peptide 1b by factors of up to 25. This observation is also consistent with the amide hydrogens of these residues participating in hydrogen bonds. Interestingly, hydrogen bonds from Asp4 $H^N$ to Thr1 $O^{\gamma 2}$ were present in 80% of the structures, indicating that an N-cap hydrogen bonding interaction (Harper, E. T.; Rose, G. D. *Biochemistry* 1993, 32: 7605–7609) was present even in this short peptide. However, the amide proton of Asp4 was not noticeably protected from exchange (Table 4), hence this hydrogen bond may be more transient.

TABLE 4

Amide hydrogen exchange rates constants[a] and protection factors[b] for peptide 1b and 1c

| Residue | log k (1b) | log k (1c) | Protection Factor |
|---|---|---|---|
| Thr1 | −2.44 | −2.48 | approx. 1 |
| Asn2 | n.d. | n.d. | — |
| Gln3 | n.d. | n.d. | — |
| Asp4 | −2.72 | −2.84 | 1.3 |
| Leu5 | −2.69 | −3.51 | 6.7 |
| Ala6 | −2.73 | −3.77 | 10.9 |
| Ala7 | −2.51 | −3.55 | 11.1 |
| Arg8 | n.d. | −3.33 | >26 |
| Arg9 | n.d. | −3.21 | >20 |
| Gln10 | n.d. | −3.29 | >25 |
| Gln11 | n.d. | −1.83 | approx. 1.0 |
| Gln12 | n.d. | n.d. | — |

With the exception of the $\psi$ angles of Ala6 and Gln10, the backbone dihedral angles throughout the tethered region were close to those expected for an ideal $\alpha$ helix (mean $\phi = -63° \pm 8°$, mean $\psi = -42° \pm 8°$) indicating that any deviation from ideality was very slight. The $\psi$ of Ala6 is was 15° lower than expected for an $\alpha$ helix and was more similar to that expected for a $3_{10}$ helix; the higher value of $\psi$ for Gln10 reflected the fraying beyond the tethered region. The slight distortion at Ala6 could be the result of the short tether present in this peptide (only three methylene groups). Although the diamide linkage was not well defined by the NMR data, the side-chains of Gln3 and Gln10 adopted conformations close to those predicted by the modeling experiments described above (Gln3$\chi_1 = -173° \pm 17°$, $\chi_2 = 34° \pm 47°$; Gln10$\chi_1 = -71° \pm 7°$, $\chi_2 = 174° \pm 22°$). The overall conclusion was that in solution, 1c adopted an $\alpha$ helical structure from Asp2 to Gln10 with an N-terminal capping box and a very slight distortion in the central turn of the helix.

Circular Dichroism

CD spectra were acquired on aqueous solutions of 1–4 between 20 and 120 micromoles/liter ($\mu$M) at 280 K, pH 5. Spectra of peptides 1 and 3 (apamin sequence) are shown in FIG. 8 and those of peptides 2 and 4 (C-peptide sequence) in FIG. 8. Numerical values for percent helicity, calculated from the per-residue molar ellipticity of the peptides at 222 nanometers (nm), are shown above in Table 3.

The CD data supported the conclusions derived from the NMR studies. Both tethering methods substantially enhanced the helicity of the C-peptide sequence (FIG. 8). However, only the diamide method was capable of rendering the apamin sequence helical under the conditions used; the thiolysine-constrained peptide 3b did not appear to be helical (FIG. 7). The CD spectrum of 4b, in spite of substantial negative ellipticity at 222 nm, showed several features which indicated a lesser degree of helicity than those of 2c–2e: the short-wavelength minimum in 4b was shifted from 208 nm (a typical value for an $\alpha$ helix) to 204 nm, and the observable shoulder of the 190 nm maximum was much smaller than those of 2c–2e.

Thermal denaturation experiments were performed on the apamin-based peptides 1b–1e. In the initial experiment, CD spectra of peptides 1b–1e were taken at 10° C. intervals from 7° C. (280 K) to 57° C. (330 K). Given that 1c–1e showed good retention of helicity in this temperature range, spectra of 1c were taken up to 97° C. (370 K), where some loss of helicity was observed (FIG. 6). The molar ellipticity of 1c at 97° C. and 222 nm was still substantially more negative than that of the non-helical control peptide 1b at 7° C. and 222 nm.

Experiments to examine the effects of heating and recooling the peptides were complicated by several factors: the CD spectrometer showed a baseline drift over long experiments; the concentration of the samples changed because of evaporation at higher operating temperatures; and there appeared to be some variation in sample behavior depending on the rates of heating and cooling. A set of CD spectra of 1c was acquired before, during, and after heating at 87° C. for one day. The effect of baseline drift was reduced by linear normalization of the spectra based on $\Theta_{245}$. The effect of concentration change due to sample evaporation was corrected by normalizing the post-heating spectrum to the same amplitude as the pre-heating spectrum at wavelength ($\lambda$) of 204 nm. This wavelength was chosen as the point where an $\alpha$ helix and a random coil have equal contributions to the ellipticity, and hence interconversion of a peptide between these conformations will not affect the magnitude of the ellipticity. The resulting spectra are shown in FIG. 9. The close match in curve shape between the pre- and post-heating spectra indicated that most or all of the helical structure was regained on cooling after the partial denaturation induced by heating at 87° C. The small difference in overall amplitude could be due to a small amount of permanent denaturation or could be an artifact of the normalization procedure. This experiment demonstrated that the $\alpha$ helix of 1c was stable to relatively harsh conditions, a feature which improves its general utility.

Conclusion

A new method for constraining small peptides to an $\alpha$ helical conformation has been devised. This I to I+7 amide-based tether is successful as a general method for inducing $\alpha$ helicity in small peptides and possesses several desirable features. First, it allows the maximum possible sequence variability. Any residue except the two tethering residues themselves may be changed. Second, the helicity induced by this method approaches 100% in aqueous solution at room temperature (RT). The comparison of helical peptides 1c–1e with non-helical peptide 1b shows that the helicity is achieved by introduction of the linker rather than being a property of the primary sequence. Third, these tethered peptides are synthesized by standard solid-phase (Merrifield) chemistry and require only inexpensive, commercially available reagents. Fourth, the method can be used for peptides as short as eight residues. Fifth, it poses no chemical requirements as to environment and has been shown to induce good helicity despite changes in temperature and buffer conditions. This method is generally useful for studies of biologically active helical regions of proteins, for the experimental study of helix formation, propagation, and stability, and for physical organic experiments on the interactions of helical peptides with their environments.

Example 2

The peptide cyclized peptide FNM(5)QQRRFY(6)ALH (FIG. 11) was synthesized using Fmoc chemistry with standard solid phase protocols in which Fmoc-glutamic acid, δ-(5-allyloxycarbonyl-1,5-diaminopentane)(5) (synthesized as described below) and Fmoc glutamic acid δ-allyl ester (6) (commercially available from Millipore) are incorporated as standard amino acids in peptide synthesis, followed by cyclization as shown in FIG. 11. Fmoc-glutamic acid, δ-(5-allyloxycarbonyl-1,5-diaminopentane) (5) was synthesized as shown in Scheme 1 below.

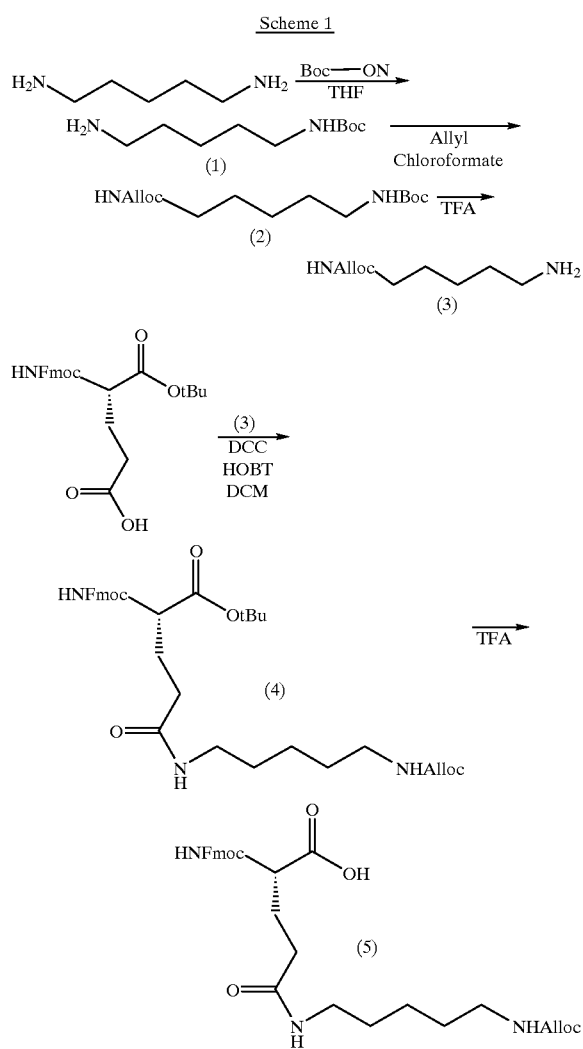

Mono-t-butyloxycarbonyl (BOC) 1,5-pentanediamine was synthesized by using 1,5-diaminopentane (12.5 g, 122 mmol) in place of 1,3-diaminopropane in the synthesis of mono-allyloxycarbonyl-1,3-diaminopropane described in Example 1 above, yielding 10 g (49 mmol) of mono-tert-butyloxycarbonyl-1,5-diaminopentane (1). The mono-tert-butyloxycarbonyl-1,5-diaminopentane (1) (5.8 g, 28.7 mmol) was dissolved in 75 mL of dichloromethane with 7.5 mL of diisopropylethylamine and cooled to 0° C. A solution of allyl chloroformate (3.3 mL) in dichloromethane (25 mL) was added over five minutes. The reaction was allowed to warm to room temperature for one hour and then solvent was removed by rotary evaporation. The residue was dissolved in 100 mL of ethyl acetate and washed with three 100 mL portions of 10% citric acid, once with 100 mL saturated aqueous sodium bicarbonate and once with 100 mL of saturated aqueous sodium chloride. The organic phase was dried over magnesium sulfate and solvent was removed by rotary evaporation. The resulting oil (2) was treated with 25 mL of trifluoroacetic acid for 30 minutes. The trifluoroacetic acid was removed by rotary evaporation and the resulting reside was twice dissolved in dichloromethane and then evaporated to remove residual solvent. The residue was dissolved in 50 mL of 3N hydrochloric acid and washed with two 50 mL portions of dichloromethane. The aqueous phase was cooled in an ice bath and the pH was adjusted to approximately 13 with 50% aqueous sodium hydroxide. The basic aqueous phase was extracted with three 100 mL portions of dichloromethane, the combined organics were washed with 100 mL of saturated aqueous sodium chloride and then dried over potassium carbonate. The mixture was filtered, the solvent removed first by rotary evaporation and then by high vacuum to yield 3.95 g of mono-allyloxycarbonyl-1,5-diaminopentane (3) as a colorless oil.

Fmoc-Glutamic acid, α-tert-butyl ester, 9.0 g (21.1 mmol, Bachem Calif.) was dissolved in 100 mL of dichloromethane. Dicyclohexyl carbodiimide (4.4 g, 21.3 mol) and N-hydroxybenzotriazole (0.3 g, 2.1 mmol) was added to this solution, followed by the mono-allyloxycarbonyl-1,5-diaminopentane (3) (3.95 g, 21.2 mmol). The reaction was stirred at 25° C. for 14 hours, then cooled to 0° C. for one hour. Insoluble material was removed by filtration, and the filtrate was concentrated by rotary evaporation. The residue was dissolved in 150 mL of ethyl acetate and washed twice with 100 mL of 10% aqueous citric acid, twice with 100 mL of saturated aqueous sodium bicarbonate and once with 100 mL brine. After drying over magnesium sulfate and filtering the solvent was removed by rotary evaporation. The residue was dissolved in approximately 75 mL of ethyl acetate with heating and 2:1 hexanes:ethyl acetate was added until the solution became cloudy. After standing for several hours the crystalline precipitate was removed by filtration, the white crystals were washed with 2:1 hexanes:ethyl acetate and dried under vacuum to yield 11.4 g of (4) (90%).

The tert-butyl ester (4), 11 g, 18.5 mmol) was dissolved in 50 mL of trifluoroacetic acid with stirring. After 45 minutes, the trifluoroacetic acid was removed by rotary evaporation; residual trifluoroacetic acid was removed by evaporation from 50 mL of dichloromethane three times. The residue was dissolved in 75 mL of ethyl acetate with heating, filtered through celite, and 3:1 hexanes:ethyl acetate was added until a haze developed. Crystals were allowed to grow at 25° C. for three hours, then cooled to 0° C. for one hour. The crystals were isolated by filtration and washed with 3:1 hexanes:ethyl acetate, then dried under vacuum to yield 9.5 g (95%) of (5) as off white crystals.

Following peptide synthesis of FNM(5)QQRRFY(6) ALH, the N-terminus of the solid phase peptide was coupled to mono tert-butyl-succinic acid the allyl and allyloxycarbonyl protecting groups were removed using 500 mg Pd(PPh$_3$)$_2$Cl$_2$ in 20 mL of 20% piperidine in dimethyl acetamide for 1.5 hours at room temperature. The resin was then washed with 20% piperidine in dimethyl acetamide, dimethyl acetamide, dichloromethane and finally with 0.5% trifluoroacetic acid in dichloromethane. The resin was suspended in dichloromethane and 1.5 equivalents of HATU with 3 eq N,N-diisopropylethylamine in 5 mL of dimethyl acetamide was added. After two hours the resin was checked for free amines by ninhydrin test and found to be negative. The peptide was cleaved from the resin with 95% trifluoroacetic acid 5% triethylsilane and purified using reverse phase HPLC.

The helical structure of the cyclized peptide shown in FIG. 11 was confirmed by circular dichroism (CD) and nuclear magnetic resonance (NMR). Both of these methods indicated that the locked helix peptide displayed predominantly α-helical character. The locked helix peptide was determined to bind IgG with an affinity (Kd) of approximately 100 μM both by microcalorimetry and surface plasmon resonance. A control peptide lacking the locking portion of the molecule did not exhibit IgG binding detectable by microcalorimetry.

Example 3

To confirm that the covalent locking mechanism is fully functional and that peptides constrained by this technique are able to bind ligand with high affinity, a 33 amino acid peptide based on helix 1 of the Z domain of protein A was synthesized with the i to i+7 linkage as shown in Scheme 2 below:

Scheme 2 suc-FNM (5) QQARFY (6)
ALHDPNLNEEQRNAKIKSIRDD-nh2 where (5) and (6) are the allyloxycarbonyl and allyl protected amino acids described in Example 2 above. The peptide was synthesized and cyclized as described in Example 2 above. The helicity of the peptide was verified by CD and NMR, and thermal denaturation of the peptide as monitored by CD indicated that the peptide only partly unfolds at 90° C., consistent with the stability of the covalent linkage. The IgG binding affinity (Kd) of this peptide (as measured by surface plasmon resonance) was determined to be approximately 20 nM.

Example 4

Linear peptides derived from the ectodomain of the HIV-1 envelope protein gp41 are known to inhibit viral fusion events. The most potent of these (DP178) corresponds to a membrane proximal region of gp41, which is predicted to be α-helical. However, DP178 itself lacks discernable structure in solution, rendering mechanistic interpretation of its activity difficult. By applying the helix locking chemistry taught herin, constrained versions of DP178 were made to determine whether helicity is necessary or sufficient for its infectivity inhibition activty and to define a likely mode of action for this molecule in primary infection (as measured using viral infectivity assays).

By constraining DP178 analogs into a helical conformation we show that helicity is necessary, but not sufficient, for inhibitory potency. The correct face of the helix must also be exposed. Two recent crystal structures of gp41 indicate that this face is buried in a groove formed by a coiled-coil trimer. Taken together, these results indicate that DP178 inhibits infectivity by blocking this groove, and that the conformation of gp41 observed by crystallography represents the fusogenic state.

A series of analogs of DP178 in which segments of the amide backbone were constrained to be helical (FIG. 12) were prepared. Because short α-helices are usually unstructured in solution (Marqusee et al. *Proc. Natl. Acad. Sci. USA* 86: 5286–5290 (1989)), a covalent crosslink between amino acid side chains at positions i and i+7 of the polypeptide chain as taught herein (see also Phelan et al., *J. Am. Chem. Soc.* 119: 455–460 (1997), which is incorportated herein by reference) which lock the intervening residues into a stable α-helical conformation.

A truncated form of DP178, designated HIV35 (FIG. 12) was used as a reference. In the absence of detailed information regarding the associaton of DP178 with DP107, the coiled-coil propensities (Lupas et al., *Science* 252: 1162–1164 (1991)) for 29 distinct gp160 sequences were computed in order to determine whether the region corresponding to DP178 scored as a coiled-coil. The N-terminal 27 residues of DP178, selected for the reference peptide HIV35, maintained a high overall score with a consistent heptad register. The "a–d" face predicted by the scoring algorithm corresponded to the face seen to pack against the trimer core. This corresponding region is entirely helical in the x-ray structures, and packs against the trimer core using a 4–3 heptad repeat akin to that found in coiled-coils. Using the helical locking chemistry and methods taught herin we enforced the exposure of this repeat (positions "a" and "d" of the heptad) by introducing crosslinks between pairs of adjacent residues on the opposite face of the helix (position "f"). Thus, "f" to "f" (tethers) locks were made to constrain the potential helix. Analogs of HIV35 (FIG. 12) were prepared containing either one (HIV24) or two (HIV31) tethers to impart increasing helicity. A control peptide (HIV30) was prepared in which a tether was introduced between successive "d" residues to stabilize helicity while blocking potential binding interactions across the "a–d" face.

Linear peptides were synthesized according to standard solid phase techniques using Fmoc chemistry (Fields et al., *Int. J. Peptide Protein Res.* 35: 161–214 (1990)) as taught herein. In particular, helix dipole effects were minimized by blocking the C-termini as amides and the N-termini as succinate groups. After formation of the lactam bridges as taught herein (see also Phelan et al., *J. Am. Chem. Soc.* 119: 455–460 (1997)), the peptides were cleaved from the resin and purified to homogeneity using preparative reversed phase HPLC with water/acetonitrile/0.1% TFA gradients in the mobile phase. The identity of each peptide was confirmed by electrospray mass spectrometry: HIV 24, calculated mass 3396.8, observed, 3396.0; HIV 30, calculated mass 3413.7, observed, 3413.8; HIV 31, calculated mass 3520.0, observed, 3520.7; HIV 35, calculated mass 3330.8, observed, 3330.5.

Circular dichroism analysis (FIG. 13) confirms that the locking strategy markedly increases the helicity of the DP178 truncations. CD spectra were recorded on an AVIV 62DS CD spectrometer using 0.05 cm pathlength cuvettes. Spectra were gathered by averaging data from three runs spanning 250 nm to 190 nm in 1.0 nm increments, with 2 second averaging time at each wavelength. Peptide concentrations were approximately 200 μM in a solution of 10 mM Tris HCl pH 7.5 with 6% acetonitrile (v/v). For conversion of raw data to molar ellipticity values, precise concentrations were determined by measuring $A_{276}$ and $A_{280}$ (Edelhoch, *Biochemistry* 6: 1948–1954 (1967)); these values were confirmed by quantitative amino acid analysis.

The unconstrained peptide HIV35 has an almost featureless spectrum, similar to that reported for DP178 (Lawless, et al., *Biochemistry* 35: 13697–13708 (1996)). The CD spectra of peptides containing a single constraint (HIV24 and HIV30) display minima at 209 and 222 nm characteristic of α-helices. The intensity ratios of these two regions are skewed from ideality, suggesting that regions of the peptide backbone outside the constrained segment are disordered. By contrast, the doubly-constrained analog HIV31 appears to be largely helical by CD, giving the shape and intensity profile of a typical α-helix.

Viral infectivity assays were used to characterize the locked-helix constructs. Normal human peripheral blood mononuclear cells (PBMCs) were stimulated with phytohemagglutinin (PHA) in RPMI 1640 medium containing interleukin 2 for 24 hours. The PHA medium was removed and the cells grown overnight in RPMI 1640 with glutamine, 20% heat inactivated fetal calf serum, and gentamicin. At the start of the assay, pre-titered virus stocks were equilibrated with peptides for one hour before adding to the PBMCs ($2.5 \times 10^5$ cells per well). Cells were grown for three days, rinsed to remove extracellular virus and peptides, then supplemented with fresh medium and grown for an additional four days. After seven days the cells were lysed and p24 antigen was determined by ELISA. Peptides were run in triplicate at each concentration. Viral titers were determined in duplicate for each run. Each assay also included the following controls, in triplicate: Uninfected cells as a negative control, infected cells without peptide as a positive control, and virus innoculum without cells to establish a baseline p24 level. Peptides were tested for cytotoxicity by incubating them at the highest assay concentration (approximately 100 μM) with uninfected cells and then growing the cells as described above. After 7 days the cell counts were estimated by microscopy and compared to an identical batch of cells which were not treated with the peptides; none of the peptides inhibited normal cell growth under these conditions.

When tested in viral infectivity assays, the peptides displayed a striking pattern of relative potency that extended across both syncitium inducing (SI) and non-syncitium inducing (NSI) strains of HIV-1 (Zhang et al., *Nature* 383: 768 (1996)). As shown in FIGS. 14A and 14B, truncating the hydrophobic C-terminus of DP178 (HIV35) caused a dramatic drop in activity, which was partially restored when a single restraint, i.e. constrained helical peptide, (and partial α-helical character) was introduced (HIV24). Adding a second restraint (HIV31) imparted strong helical character and enhanced the potency of the peptide to levels comparable to DP178. Thus, the additional stabilization afforded by preorganizing HIV31 into an active helical conformation offset the loss of binding energy caused by deleting the C-terminus. By contrast, a single restraint that induced helicity while blocking the "a–d" face (HIV30) completely ablated activity.

A series of shorter constrained peptides spanning positions 631–644, 643–656, 649–662, 656–669, and 663–678 of HIV-1$_{LAI}$, tethered between adjacent residues at the "f" positions of the heptad, were prepared to determine whether a subset of HIV35 or its N- and C-terminal flanking regions was sufficient to block infectivity. All peptides, whether constrained or unconstrained, failed to show significant activity. Peptide 631–644 contains the hydrophobic cluster observed in the x-ray structure to pack into a cavity in the trimer core (Chan et al., *Cell* 89:263–273 (1997)).

The relative activities of HIV35, HIV24, and HIV31 demonstrate a clear correlation between helicity and inhibitory potency. The widely disparate activities of HIV30 and HIV24 indicate that peptide inhibition also requires exposure of the face of the helix seen by crystallography to pack against the N-terminal trimer core of gp41.

The data presented herin, combined with prior model studies on isolated peptides and the recently published crystal structures, strongly support the hypothesis that the peptides inhibit viral infectivity by binding to the resting state of gp41 and preventing formation of the fusogenic state. Peptide HIV31 is conformationally constrained to be largely helical, and is likely to interact as such with an accessible cognate surface in the resting state of gp41. Because x-ray analysis shows that the face of HIV31 required for inhibiting viral fusion is buried in the groove formed by the N-terminal trimer core, we believe (without being bound to any particular theory) that this groove represents the cognate surface for the peptides.

Figure 15:
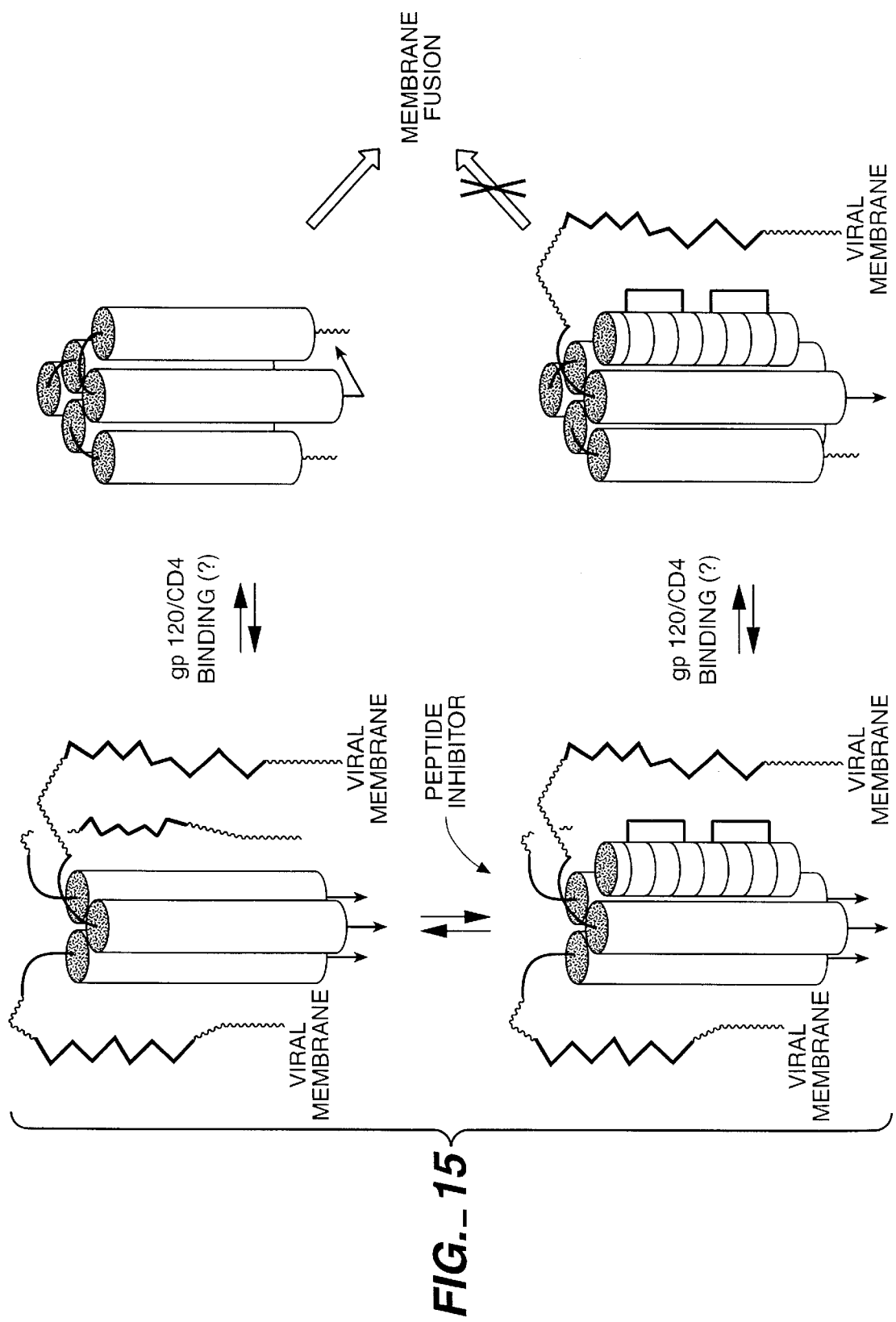
FIG. 15 is a schematic of a proposed mechanism for assembly of the fusogenic state of gp41 (top) and inhibition by constrained peptides (bottom).

FIG. 15 outlines schematically a current model for assembly of the fusgenic state of gp41, and the mechanism by which the constrained helices inhibit this process. The model is presented without meaning to be limiting to the invention and without binding the inventors to any particular theory of operation of the invention. The resting state of gp41 (upper left) is presumed to be constitutively trimerized, featuring a coiled-coil bundle near the N-terminal fusion peptide (arrow). The region corresponding to the C-terminus of the ectodomain (dark lines) is not initially bound to the trimer bundle, and has an unknown conformation. A conformational shift resulting from the binding of gp120to either CD4, a co-receptor, or both, may then allow association of the C-terminal portion of gp41 with the N-terminal bundle. The resulting antiparallel helical array (top right) observed in the x-ray structures is presumably the fusogenic state of gp41. Rearrangement to this state can be blocked if the trimer grooves are occupied by inhibitory peptides (bottom left). Once blocked in this manner, a subsequent conformational shift in the gp41 cluster would sequester the protein off-pathway (bottom right).

Peptides DP178 and HIV24 effectively inhibit the infectivity of genetically distant and phenotypically distinct subtypes of HIV-1 (Gao et al., *Journal of Virology* 70:1651–1667 (1996)). Moreover, the surface to which they are proposed to bind is one of the most highly conserved regions in the HIV-1 genome. We have assayed DP178 against other strains and found it to have similar inhibitory potency against the laboratory-adapted strain MN/H9 and primary isolates 301660 and Th009. Strain Th009 is from subtype E and is genetically distant from the predominant North American subtype B (e.g. JRCSF) (Zhang et al., *Nature* 383:768 (1996)). These results are in accord with observations from other labs (Wild et al., *Proc. Natl. Acad. Sci. USA* 89:10537–10541 (1992); Wild et al., *Proc. Natl. Acad. Sci. USA* 91: 9770–9774(1994); Jiang et al., *Nature* 365:113 (1993)). In addition to JRCSF and BZ167, we tested HIV24 against Th009 and found it to have comparable potency, suggesting that the membrane fusion mechanism proposed extends to widely disparate strains of HIV-1.

Other agents, such as antibodies, which target this surface may thus hold promise for the therapeutic treatment of AIDS.

Example 5

To prepare a vaccine that would be effective against HIV infection, either as a prophylactic or post-infection therapeutic (optionally in combination with anti-HIV drugs or other subunit vaccines), constrained α-helical peptides from the 633–678 region of gp41 were prepared and used as immunogens.

Variants of HIV 24 were prepared with the sequence "Gly Gly Cys" at the C-terminus or "Cys Gly Gly" at the N-terminus. These peptides were conjugated to KLH using a heterobifunctional crosslinker such as 4-(N-

Maleimidomethyl)-cyclohexane-1-carboxylic acid 3-sulfo-N-hydroxysuccinimide ester, available from Sigma, or its equivalent (e.g. "Sulfo-MBS" from Pierce). Immunizations were performed as described below.

Polyclonal antibodies were generated in female guinea pigs (Hartley Strain from Simonson Labs) against KLH-conjugated HIV peptides. Fifty μg peptide in 250 μL PBS was emulsified with 250 μL Freund's adjuvant (complete adjuvant for the primary injection and incomplete adjuvant for all boosts). Injections of 70–100 μg peptide/kg body weight were administered with a combination of subcutaneous and intramuscular sites in a three-week cycle. Bleeds were taken on the second and third weeks following each boost.

Sera from immunized animals was loaded on a Protein A column to provide, on elution, purified total Ig. Antibodies selective for the locked helices were obtained by passing the total Ig pool over an affinity column containing support loaded with immobilized locked helices. This support was prepared by first reacting the cysteine-containing peptides described above (HIV 26, 27, 28, and 29) with biotin-maleimide (also from Sigma; N-biotinyl-N'-[6-maleimidohexanoyl]-hydrazide) to afford peptides biotinylated at either terminus. These peptides were loaded onto a resin pre-loaded with streptavidin (Pierce, "Ultralink Avidin") to provide the affinity gel described.

The total Ig pool from the protein A column was passed over the appropriate affinity column (i.e. the one with the matching hapten immobilized). Nonspecific antibodies were eluted in the flow-through and saved as negative controls. Specific antibodies were eluted as from the Protein A column, dialyzed into assay buffer, and stored.

Surprisingly, the antibody titers observed were quite high for gp41 subunit peptides. This is particularly surprising since this region of gp41 (633–678) is not known in the art to generate HIV neutralizing antibodies.

The affinity purified polyclonal antibodies are tested in the viral infectivity assays used to evaluate the peptides. The haptens used to generate polyclonal antibody preparations that inhibit infectivity are desirable immunogenic agents for use in a vaccine. Most preferred are candidates that elicit broadly cross-reactive antibodies able to neutralize a variety of diverse HIV-1 isolates in vitro.

Candidate HIV-1 vaccines can be tested in available animal models, for example, in chimpanzees as described by Berman et al., *J. Virol.* 7:4464–9 (1992); Haigwood et al., *J. Virol.* 66:172–82 (1992) and Salmon-Ceron et al., *AIDS Res. and Human Retroviruses* 11:1479–86 (1995) for gp 120 subunit vaccines. Most preferred are candidates that elicit broadly cross-reactive antibodies able to neutralize a variety of diverse HIV-1 isolates in these animal studies, providing protection from challenge by homologous and heterologous strains of HIV-1. Successful protection of chimpanzees is encouraging and has historically proved to be a reliable indicator of vaccine efficacy.

SEQUENCE LISTING

```
(1) GENERAL INFORMATION:

(iii) NUMBER OF SEQUENCES: 113

(2) INFORMATION FOR SEQ ID NO: 1:

(i) SEQUENCE CHARACTERISTICS:
          (A) LENGTH: 36 amino acids
          (B) TYPE: Amino Acid
          (D) TOPOLOGY: Linear (ii) MOLECULE TYPE: DP178

(xi) SEQUENCE DESCRIPTION: SEQ ID NO: 1:

Tyr Thr Ser Leu Ile His Ser Leu Ile Glu Glu Ser Gln Asn Gln
  1               5                  10                  15

Gln Glu Lys Asn Glu Gln Glu Leu Leu Glu Leu Asp Lys Trp Ala
                 20                  25                  30

Ser Leu Trp Asn Trp Phe
                 35  36

(2) INFORMATION FOR SEQ ID NO: 2:

(i) SEQUENCE CHARACTERISTICS:
          (A) LENGTH: 27 amino acids
          (B) TYPE: Amino Acid
          (D) TOPOLOGY: Linear (xi) SEQUENCE DESCRIPTION: SEQ ID NO: 2:

Tyr Thr Ser Leu Ile His Ser Leu Ile Glu Glu Ser Gln Asn Gln
  1               5                  10                  15

Gln Glu Lys Asn Glu Gln Glu Leu Leu Glu Leu Asp
```

```
                20              25      27

(2) INFORMATION FOR SEQ ID NO: 3:

(i) SEQUENCE CHARACTERISTICS:
        (A) LENGTH: 27 amino acids
        (B) TYPE: Amino Acid
        (D) TOPOLOGY: Linear (xi) SEQUENCE DESCRIPTION: SEQ ID NO: 3:

Tyr Thr Ser Leu Ile His Ser Leu Ile Xaa Glu Ser Gln Asn Gln
 1               5                  10                  15

Gln Xaa Lys Asn Glu Gln Glu Leu Leu Glu Leu Asp
                20              25      27

(2) INFORMATION FOR SEQ ID NO: 4:

(i) SEQUENCE CHARACTERISTICS:
        (A) LENGTH: 27 amino acids
        (B) TYPE: Amino Acid
        (D) TOPOLOGY: Linear (xi) SEQUENCE DESCRIPTION: SEQ ID NO: 4:

Tyr Thr Xaa Leu Ile His Ser Leu Ile Xaa Glu Ser Gln Asn Gln
 1               5                  10                  15

Gln Xaa Lys Asn Glu Gln Glu Leu Xaa Glu Leu Asp
                20              25      27

(2) INFORMATION FOR SEQ ID NO: 5:

(i) SEQUENCE CHARACTERISTICS:
        (A) LENGTH: 27 amino acids
        (B) TYPE: Amino Acid
        (D) TOPOLOGY: Linear (xi) SEQUENCE DESCRIPTION: SEQ ID NO: 5:

Tyr Thr Ser Leu Ile His Ser Xaa Ile Glu Glu Ser Gln Asn Xaa
 1               5                  10                  15

Gln Glu Lys Asn Glu Gln Glu Leu Leu Glu Leu Asp
                20              25      27

(2) INFORMATION FOR SEQ ID NO: 6:

(i) SEQUENCE CHARACTERISTICS:
        (A) LENGTH: 269 amino acids
        (B) TYPE: Amino Acid
        (D) TOPOLOGY: Linear (xi) SEQUENCE DESCRIPTION: SEQ ID NO: 6:

Gly Gly Gly Asp Met Arg Asp Asn Trp Arg Ser Glu Leu Tyr Lys
 1               5                  10                  15

Tyr Lys Val Val Lys Ile Glu Pro Leu Gly Val Ala Pro Thr Lys
                20                  25                  30

Ala Lys Arg Arg Val Val Gln Arg Glu Lys Arg Ala Val Gly Xaa
                35                  40                  45

Ile Gly Ala Met Phe Leu Gly Phe Leu Gly Ala Ala Gly Ser Thr
                50                  55                  60

Met Gly Ala Ala Ser Met Thr Leu Thr Val Gln Ala Arg Gln Leu
                65                  70                  75

Leu Ser Gly Ile Val Gln Gln Gln Asn Asn Leu Leu Arg Ala Ile
                80                  85                  90

Glu Ala Gln Gln His Leu Leu Gln Leu Thr Val Trp Gly Ile Lys
```

-continued

```
                        95                  100                 105

Gln Leu Gln Ala Arg Val Leu Ala Val Glu Arg Tyr Leu Lys Asp
                110                 115                 120

Gln Gln Leu Leu Gly Ile Trp Gly Cys Ser Gly Lys Leu Ile Cys
                125                 130                 135

Thr Thr Ala Val Pro Trp Asn Ala Ser Trp Ser Asn Lys Ser Leu
                140                 145                 150

Xaa Xaa Ile Trp Xaa Asn Met Thr Trp Met Glu Trp Glu Arg Glu
                155                 160                 165

Ile Asp Asn Tyr Thr Xaa Leu Ile Tyr Thr Leu Ile Glu Glu Ser
                170                 175                 180

Gln Asn Gln Gln Glu Lys Asn Glu Gln Glu Leu Leu Glu Leu Asp
                185                 190                 195

Lys Trp Ala Ser Leu Trp Asn Trp Phe Xaa Ile Thr Asn Trp Leu
                200                 205                 210

Trp Tyr Ile Lys Ile Phe Ile Met Ile Val Gly Gly Leu Val Gly
                215                 220                 225

Leu Arg Ile Val Phe Ala Val Leu Ser Ile Val Asn Arg Val Arg
                230                 235                 240

Gln Gly Tyr Ser Pro Leu Ser Phe Gln Thr Xaa Leu Pro Ala Pro
                245                 250                 255

Arg Gly Pro Asp Arg Pro Glu Gly Ile Glu Glu Gly Gly
                260                 265             269

(2) INFORMATION FOR SEQ ID NO: 7:

(i) SEQUENCE CHARACTERISTICS:
        (A) LENGTH: 268 amino acids
        (B) TYPE: Amino Acid
        (D) TOPOLOGY: Linear (ii) MOLECULE TYPE: HIV-JRCSF (xi) SEQUENCE DESCRIPTION: SEQ ID NO: 7:

Gly Gly Gly Asp Met Arg Asp Asn Trp Arg Ser Glu Leu Tyr Lys
 1               5                  10                  15

Tyr Lys Val Val Lys Ile Glu Pro Leu Gly Val Ala Pro Thr Lys
                20                  25                  30

Ala Lys Arg Arg Val Val Gln Arg Glu Lys Arg Ala Val Gly Ile
                35                  40                  45

Gly Ala Leu Phe Leu Gly Phe Leu Gly Ala Ala Gly Ser Thr Met
                50                  55                  60

Gly Ala Arg Ser Met Thr Leu Thr Val Gln Ala Arg Gln Leu Leu
                65                  70                  75

Ser Gly Ile Val Gln Gln Gln Asn Asn Leu Leu Arg Ala Ile Glu
                80                  85                  90

Ala Gln Gln His Met Leu Gln Leu Thr Val Trp Gly Ile Lys Gln
                95                  100                 105

Leu Gln Ala Arg Val Leu Ala Val Glu Arg Tyr Leu Lys Asp Gln
                110                 115                 120

Gln Leu Met Gly Ile Trp Gly Cys Ser Gly Lys Leu Ile Cys Thr
                125                 130                 135

Thr Ala Val Pro Trp Asn Thr Ser Trp Ser Asn Lys Ser Leu Asp
                140                 145                 150

Ser Ile Trp Asn Asn Met Thr Trp Met Glu Trp Glu Lys Glu Ile
                155                 160                 165
```

```
Glu Asn Tyr Thr Asn Thr Ile Tyr Thr Leu Ile Glu Glu Ser Gln
                170                 175                 180

Ile Gln Gln Glu Lys Asn Glu Gln Glu Leu Leu Glu Leu Asp Lys
            185                 190                 195

Trp Ala Ser Leu Trp Asn Trp Phe Gly Ile Thr Lys Trp Leu Trp
            200                 205                 210

Tyr Ile Lys Ile Phe Ile Met Ile Val Gly Gly Leu Ile Gly Leu
            215                 220                 225

Arg Ile Val Phe Ser Val Leu Ser Ile Val Asn Arg Val Arg Gln
            230                 235                 240

Gly Tyr Ser Pro Leu Ser Phe Gln Thr Leu Leu Pro Ala Thr Arg
            245                 250                 255

Gly Pro Asp Arg Pro Glu Gly Ile Glu Glu Glu Gly Gly
            260                 265             268

(2) INFORMATION FOR SEQ ID NO: 8:

(i) SEQUENCE CHARACTERISTICS:
        (A) LENGTH: 268 amino acids
        (B) TYPE: Amino Acid
        (D) TOPOLOGY: Linear (xi) SEQUENCE DESCRIPTION: SEQ ID NO: 8:

Gly Gly Gly Asp Met Arg Asp Asn Trp Arg Ser Glu Leu Tyr Lys
 1               5                  10                  15

Tyr Lys Val Val Lys Ile Glu Pro Leu Gly Val Ala Pro Thr Lys
            20                  25                  30

Ala Lys Arg Arg Val Val Gln Arg Glu Lys Arg Ala Val Gly Ile
            35                  40                  45

Gly Ala Val Phe Leu Gly Phe Leu Gly Ala Ala Gly Ser Thr Met
            50                  55                  60

Gly Ala Ala Ser Met Thr Leu Thr Val Gln Ala Arg Leu Leu Leu
            65                  70                  75

Ser Gly Ile Val Gln Gln Gln Asn Asn Leu Leu Arg Ala Ile Glu
            80                  85                  90

Ala Gln Gln Arg Met Leu Gln Leu Thr Val Trp Gly Ile Lys Gln
            95                  100                 105

Leu Gln Ala Arg Val Leu Ala Val Glu Arg Tyr Leu Gly Asp Gln
            110                 115                 120

Gln Leu Leu Gly Ile Trp Gly Cys Ser Gly Lys Leu Ile Cys Thr
            125                 130                 135

Thr Ala Val Pro Trp Asn Ala Ser Trp Ser Asn Lys Ser Leu Asp
            140                 145                 150

Arg Ile Trp Asn Asn Met Thr Trp Met Glu Trp Glu Arg Glu Ile
            155                 160                 165

Asp Asn Tyr Thr Ser Glu Ile Tyr Thr Leu Ile Glu Glu Ser Gln
            170                 175                 180

Asn Gln Gln Glu Lys Asn Glu Gln Glu Leu Leu Glu Leu Asp Lys
            185                 190                 195

Trp Ala Ser Leu Trp Asn Trp Phe Asp Ile Thr Lys Trp Leu Trp
            200                 205                 210

Tyr Ile Lys Ile Phe Ile Met Ile Val Gly Gly Leu Val Gly Leu
            215                 220                 225

Arg Leu Val Phe Thr Val Leu Ser Ile Val Asn Arg Val Arg Gln
            230                 235                 240
```

```
Gly Tyr Ser Pro Leu Ser Phe Gln Thr Leu Leu Pro Ala Pro Arg
                245                 250                 255

Gly Pro Asp Arg Pro Glu Gly Ile Glu Glu Glu Gly Gly
                260                 265         268
```

(2) INFORMATION FOR SEQ ID NO: 9:

(i) SEQUENCE CHARACTERISTICS:
        (A) LENGTH: 268 amino acids
        (B) TYPE: Amino Acid
        (D) TOPOLOGY: Linear (xi) SEQUENCE DESCRIPTION: SEQ ID NO: 9:

```
Gly Gly Gly Asp Met Arg Asp Asn Trp Arg Ser Glu Leu Tyr Lys
 1               5                  10                  15

Tyr Lys Val Val Lys Ile Glu Pro Leu Gly Val Ala Pro Thr Arg
                 20                  25                  30

Ala Lys Arg Arg Val Val Gln Arg Glu Lys Arg Ala Val Gly Leu
                 35                  40                  45

Gly Ala Leu Phe Leu Gly Phe Leu Gly Ala Ala Gly Ser Thr Met
                 50                  55                  60

Gly Ala Arg Ser Met Thr Leu Thr Val Gln Ala Arg Gln Leu Leu
                 65                  70                  75

Ser Gly Ile Val Gln Gln Gln Asn Asn Leu Leu Arg Ala Ile Glu
                 80                  85                  90

Ala Gln Gln His Leu Leu Gln Leu Thr Val Trp Gly Ile Lys Gln
                 95                 100                 105

Leu Gln Ala Arg Val Leu Ala Val Glu Arg Tyr Leu Arg Asp Gln
                110                 115                 120

Gln Leu Leu Glu Ile Trp Gly Cys Ser Gly Lys Leu Ile Cys Thr
                125                 130                 135

Thr Thr Val Pro Trp Asn Ala Ser Trp Ser Asn Lys Ser Leu Asn
                140                 145                 150

Gln Ile Trp Asp Asn Met Thr Trp Met Glu Trp Glu Arg Glu Ile
                155                 160                 165

Asp Asn Tyr Thr Ser Leu Ile Tyr Thr Leu Ile Glu Glu Ser Gln
                170                 175                 180

Asn Gln Gln Glu Lys Asn Glu Gln Glu Leu Leu Glu Leu Asp Lys
                185                 190                 195

Trp Ala Ser Leu Trp Asn Trp Phe Asn Ile Thr Asn Trp Leu Trp
                200                 205                 210

Tyr Ile Lys Ile Phe Ile Met Ile Val Gly Gly Leu Val Gly Leu
                215                 220                 225

Arg Ile Val Phe Ser Val Leu Ser Ile Val Asn Arg Val Arg Gln
                230                 235                 240

Gly Tyr Ser Pro Leu Ser Phe Gln Thr Arg Leu Pro Ala Arg Arg
                245                 250                 255

Glu Pro Asp Arg Pro Glu Gly Ile Glu Glu Glu Gly Gly
                260                 265         268
```

(2) INFORMATION FOR SEQ ID NO: 10:

(i) SEQUENCE CHARACTERISTICS:
        (A) LENGTH: 268 amino acids
        (B) TYPE: Amino Acid
        (D) TOPOLOGY: Linear -continued (xi) SEQUENCE DESCRIPTION: SEQ ID NO: 10:

```
Gly Gly Gly Asn Met Arg Asp Asn Trp Arg Ser Glu Leu Tyr Lys
 1               5                   10                  15

Tyr Lys Val Val Lys Ile Glu Pro Leu Gly Val Ala Pro Thr Lys
                20                  25                  30

Ala Lys Arg Arg Val Val Gln Arg Glu Lys Arg Ala Val Gly Leu
                35                  40                  45

Gly Ala Leu Phe Leu Gly Phe Leu Gly Ala Ala Gly Ser Thr Met
                50                  55                  60

Gly Ala Ala Ser Leu Thr Leu Thr Val Gln Ala Arg Leu Leu Leu
                65                  70                  75

Ser Gly Ile Val Gln Gln Gln Asn Asn Leu Leu Met Ala Ile Glu
                80                  85                  90

Ala Gln Gln His Met Leu Glu Leu Thr Val Trp Gly Ile Lys Gln
                95                 100                 105

Leu Gln Ala Arg Val Leu Ala Val Glu Arg Tyr Leu Lys Asp Gln
               110                 115                 120

Gln Leu Leu Gly Ile Trp Gly Cys Ser Gly Lys Leu Ile Cys Thr
               125                 130                 135

Thr Ala Val Pro Trp Asn Ala Ser Trp Ser Asn Lys Ser Leu Ser
               140                 145                 150

Asp Ile Trp Asp Asn Met Thr Trp Met Glu Trp Glu Arg Glu Ile
               155                 160                 165

Asp Asn Tyr Thr Asn Leu Ile Tyr Ser Leu Ile Glu Asp Ser Gln
               170                 175                 180

Ile Gln Gln Glu Lys Asn Glu Lys Glu Leu Leu Glu Leu Asp Lys
               185                 190                 195

Trp Ala Ser Leu Trp Asn Trp Phe Asn Ile Thr Asn Trp Leu Trp
               200                 205                 210

Tyr Ile Lys Ile Phe Ile Met Ile Val Gly Gly Leu Ile Gly Leu
               215                 220                 225

Arg Ile Val Phe Ala Val Leu Ser Ile Val Asn Arg Val Arg Gln
               230                 235                 240

Gly Tyr Ser Pro Leu Ser Phe Gln Thr Arg Leu Pro Gly Arg Arg
               245                 250                 255

Gly Pro Asp Arg Pro Glu Gly Ile Glu Glu Gly Gly
               260                 265         268
```

(2) INFORMATION FOR SEQ ID NO: 11:

(i) SEQUENCE CHARACTERISTICS:
        (A) LENGTH: 267 amino acids
        (B) TYPE: Amino Acid
        (D) TOPOLOGY: Linear (xi) SEQUENCE DESCRIPTION: SEQ ID NO: 11:

```
Gly Gly Gly Asn Met Arg Asp Asn Trp Arg Ser Glu Leu Tyr Lys
 1               5                   10                  15

Tyr Lys Val Val Lys Ile Glu Leu Leu Gly Val Ala Pro Thr Lys
                20                  25                  30

Ala Lys Arg Arg Val Val Gln Arg Glu Lys Arg Ala Val Gly Ile
                35                  40                  45

Gly Ala Val Phe Leu Gly Phe Leu Gly Ala Ala Gly Ser Thr Met
                50                  55                  60

Gly Ala Ser Met Thr Leu Thr Val Gln Ala Arg Leu Leu Leu Ser
```

```
                    65                  70                  75
Gly Ile Val Gln Gln Gln Asn Asn Leu Leu Arg Ala Ile Glu Gly
                    80                  85                  90

Gln Gln His Leu Leu Gln Leu Thr Val Trp Gly Ile Lys Gln Leu
                    95                 100                 105

Gln Ala Arg Ile Leu Ala Val Glu Arg Tyr Leu Lys Asp Gln Gln
                   110                 115                 120

Leu Leu Gly Ile Trp Gly Cys Ser Gly Lys Leu Ile Cys Thr Thr
                   125                 130                 135

Ala Val Pro Trp Asn Ala Ser Trp Ser Asn Lys Ser Leu Glu Glu
                   140                 145                 150

Ile Trp Asp Asn Met Thr Trp Met Glu Trp Glu Arg Glu Ile Asp
                   155                 160                 165

Asn Tyr Thr Ser Leu Ile Tyr Thr Leu Ile Glu Glu Ser Gln Asn
                   170                 175                 180

Gln Gln Glu Lys Asn Glu Gln Glu Leu Leu Gly Leu Asp Lys Trp
                   185                 190                 195

Ala Ser Leu Trp Asn Trp Phe Thr Ile Thr Asn Trp Leu Trp Tyr
                   200                 205                 210

Ile Arg Ile Phe Ile Met Ile Val Gly Gly Leu Val Gly Leu Arg
                   215                 220                 225

Ile Val Phe Thr Val Leu Ser Ile Val Asn Arg Val Arg Gln Gly
                   230                 235                 240

Tyr Ser Pro Leu Ser Phe Gln Thr Arg Leu Pro Ala Pro Arg Gly
                   245                 250                 255

Pro Asp Arg Pro Glu Gly Ile Glu Glu Glu Gly Gly
                   260                 265     267

(2) INFORMATION FOR SEQ ID NO: 12:

(i) SEQUENCE CHARACTERISTICS:
        (A) LENGTH: 269 amino acids
        (B) TYPE: Amino Acid
        (D) TOPOLOGY: Linear (xi) SEQUENCE DESCRIPTION: SEQ ID NO: 12:

Gly Gly Gly Asp Met Arg Asp Asn Trp Arg Ser Glu Leu Tyr Lys
 1               5                  10                  15

Tyr Lys Val Val Lys Ile Glu Pro Leu Gly Val Ala Pro Thr Lys
                    20                  25                  30

Ala Lys Arg Arg Val Val Gln Arg Glu Lys Arg Ala Val Gly Thr
                    35                  40                  45

Ile Gly Ala Met Phe Leu Gly Phe Leu Gly Ala Ala Gly Ser Thr
                    50                  55                  60

Met Gly Ala Thr Ser Met Thr Leu Thr Val Gln Ala Arg Leu Leu
                    65                  70                  75

Leu Ser Gly Ile Val Gln Gln Gln Asn Asn Leu Leu Arg Ala Ile
                    80                  85                  90

Glu Ala Gln Gln His Leu Leu Gln Leu Thr Val Trp Gly Ile Lys
                    95                 100                 105

Gln Leu Gln Ala Arg Val Leu Ala Val Glu Arg Tyr Leu Arg Asp
                   110                 115                 120

Gln Gln Leu Leu Gly Ile Trp Gly Cys Ser Gly Lys Leu Ile Cys
                   125                 130                 135

Thr Thr Thr Val Pro Trp Asn Thr Ser Trp Ser Asn Lys Ser Leu
```

```
                    140                 145                 150
Asp Lys Ile Trp Gly Asn Met Thr Trp Met Glu Trp Glu Arg Glu
                155                 160                 165
Ile Asp Asn Tyr Thr Ser Leu Ile Tyr Thr Leu Ile Glu Glu Ser
                170                 175                 180
Gln Asn Gln Gln Glu Lys Asn Glu Gln Glu Leu Leu Glu Leu Asp
                185                 190                 195
Lys Trp Ala Ser Leu Trp Asn Trp Phe Asn Ile Thr Asn Trp Leu
                200                 205                 210
Trp Tyr Ile Lys Ile Phe Ile Met Ile Val Gly Gly Leu Val Gly
                215                 220                 225
Leu Arg Ile Val Phe Thr Val Leu Ser Ile Val Asn Arg Val Arg
                230                 235                 240
Gln Gly Tyr Ser Pro Leu Ser Phe Gln Thr Arg Leu Pro Ser Gln
                245                 250                 255
Arg Gly Pro Asp Arg Pro Glu Gly Ile Glu Glu Gly Gly
                260                 265                 269

(2) INFORMATION FOR SEQ ID NO: 13:

(i) SEQUENCE CHARACTERISTICS:
        (A) LENGTH: 268 amino acids
        (B) TYPE: Amino Acid
        (D) TOPOLOGY: Linear (xi) SEQUENCE DESCRIPTION: SEQ ID NO: 13:

Gly Gly Gly Asp Met Arg Asp Asn Trp Arg Ser Glu Leu Tyr Lys
 1               5                  10                  15
Tyr Lys Val Val Lys Ile Glu Pro Leu Gly Val Ala Pro Thr Lys
                20                  25                  30
Ala Lys Arg Arg Val Val Gln Arg Glu Lys Arg Ala Val Gly Ile
                35                  40                  45
Gly Ala Val Phe Leu Gly Phe Leu Gly Ala Ala Gly Ser Thr Met
                50                  55                  60
Gly Ala Ala Ala Met Thr Leu Thr Val Gln Ala Arg Leu Leu Leu
                65                  70                  75
Ser Gly Ile Val Gln Gln Gln Asn Asn Leu Leu Arg Ala Ile Glu
                80                  85                  90
Ala Gln Gln His Leu Leu Gln Leu Thr Val Trp Gly Ile Lys Gln
                95                  100                 105
Leu Gln Ala Arg Val Leu Ala Val Glu Arg Tyr Leu Arg Asp Gln
                110                 115                 120
Gln Leu Leu Gly Ile Trp Gly Cys Ser Gly Lys Leu Ile Cys Thr
                125                 130                 135
Thr Ala Val Pro Trp Asn Ala Ser Trp Ser Asn Lys Ser Leu Asn
                140                 145                 150
Lys Ile Trp Asp Asn Met Thr Trp Ile Glu Trp Asp Arg Glu Ile
                155                 160                 165
Asn Asn Tyr Thr Ser Ile Ile Tyr Ser Leu Ile Glu Glu Ser Gln
                170                 175                 180
Asn Gln Gln Glu Lys Asn Glu Gln Glu Leu Leu Glu Leu Asp Lys
                185                 190                 195
Trp Ala Ser Leu Trp Asn Trp Phe Asp Ile Thr Lys Trp Leu Trp
                200                 205                 210
Tyr Ile Lys Ile Phe Ile Met Ile Val Gly Gly Leu Ile Gly Leu
```

```
            215                 220                 225
Arg Ile Val Phe Ser Val Leu Ser Ile Val Asn Arg Val Arg Gln
                230                 235                 240

Gly Tyr Ser Pro Leu Ser Phe Gln Thr His Leu Pro Ser Ser Arg
                245                 250                 255

Gly Pro Asp Arg Pro Gly Gly Ile Glu Glu Glu Gly Gly
                260                 265         268
```

(2) INFORMATION FOR SEQ ID NO: 14:

(i) SEQUENCE CHARACTERISTICS:
        (A) LENGTH: 268 amino acids
        (B) TYPE: Amino Acid
        (D) TOPOLOGY: Linear (xi) SEQUENCE DESCRIPTION: SEQ ID NO: 14:

```
Gly Gly Gly Asp Met Arg Asp Asn Trp Arg Ser Glu Leu Tyr Lys
  1             5                  10                  15

Tyr Lys Val Val Lys Ile Glu Pro Leu Gly Val Ala Pro Thr Lys
                20                  25                  30

Ala Lys Arg Arg Val Val Gln Arg Glu Lys Arg Ala Val Gly Leu
                35                  40                  45

Gly Ala Leu Phe Leu Gly Phe Leu Gly Ala Ala Gly Ser Thr Met
                50                  55                  60

Gly Ala Ala Ser Ile Thr Leu Thr Val Gln Ala Arg Gln Leu Leu
                65                  70                  75

Ser Gly Ile Val Gln Gln Gln Asn Asn Leu Leu Arg Ala Ile Glu
                80                  85                  90

Ala Gln Gln His Leu Leu Gln Leu Thr Val Trp Gly Ile Lys Gln
                95                 100                 105

Leu Gln Ala Arg Val Leu Ala Val Glu Arg Tyr Leu Arg Asp Gln
               110                 115                 120

Gln Leu Leu Gly Ile Trp Gly Cys Ser Gly Lys Leu Ile Cys Thr
               125                 130                 135

Thr Thr Val Pro Trp Asn Thr Ser Trp Ser Asn Lys Ser Leu Asn
               140                 145                 150

Glu Ile Trp Asp Asn Met Thr Trp Met Lys Trp Glu Arg Glu Ile
               155                 160                 165

Asp Asn Tyr Thr His Ile Ile Tyr Ser Leu Ile Glu Gln Ser Gln
               170                 175                 180

Asn Gln Gln Glu Lys Asn Glu Gln Glu Leu Leu Ala Leu Asp Lys
               185                 190                 195

Trp Ala Ser Leu Trp Asn Trp Phe Asp Ile Thr Lys Trp Leu Trp
               200                 205                 210

Tyr Ile Lys Ile Phe Ile Met Ile Val Gly Gly Leu Ile Gly Leu
               215                 220                 225

Arg Ile Val Phe Val Val Leu Ser Ile Val Asn Arg Val Arg Gln
               230                 235                 240

Gly Tyr Ser Pro Leu Ser Phe Gln Thr His Leu Pro Ala Gln Arg
               245                 250                 255

Gly Pro Asp Arg Pro Asp Gly Ile Glu Glu Glu Gly Gly
               260                 265         268
```

(2) INFORMATION FOR SEQ ID NO: 15:

(i) SEQUENCE CHARACTERISTICS:

(A) LENGTH: 267 amino acids
        (B) TYPE: Amino Acid
        (D) TOPOLOGY: Linear (xi) SEQUENCE DESCRIPTION: SEQ ID NO: 15:

Gly Gly Gly Asp Met Arg Asp Asn Trp Arg Ser Glu Leu Tyr Lys
 1               5                  10                  15

Tyr Lys Val Val Thr Ile Glu Pro Leu Gly Val Ala Pro Thr Lys
                20                  25                  30

Ala Lys Arg Arg Val Val Gln Arg Glu Lys Arg Ala Ala Ile Gly
                35                  40                  45

Ala Leu Phe Leu Gly Phe Leu Gly Ala Ala Gly Ser Thr Met Gly
                50                  55                  60

Ala Ala Ser Val Thr Leu Thr Val Gln Ala Arg Leu Leu Leu Ser
                65                  70                  75

Gly Ile Val Gln Gln Gln Asn Asn Leu Leu Arg Ala Ile Glu Ala
                80                  85                  90

Gln Gln His Met Leu Gln Leu Thr Val Trp Gly Ile Lys Gln Leu
                95                 100                 105

Gln Ala Arg Val Leu Ala Val Glu Arg Tyr Leu Lys Asp Gln Gln
               110                 115                 120

Leu Leu Gly Phe Trp Gly Cys Ser Gly Lys Leu Ile Cys Thr Thr
               125                 130                 135

Thr Val Pro Trp Asn Ala Ser Trp Ser Asn Lys Ser Leu Asp Asp
               140                 145                 150

Ile Trp Asn Asn Met Thr Trp Met Gln Trp Glu Arg Glu Ile Asp
               155                 160                 165

Asn Tyr Thr Ser Leu Ile Tyr Ser Leu Leu Glu Lys Ser Gln Thr
               170                 175                 180

Gln Gln Glu Lys Asn Glu Gln Glu Leu Leu Glu Leu Asp Lys Trp
               185                 190                 195

Ala Ser Leu Trp Asn Trp Phe Asp Ile Thr Asn Trp Leu Trp Tyr
               200                 205                 210

Ile Lys Ile Phe Ile Met Ile Val Gly Gly Leu Val Gly Leu Arg
               215                 220                 225

Ile Val Phe Ala Val Leu Ser Ile Val Asn Arg Val Arg Gln Gly
               230                 235                 240

Tyr Ser Pro Leu Ser Leu Gln Thr Arg Pro Pro Val Pro Arg Gly
               245                 250                 255

Pro Asp Arg Pro Glu Gly Ile Glu Glu Glu Gly Gly
               260                 265     267

(2) INFORMATION FOR SEQ ID NO: 16:

(i) SEQUENCE CHARACTERISTICS:
        (A) LENGTH: 268 amino acids
        (B) TYPE: Amino Acid
        (D) TOPOLOGY: Linear (xi) SEQUENCE DESCRIPTION: SEQ ID NO: 16:

Gly Gly Gly Asp Met Arg Asp Asn Trp Arg Ser Glu Leu Tyr Lys
 1               5                  10                  15

Tyr Lys Val Val Lys Ile Glu Pro Leu Gly Val Ala Pro Thr Lys
                20                  25                  30

Ala Lys Arg Arg Val Val Gln Arg Glu Lys Arg Ala Val Gly Ile
                35                  40                  45

```
Gly Ala Leu Phe Leu Gly Phe Leu Gly Ala Ala Gly Ser Thr Met
                50                  55                  60

Gly Ala Ala Ser Met Thr Leu Thr Val Gln Ala Arg Gln Leu Leu
                65                  70                  75

Ser Gly Ile Val Gln Gln Gln Asn Asn Leu Leu Arg Ala Ile Glu
                80                  85                  90

Ala Gln Gln His Leu Leu Gln Leu Thr Val Trp Gly Ile Lys Gln
                95                  100                 105

Leu Gln Ala Arg Ile Leu Ala Val Glu Arg Tyr Leu Lys Asp Gln
                110                 115                 120

Gln Leu Leu Gly Ile Trp Gly Cys Ser Gly Lys Leu Ile Cys Thr
                125                 130                 135

Thr Ala Val Pro Trp Asn Ala Ser Trp Ser Asn Lys Ser Leu Glu
                140                 145                 150

Gln Ile Trp Asn His Thr Thr Trp Met Glu Trp Asp Arg Glu Ile
                155                 160                 165

Asn Asn Tyr Thr Ser Leu Ile His Ser Leu Ile Glu Glu Ser Gln
                170                 175                 180

Asn Gln Gln Glu Lys Asn Glu Gln Glu Leu Leu Glu Leu Asp Lys
                185                 190                 195

Trp Ala Ser Leu Trp Asn Trp Phe Asn Ile Thr Asn Trp Leu Trp
                200                 205                 210

Tyr Ile Lys Leu Phe Ile Met Ile Val Gly Gly Leu Val Gly Leu
                215                 220                 225

Arg Ile Val Phe Ala Val Leu Ser Ile Val Asn Arg Val Arg Gln
                230                 235                 240

Gly Tyr Ser Pro Leu Ser Phe Gln Thr His Leu Pro Thr Pro Arg
                245                 250                 255

Gly Pro Asp Arg Pro Glu Gly Ile Glu Glu Glu Gly Gly
                260                 265         268

(2) INFORMATION FOR SEQ ID NO: 17:

(i) SEQUENCE CHARACTERISTICS:
        (A) LENGTH: 268 amino acids
        (B) TYPE: Amino Acid
        (D) TOPOLOGY: Linear (xi) SEQUENCE DESCRIPTION: SEQ ID NO: 17:

Gly Gly Gly Asp Met Arg Asp Asn Trp Arg Ser Glu Leu Tyr Lys
 1               5                   10                  15

Tyr Lys Val Val Lys Ile Glu Pro Leu Gly Val Ala Pro Thr Lys
                20                  25                  30

Ala Lys Arg Arg Val Val Gln Arg Glu Lys Arg Ala Val Gly Ile
                35                  40                  45

Gly Ala Leu Phe Leu Gly Phe Leu Gly Ala Ala Gly Ser Thr Met
                50                  55                  60

Gly Ala Arg Ser Met Thr Leu Thr Val Gln Ala Arg Gln Leu Leu
                65                  70                  75

Ser Gly Ile Val Gln Gln Gln Asn Asn Leu Leu Arg Ala Ile Glu
                80                  85                  90

Ala Gln Gln His Leu Leu Gln Leu Thr Val Trp Gly Ile Lys Gln
                95                  100                 105

Leu Gln Ala Arg Ile Leu Ala Val Glu Arg Tyr Leu Lys Asp Gln
                110                 115                 120
```

```
Gln Leu Leu Gly Ile Trp Gly Cys Ser Gly Lys Leu Ile Cys Thr
                125                 130                 135

Thr Ala Val Pro Trp Asn Ala Ser Trp Ser Asn Lys Ser Leu Glu
                140                 145                 150

Gln Ile Trp Asn Asn Met Thr Trp Met Glu Trp Asp Arg Glu Ile
                155                 160                 165

Asn Asn Tyr Thr Ser Leu Ile His Ser Leu Ile Glu Glu Ser Gln
                170                 175                 180

Asn Gln Gln Glu Lys Asn Glu Gln Glu Leu Leu Glu Leu Asp Lys
                185                 190                 195

Trp Ala Ser Leu Trp Asn Trp Phe Asn Ile Thr Asn Trp Leu Trp
                200                 205                 210

Tyr Ile Lys Ile Phe Ile Met Ile Val Gly Gly Leu Val Gly Leu
                215                 220                 225

Arg Ile Val Phe Ala Val Leu Ser Ile Val Asn Arg Val Arg Gln
                230                 235                 240

Gly Tyr Ser Pro Leu Ser Phe Gln Thr His Leu Pro Thr Pro Arg
                245                 250                 255

Gly Pro Asp Arg Pro Glu Gly Ile Glu Glu Glu Gly Gly
                260                 265         268

(2) INFORMATION FOR SEQ ID NO: 18:

(i) SEQUENCE CHARACTERISTICS:
        (A) LENGTH: 268 amino acids
        (B) TYPE: Amino Acid
        (D) TOPOLOGY: Linear (xi) SEQUENCE DESCRIPTION: SEQ ID NO: 18:

Gly Gly Gly Asp Met Arg Asp Asn Trp Arg Ser Glu Leu Tyr Lys
 1               5                  10                  15

Tyr Lys Val Val Lys Ile Glu Pro Leu Gly Val Ala Pro Thr Lys
                20                  25                  30

Ala Lys Arg Arg Val Val Gln Arg Glu Lys Arg Ala Val Gly Ile
                35                  40                  45

Gly Ala Leu Phe Leu Gly Phe Leu Gly Ala Ala Gly Ser Thr Met
                50                  55                  60

Gly Cys Thr Ser Met Thr Leu Thr Val Gln Ala Arg Gln Leu Leu
                65                  70                  75

Ser Asp Ile Val Gln Gln Asn Asn Leu Leu Arg Ala Ile Glu
                80                  85                  90

Ala Gln Gln His Leu Leu Gln Leu Thr Val Trp Gly Ile Lys Gln
                95                  100                 105

Leu Gln Ala Arg Ile Leu Ala Val Glu Arg Tyr Leu Lys Asp Gln
                110                 115                 120

Gln Leu Leu Gly Ile Trp Gly Cys Ser Gly Lys Leu Ile Cys Thr
                125                 130                 135

Thr Ala Val Pro Trp Asn Ala Ser Trp Ser Asn Lys Ser Leu Glu
                140                 145                 150

Gln Ile Trp Asn Asn Met Thr Trp Met Glu Trp Asp Arg Glu Ile
                155                 160                 165

Asn Asn Tyr Thr Ser Leu Ile His Ser Leu Ile Glu Glu Ser Gln
                170                 175                 180

Asn Gln Gln Glu Lys Asn Glu Gln Glu Leu Leu Glu Leu Asp Lys
                185                 190                 195
```

```
Trp Ala Ser Leu Trp Asn Trp Phe Asn Ile Thr Asn Trp Leu Trp
                200                 205                 210

Tyr Ile Lys Leu Phe Ile Met Ile Val Gly Gly Leu Val Gly Leu
                215                 220                 225

Arg Ile Val Phe Ala Val Leu Ser Ile Val Asn Arg Val Arg Gln
                230                 235                 240

Gly Tyr Ser Pro Leu Ser Phe Gln Thr His Leu Pro Ile Pro Arg
                245                 250                 255

Gly Pro Asp Arg Pro Glu Gly Ile Glu Glu Glu Gly Gly
                260                 265     268

(2) INFORMATION FOR SEQ ID NO: 19:

(i) SEQUENCE CHARACTERISTICS:
        (A) LENGTH: 268 amino acids
        (B) TYPE: Amino Acid
        (D) TOPOLOGY: Linear (xi) SEQUENCE DESCRIPTION: SEQ ID NO: 19:

Gly Gly Gly Asp Met Arg Asp Asn Trp Arg Ser Glu Leu Tyr Lys
 1               5                  10                  15

Tyr Lys Val Val Lys Ile Glu Thr Leu Gly Val Ala Pro Thr Lys
                20                  25                  30

Ala Lys Arg Arg Val Val Gln Arg Glu Lys Arg Ala Val Gly Ile
                35                  40                  45

Gly Ala Leu Phe Leu Gly Phe Leu Gly Ala Ala Gly Ser Thr Met
                50                  55                  60

Gly Ala Ala Ser Met Thr Leu Thr Val Gln Ala Arg Gln Leu Leu
                65                  70                  75

Ser Gly Ile Val Gln Gln Gln Asn Asn Leu Leu Arg Ala Ile Glu
                80                  85                  90

Ala Gln Gln His Leu Leu Gln Leu Thr Val Trp Gly Ile Lys Gln
                95                 100                 105

Leu Gln Ala Arg Ile Leu Ala Val Glu Arg Tyr Leu Lys Asp Gln
                110                 115                 120

Gln Leu Leu Gly Ile Trp Gly Cys Ser Gly Lys Leu Ile Cys Thr
                125                 130                 135

Thr Ala Val Pro Trp Asn Ala Ser Trp Ser Asn Lys Ser Leu Glu
                140                 145                 150

Gln Phe Trp Asn Asn Met Thr Trp Met Glu Trp Asp Arg Glu Ile
                155                 160                 165

Asn Asn Tyr Thr Ser Leu Ile His Ser Leu Ile Asp Glu Ser Gln
                170                 175                 180

Asn Gln Gln Glu Lys Asn Glu Gln Glu Leu Leu Glu Leu Asp Lys
                185                 190                 195

Trp Ala Ser Leu Trp Asn Trp Phe Asn Ile Thr Asn Trp Leu Trp
                200                 205                 210

Tyr Ile Lys Ile Phe Ile Met Ile Val Gly Gly Leu Val Gly Leu
                215                 220                 225

Arg Ile Val Phe Ala Val Leu Ser Ile Val Asn Arg Val Arg Gln
                230                 235                 240

Gly Tyr Ser Pro Leu Ser Phe Gln Thr His Leu Pro Asn Arg Gly
                245                 250                 255

Gly Pro Asp Arg Pro Glu Gly Ile Glu Glu Glu Gly Gly
                260                 265     268
```

-continued (2) INFORMATION FOR SEQ ID NO: 20:

(i) SEQUENCE CHARACTERISTICS:
        (A) LENGTH: 269 amino acids
        (B) TYPE: Amino Acid
        (D) TOPOLOGY: Linear (xi) SEQUENCE DESCRIPTION: SEQ ID NO: 20:

```
Gly Gly Gly Asp Met Arg Asp Asn Trp Arg Ser Glu Leu Tyr Lys
 1               5                  10                  15

Tyr Lys Val Val Lys Ile Glu Pro Leu Gly Val Ala Pro Thr Lys
                20                  25                  30

Ala Lys Arg Arg Val Val Gln Arg Glu Lys Arg Ala Val Gly Ala
                35                  40                  45

Ile Gly Ala Leu Phe Leu Gly Phe Leu Gly Ala Ala Gly Ser Thr
                50                  55                  60

Met Gly Ala Val Ala Leu Thr Leu Thr Val Gln Thr Arg Gln Leu
                65                  70                  75

Leu Ser Gly Ile Val Gln Gln Gln Asn Asn Leu Leu Arg Ala Ile
                80                  85                  90

Glu Ala Gln Gln His Leu Leu Gln Leu Thr Val Trp Gly Ile Lys
                95                 100                 105

Gln Leu Gln Ala Arg Val Leu Ala Val Glu Arg Tyr Leu Lys Asp
               110                 115                 120

Gln Gln Leu Leu Gly Ile Trp Gly Cys Ser Gly Lys Leu Ile Cys
               125                 130                 135

Thr Thr Ala Val Pro Trp Asn Ala Ser Trp Ser Asn Lys Ser Leu
               140                 145                 150

Asp Lys Ile Trp Asn Asn Met Thr Trp Met Glu Trp Glu Arg Glu
               155                 160                 165

Ile Asp Asn Tyr Thr Asn Leu Ile Tyr Thr Leu Ile Glu Glu Ser
               170                 175                 180

Gln Asn Gln Gln Glu Lys Asn Glu Lys Asp Leu Leu Glu Leu Asp
               185                 190                 195

Thr Trp Ala Ser Leu Trp Asn Trp Phe Asp Ile Thr Asn Trp Leu
               200                 205                 210

Trp Tyr Ile Lys Ile Phe Ile Met Ile Ile Gly Gly Leu Ile Gly
               215                 220                 225

Leu Arg Ile Val Phe Thr Ile Leu Ser Leu Val Asn Arg Val Arg
               230                 235                 240

Gln Gly Tyr Ser Pro Leu Ser Phe Gln Thr Arg Phe Pro Val Pro
               245                 250                 255

Arg Gly Pro Asp Arg Pro Glu Gly Ile Glu Glu Glu Gly Gly
               260                 265             269
```

(2) INFORMATION FOR SEQ ID NO: 21:

(i) SEQUENCE CHARACTERISTICS:
        (A) LENGTH: 269 amino acids
        (B) TYPE: Amino Acid
        (D) TOPOLOGY: Linear (xi) SEQUENCE DESCRIPTION: SEQ ID NO: 21:

```
Gly Gly Gly Asp Met Arg Asp Asn Trp Arg Ser Glu Leu Tyr Lys
 1               5                  10                  15

Tyr Lys Val Val Lys Ile Glu Pro Leu Gly Val Ala Pro Thr Lys
                20                  25                  30
```

```
Ala Lys Arg Arg Val Val Gln Arg Glu Lys Arg Ala Val Gly Ala
             35                  40                  45

Leu Gly Ala Leu Phe Leu Gly Phe Leu Gly Ala Ala Gly Ser Thr
             50                  55                  60

Met Gly Ala Ala Ser Met Ala Leu Thr Val Gln Thr Arg Gln Leu
             65                  70                  75

Met Ser Gly Ile Val Gln Gln Asn Asn Leu Leu Lys Ala Ile
             80                  85                  90

Glu Ala Gln Gln His Leu Leu Gln Leu Thr Val Trp Gly Ile Lys
             95                 100                 105

Gln Leu Gln Ala Arg Val Leu Ala Val Glu Arg Tyr Leu Lys Asp
            110                 115                 120

Gln Gln Leu Leu Arg Ile Trp Gly Cys Ser Gly Lys Leu Ile Cys
            125                 130                 135

Thr Thr Thr Val Pro Trp Asn Ala Ser Trp Ser Asn Lys Ser Leu
            140                 145                 150

Asp Lys Ile Trp Asp Asn Met Thr Trp Met Glu Trp Glu Arg Glu
            155                 160                 165

Ile Asp Asn Tyr Thr Gly Leu Ile Tyr Thr Leu Ile Glu Glu Ser
            170                 175                 180

Gln Ile Gln Gln Glu Lys Asn Glu Gln Glu Leu Leu Glu Leu Asp
            185                 190                 195

Lys Trp Ala Ser Leu Trp Asn Trp Phe Asp Ile Thr Lys Trp Leu
            200                 205                 210

Trp Tyr Ile Lys Ile Phe Ile Met Ile Val Gly Gly Leu Ile Gly
            215                 220                 225

Leu Arg Ile Val Phe Thr Val Leu Ser Ile Val Asn Arg Val Arg
            230                 235                 240

Gln Gly Tyr Ser Pro Leu Ser Phe Gln Thr Arg Leu Pro Ala Gln
            245                 250                 255

Arg Gly Pro Asp Arg Pro Glu Gly Ile Glu Glu Glu Gly Gly
            260                 265             269

(2) INFORMATION FOR SEQ ID NO: 22:

(i) SEQUENCE CHARACTERISTICS:
        (A) LENGTH: 269 amino acids
        (B) TYPE: Amino Acid
        (D) TOPOLOGY: Linear (xi) SEQUENCE DESCRIPTION: SEQ ID NO: 22:

Gly Gly Gly Asp Met Arg Asp Asn Trp Arg Ser Glu Leu Tyr Lys
 1               5                  10                  15

Tyr Lys Val Val Lys Ile Glu Pro Leu Gly Val Ala Pro Thr Lys
             20                  25                  30

Ala Lys Arg Arg Val Val Gln Arg Glu Lys Arg Ala Val Gly Thr
             35                  40                  45

Ile Gly Ala Met Phe Leu Gly Phe Leu Gly Ala Ala Gly Ser Thr
             50                  55                  60

Met Gly Ala Ala Ser Ile Thr Leu Thr Val Gln Ala Arg Leu Leu
             65                  70                  75

Leu Ser Gly Ile Val Gln Gln Gln Asn Asn Leu Leu Arg Ala Ile
             80                  85                  90

Glu Ala Gln Gln His Leu Leu Gln Leu Thr Val Trp Gly Ile Lys
             95                 100                 105
```

```
Gln Leu Gln Ala Arg Val Leu Ala Leu Glu Arg Tyr Leu Arg Asp
            110                 115                 120

Gln Gln Leu Leu Gly Ile Trp Gly Cys Ser Gly Lys Leu Ile Cys
            125                 130                 135

Thr Thr Ala Val Pro Trp Asn Ala Ser Trp Ser Asn Lys Thr Leu
            140                 145                 150

Asp Met Ile Trp Asp Asn Met Thr Trp Met Glu Trp Glu Arg Glu
            155                 160                 165

Ile Glu Asn Tyr Thr Gly Leu Ile Tyr Thr Leu Ile Glu Glu Ser
            170                 175                 180

Gln Asn Gln Gln Glu Lys Asn Glu Gln Asp Leu Leu Ala Leu Asp
            185                 190                 195

Lys Trp Ala Ser Leu Trp Asn Trp Phe Asp Ile Ser Asn Trp Leu
            200                 205                 210

Trp Tyr Ile Lys Ile Phe Ile Met Ile Val Gly Gly Leu Ile Gly
            215                 220                 225

Leu Arg Ile Val Phe Thr Val Leu Ser Ile Val Asn Arg Val Arg
            230                 235                 240

Gln Gly Tyr Ser Pro Leu Ser Phe Gln Thr His Leu Pro Ala Pro
            245                 250                 255

Arg Gly Pro Asp Arg Pro Glu Gly Ile Glu Glu Gly Gly
            260                 265             269
```

(2) INFORMATION FOR SEQ ID NO: 23:

(i) SEQUENCE CHARACTERISTICS:
        (A) LENGTH: 269 amino acids
        (B) TYPE: Amino Acid
        (D) TOPOLOGY: Linear (xi) SEQUENCE DESCRIPTION: SEQ ID NO: 23:

```
Gly Gly Gly Asn Met Arg Asp Asn Trp Arg Ser Lys Leu Tyr Lys
 1               5                  10                  15

Tyr Lys Val Val Lys Ile Glu Pro Leu Gly Val Ala Pro Thr Lys
            20                  25                  30

Ala Lys Arg Arg Val Val Gln Arg Lys Lys Arg Ala Val Gly Thr
            35                  40                  45

Ile Gly Ala Met Phe Leu Gly Phe Leu Gly Ala Ala Gly Ser Thr
            50                  55                  60

Met Gly Ala Ala Ser Met Thr Leu Thr Val Gln Ala Arg Leu Leu
            65                  70                  75

Leu Ser Gly Ile Val Gln Gln Gln Asn Asn Leu Leu Arg Ala Ile
            80                  85                  90

Glu Ala Gln Gln His Leu Leu Gln Leu Thr Val Trp Gly Ile Lys
            95                 100                 105

Gln Leu Gln Ala Arg Val Leu Ala Val Glu Arg Tyr Leu Gln Asp
            110                 115                 120

Gln Gln Leu Leu Gly Ile Trp Gly Cys Ser Gly Lys Leu Ile Cys
            125                 130                 135

Thr Thr Thr Val Pro Trp Asn Ala Ser Trp Ser Asn Lys Ser Leu
            140                 145                 150

Asp Glu Ile Xaa Asn Asn Met Thr Trp Met Gln Trp Glu Arg Glu
            155                 160                 165

Ile Ser Asn Tyr Thr Ser Leu Ile Tyr Thr Leu Ile Glu Glu Ser
            170                 175                 180
```

```
Gln Asn Gln Gln Glu Lys Asn Glu Leu Glu Leu Leu Glu Leu Asp
                185                 190                 195

Lys Trp Ala Ser Leu Xaa Asn Trp Phe Asp Ile Thr Asn Trp Leu
                200                 205                 210

Trp Ser Ile Lys Ile Phe Ile Met Ile Val Ala Gly Leu Val Gly
                215                 220                 225

Leu Arg Ile Val Phe Ala Val Leu Ser Ile Val Asn Arg Val Arg
                230                 235                 240

Gln Gly Tyr Ser Pro Leu Ser Phe Gln Thr Arg Leu Pro Thr Pro
                245                 250                 255

Arg Gly Pro Asp Arg Pro Gly Gly Ile Glu Glu Glu Gly Gly
                260                 265             269
```

(2) INFORMATION FOR SEQ ID NO: 24:

(i) SEQUENCE CHARACTERISTICS:
        (A) LENGTH: 269 amino acids
        (B) TYPE: Amino Acid
        (D) TOPOLOGY: Linear (xi) SEQUENCE DESCRIPTION: SEQ ID NO: 24:

```
Gly Gly Gly Asp Met Arg Asp Asn Trp Arg Ser Glu Leu Tyr Lys
 1               5                  10                  15

Tyr Lys Val Val Lys Ile Glu Pro Leu Gly Val Ala Pro Thr Lys
                20                  25                  30

Ala Lys Arg Arg Val Val Gln Arg Glu Lys Arg Ala Val Gly Leu
                35                  40                  45

Ile Gly Ala Leu Phe Leu Gly Phe Leu Gly Ala Ala Gly Ser Thr
                50                  55                  60

Met Gly Ala Ala Ser Met Thr Leu Thr Val Gln Ala Arg Gln Leu
                65                  70                  75

Leu Ser Gly Ile Val Gln Gln Gln Ser Asn Leu Leu Arg Ala Ile
                80                  85                  90

Glu Ala Gln Gln His Leu Leu Gln Leu Thr Val Trp Gly Ile Lys
                95                 100                 105

Gln Leu Gln Ala Arg Val Leu Ala Val Glu Arg Tyr Leu Lys Asp
                110                 115                 120

Gln Gln Leu Leu Gly Ile Trp Gly Cys Ser Gly Lys Leu Val Cys
                125                 130                 135

Thr Thr Thr Val Pro Trp Asn Ala Ser Trp Ser Asn Lys Ser Leu
                140                 145                 150

Asn Gln Ile Trp Asp Asn Met Thr Trp Met Glu Trp Glu Arg Glu
                155                 160                 165

Ile Asp Asn Tyr Thr Gly Leu Ile Tyr Arg Leu Ile Glu Glu Ser
                170                 175                 180

Gln Asn Gln Gln Glu Gln Asn Glu Gln Asp Leu Leu Lys Leu Asp
                185                 190                 195

Thr Trp Ala Ser Leu Trp Asn Trp Phe Ser Ile Thr Lys Trp Leu
                200                 205                 210

Trp Tyr Ile Lys Ile Phe Ile Met Ile Val Gly Gly Leu Ile Gly
                215                 220                 225

Leu Arg Ile Ile Phe Ala Val Leu Ser Ile Val Asn Arg Val Arg
                230                 235                 240

Gln Gly Tyr Ser Pro Leu Ser Phe Gln Thr Leu Leu Pro Ala Pro
                245                 250                 255
```

Arg Gly Pro Asp Arg Pro Glu Gly Ile Glu Glu Glu Gly Gly
          260                 265                 269

(2) INFORMATION FOR SEQ ID NO: 25:

(i) SEQUENCE CHARACTERISTICS:
        (A) LENGTH: 269 amino acids
        (B) TYPE: Amino Acid
        (D) TOPOLOGY: Linear (xi) SEQUENCE DESCRIPTION: SEQ ID NO: 25:

Gly Gly Gly Asn Met Arg Asp Asn Trp Arg Ser Glu Leu Tyr Lys
 1               5                  10                  15

Tyr Lys Val Val Lys Ile Glu Pro Leu Gly Val Ala Pro Thr Lys
                20                  25                  30

Ala Lys Arg Arg Val Val Gln Arg Glu Lys Arg Ala Val Gly Leu
                35                  40                  45

Leu Gly Ala Val Phe Leu Gly Phe Leu Gly Ala Ala Gly Ser Thr
                50                  55                  60

Met Gly Ala Arg Ser Met Ala Leu Thr Val Gln Ala Arg Gln Leu
                65                  70                  75

Leu Ser Gly Ile Val Gln Gln Gln Asn Asn Leu Leu Arg Ala Ile
                80                  85                  90

Glu Ala Gln Gln His Leu Leu Gln Leu Thr Val Trp Gly Ile Lys
                95                  100                 105

Gln Leu Gln Ala Arg Val Leu Ala Val Glu Arg Tyr Leu Arg Asp
                110                 115                 120

Gln Gln Leu Leu Gly Ile Trp Gly Cys Ser Gly Lys Leu Ile Cys
                125                 130                 135

Thr Thr Ala Val Pro Trp Asn Ala Ser Trp Ser Asn Lys Ser Met
                140                 145                 150

Asp Met Ile Trp Asn Asn Met Thr Trp Met Glu Trp Glu Arg Glu
                155                 160                 165

Ile Asp Asn Tyr Thr Ser Leu Ile Tyr Thr Leu Ile Glu Glu Ser
                170                 175                 180

Gln Asn Gln Gln Glu Lys Asn Glu Gln Glu Leu Leu Glu Leu Asn
                185                 190                 195

Lys Trp Glu Asn Leu Trp Ser Trp Phe Asp Ile Ser Asn Trp Leu
                200                 205                 210

Trp Tyr Ile Lys Ile Phe Ile Met Ile Val Gly Gly Leu Val Gly
                215                 220                 225

Leu Arg Ile Val Phe Ala Val Leu Ser Ile Val Asn Ser Val Arg
                230                 235                 240

Gln Gly Tyr Ser Pro Leu Ser Phe Gln Thr Arg Leu Pro Ala Pro
                245                 250                 255

Arg Gly Pro Asp Arg Pro Glu Gly Ile Glu Glu Glu Gly Gly
                260                 265                 269

(2) INFORMATION FOR SEQ ID NO: 26:

(i) SEQUENCE CHARACTERISTICS:
        (A) LENGTH: 268 amino acids
        (B) TYPE: Amino Acid
        (D) TOPOLOGY: Linear (xi) SEQUENCE DESCRIPTION: SEQ ID NO: 26:

Gly Gly Gly Asp Met Arg Asp Asn Trp Arg Ser Glu Leu Tyr Lys

-continued

```
  1               5                  10                 15
Tyr Lys Val Val Lys Ile Glu Pro Leu Gly Val Ala Pro Thr Lys
                 20                 25                 30
Ala Lys Arg Arg Val Val Gln Arg Glu Lys Arg Ala Val Thr Leu
                 35                 40                 45
Gly Ala Met Phe Leu Gly Phe Leu Gly Ala Ala Gly Ser Thr Met
                 50                 55                 60
Gly Ala Arg Ser Leu Thr Leu Thr Val Gln Ala Arg Gln Leu Leu
                 65                 70                 75
Ser Gly Ile Val Gln Gln Gln Asn Asn Leu Leu Arg Ala Ile Glu
                 80                 85                 90
Ala Gln Gln His Leu Leu Gln Leu Thr Val Trp Gly Ile Lys Gln
                 95                100                105
Leu Gln Ala Arg Val Leu Ala Val Glu Arg Tyr Leu Lys Asp Gln
                110                115                120
Gln Leu Leu Gly Ile Trp Gly Cys Ser Gly Lys Leu Ile Cys Thr
                125                130                135
Thr Ala Val Pro Trp Asn Ala Ser Trp Ser Asn Lys Ser Leu Asp
                140                145                150
Gln Ile Trp Asn Asn Met Thr Trp Met Glu Trp Glu Arg Glu Ile
                155                160                165
Asp Asn Tyr Thr Asn Leu Ile Tyr Thr Leu Ile Glu Glu Ser Gln
                170                175                180
Asn Gln Gln Glu Lys Asn Glu Gln Glu Leu Leu Glu Leu Asp Lys
                185                190                195
Trp Ala Ser Leu Trp Asn Trp Phe Asp Ile Ser Lys Trp Leu Trp
                200                205                210
Tyr Ile Lys Ile Phe Ile Met Ile Val Gly Gly Leu Val Gly Leu
                215                220                225
Arg Ile Val Phe Thr Val Leu Ser Ile Val Asn Arg Val Arg Gln
                230                235                240
Gly Tyr Ser Pro Leu Ser Phe Gln Thr Arg Phe Pro Ala Pro Arg
                245                250                255
Gly Pro Asp Arg Pro Glu Gly Ile Glu Glu Glu Gly Gly
                260                265       268
```

(2) INFORMATION FOR SEQ ID NO: 27:

(i) SEQUENCE CHARACTERISTICS:
        (A) LENGTH: 267 amino acids
        (B) TYPE: Amino Acid
        (D) TOPOLOGY: Linear (xi) SEQUENCE DESCRIPTION: SEQ ID NO: 27:

```
Ala Gly Gly Asp Met Arg Asp Asn Trp Arg Ser Glu Leu Tyr Lys
  1               5                  10                 15
Tyr Lys Val Val Lys Ile Glu Pro Leu Gly Val Ala Pro Thr Lys
                 20                 25                 30
Ala Arg Arg Arg Val Val Gln Arg Glu Lys Arg Ala Val Gly Met
                 35                 40                 45
Leu Gly Ala Met Phe Leu Gly Phe Leu Gly Ala Ala Gly Ser Thr
                 50                 55                 60
Met Gly Ala Arg Ser Met Thr Leu Thr Val Gln Ala Arg Gln Leu
                 65                 70                 75
Leu Ser Gly Ile Val Gln Gln Gln Asn Asn Leu Leu Arg Ala Ile
```

```
                    80                  85                  90
Glu Ala Gln Gln His Leu Leu Gln Leu Thr Val Trp Gly Ile Lys
                    95                 100                 105
Gln Leu Gln Ala Arg Val Leu Ala Val Glu Arg Tyr Leu Lys Asp
                   110                 115                 120
Gln Gln Leu Leu Gly Ile Trp Gly Cys Ser Gly Lys Leu Ile Cys
                   125                 130                 135
Thr Thr Thr Val Pro Trp Asn Ala Ser Trp Ser Asn Lys Ser Leu
                   140                 145                 150
Asn Glu Ile Trp Asp Asn Met Thr Trp Met Gln Trp Glu Arg Glu
                   155                 160                 165
Ile Asp Asn Tyr Thr His Leu Ile Tyr Thr Leu Ile Glu Glu Ser
                   170                 175                 180
Gln Asn Gln Gln Glu Lys Asn Glu Gln Glu Leu Leu Glu Leu Asp
                   185                 190                 195
Lys Trp Leu Trp Ser Trp Phe Ser Ile Thr Asn Trp Leu Trp Tyr
                   200                 205                 210
Ile Arg Ile Phe Ile Ile Val Gly Gly Leu Val Gly Leu Arg
                   215                 220                 225
Ile Val Phe Ala Val Leu Ser Ile Val Asn Arg Val Arg Gln Gly
                   230                 235                 240
Tyr Ser Pro Leu Ser Phe Gln Thr Arg Leu Pro Thr Gln Arg Gly
                   245                 250                 255
Pro Asp Arg Pro Glu Gly Ile Glu Glu Glu Gly Gly
                   260                 265     267

(2) INFORMATION FOR SEQ ID NO: 28:

(i) SEQUENCE CHARACTERISTICS:
        (A) LENGTH: 269 amino acids
        (B) TYPE: Amino Acid
        (D) TOPOLOGY: Linear (xi) SEQUENCE DESCRIPTION: SEQ ID NO: 28:

Ala Gly Gly Asn Met Lys Asp Asn Trp Arg Ser Glu Leu Tyr Lys
 1               5                  10                  15
Tyr Lys Val Val Lys Ile Glu Pro Leu Gly Val Ala Pro Thr Lys
                    20                  25                  30
Ala Lys Arg Arg Val Val Gln Arg Glu Lys Arg Ala Val Gly Val
                    35                  40                  45
Ile Gly Ala Met Phe Leu Gly Phe Leu Gly Ala Ala Gly Ser Thr
                    50                  55                  60
Met Gly Ala Ala Ser Ile Thr Leu Thr Val Gln Ala Arg Lys Leu
                    65                  70                  75
Leu Ser Gly Ile Val Gln Gln Gln Asn Asn Leu Leu Arg Ala Ile
                    80                  85                  90
Glu Ala Gln Gln His Leu Leu Gln Leu Thr Val Trp Gly Ile Lys
                    95                 100                 105
Gln Leu Gln Ala Arg Val Leu Ala Val Glu Arg Tyr Leu Arg Asp
                   110                 115                 120
Gln Gln Leu Leu Gly Ile Trp Gly Cys Ser Gly Lys Leu Ile Cys
                   125                 130                 135
Thr Thr Thr Val Pro Trp Asn Thr Ser Trp Ser Asn Lys Ser Leu
                   140                 145                 150
Asp Lys Ile Trp Asn Asn Met Thr Trp Met Glu Trp Glu Arg Glu
```

-continued

```
                  155                 160                 165
Ile Asp Asn Tyr Thr Ser Leu Ile Tyr Thr Leu Leu Glu Glu Ser
                  170                 175                 180

Gln Asn Gln Gln Glu Lys Asn Glu Gln Glu Leu Leu Glu Leu Asp
                  185                 190                 195

Lys Trp Ala Ser Leu Trp Asn Trp Phe Ser Ile Thr Asn Trp Leu
                  200                 205                 210

Trp Tyr Ile Arg Ile Phe Ile Met Ile Val Gly Gly Leu Ile Gly
                  215                 220                 225

Leu Arg Ile Ile Phe Ala Val Leu Ser Ile Val Asn Arg Val Arg
                  230                 235                 240

Gln Gly Tyr Ser Pro Leu Ser Phe Gln Thr Leu Ile Pro Ala Gln
                  245                 250                 255

Arg Gly Pro Asp Arg Pro Glu Gly Ile Glu Glu Gly Gly
                  260                 265             269
```

(2) INFORMATION FOR SEQ ID NO: 29:

(i) SEQUENCE CHARACTERISTICS:
        (A) LENGTH: 269 amino acids
        (B) TYPE: Amino Acid
        (D) TOPOLOGY: Linear (xi) SEQUENCE DESCRIPTION: SEQ ID NO: 29:

```
Gly Gly Gly Asp Met Arg Asp Asn Trp Arg Ser Glu Leu Tyr Lys
 1               5                  10                  15

Tyr Lys Val Val Lys Ile Glu Pro Leu Gly Val Ala Pro Thr Lys
                  20                  25                  30

Ala Lys Arg Arg Val Val Gln Arg Glu Lys Arg Ala Val Gly Met
                  35                  40                  45

Leu Gly Ala Met Phe Leu Gly Phe Leu Gly Ala Ala Gly Ser Thr
                  50                  55                  60

Met Gly Ala Thr Ser Met Ala Leu Thr Val Gln Ala Arg Gln Leu
                  65                  70                  75

Leu Ser Gly Ile Val Gln Gln Gln Asn Asn Leu Leu Arg Ala Ile
                  80                  85                  90

Lys Ala Gln Gln His Leu Leu Gln Leu Thr Val Trp Gly Ile Lys
                  95                 100                 105

Gln Leu Gln Ala Arg Ile Leu Ala Val Glu Arg Tyr Leu Lys Asp
                  110                 115                 120

Gln Gln Leu Leu Gly Phe Trp Gly Cys Ser Gly Lys Leu Ile Cys
                  125                 130                 135

Thr Thr Ala Val Pro Trp Asn Ala Ser Trp Ser Asn Lys Thr Leu
                  140                 145                 150

Asp Gln Ile Trp Asn Asn Met Thr Trp Met Glu Trp Asp Arg Glu
                  155                 160                 165

Ile Asp Asn Tyr Thr His Leu Ile Tyr Thr Leu Ile Glu Glu Ser
                  170                 175                 180

Gln Asn Gln Gln Glu Lys Asn Gln Gln Glu Leu Leu Gln Leu Asp
                  185                 190                 195

Lys Trp Ala Ser Leu Trp Thr Trp Ser Asp Ile Thr Lys Trp Leu
                  200                 205                 210

Trp Tyr Ile Lys Ile Phe Ile Met Ile Val Gly Gly Leu Ile Gly
                  215                 220                 225

Leu Arg Ile Val Phe Ala Val Leu Ser Ile Val Asn Arg Val Arg
```

```
                    230                 235                 240
Gln Gly Tyr Ser Pro Leu Ser Phe Gln Thr Leu Leu Pro Asn Pro
                245                 250                 255
Arg Gly Pro Asp Arg Pro Glu Gly Thr Glu Glu Gly Gly
                260                 265             269

(2) INFORMATION FOR SEQ ID NO: 30:

(i) SEQUENCE CHARACTERISTICS:
        (A) LENGTH: 269 amino acids
        (B) TYPE: Amino Acid
        (D) TOPOLOGY: Linear (xi) SEQUENCE DESCRIPTION: SEQ ID NO: 30:

Gly Gly Gly Asp Met Arg Asp Asn Trp Arg Ser Glu Leu Tyr Lys
 1               5                  10                  15
Tyr Lys Val Ile Lys Ile Glu Pro Leu Gly Ile Ala Pro Thr Lys
                20                  25                  30
Ala Lys Arg Arg Val Val Gln Arg Glu Lys Arg Ala Val Gly Ile
                35                  40                  45
Val Gly Ala Met Phe Leu Gly Phe Leu Gly Ala Ala Gly Ser Thr
                50                  55                  60
Met Gly Ala Val Ser Leu Thr Leu Thr Val Gln Ala Arg Gln Leu
                65                  70                  75
Leu Ser Gly Ile Val Gln Gln Gln Asn Asn Leu Leu Arg Ala Ile
                80                  85                  90
Glu Ala Gln Gln His Leu Leu Gln Leu Thr Val Trp Gly Ile Lys
                95                 100                 105
Gln Leu Gln Ala Arg Val Leu Ala Val Glu Arg Tyr Leu Arg Asp
               110                 115                 120
Gln Gln Leu Leu Gly Ile Trp Gly Cys Ser Gly Lys Leu Ile Cys
               125                 130                 135
Thr Thr Ala Val Pro Trp Asn Ala Ser Trp Ser Asn Lys Ser Leu
               140                 145                 150
Glu Asp Ile Trp Asp Asn Met Thr Trp Met Gln Trp Glu Arg Glu
               155                 160                 165
Ile Asp Asn Tyr Thr Asn Thr Ile Tyr Thr Leu Leu Glu Glu Ser
               170                 175                 180
Gln Asn Gln Gln Glu Lys Asn Glu Gln Glu Leu Leu Glu Leu Asp
               185                 190                 195
Lys Trp Ala Ser Leu Trp Asn Trp Phe Ser Ile Thr Asn Trp Leu
               200                 205                 210
Trp Tyr Ile Lys Ile Phe Ile Met Ile Val Gly Gly Leu Val Gly
               215                 220                 225
Leu Arg Ile Val Phe Ala Val Leu Ser Ile Val Asn Arg Val Arg
               230                 235                 240
Gln Gly Tyr Ser Pro Leu Ser Phe Gln Thr Arg Leu Pro Val Pro
               245                 250                 255
Arg Gly Pro Asp Arg Pro Asp Gly Ile Glu Glu Glu Gly Gly
               260                 265             269

(2) INFORMATION FOR SEQ ID NO: 31:

(i) SEQUENCE CHARACTERISTICS:
        (A) LENGTH: 269 amino acids
        (B) TYPE: Amino Acid
        (D) TOPOLOGY: Linear
```

(xi) SEQUENCE DESCRIPTION: SEQ ID NO: 31:

```
Gly Gly Gly Asp Met Arg Asp Asn Trp Arg Ser Glu Leu Tyr Lys
  1               5                  10                  15

Tyr Lys Val Val Lys Ile Glu Pro Leu Gly Ile Ala Pro Thr Lys
                 20                  25                  30

Ala Lys Arg Arg Val Val Gln Arg Glu Lys Arg Ala Val Gly Ile
                 35                  40                  45

Ile Gly Ala Met Phe Leu Gly Phe Leu Gly Ala Ala Gly Ser Thr
                 50                  55                  60

Met Gly Ala Arg Ser Met Thr Leu Thr Val Gln Ala Arg Lys Leu
                 65                  70                  75

Leu Ser Gly Ile Val Gln Gln Asn Asn Leu Leu Arg Ala Ile
                 80                  85                  90

Glu Ala Gln Gln His Leu Leu Gln Leu Thr Val Trp Gly Ile Lys
                 95                 100                 105

Gln Leu Gln Ala Arg Val Leu Ala Val Glu Arg Tyr Leu Arg Asp
                110                 115                 120

Gln Gln Leu Leu Gly Ile Trp Gly Cys Ser Gly Lys Leu Ile Cys
                125                 130                 135

Thr Thr Ala Val Pro Trp Asn Thr Ser Trp Ser Asn Lys Ser Met
                140                 145                 150

Glu Asp Ile Trp Asp Asn Met Thr Trp Met Gln Trp Glu Lys Glu
                155                 160                 165

Ile Asp Asn Tyr Thr Asn Thr Ile Tyr Thr Leu Leu Glu Glu Ser
                170                 175                 180

Gln Asn Gln Gln Glu Lys Asn Glu Gln Glu Leu Leu Glu Leu Asp
                185                 190                 195

Lys Trp Ala Ser Leu Trp Asn Trp Phe Asn Ile Thr Asn Trp Leu
                200                 205                 210

Trp Tyr Ile Lys Ile Phe Ile Met Ile Val Gly Gly Leu Val Gly
                215                 220                 225

Leu Arg Ile Val Phe Ala Val Leu Ser Val Val Asn Arg Val Arg
                230                 235                 240

Gln Gly Tyr Ser Pro Leu Ser Phe Gln Thr Arg Leu Pro Thr Pro
                245                 250                 255

Arg Gly Pro Asp Arg Pro Asp Gly Ile Glu Glu Glu Gly Gly
                260                 265             269
```

(2) INFORMATION FOR SEQ ID NO: 32:

(i) SEQUENCE CHARACTERISTICS:
        (A) LENGTH: 269 amino acids
        (B) TYPE: Amino Acid
        (D) TOPOLOGY: Linear (xi) SEQUENCE DESCRIPTION: SEQ ID NO: 32:

```
Gly Gly Gly Asn Met Arg Asp Asn Trp Arg Asn Glu Leu Tyr Lys
  1               5                  10                  15

Tyr Lys Val Val Lys Ile Glu Pro Leu Gly Val Ala Pro Thr Lys
                 20                  25                  30

Ala Lys Arg Arg Val Val Gln Arg Glu Lys Arg Ala Val Gly Met
                 35                  40                  45

Leu Gly Ala Met Phe Leu Gly Phe Leu Gly Ala Ala Gly Ser Thr
                 50                  55                  60
```

```
Met Gly Ala Arg Ser Leu Thr Leu Thr Val Gln Ala Arg Gln Leu
                65                  70                  75
Leu Ser Gly Ile Val Gln Gln Gln Asn Asn Leu Leu Arg Ala Ile
                80                  85                  90
Glu Ala Gln Gln His Leu Leu Gln Leu Thr Val Trp Gly Ile Lys
                95                 100                 105
Gln Leu Gln Ala Arg Val Leu Ala Val Glu Arg Tyr Leu Arg Asp
               110                 115                 120
Gln Gln Leu Leu Gly Ile Trp Gly Cys Ser Gly Lys Leu Ile Cys
               125                 130                 135
Thr Thr Thr Val Pro Trp Asn Ala Ser Trp Ser Asn Lys Thr Leu
               140                 145                 150
Asp Gln Ile Trp Asn Asn Met Thr Trp Met Glu Trp Glu Arg Glu
               155                 160                 165
Ile Asp Asn Tyr Thr Ser Leu Ile Tyr Thr Leu Ile Glu Gln Ser
               170                 175                 180
Gln Asn Gln Gln Glu Lys Asn Glu Gln Glu Leu Leu Glu Leu Asp
               185                 190                 195
Lys Trp Ala Ser Leu Trp Ser Trp Tyr Asp Ile Ser Asn Trp Leu
               200                 205                 210
Trp Tyr Ile Lys Ile Phe Ile Met Ile Val Gly Gly Leu Ile Gly
               215                 220                 225
Leu Arg Ile Val Phe Ala Val Leu Ser Ile Val Asn Arg Val Arg
               230                 235                 240
Gln Gly Tyr Ser Pro Leu Ser Phe Gln Thr Leu Leu Pro Ala Thr
               245                 250                 255
Arg Gly Pro Arg Gln Pro Glu Glu Ile Glu Glu Glu Gly Gly
               260                 265                 269

(2) INFORMATION FOR SEQ ID NO: 33:

(i) SEQUENCE CHARACTERISTICS:
        (A) LENGTH: 269 amino acids
        (B) TYPE: Amino Acid
        (D) TOPOLOGY: Linear (xi) SEQUENCE DESCRIPTION: SEQ ID NO: 33:

Gly Gly Gly Asn Met Arg Asp Asn Trp Arg Ser Glu Leu Tyr Lys
 1               5                  10                  15
Tyr Lys Val Val Arg Ile Glu Pro Leu Gly Val Ala Pro Thr Arg
                20                  25                  30
Ala Lys Arg Arg Val Val Gln Arg Glu Lys Arg Ala Val Gly Thr
                35                  40                  45
Ile Gly Ala Met Phe Leu Gly Phe Leu Gly Ala Ala Gly Ser Thr
                50                  55                  60
Met Gly Ala Gly Ser Ile Thr Leu Thr Val Gln Ala Arg His Leu
                65                  70                  75
Leu Ser Gly Ile Val Gln Gln Gln Asn Asn Leu Leu Arg Ala Ile
                80                  85                  90
Glu Ala Gln Gln His Leu Leu Gln Leu Thr Val Trp Gly Ile Lys
                95                 100                 105
Gln Leu Gln Ala Arg Val Leu Ala Val Glu Arg Tyr Leu Arg Asp
               110                 115                 120
Gln Gln Leu Leu Gly Ile Trp Gly Cys Ser Gly Lys Leu Ile Cys
               125                 130                 135
```

```
Thr Thr Thr Val Pro Trp Asn Ala Ser Trp Ser Asn Lys Ser Leu
            140                 145                 150

Asn Met Ile Trp Asn Asn Met Thr Trp Met Gln Trp Glu Arg Glu
            155                 160                 165

Ile Asp Asn Tyr Thr Gly Ile Ile Tyr Asn Leu Leu Glu Glu Ser
            170                 175                 180

Gln Asn Gln Gln Glu Lys Asn Glu Gln Glu Leu Leu Glu Leu Asp
            185                 190                 195

Lys Trp Ala Asn Leu Trp Asn Trp Phe Asp Ile Thr Gln Trp Leu
            200                 205                 210

Trp Tyr Ile Arg Ile Phe Ile Met Ile Val Gly Gly Leu Val Gly
            215                 220                 225

Leu Lys Ile Val Phe Ala Val Leu Ser Ile Val Asn Arg Val Arg
            230                 235                 240

Gln Gly Tyr Ser Pro Leu Ser Phe Gln Thr His Leu Pro Ala Pro
            245                 250                 255

Arg Gly Pro Asp Arg Pro Glu Gly Ile Glu Gly Glu Gly Gly
            260                 265                 269
```

(2) INFORMATION FOR SEQ ID NO: 34:

(i) SEQUENCE CHARACTERISTICS:
        (A) LENGTH: 269 amino acids
        (B) TYPE: Amino Acid
        (D) TOPOLOGY: Linear (xi) SEQUENCE DESCRIPTION: SEQ ID NO: 34:

```
Gly Gly Gly Asn Met Arg Asp Asn Trp Arg Ser Glu Leu Tyr Lys
 1               5                  10                  15

Tyr Lys Val Val Arg Ile Glu Pro Leu Gly Val Ala Pro Thr Lys
            20                  25                  30

Ala Lys Arg Arg Val Val Gln Arg Glu Lys Arg Ala Val Gly Thr
            35                  40                  45

Ile Gly Ala Met Phe Leu Gly Phe Leu Gly Ala Ala Gly Ser Thr
            50                  55                  60

Met Gly Ala Gly Ser Leu Thr Leu Thr Val Gln Ala Arg Gln Leu
            65                  70                  75

Leu Ser Gly Ile Val Gln Gln Gln Asn Asn Leu Leu Arg Ala Ile
            80                  85                  90

Asp Ala Gln Gln His Leu Leu Gln Leu Thr Val Trp Gly Ile Lys
            95                  100                 105

Gln Leu Gln Ala Arg Val Leu Ala Val Glu Arg Tyr Leu Arg Asp
            110                 115                 120

Gln Gln Leu Leu Gly Ile Trp Gly Cys Ser Gly Lys Leu Ile Cys
            125                 130                 135

Thr Thr Thr Val Pro Trp Asn Ala Ser Trp Ser Asn Lys Ser Met
            140                 145                 150

Asn Gln Ile Trp Asp Asn Leu Thr Trp Met Glu Trp Glu Arg Glu
            155                 160                 165

Ile Asp Asn Tyr Thr Ser Ile Ile Tyr Ser Leu Ile Glu Glu Ser
            170                 175                 180

Gln Asn Gln Gln Gly Lys Asn Glu Gln Glu Leu Leu Glu Leu Asp
            185                 190                 195

Lys Trp Ala Ser Leu Trp Asn Trp Phe Asp Ile Thr Asn Trp Leu
            200                 205                 210
```

-continued

```
Trp Tyr Ile Lys Ile Phe Ile Met Ile Val Gly Gly Leu Ile Gly
                215                 220                 225

Leu Arg Ile Val Phe Thr Val Leu Ser Ile Val Asn Arg Val Arg
                230                 235                 240

Gln Gly Tyr Ser Pro Leu Ser Phe Gln Thr His Leu Pro Thr Pro
                245                 250                 255

Arg Gly Pro Asp Arg Pro Glu Gly Ile Glu Glu Glu Gly Gly
                260                 265             269
```

(2) INFORMATION FOR SEQ ID NO: 35:

(i) SEQUENCE CHARACTERISTICS:
        (A) LENGTH: 268 amino acids
        (B) TYPE: Amino Acid
        (D) TOPOLOGY: Linear (xi) SEQUENCE DESCRIPTION: SEQ ID NO: 35:

```
Gly Gly Gly Asn Met Arg Asp Asn Trp Arg Ser Glu Leu Tyr Lys
 1               5                  10                  15

Tyr Lys Val Val Lys Ile Glu Pro Leu Gly Val Ala Pro Thr Xaa
                 20                  25                  30

Ala Lys Arg Arg Val Val Gln Arg Glu Lys Arg Ala Val Gly Ile
                 35                  40                  45

Gly Ala Ala Ser Pro Gly Phe Leu Gly Ala Ala Gly Ser Thr Met
                 50                  55                  60

Xaa Ala Ala Pro Thr Thr Leu Thr Val Gln Pro Arg Gln Leu Leu
                 65                  70                  75

Ser Gly Ile Val Gln Gln Gln Asn Asn Leu Leu Arg Ala Ile Glu
                 80                  85                  90

Ala Gln Gln His Leu Leu Gln Leu Thr Val Trp Gly Ile Lys Gln
                 95                 100                 105

Leu Gln Ala Arg Val Leu Ala Val Glu Arg Tyr Leu Lys Asp Gln
                110                 115                 120

Gln Leu Leu Gly Ile Trp Gly Cys Ser Gly Lys Leu Ile Cys Thr
                125                 130                 135

Thr Thr Val Pro Trp Asn Ala Ser Trp Ser Asn Lys Ser Leu Asp
                140                 145                 150

Glu Ile Trp Asn Asn Met Thr Trp Met Glu Trp Arg Glu Ile
                155                 160                 165

Asn Asn Tyr Thr Gly Leu Ile Tyr Thr Leu Ile Glu Glu Ser Gln
                170                 175                 180

Xaa Gln Gln Glu Lys Asn Glu Leu Asp Leu Leu Glu Leu Asp Lys
                185                 190                 195

Trp Ala Ser Leu Trp Asn Trp Phe Asp Ile Thr Asn Xaa Leu Trp
                200                 205                 210

Tyr Ile Lys Ile Phe Ile Met Ile Val Gly Gly Leu Val Gly Leu
                215                 220                 225

Arg Ile Ile Phe Thr Val Leu Ser Ile Val Asn Arg Val Arg Gln
                230                 235                 240

Gly Tyr Ser Pro Leu Ser Phe Gln Thr His Leu Pro Xaa Pro Arg
                245                 250                 255

Gly Pro Asp Arg Pro Gly Gly Ile Glu Glu Glu Gly Gly
                260                 265             268
```

(2) INFORMATION FOR SEQ ID NO: 36:

(i) SEQUENCE CHARACTERISTICS:
    (A) LENGTH: 269 amino acids
    (B) TYPE: Amino Acid
    (D) TOPOLOGY: Linear (xi) SEQUENCE DESCRIPTION: SEQ ID NO: 36:

```
Gly Gly Gly Asp Met Arg Asp Asn Trp Arg Ser Glu Leu Tyr Lys
 1               5                  10                  15

Tyr Lys Val Val Arg Ile Glu Pro Leu Gly Ile Ala Pro Thr Arg
                20                  25                  30

Ala Lys Arg Arg Val Val Gln Arg Glu Lys Arg Ala Val Gly Thr
                35                  40                  45

Leu Gly Ala Met Phe Leu Gly Phe Leu Gly Ala Ala Gly Ser Thr
                50                  55                  60

Met Gly Ala Ala Ser Val Ala Leu Thr Val Gln Ala Arg Gln Leu
                65                  70                  75

Leu Ser Gly Ile Val Gln Gln Gln Asn Asn Leu Leu Arg Ala Ile
                80                  85                  90

Glu Ala Gln Gln His Met Leu Gln Leu Thr Val Trp Gly Ile Lys
                95                 100                 105

Gln Leu Gln Ala Arg Val Leu Ala Val Glu Arg Tyr Leu Gly Asp
               110                 115                 120

Gln Gln Leu Leu Gly Ile Trp Gly Cys Ser Gly Lys Leu Ile Cys
               125                 130                 135

Thr Thr Thr Val Pro Trp Asn Thr Ser Trp Ser Asn Lys Ser Leu
               140                 145                 150

Asp Asp Ile Trp Thr Asn Met Thr Trp Met Glu Trp Lys Arg Glu
               155                 160                 165

Ile Asp Asn Tyr Thr Ser Leu Ile Tyr Thr Leu Ile Glu Glu Ser
               170                 175                 180

Gln Arg Gln Gln Glu Lys Asn Glu Gln Glu Leu Leu Glu Leu Asp
               185                 190                 195

Lys Trp Asp Ser Leu Trp Asn Trp Phe Thr Ile Ser Lys Trp Leu
               200                 205                 210

Trp Tyr Ile Lys Ile Phe Ile Met Ile Val Ala Gly Leu Val Gly
               215                 220                 225

Leu Arg Ile Val Phe Ala Val Leu Ser Ile Val Asn Lys Val Arg
               230                 235                 240

Gln Gly Tyr Ser Pro Val Ser Phe Gln Thr Arg Leu Pro Ala Gln
               245                 250                 255

Arg Gly Pro Asp Arg Pro Glu Glu Ile Glu Glu Glu Gly Gly
               260                 265             269
```

(2) INFORMATION FOR SEQ ID NO: 37:

(i) SEQUENCE CHARACTERISTICS:
        (A) LENGTH: 269 amino acids
        (B) TYPE: Amino Acid
        (D) TOPOLOGY: Linear (xi) SEQUENCE DESCRIPTION: SEQ ID NO: 37:

```
Gly Gly Gly Asp Met Arg Asp Asn Trp Arg Ser Glu Leu Tyr Lys
 1               5                  10                  15

Tyr Lys Val Val Lys Ile Glu Pro Leu Gly Val Ala Pro Thr Lys
                20                  25                  30

Pro Lys Arg Arg Val Val Gln Arg Glu Lys Arg Ala Val Gly Thr
                35                  40                  45
```

```
Ile Gly Ala Met Phe Leu Gly Phe Leu Gly Thr Ala Gly Ser Thr
                50                  55                  60

Met Gly Ala Ala Ser Ile Thr Leu Thr Val Gln Ala Arg Gln Leu
                65                  70                  75

Leu Ser Gly Ile Val Gln Gln Arg Asn Leu Leu Arg Ala Ile
                80                  85                  90

Glu Ala Gln Gln His Leu Leu Gln Leu Thr Val Trp Gly Ile Lys
                95                  100                 105

Gln Leu Gln Ala Arg Val Leu Ala Val Glu Arg Tyr Leu Lys Asp
                110                 115                 120

Gln Gln Leu Leu Gly Ile Trp Gly Cys Ser Gly Lys Leu Ile Cys
                125                 130                 135

Thr Thr Ala Val Pro Trp Asn Ala Ser Trp Ser Asn Lys Ser Leu
                140                 145                 150

Asp Lys Ile Trp Asn Asn Met Thr Trp Met Glu Trp Glu Arg Glu
                155                 160                 165

Ile Asp Asn Tyr Thr Arg Glu Ile Tyr Thr Leu Ile Glu Glu Ser
                170                 175                 180

Gln Asn Gln Gln Glu Lys Asn Glu Leu Glu Leu Leu Glu Leu Asp
                185                 190                 195

Lys Trp Ala Ser Leu Trp Asn Trp Phe Asp Ile Thr Lys Trp Leu
                200                 205                 210

Trp Tyr Ile Lys Ile Phe Ile Met Ile Val Gly Gly Leu Val Gly
                215                 220                 225

Leu Arg Ile Val Phe Ala Val Leu Ser Ile Val Asn Arg Val Arg
                230                 235                 240

Gln Gly Tyr Ser Pro Leu Ser Leu Gln Thr Arg Phe Pro Ala Gln
                245                 250                 255

Arg Gly Pro Gly Gly Pro Glu Gly Ile Glu Glu Glu Gly Gly
                260                 265             269

(2) INFORMATION FOR SEQ ID NO: 38:

(i) SEQUENCE CHARACTERISTICS:
        (A) LENGTH: 267 amino acids
        (B) TYPE: Amino Acid
        (D) TOPOLOGY: Linear (xi) SEQUENCE DESCRIPTION: SEQ ID NO: 38:

Gly Gly Gly Asp Met Arg Asp Asn Trp Arg Ser Glu Leu Tyr Lys
 1               5                  10                  15

Tyr Lys Val Val Lys Ile Glu Pro Leu Gly Ile Ala Pro Thr Lys
                20                  25                  30

Ala Lys Arg Arg Val Val Gln Arg Glu Lys Arg Ala Val Gly Ile
                35                  40                  45

Gly Ala Val Phe Leu Gly Phe Leu Gly Ala Ala Gly Ser Thr Met
                50                  55                  60

Gly Ala Ala Ala Met Thr Leu Thr Val Gln Ala Arg Leu Leu Leu
                65                  70                  75

Thr Gly Ile Val Gln Gln Gln Asn Asn Leu Leu Lys Ala Ile Glu
                80                  85                  90

Ala Gln Gln His Leu Leu Gln Leu Thr Val Trp Gly Ile Lys Gln
                95                  100                 105

Leu Gln Ala Arg Val Leu Ala Val Glu Arg Tyr Leu Lys Asp Gln
                110                 115                 120
```

```
Gln Leu Leu Gly Ile Trp Gly Cys Ser Gly Lys Leu Ile Cys Thr
            125                 130                 135

Thr Thr Val Pro Trp Asn Thr Ser Trp Ser Asn Lys Ser Leu Asp
            140                 145                 150

Lys Ile Trp Gly Asn Met Thr Trp Met Glu Trp Glu Arg Glu Ile
            155                 160                 165

Asp Asn Tyr Thr Gly Leu Ile Tyr Thr Leu Ile Glu Glu Ser Gln
            170                 175                 180

Asn Gln Gln Glu Lys Asn Glu Gln Glu Leu Leu Glu Leu Asp Lys
            185                 190                 195

Trp Ala Ser Leu Trp Asn Trp Phe Thr Ile Thr Asn Trp Leu Trp
            200                 205                 210

Tyr Ile Lys Ile Phe Ile Met Ile Val Gly Gly Leu Ile Gly Leu
            215                 220                 225

Arg Ile Val Phe Ala Val Leu Ser Ile Val Asn Arg Val Arg Gln
            230                 235                 240

Gly Tyr Ser Pro Leu Ser Phe Gln Thr Arg Leu Pro Ala Pro Arg
            245                 250                 255

Gly Pro Asp Arg Pro Glu Gly Ile Glu Glu Gly
            260                 265     267

(2) INFORMATION FOR SEQ ID NO: 39:

(i) SEQUENCE CHARACTERISTICS:
        (A) LENGTH: 268 amino acids
        (B) TYPE: Amino Acid
        (D) TOPOLOGY: Linear (xi) SEQUENCE DESCRIPTION: SEQ ID NO: 39:

Gly Gly Gly Asp Met Arg Glu Asn Trp Arg Ser Glu Leu Tyr Lys
 1               5                  10                  15

Tyr Lys Val Val Lys Ile Glu Pro Leu Gly Val Ala Pro Thr Lys
            20                  25                  30

Ala Lys Arg Arg Val Val Gln Arg Glu Lys Arg Ala Val Gly Phe
            35                  40                  45

Gly Ala Met Phe Leu Gly Phe Leu Gly Ala Ala Gly Ser Thr Met
            50                  55                  60

Gly Ala Ala Ser Met Thr Leu Thr Val Gln Ala Arg Leu Leu Leu
            65                  70                  75

Ser Gly Ile Val Gln Gln Gln Ser Asn Leu Leu Arg Ala Ile Glu
            80                  85                  90

Ala Gln Gln His Leu Leu Gln Leu Thr Val Trp Gly Ile Lys Gln
            95                  100                 105

Leu Gln Ala Arg Val Leu Ala Val Glu Arg Tyr Leu Lys Asp Gln
            110                 115                 120

Gln Leu Leu Gly Ile Trp Gly Cys Ser Gly Lys Leu Ile Cys Thr
            125                 130                 135

Thr Asn Val Pro Trp Asn Lys Thr Trp Ser Asn Lys Ser Leu Asp
            140                 145                 150

Gln Ile Trp Gln Asn Met Thr Trp Met Gln Trp Glu Arg Glu Ile
            155                 160                 165

Asp Lys Tyr Thr Asp Val Ile Tyr Thr Leu Ile Gly Glu Ser Gln
            170                 175                 180

Asn Gln Gln Glu Lys Asn Glu Gln Glu Leu Leu Glu Leu Asp Lys
            185                 190                 195
```

```
Trp Ala Ser Leu Trp Asn Trp Phe Asp Ile Thr Gln Trp Leu Trp
            200                 205                 210

Tyr Ile Lys Ile Phe Ile Met Ile Val Gly Gly Leu Val Gly Leu
            215                 220                 225

Arg Ile Val Phe Ser Val Leu Ser Ile Val Asn Arg Val Arg Gln
            230                 235                 240

Gly Tyr Ser Pro Leu Ser Phe Gln Thr Arg Leu Pro Ala Ala Arg
            245                 250                 255

Gly Pro Asp Arg Pro Glu Gly Ile Glu Glu Glu Gly Gly
            260                 265         268
```

(2) INFORMATION FOR SEQ ID NO: 40:

(i) SEQUENCE CHARACTERISTICS:
        (A) LENGTH: 268 amino acids
        (B) TYPE: Amino Acid
        (D) TOPOLOGY: Linear (xi) SEQUENCE DESCRIPTION: SEQ ID NO: 40:

```
Gly Gly Gly Asn Met Lys Asp Asn Trp Arg Ser Glu Leu Tyr Lys
 1               5                  10                  15

Tyr Lys Val Val Arg Ile Glu Pro Leu Gly Ile Ala Pro Thr Arg
            20                  25                  30

Ala Lys Arg Arg Val Val Gln Arg Glu Lys Arg Ala Ala Gly Leu
            35                  40                  45

Gly Val Met Phe Leu Gly Phe Leu Gly Ala Ala Gly Ser Thr Met
            50                  55                  60

Gly Ala Ala Ser Ile Ala Leu Thr Val Gln Ala Arg Gln Leu Leu
            65                  70                  75

Ser Gly Ile Val Gln Gln Gln Asn Asn Leu Leu Arg Ala Ile Glu
            80                  85                  90

Ala Gln Gln His Met Leu Gln Leu Thr Val Trp Gly Ile Lys Gln
            95                  100                 105

Leu Gln Ala Arg Val Leu Ala Val Glu Arg Tyr Leu Arg Asp Gln
            110                 115                 120

Gln Leu Leu Gly Ile Trp Gly Cys Ser Gly Lys Leu Ile Cys Thr
            125                 130                 135

Thr Thr Val Pro Trp Asn Ala Ser Trp Ser Asn Lys Ser His Asp
            140                 145                 150

Gln Ile Trp Gln Asn Met Thr Trp Met Gln Trp Glu Lys Glu Ile
            155                 160                 165

Asp Asn Tyr Thr Ser Leu Ile Tyr Asn Leu Ile Glu Val Ser Gln
            170                 175                 180

Asn Gln Gln Glu Lys Asn Glu Gln Glu Leu Leu Glu Leu Asp Lys
            185                 190                 195

Trp Ala Ser Leu Trp Asn Trp Phe Asp Ile Thr Asn Trp Leu Trp
            200                 205                 210

Tyr Ile Lys Ile Phe Ile Met Ile Val Gly Gly Leu Ile Gly Leu
            215                 220                 225

Arg Ile Val Phe Ile Val Leu Ser Ile Val Asn Arg Val Arg Gln
            230                 235                 240

Gly Tyr Ser Pro Leu Ser Phe Gln Thr His Leu Pro Ala Arg Arg
            245                 250                 255

Gly Pro Asp Arg Pro Glu Gly Ile Glu Glu Glu Gly Gly
            260                 265         268
```

(2) INFORMATION FOR SEQ ID NO: 41:

(i) SEQUENCE CHARACTERISTICS:
        (A) LENGTH: 268 amino acids
        (B) TYPE: Amino Acid
        (D) TOPOLOGY: Linear (xi) SEQUENCE DESCRIPTION: SEQ ID NO: 41:

```
Gly Gly Gly Asn Met Arg Asp Asn Trp Arg Ser Glu Leu Tyr Lys
 1               5                  10                  15

Tyr Lys Val Val Lys Ile Glu Pro Leu Gly Val Ala Pro Thr Arg
                20                  25                  30

Ala Lys Arg Arg Val Val Gln Arg Glu Lys Arg Ala Val Gly Ile
                35                  40                  45

Gly Ala Met Phe Leu Gly Phe Leu Gly Ala Ala Gly Ser Thr Met
                50                  55                  60

Gly Ala Ala Ser Leu Thr Leu Thr Val Gln Ala Arg Leu Leu Leu
                65                  70                  75

Ser Gly Ile Val Gln Gln Gln Asn Asn Leu Leu Arg Ala Ile Glu
                80                  85                  90

Ala Gln Gln His Leu Leu Gln Leu Thr Val Trp Gly Ile Lys Gln
                95                 100                 105

Leu Gln Ala Arg Val Leu Ala Val Glu Arg Tyr Leu Lys Asp Gln
               110                 115                 120

Gln Leu Leu Gly Ile Trp Gly Cys Ser Gly Lys Leu Ile Cys Thr
               125                 130                 135

Thr Thr Val Pro Trp Asn Thr Ser Trp Ser Asn Lys Ser Leu Asp
               140                 145                 150

Gln Ile Trp Gly Asn Met Thr Trp Met Gln Trp Glu Arg Glu Ile
               155                 160                 165

Asp Asn Tyr Thr Gly Leu Ile Tyr Thr Leu Ile Glu Glu Ser Gln
               170                 175                 180

Asn Gln Gln Glu Lys Asn Glu Gln Glu Leu Leu Glu Leu Asp Lys
               185                 190                 195

Trp Ala Ser Leu Trp Asn Trp Phe Asn Ile Thr Asn Trp Leu Trp
               200                 205                 210

Tyr Ile Lys Ile Phe Ile Met Ile Val Ala Gly Leu Val Gly Leu
               215                 220                 225

Arg Val Val Phe Ile Val Leu Ser Ile Val Asn Arg Val Arg Gln
               230                 235                 240

Gly Tyr Ser Pro Leu Ser Phe Gln Thr His His Pro Ala Leu Arg
               245                 250                 255

Gly Pro Asp Arg Pro Glu Gly Ile Glu Glu Glu Gly Gly
               260                 265         268
```

(2) INFORMATION FOR SEQ ID NO: 42:

(i) SEQUENCE CHARACTERISTICS:
        (A) LENGTH: 269 amino acids
        (B) TYPE: Amino Acid
        (D) TOPOLOGY: Linear (xi) SEQUENCE DESCRIPTION: SEQ ID NO: 42:

```
Gly Gly Gly Asp Met Arg Asp Asn Trp Arg Ser Glu Leu Tyr Lys
 1               5                  10                  15

Tyr Lys Val Val Lys Ile Glu Pro Leu Gly Val Ala Pro Thr Lys
```

```
                    20                  25                  30

Ala Lys Arg Arg Val Val Gln Arg Glu Lys Arg Ala Val Gly Ile
                    35                  40                  45

Val Gly Ala Met Phe Leu Gly Phe Leu Gly Ala Ala Gly Ser Thr
                    50                  55                  60

Met Gly Ala Ala Ser Met Thr Leu Thr Val Gln Ala Arg Leu Leu
                    65                  70                  75

Leu Ser Gly Ile Val Gln Gln Asn Asn Leu Leu Arg Ala Ile
                    80                  85                  90

Glu Ala Gln Gln His Leu Leu Gln Leu Thr Val Trp Gly Ile Lys
                    95                 100                 105

Gln Leu Gln Ala Arg Val Leu Ala Val Glu Arg Tyr Leu Lys Asp
                   110                 115                 120

Gln Gln Leu Leu Gly Ile Trp Gly Cys Ser Gly Lys Leu Ile Cys
                   125                 130                 135

Thr Thr Thr Val Pro Trp Asn Thr Ser Trp Ser Asn Lys Ser Leu
                   140                 145                 150

Ser Glu Ile Trp Asp Asn Met Thr Trp Met Gln Trp Glu Arg Glu
                   155                 160                 165

Ile Asp Asn Tyr Thr Ser Leu Ile Tyr Thr Leu Ile Glu Glu Ser
                   170                 175                 180

Gln Asn Gln Gln Glu Lys Asn Glu Gln Glu Leu Leu Glu Leu Asp
                   185                 190                 195

Lys Trp Ala Gly Leu Trp Asn Trp Phe Glu Ile Thr Asn Trp Leu
                   200                 205                 210

Trp Tyr Ile Lys Ile Phe Ile Met Ile Val Gly Gly Leu Val Gly
                   215                 220                 225

Leu Arg Ile Val Phe Ala Val Leu Ser Ile Val Asn Arg Val Arg
                   230                 235                 240

Gln Gly Tyr Ser Pro Val Ser Phe Gln Thr His Leu Pro Ala Pro
                   245                 250                 255

Arg Gly Pro Asp Arg Pro Glu Gly Ile Glu Glu Glu Gly Gly
                   260                 265                 269

(2) INFORMATION FOR SEQ ID NO: 43:

(i) SEQUENCE CHARACTERISTICS:
        (A) LENGTH: 269 amino acids
        (B) TYPE: Amino Acid
        (D) TOPOLOGY: Linear (xi) SEQUENCE DESCRIPTION: SEQ ID NO: 43:

Gly Gly Gly Asp Met Arg Asp Asn Trp Arg Ser Glu Leu Tyr Lys
 1               5                  10                  15

Tyr Lys Val Val Lys Ile Glu Pro Leu Gly Val Ala Pro Thr Arg
                    20                  25                  30

Ala Lys Arg Arg Val Val Gln Arg Glu Lys Arg Ala Val Gly Ala
                    35                  40                  45

Leu Gly Ala Met Phe Leu Gly Phe Leu Gly Ala Ala Gly Ser Thr
                    50                  55                  60

Met Gly Ala Ala Ser Met Thr Leu Thr Val Gln Ala Arg Gln Leu
                    65                  70                  75

Leu Ser Gly Ile Val Gln Gln Asn Asn Leu Leu Arg Ala Ile
                    80                  85                  90

Glu Ala Gln Gln His Leu Leu Gln Leu Thr Val Trp Gly Ile Lys
```

-continued

```
                  95                  100                 105

Gln Leu Gln Ala Arg Ile Leu Ala Val Glu Arg Tyr Leu Lys Asp
                110                 115                 120

Gln Gln Leu Leu Gly Ile Trp Gly Cys Ser Gly Lys Leu Ile Cys
                125                 130                 135

Thr Thr Ala Val Pro Trp Asn Thr Ser Trp Ser Asn Lys Ser Leu
                140                 145                 150

Glu Lys Ile Trp Asn Asn Met Thr Trp Met Glu Trp Glu Arg Glu
                155                 160                 165

Ile Asp Asn Tyr Thr Gly Leu Ile Tyr Ser Leu Ile Glu Glu Ser
                170                 175                 180

Gln Asn Gln Gln Glu Lys Asn Glu Gln Asp Leu Leu Glu Leu Asp
                185                 190                 195

Lys Trp Ala Ser Leu Trp Asn Trp Phe Asn Ile Thr Lys Trp Leu
                200                 205                 210

Trp Tyr Ile Lys Ile Phe Ile Met Ile Val Gly Gly Leu Ile Gly
                215                 220                 225

Leu Arg Ile Val Phe Ala Val Leu Ser Ile Val Asn Arg Val Arg
                230                 235                 240

Gln Gly Tyr Ser Pro Leu Ser Phe Gln Thr Leu Leu Pro Ala Gln
                245                 250                 255

Arg Gly Pro Asp Arg Pro Gly Gly Ile Glu Glu Glu Gly Gly
                260                 265             269

(2) INFORMATION FOR SEQ ID NO: 44:

(i) SEQUENCE CHARACTERISTICS:
        (A) LENGTH: 269 amino acids
        (B) TYPE: Amino Acid
        (D) TOPOLOGY: Linear (xi) SEQUENCE DESCRIPTION: SEQ ID NO: 44:

Gly Gly Gly Asp Met Arg Asp Asn Trp Arg Ser Glu Leu Tyr Lys
  1               5                  10                  15

Tyr Lys Val Val Lys Ile Glu Pro Leu Gly Val Ala Pro Thr Lys
                 20                  25                  30

Ala Lys Lys Arg Val Val Gln Arg Glu Lys Arg Ala Val Gly Val
                 35                  40                  45

Leu Gly Ala Met Phe Leu Gly Phe Leu Gly Ala Ala Gly Ser Thr
                 50                  55                  60

Met Gly Ala Ala Ser Met Thr Leu Thr Val Gln Ala Arg Gln Leu
                 65                  70                  75

Leu Ser Gly Ile Val Gln Gln Gln Asn Asn Leu Leu Arg Ala Ile
                 80                  85                  90

Glu Ala Gln Gln His Leu Leu Gln Leu Thr Val Trp Gly Ile Lys
                 95                 100                 105

Gln Leu Gln Ala Arg Ile Leu Ala Met Glu Arg Tyr Leu Lys Asp
                110                 115                 120

Gln Gln Leu Leu Gly Ile Trp Gly Cys Ser Gly Lys Leu Ile Cys
                125                 130                 135

Thr Thr Ala Val Pro Trp Asn Thr Ser Trp Ser Asn Lys Ser Leu
                140                 145                 150

Glu Lys Ile Trp Asn Asn Met Thr Trp Met Glu Trp Glu Arg Glu
                155                 160                 165

Ile Asp Asn Tyr Thr Gly Leu Ile Tyr Ser Leu Ile Gly Glu Ser
```

```
                        170                 175                 180

Gln Asn Gln Gln Glu Lys Asn Glu Gln Asp Leu Leu Glu Leu Asp
                185                 190                 195

Lys Trp Ala Ser Leu Trp Asn Trp Phe Asn Ile Thr Lys Trp Leu
            200                 205                 210

Trp Tyr Ile Lys Ile Phe Ile Met Ile Val Gly Gly Leu Val Gly
        215                 220                 225

Leu Arg Ile Val Phe Ala Val Leu Ser Ile Val Asn Arg Val Arg
    230                 235                 240

Gln Gly Tyr Ser Pro Leu Ser Phe Gln Thr Leu Leu Pro Ala Gln
                245                 250                 255

Arg Gly Pro Asp Arg Pro Gly Gly Ile Glu Glu Glu Gly Gly
                260                 265             269

(2) INFORMATION FOR SEQ ID NO: 45:

(i) SEQUENCE CHARACTERISTICS:
        (A) LENGTH: 269 amino acids
        (B) TYPE: Amino Acid
        (D) TOPOLOGY: Linear (xi) SEQUENCE DESCRIPTION: SEQ ID NO: 45:

Gly Gly Gly Asp Met Lys Asp Asn Trp Arg Ser Glu Leu Tyr Lys
 1               5                  10                  15

Tyr Lys Val Val Lys Ile Glu Pro Leu Gly Val Ala Pro Thr Lys
                20                  25                  30

Ala Lys Ser Arg Val Val Gln Arg Glu Lys Arg Ala Val Gly Val
            35                  40                  45

Leu Gly Ala Met Phe Leu Gly Leu Leu Gly Ala Ala Gly Ser Thr
        50                  55                  60

Met Gly Ala Ala Ser Met Thr Leu Thr Val Gln Ala Arg Gln Leu
    65                  70                  75

Leu Ser Gly Ile Val Gln Gln Gln Asn Asn Leu Leu Arg Ala Ile
                80                  85                  90

Glu Ala Gln Gln His Leu Ser Gln Leu Thr Val Trp Gly Ile Lys
                95                  100                 105

Gln Leu Gln Ala Arg Val Leu Ala Val Glu Arg Tyr Leu Lys Asp
            110                 115                 120

Gln Gln Leu Leu Gly Ile Trp Gly Cys Ser Gly Lys Leu Ile Cys
        125                 130                 135

Pro Thr Ala Val Pro Trp Asn Ala Ser Trp Ser Asn Arg Ser Leu
    140                 145                 150

Gln Tyr Ile Trp Asn Asn Met Thr Trp Ile Glu Trp Glu Arg Glu
                155                 160                 165

Ile Asp Asn Tyr Thr Asp Ile Ile Tyr Ser Leu Ile Glu Lys Ser
                170                 175                 180

Gln Asn Gln Gln Glu Lys Asn Glu Gln Glu Leu Leu Glu Leu Asp
            185                 190                 195

Gln Trp Ala Ser Leu Trp Asn Trp Phe Ser Ile Thr Lys Trp Leu
        200                 205                 210

Trp Tyr Ile Lys Leu Phe Ile Met Ile Val Gly Gly Leu Ile Gly
    215                 220                 225

Leu Arg Ile Val Phe Ala Ile Leu Ser Ile Val Asn Arg Ala Arg
                230                 235                 240

Gln Gly Tyr Ser Pro Leu Ser Phe Gln Thr Leu Leu Pro Ala Pro
```

```
                       245                 250                 255
Arg Gly Leu Asp Arg Pro Glu Gly Ile Gly Glu Gly Gly
                260                 265             269

(2) INFORMATION FOR SEQ ID NO: 46:

(i) SEQUENCE CHARACTERISTICS:
        (A) LENGTH: 269 amino acids
        (B) TYPE: Amino Acid
        (D) TOPOLOGY: Linear (xi) SEQUENCE DESCRIPTION: SEQ ID NO: 46:

Gly Gly Gly Asp Met Arg Asp Asn Trp Arg Ser Glu Leu Tyr Lys
  1               5                  10                  15

Tyr Lys Val Val Lys Ile Glu Pro Leu Gly Val Ala Pro Thr Lys
                 20                  25                  30

Ala Lys Arg Arg Val Val Gln Arg Glu Lys Arg Ala Val Gly Thr
                 35                  40                  45

Leu Gly Ala Met Phe Leu Gly Phe Leu Gly Ala Ala Gly Ser Thr
                 50                  55                  60

Met Gly Ala Ala Ser Met Thr Leu Thr Val Gln Ala Arg Leu Leu
                 65                  70                  75

Leu Ser Gly Ile Val Gln Gln Gln Asn Asn Leu Leu Arg Ala Ile
                 80                  85                  90

Glu Ala Gln Gln His Leu Leu Gln Leu Thr Val Trp Gly Ile Lys
                 95                 100                 105

Gln Leu Gln Ala Arg Val Leu Ala Val Glu Arg Tyr Leu Lys Asp
                110                 115                 120

Arg Gln Leu Leu Gly Ile Trp Gly Cys Ser Gly Lys Pro Ile Cys
                125                 130                 135

Thr Thr Ser Val Pro Trp Asn Ser Ser Trp Ser Asn Lys Ser Leu
                140                 145                 150

Glu Gln Ile Trp Asn Asn Met Thr Trp Leu Glu Trp Glu Arg Glu
                155                 160                 165

Ile Asp Asn Tyr Thr Ser Leu Ile Tyr Ser Leu Ile Lys Glu Ser
                170                 175                 180

Gln Asn Gln Gln Glu Lys Asn Glu Gln Glu Leu Leu Glu Leu Asp
                185                 190                 195

Lys Trp Ala Ser Leu Trp Asn Trp Phe Asn Ile Thr Glu Trp Leu
                200                 205                 210

Trp Tyr Ile Lys Ile Phe Ile Met Ile Val Gly Gly Leu Val Gly
                215                 220                 225

Leu Arg Ile Val Phe Thr Val Leu Ser Ile Val Asn Arg Val Arg
                230                 235                 240

Gln Gly Tyr Ser Pro Leu Ser Phe Gln Thr Arg Leu Pro Ala Pro
                245                 250                 255

Arg Gly Pro Asp Arg Pro Glu Gly Ile Glu Glu Glu Gly Gly
                260                 265             269

(2) INFORMATION FOR SEQ ID NO: 47:

(i) SEQUENCE CHARACTERISTICS:
        (A) LENGTH: 269 amino acids
        (B) TYPE: Amino Acid
        (D) TOPOLOGY: Linear (xi) SEQUENCE DESCRIPTION: SEQ ID NO: 47:
```

```
Gly Gly Gly Asp Met Arg Asp Asn Trp Arg Ser Glu Leu Tyr Lys
 1               5                  10                  15

Tyr Lys Val Val Lys Ile Glu Pro Leu Gly Val Ala Pro Thr Lys
                20                  25                  30

Ala Lys Arg Arg Val Val Gln Arg Glu Lys Arg Ala Val Gly Val
                35                  40                  45

Ile Gly Ala Met Phe Leu Gly Phe Leu Gly Ala Ala Gly Ser Thr
                50                  55                  60

Met Gly Ala Ala Ser Met Ala Leu Thr Val Gln Ala Arg Gln Leu
                65                  70                  75

Leu Ser Gly Ile Val Gln Gln Asn Asn Leu Leu Arg Ala Ile
                80                  85                  90

Glu Ala Gln Gln His Leu Leu Gln Leu Thr Val Trp Gly Ile Lys
                95                  100                 105

Gln Leu Gln Ala Arg Val Leu Ala Val Glu Arg Tyr Leu Lys Asp
                110                 115                 120

Gln Gln Leu Leu Gly Ile Trp Gly Cys Ser Gly Lys Leu Ile Cys
                125                 130                 135

Thr Thr Ala Val Pro Trp Asn Thr Ser Trp Ser Asn Lys Ser Leu
                140                 145                 150

Glu Glu Ile Trp Asp Asn Met Thr Trp Met Glu Trp Glu Arg Glu
                155                 160                 165

Ile Asn Asn Tyr Thr Gly Leu Ile Tyr Thr Leu Ile Glu Gln Ser
                170                 175                 180

Gln Asn Gln Gln Glu Lys Asn Glu Gln Glu Leu Leu Ala Leu Asp
                185                 190                 195

Thr Trp Ala Ser Leu Trp Asn Trp Phe Ser Ile Ser Asn Trp Leu
                200                 205                 210

Trp Tyr Ile Arg Ile Phe Ile Met Ile Val Gly Gly Leu Val Gly
                215                 220                 225

Leu Arg Ile Val Phe Ala Val Leu Ser Ile Val Asn Arg Val Arg
                230                 235                 240

Gln Gly Tyr Ser Pro Leu Ser Phe Gln Thr Arg Leu Pro Thr Pro
                245                 250                 255

Arg Gly Pro Asp Arg Pro Glu Gly Ile Glu Glu Glu Gly Gly
                260                 265             269
```

(2) INFORMATION FOR SEQ ID NO: 48:

(i) SEQUENCE CHARACTERISTICS:
        (A) LENGTH: 269 amino acids
        (B) TYPE: Amino Acid
        (D) TOPOLOGY: Linear (xi) SEQUENCE DESCRIPTION: SEQ ID NO: 48:

```
Gly Gly Gly Asp Met Arg Asp Asn Trp Arg Ser Glu Leu Tyr Lys
 1               5                  10                  15

Tyr Lys Val Val Lys Ile Glu Pro Ile Gly Val Ala Pro Thr Lys
                20                  25                  30

Ala Lys Arg Arg Val Val Gln Arg Glu Lys Arg Ala Val Gly Thr
                35                  40                  45

Ile Gly Val Met Phe Leu Gly Phe Leu Gly Ala Ala Gly Ser Thr
                50                  55                  60

Met Gly Ala Ala Ser Ile Thr Leu Thr Val Gln Ala Arg Gln Leu
                65                  70                  75
```

```
Leu Ser Gly Ile Val Gln Gln Gln Asn Asn Leu Leu Arg Ala Ile
                80                  85                  90

Lys Ala Gln Gln His Leu Leu Gln Leu Thr Val Trp Gly Ile Lys
                95                 100                 105

Gln Leu Gln Ala Arg Val Leu Ala Ile Glu Arg Phe Leu Arg Asp
               110                 115                 120

Gln Gln Leu Leu Gly Ile Trp Gly Cys Ser Gly Lys Leu Ile Cys
               125                 130                 135

Thr Thr Thr Val Pro Trp Asn Thr Ser Trp Ser Asn Lys Ser Leu
               140                 145                 150

Lys Gln Ile Trp Asp Asn Leu Thr Trp Met Glu Trp Glu Arg Glu
               155                 160                 165

Ile Asp Asn Tyr Thr Gly Ile Ile Phe Asn Leu Ile Glu Glu Ala
               170                 175                 180

Gln Asn Gln Gln Glu Lys Asn Glu Gln Asp Leu Leu Glu Leu Asp
               185                 190                 195

Lys Trp Ala Gly Leu Trp Asn Trp Phe Ser Ile Thr Asn Trp Leu
               200                 205                 210

Trp Tyr Ile Lys Ile Phe Ile Met Ile Val Gly Gly Leu Ile Gly
               215                 220                 225

Leu Arg Ile Val Phe Ala Val Leu Ser Ile Val Asn Arg Val Arg
               230                 235                 240

Gln Gly Tyr Ser Pro Leu Ser Phe Gln Thr His Leu Pro Thr Pro
               245                 250                 255

Arg Gly Pro Asp Arg Pro Glu Gly Thr Gly Glu Glu Gly Gly
               260                 265                 269

(2) INFORMATION FOR SEQ ID NO: 49:

(i) SEQUENCE CHARACTERISTICS:
        (A) LENGTH: 233 amino acids
        (B) TYPE: Amino Acid
        (D) TOPOLOGY: Linear (xi) SEQUENCE DESCRIPTION: SEQ ID NO: 49:

Gly Gly Gly Asp Met Arg Asp Asn Trp Arg Ser Glu Leu Tyr Lys
 1               5                  10                  15

Tyr Lys Val Val Arg Ile Glu Pro Leu Gly Ile Ala Pro Thr Lys
                20                  25                  30

Ala Lys Arg Arg Val Val Gln Arg Glu Lys Arg Ala Val Gly Ile
                35                  40                  45

Gly Ala Met Phe Leu Gly Phe Leu Gly Ala Ala Gly Ser Thr Met
                50                  55                  60

Gly Ala Ala Ser Ile Thr Leu Thr Val Gln Ala Arg Leu Leu Leu
                65                  70                  75

Ser Gly Ile Val Gln Gln Gln Asn Asn Leu Leu Arg Ala Ile Glu
                80                  85                  90

Ala Gln Gln His Leu Leu Gln Leu Thr Val Trp Gly Ile Lys Gln
                95                 100                 105

Leu Gln Ala Arg Val Leu Ala Val Glu Arg Tyr Leu Arg Asp Gln
               110                 115                 120

Gln Leu Leu Gly Ile Trp Gly Cys Ser Gly Lys Leu Ile Cys Thr
               125                 130                 135

Thr Ala Val Pro Trp Asn Ala Ser Trp Ser Asn Lys Ser Leu Asp
               140                 145                 150
```

-continued

```
Gln Ile Trp Asp Asn Met Thr Trp Met Gln Trp Glu Arg Glu Ile
                155                 160                 165

Glu Asn Tyr Thr Ser Leu Ile Tyr Asn Leu Ile Glu Glu Ser Gln
                170                 175                 180

Asn Gln Gln Glu Lys Asn Glu Gln Asp Leu Leu Glu Leu Asp Lys
                185                 190                 195

Trp Ala Ser Leu Trp Ser Trp Phe Ser Ile Thr Asn Trp Leu Trp
                200                 205                 210

Tyr Ile Arg Ile Phe Ile Met Ile Val Gly Gly Leu Ile Gly Leu
                215                 220                 225

Arg Ile Val Phe Ala Val Leu Ser
                230         233
```

(2) INFORMATION FOR SEQ ID NO: 50:

(i) SEQUENCE CHARACTERISTICS:
        (A) LENGTH: 233 amino acids
        (B) TYPE: Amino Acid
        (D) TOPOLOGY: Linear (xi) SEQUENCE DESCRIPTION: SEQ ID NO: 50:

```
Gly Gly Gly Asp Met Arg Asp Asn Trp Arg Ser Glu Leu Tyr Lys
 1              5                  10                  15

Tyr Lys Val Val Lys Ile Glu Pro Leu Gly Val Ala Pro Thr Lys
                20                  25                  30

Ala Lys Arg Arg Val Val Gln Arg Glu Lys Arg Ala Val Gly Ile
                35                  40                  45

Gly Ala Val Phe Leu Gly Phe Leu Gly Ala Ala Gly Ser Thr Met
                50                  55                  60

Gly Ala Ala Ser Ile Thr Leu Thr Val Gln Ala Arg Leu Leu Leu
                65                  70                  75

Ser Gly Ile Val Gln Gln Gln Asn Asn Leu Leu Arg Ala Ile Glu
                80                  85                  90

Ala Gln Gln His Leu Leu Gln Leu Thr Val Trp Gly Ile Lys Gln
                95                  100                 105

Leu Gln Ala Arg Val Leu Ala Val Glu Arg Tyr Leu Arg Asp Gln
                110                 115                 120

Gln Leu Leu Gly Ile Trp Gly Cys Ser Gly Lys Leu Ile Cys Thr
                125                 130                 135

Thr Ala Val Pro Trp Asn Ser Ser Trp Ser Asn Lys Ser Leu Asp
                140                 145                 150

Gln Ile Trp Asn Asn Met Thr Trp Met Gln Trp Glu Arg Glu Ile
                155                 160                 165

Glu Asn Tyr Thr Ser Leu Ile Tyr Asn Leu Ile Glu Glu Ser Gln
                170                 175                 180

Asn Gln Gln Glu Lys Asn Glu Gln Glu Leu Leu Glu Leu Asp Lys
                185                 190                 195

Trp Ala Ser Leu Trp Asn Trp Phe Ser Ile Thr Asn Trp Leu Trp
                200                 205                 210

Tyr Ile Lys Ile Phe Ile Ile Ile Val Gly Gly Leu Ile Gly Leu
                215                 220                 225

Arg Ile Val Phe Ala Val Leu Ser
                230         233
```

(2) INFORMATION FOR SEQ ID NO: 51:

```
    (i) SEQUENCE CHARACTERISTICS:
        (A) LENGTH: 233 amino acids
        (B) TYPE: Amino Acid
        (D) TOPOLOGY: Linear (xi) SEQUENCE DESCRIPTION: SEQ ID NO: 51:

Ala Gly Gly Asp Met Arg Asp Asn Trp Arg Ser Glu Leu Tyr Lys
 1               5                  10                  15

Tyr Lys Val Ile Gln Ile Glu Pro Leu Gly Val Ala Pro Thr Lys
                20                  25                  30

Ala Lys Arg Arg Val Val Gln Arg Glu Lys Arg Ala Val Gly Ile
                35                  40                  45

Gly Ala Val Leu Phe Gly Phe Leu Gly Ala Ala Gly Ser Thr Met
                50                  55                  60

Gly Ala Ala Ser Leu Thr Leu Thr Val Gln Ala Arg Gln Leu Leu
                65                  70                  75

Ser Gly Ile Val Gln Gln Gln Asn Asn Leu Leu Arg Ala Ile Glu
                80                  85                  90

Ala Gln Gln His Leu Leu Gln Leu Thr Val Trp Gly Ile Lys Gln
                95                 100                 105

Leu Gln Ala Arg Val Leu Ala Leu Glu Arg Tyr Leu Lys Asp Gln
               110                 115                 120

Gln Leu Leu Gly Ile Trp Gly Cys Ser Gly Lys Leu Ile Cys Thr
               125                 130                 135

Thr Ala Val Pro Trp Asn Ala Ser Trp Ser Asn Lys Ser Leu Asn
               140                 145                 150

Asp Ile Trp Asp Asn Met Thr Trp Met Gln Trp Asp Arg Glu Ile
               155                 160                 165

Asn Lys Tyr Thr Asp Ser Ile Tyr Gln Leu Ile Glu Glu Ser Gln
               170                 175                 180

Asn Gln Gln Glu Lys Asn Glu Gln Asp Leu Leu Lys Leu Asp Glu
               185                 190                 195

Trp Ala Ser Leu Trp Asn Trp Phe Ser Ile Ser Lys Trp Leu Trp
               200                 205                 210

Tyr Ile Lys Ile Phe Ile Met Ile Val Gly Gly Leu Val Gly Leu
               215                 220                 225

Arg Ile Val Phe Ala Val Leu Ser
               230         233

(2) INFORMATION FOR SEQ ID NO: 52:

(i) SEQUENCE CHARACTERISTICS:
        (A) LENGTH: 105 amino acids
        (B) TYPE: Amino Acid
        (D) TOPOLOGY: Linear (xi) SEQUENCE DESCRIPTION: SEQ ID NO: 52:

Gly Gly Gly Asp Met Arg Asp Asn Trp Arg Ser Glu Leu Tyr Lys
 1               5                  10                  15

Tyr Lys Val Val Lys Ile Glu Pro Leu Gly Val Ala Pro Thr Arg
                20                  25                  30

Ala Lys Arg Arg Val Val Gln Arg Glu Arg Arg Ala Val Gly Ala
                35                  40                  45

Leu Gly Ala Met Phe Leu Gly Phe Leu Gly Ala Ala Gly Ser Thr
                50                  55                  60

Met Gly Ala Ala Ser Leu Thr Leu Thr Val Gln Ala Arg Gln Leu
                65                  70                  75
```

Leu Ser Gly Ile Val Gln Gln Gln Asn Asn Leu Leu Lys Ala Ile
            80                  85                  90

Glu Ala Gln Gln His Leu Leu Gln Leu Thr Val Trp Gly Ile Lys
            95                 100                 105

(2) INFORMATION FOR SEQ ID NO: 53:

(i) SEQUENCE CHARACTERISTICS:
        (A) LENGTH: 105 amino acids
        (B) TYPE: Amino Acid
        (D) TOPOLOGY: Linear (xi) SEQUENCE DESCRIPTION: SEQ ID NO: 53:

Gly Gly Gly Asp Met Lys Asp Asn Trp Arg Ser Lys Leu Tyr Lys
 1            5                  10                  15

Tyr Lys Val Val Lys Ile Glu Pro Leu Gly Val Ala Pro Thr Arg
            20                  25                  30

Ala Lys Arg Arg Val Val Gln Arg Glu Lys Arg Ala Val Gly Thr
            35                  40                  45

Ile Gly Ala Met Phe Leu Gly Phe Leu Gly Ala Ala Gly Ser Thr
            50                  55                  60

Met Gly Ala Ala Ser Ile Thr Leu Met Val Gln Ala Arg Gln Leu
            65                  70                  75

Leu Ser Gly Ile Val Gln Gln Gln Arg Asn Leu Leu Arg Ala Ile
            80                  85                  90

Glu Ala Gln Gln His Leu Leu Gln Leu Thr Val Trp Gly Ile Lys
            95                 100                 105

(2) INFORMATION FOR SEQ ID NO: 54:

(i) SEQUENCE CHARACTERISTICS:
        (A) LENGTH: 105 amino acids
        (B) TYPE: Amino Acid
        (D) TOPOLOGY: Linear (xi) SEQUENCE DESCRIPTION: SEQ ID NO: 54:

Gly Gly Gly Asp Met Arg Asp Asn Trp Arg Ser Glu Leu Tyr Lys
 1            5                  10                  15

Tyr Lys Val Val Lys Ile Glu Pro Leu Gly Val Ala Pro Thr Arg
            20                  25                  30

Ala Lys Arg Arg Val Val Gln Arg Glu Arg Arg Ala Val Gly Ala
            35                  40                  45

Leu Gly Ala Met Phe Leu Gly Phe Leu Gly Ala Ala Gly Ser Thr
            50                  55                  60

Met Gly Ala Ala Ser Leu Thr Leu Thr Val Gln Ala Arg Gln Leu
            65                  70                  75

Leu Ser Gly Ile Val Gln Gln Gln Asn Asn Leu Leu Lys Ala Ile
            80                  85                  90

Glu Ala Gln Gln His Leu Leu Gln Leu Thr Val Trp Gly Ile Lys
            95                 100                 105

(2) INFORMATION FOR SEQ ID NO: 55:

(i) SEQUENCE CHARACTERISTICS:
        (A) LENGTH: 105 amino acids
        (B) TYPE: Amino Acid
        (D) TOPOLOGY: Linear (xi) SEQUENCE DESCRIPTION: SEQ ID NO: 55:

```
Gly Gly Gly Asp Met Lys Asp Asn Trp Arg Ser Lys Leu Tyr Lys
 1               5                  10                  15

Tyr Lys Val Val Lys Ile Glu Pro Leu Gly Val Ala Pro Thr Arg
                20                  25                  30

Ala Lys Arg Arg Val Val Gln Arg Glu Lys Arg Ala Val Gly Thr
                35                  40                  45

Ile Gly Ala Met Phe Leu Gly Phe Leu Gly Ala Ala Gly Ser Thr
                50                  55                  60

Met Gly Ala Ala Ser Ile Thr Leu Met Val Gln Ala Arg Gln Leu
                65                  70                  75

Leu Ser Gly Ile Val Gln Gln Gln Arg Asn Leu Leu Arg Ala Ile
                80                  85                  90

Glu Ala Gln Gln His Leu Leu Gln Leu Thr Val Trp Gly Ile Lys
                95                 100                 105

(2) INFORMATION FOR SEQ ID NO: 56:

(i) SEQUENCE CHARACTERISTICS:
        (A) LENGTH: 93 amino acids
        (B) TYPE: Amino Acid
        (D) TOPOLOGY: Linear (xi) SEQUENCE DESCRIPTION: SEQ ID NO: 56:

Gly Gly Gly Asn Met Arg Asp Asn Trp Arg Ser Glu Leu Tyr Lys
 1               5                  10                  15

Tyr Lys Val Val Lys Ile Glu Pro Leu Gly Val Ala Pro Thr Arg
                20                  25                  30

Ala Lys Arg Arg Val Val Gln Arg Glu Lys Arg Ala Val Gly Ile
                35                  40                  45

Gly Ala Val Phe Leu Gly Phe Leu Gly Ala Ala Gly Ser Thr Met
                50                  55                  60

Gly Ala Arg Ser Met Thr Leu Thr Val Gln Ala Arg Leu Leu Leu
                65                  70                  75

Ser Gly Ile Val Gln Gln Gln Asn Asn Leu Leu Arg Ala Ile Glu
                80                  85                  90

Ala Gln Gln
        93

(2) INFORMATION FOR SEQ ID NO: 57:

(i) SEQUENCE CHARACTERISTICS:
        (A) LENGTH: 94 amino acids
        (B) TYPE: Amino Acid
        (D) TOPOLOGY: Linear (xi) SEQUENCE DESCRIPTION: SEQ ID NO: 57:

Gly Gly Gly Asn Met Arg Asp Asn Trp Arg Ser Glu Leu Tyr Lys
 1               5                  10                  15

Tyr Lys Val Val Lys Ile Glu Pro Leu Gly Val Ala Pro Thr Arg
                20                  25                  30

Ala Lys Arg Arg Val Val Gln Arg Glu Lys Arg Ala Val Gly Ile
                35                  40                  45

Gly Ala Val Phe Leu Gly Phe Leu Gly Ala Ala Gly Ser Thr Met
                50                  55                  60

Gly Ala Arg Ser Met Thr Leu Thr Val Gln Ala Arg Leu Leu Leu
                65                  70                  75

Ser Gly Ile Val Gln Gln Gln Asn Asn Leu Leu Arg Ala Ile Glu
                80                  85                  90
```

Ala Gln Gln His
            94

(2) INFORMATION FOR SEQ ID NO: 58:

(i) SEQUENCE CHARACTERISTICS:
        (A) LENGTH: 79 amino acids
        (B) TYPE: Amino Acid
        (D) TOPOLOGY: Linear (xi) SEQUENCE DESCRIPTION: SEQ ID NO: 58:

Gly Gly Gly Asp Met Arg Asp Asn Trp Arg Ser Glu Leu Tyr Lys
 1               5                  10                  15

Tyr Lys Val Val Arg Ile Glu Pro Leu Gly Ile Ala Pro Thr Arg
                20                  25                  30

Ala Lys Arg Arg Glu Val Gln Arg Glu Lys Arg Ala Val Gly Thr
                35                  40                  45

Leu Gly Ala Met Phe Leu Gly Phe Leu Gly Ala Ala Gly Ser Thr
                50                  55                  60

Met Gly Ala Ala Ser Val Ala Leu Thr Val Pro Leu Arg Arg Ile
                65                  70                  75

Arg Ser Cys Xaa
            79

(2) INFORMATION FOR SEQ ID NO: 59:

(i) SEQUENCE CHARACTERISTICS:
        (A) LENGTH: 79 amino acids
        (B) TYPE: Amino Acid
        (D) TOPOLOGY: Linear (xi) SEQUENCE DESCRIPTION: SEQ ID NO: 59:

Gly Gly Gly Asp Met Arg Asp Asn Trp Arg Ser Glu Leu Tyr Lys
 1               5                  10                  15

Tyr Lys Val Val Arg Ile Glu Pro Leu Gly Val Ala Pro Thr Lys
                20                  25                  30

Ala Lys Arg Arg Val Val Gln Gly Glu Lys Arg Ala Val Gly Thr
                35                  40                  45

Ile Gly Ala Met Phe Leu Gly Phe Leu Gly Ala Ala Gly Ser Thr
                50                  55                  60

Met Gly Ala Arg Ser Ile Thr Leu Thr Val Pro Leu Arg Arg Ile
                65                  70                  75

Arg Ser Cys Xaa
            79

(2) INFORMATION FOR SEQ ID NO: 60:

(i) SEQUENCE CHARACTERISTICS:
        (A) LENGTH: 79 amino acids
        (B) TYPE: Amino Acid
        (D) TOPOLOGY: Linear (xi) SEQUENCE DESCRIPTION: SEQ ID NO: 60:

Gly Gly Gly Asp Met Arg Asp Asn Trp Arg Ser Glu Leu Tyr Lys
 1               5                  10                  15

Tyr Lys Val Val Arg Ile Glu Pro Leu Gly Val Ala Pro Thr Lys
                20                  25                  30

Ala Lys Arg Arg Val Val Gln Arg Glu Lys Arg Ala Val Gly Thr
                35                  40                  45

```
Ile Gly Ala Met Phe Leu Gly Phe Leu Gly Ala Ala Gly Ser Thr
            50                      55                      60

Met Gly Ala Ala Ser Ile Thr Leu Thr Val Pro Val Arg Arg Ile
                65                      70                      75

Arg Ser Cys Xaa
            79

(2) INFORMATION FOR SEQ ID NO: 61:

(i) SEQUENCE CHARACTERISTICS:
        (A) LENGTH: 55 amino acids
        (B) TYPE: Amino Acid
        (D) TOPOLOGY: Linear (xi) SEQUENCE DESCRIPTION: SEQ ID NO: 61:

Gly Gly Gly Asp Met Arg Asp Asn Trp Arg Ser Glu Leu Tyr Lys
 1               5                      10                      15

Tyr Lys Val Val Lys Ile Glu Pro Leu Gly Val Ala Pro Thr Arg
                20                      25                      30

Ala Lys Arg Arg Val Val Gln Arg Glu Lys Arg Ala Val Gly Thr
                35                      40                      45

Ile Gly Ala Met Phe Leu Gly Phe Leu Gly
            50                      55

(2) INFORMATION FOR SEQ ID NO: 62:

(i) SEQUENCE CHARACTERISTICS:
        (A) LENGTH: 55 amino acids
        (B) TYPE: Amino Acid
        (D) TOPOLOGY: Linear (xi) SEQUENCE DESCRIPTION: SEQ ID NO: 62:

Gly Gly Gly Asn Met Arg Asp Asn Trp Arg Ser Glu Leu Tyr Lys
 1               5                      10                      15

Tyr Lys Val Val Lys Ile Glu Pro Leu Gly Val Ala Pro Thr Arg
                20                      25                      30

Ala Lys Arg Arg Val Val Gln Arg Glu Lys Arg Ala Ile Gly Thr
                35                      40                      45

Ile Gly Ala Leu Phe Leu Gly Phe Leu Gly
            50                      55

(2) INFORMATION FOR SEQ ID NO: 63:

(i) SEQUENCE CHARACTERISTICS:
        (A) LENGTH: 54 amino acids
        (B) TYPE: Amino Acid
        (D) TOPOLOGY: Linear (xi) SEQUENCE DESCRIPTION: SEQ ID NO: 63:

Gly Gly Gly Asn Met Lys Asp Asn Trp Arg Ser Glu Leu Tyr Lys
 1               5                      10                      15

Tyr Lys Val Val Lys Ile Glu Pro Leu Gly Val Ala Pro Thr Arg
                20                      25                      30

Ala Lys Arg Arg Val Val Gln Arg Glu Lys Arg Ala Val Thr Met
                35                      40                      45

Gly Ala Leu Phe Leu Gly Phe Leu Gly
            50                  54

(2) INFORMATION FOR SEQ ID NO: 64:

(i) SEQUENCE CHARACTERISTICS:
```

(A) LENGTH: 54 amino acids
          (B) TYPE: Amino Acid
          (D) TOPOLOGY: Linear (xi) SEQUENCE DESCRIPTION: SEQ ID NO: 64:

Gly Gly Gly Asp Met Arg Asp Asn Trp Arg Ser Glu Leu Tyr Lys
 1               5                  10                  15

Tyr Lys Val Val Lys Ile Glu Pro Leu Gly Val Ala Pro Thr Arg
                20                  25                  30

Ala Lys Arg Arg Val Val Gln Arg Glu Lys Arg Ala Val Gly Leu
            35                  40                      45

Gly Ala Met Phe Leu Gly Phe Leu Gly
                50                  54

(2) INFORMATION FOR SEQ ID NO: 65:

(i) SEQUENCE CHARACTERISTICS:
          (A) LENGTH: 41 amino acids
          (B) TYPE: Amino Acid
          (D) TOPOLOGY: Linear (xi) SEQUENCE DESCRIPTION: SEQ ID NO: 65:

Gly Gly Gly Asp Met Arg Asp Asn Trp Arg Ser Glu Leu Tyr Lys
 1               5                  10                  15

Tyr Lys Val Val Lys Ile Glu Pro Leu Gly Val Ala Pro Thr Thr
                20                  25                  30

Ala Lys Arg Arg Val Met Gln Arg Glu Lys Arg
            35                  40  41

(2) INFORMATION FOR SEQ ID NO: 66:

(i) SEQUENCE CHARACTERISTICS:
          (A) LENGTH: 34 amino acids
          (B) TYPE: Amino Acid
          (D) TOPOLOGY: Linear (xi) SEQUENCE DESCRIPTION: SEQ ID NO: 66:

Gly Gly Gly Asp Met Arg Asp Asn Trp Arg Ser Glu Leu Tyr Lys
 1               5                  10                  15

Tyr Lys Val Val Lys Ile Glu Pro Leu Gly Val Ala Pro Thr Thr
                20                  25                  30

Ala Lys Arg Arg
            34

(2) INFORMATION FOR SEQ ID NO: 67:

(i) SEQUENCE CHARACTERISTICS:
          (A) LENGTH: 270 amino acids
          (B) TYPE: Amino Acid
          (D) TOPOLOGY: Linear (xi) SEQUENCE DESCRIPTION: SEQ ID NO: 67:

Gly Gly Gly Asp Met Arg Asp Asn Trp Arg Ser Glu Leu Tyr Lys
 1               5                  10                  15

Tyr Lys Val Val Lys Ile Glu Pro Leu Gly Val Ala Pro Thr Arg
                20                  25                  30

Ala Lys Arg Arg Val Val Glu Arg Glu Lys Arg Ala Val Gly Xaa
            35                  40                      45

Leu Gly Ala Val Phe Leu Gly Phe Leu Gly Ala Ala Gly Ser Thr
                50                  55                  60

Met Gly Ala Ala Ser Ile Thr Leu Thr Val Gln Ala Arg Gln Leu

```
                   65                  70                  75
Leu Ser Gly Ile Val Gln Gln Gln Ser Asn Leu Leu Arg Ala Ile
                        80                  85                  90
Glu Ala Gln Gln His Leu Leu Lys Leu Thr Val Trp Gly Ile Lys
                        95                 100                 105
Gln Leu Gln Ala Arg Val Leu Ala Val Glu Arg Tyr Leu Lys Asp
                       110                 115                 120
Gln Gln Leu Leu Gly Ile Trp Gly Cys Ser Gly Lys Leu Ile Cys
                       125                 130                 135
Thr Thr Asn Val Pro Trp Asn Ser Ser Trp Ser Asn Lys Ser Xaa
                       140                 145                 150
Gln Ser Xaa Ile Trp Asp Asn Met Thr Trp Leu Gln Trp Asp Lys
                       155                 160                 165
Glu Ile Ser Asn Tyr Thr Xaa Ile Ile Tyr Asn Leu Ile Glu Glu
                       170                 175                 180
Ser Gln Asn Gln Gln Glu Lys Asn Glu Gln Asp Leu Leu Ala Leu
                       185                 190                 195
Asp Lys Trp Ala Asn Leu Trp Asn Trp Phe Asp Ile Ser Asn Trp
                       200                 205                 210
Leu Trp Tyr Ile Xaa Ile Phe Ile Met Ile Val Gly Gly Leu Ile
                       215                 220                 225
Gly Leu Arg Ile Val Phe Ala Val Leu Ser Ile Ile Asn Arg Val
                       230                 235                 240
Arg Gln Gly Tyr Ser Pro Leu Ser Phe Gln Thr Leu Thr Pro Asn
                       245                 250                 255
Pro Arg Xaa Pro Asp Arg Pro Gly Arg Ile Glu Glu Glu Gly Gly
                       260                 265                 270

(2) INFORMATION FOR SEQ ID NO: 68:

(i) SEQUENCE CHARACTERISTICS:
        (A) LENGTH: 268 amino acids
        (B) TYPE: Amino Acid
        (D) TOPOLOGY: Linear (xi) SEQUENCE DESCRIPTION: SEQ ID NO: 68:

Thr Gly Gly Asn Met Arg Asp Asn Trp Arg Ser Glu Leu Tyr Lys
  1                   5                  10                  15
Tyr Lys Val Val Lys Ile Glu Pro Leu Gly Val Ala Pro Thr Pro
                       20                  25                  30
Ala Lys Arg Arg Val Val Gln Arg Glu Lys Arg Ala Val Gly Ile
                       35                  40                  45
Gly Ala Val Phe Ile Gly Phe Leu Gly Ala Ala Gly Ser Thr Met
                       50                  55                  60
Gly Ala Ala Ser Ile Thr Leu Thr Val Gln Ala Arg Gln Leu Leu
                       65                  70                  75
Ser Gly Ile Val Gln Gln Gln Ser Asn Leu Leu Arg Ala Ile Glu
                       80                  85                  90
Ala Gln Gln His Leu Leu Lys Leu Thr Val Trp Gly Ile Lys Gln
                       95                 100                 105
Leu Gln Ala Arg Val Leu Ala Val Glu Arg Tyr Leu Lys Asp Gln
                       110                 115                 120
Gln Leu Leu Gly Ile Trp Gly Cys Ser Gly Lys Leu Ile Cys Thr
                       125                 130                 135
Thr Asn Val Pro Trp Asn Ser Ser Trp Ser Asn Arg Thr Gln Ser
```

```
                140                 145                 150
Glu Ile Trp Asn Asn Met Thr Trp Leu Gln Trp Asp Lys Glu Ile
                155                 160                 165
Ser Asn Tyr Thr Asp Ile Ile Tyr Asn Leu Ile Glu Glu Ser Gln
                170                 175                 180
Ile Gln Gln Glu Lys Asn Glu Gln Leu Leu Ala Leu Asp Lys
                185                 190                 195
Trp Ala Asn Leu Trp Asn Trp Phe Asp Ile Ser Lys Trp Leu Trp
                200                 205                 210
Tyr Ile Arg Ile Phe Ile Met Ile Val Gly Gly Leu Ile Gly Leu
                215                 220                 225
Arg Ile Val Phe Ala Val Leu Ser Ile Ile Asn Arg Val Arg Gln
                230                 235                 240
Gly Tyr Ser Pro Leu Ser Phe Gln Ile His Thr Pro Asn Pro Arg
                245                 250                 255
Gly Pro Asp Arg Pro Glu Arg Ile Glu Glu Gly Gly
                260                 265         268

(2) INFORMATION FOR SEQ ID NO: 69:

(i) SEQUENCE CHARACTERISTICS:
        (A) LENGTH: 267 amino acids
        (B) TYPE: Amino Acid
        (D) TOPOLOGY: Linear (xi) SEQUENCE DESCRIPTION: SEQ ID NO: 69:

Gly Gly Gly Asp Met Arg Asp Asn Trp Lys Ser Glu Leu Tyr Lys
 1               5                  10                  15
Tyr Lys Val Val Lys Ile Glu Pro Leu Gly Val Ala Pro Thr Arg
                20                  25                  30
Ala Lys Arg Arg Val Val Glu Arg Glu Lys Arg Ala Val Gly Leu
                35                  40                  45
Gly Ala Ile Phe Leu Gly Phe Leu Gly Ala Ala Gly Ser Thr Met
                50                  55                  60
Gly Ala Ala Ser Ile Thr Leu Thr Val Gln Ala Arg Gln Leu Leu
                65                  70                  75
Ser Gly Ile Val Gln Gln Gln Ser Asn Leu Leu Arg Ala Ile Glu
                80                  85                  90
Ala Gln Gln His Leu Leu Lys Leu Thr Val Trp Gly Ile Lys Gln
                95                  100                 105
Leu Gln Ala Arg Val Leu Ala Val Glu Arg Tyr Leu Gln Asp Gln
                110                 115                 120
Gln Leu Leu Gly Ile Trp Gly Cys Ser Gly Lys Leu Ile Cys Thr
                125                 130                 135
Thr Thr Val Pro Trp Asn Ser Ser Trp Ser Asn Lys Ser Gln Glu
                140                 145                 150
Asp Ile Trp Asn Asn Met Thr Trp Leu Gln Trp Glu Lys Glu Ile
                155                 160                 165
Ser Ser Tyr Thr Gly Ile Ile Tyr Gln Leu Ile Glu Glu Ser Gln
                170                 175                 180
Asn Gln Gln Glu Lys Asn Glu Leu Asp Leu Leu Ala Leu Asp Lys
                185                 190                 195
Trp Ala Asn Leu Asn Trp Phe Asn Ile Ser Asn Trp Leu Trp Tyr
                200                 205                 210
Ile Arg Leu Phe Val Ile Ile Val Gly Gly Leu Ile Gly Leu Arg
```

```
                    215                 220                 225

Ile Val Phe Thr Val Leu Ser Ile Ile Asn Arg Val Arg Gln Gly
                    230                 235                 240

Tyr Ser Pro Leu Ser Phe Gln Thr Leu Ala Pro Ile Pro Glu Gly
                    245                 250                 255

Leu Gly Arg Pro Gly Arg Ile Glu Glu Glu Gly Gly
                    260                 265     267
```

(2) INFORMATION FOR SEQ ID NO: 70:

(i) SEQUENCE CHARACTERISTICS:
        (A) LENGTH: 268 amino acids
        (B) TYPE: Amino Acid
        (D) TOPOLOGY: Linear (xi) SEQUENCE DESCRIPTION: SEQ ID NO: 70:

```
Gly Gly Gly Asp Met Arg Asp Asn Trp Arg Ser Glu Leu Tyr Lys
 1               5                  10                  15

Tyr Lys Val Val Lys Ile Glu Pro Leu Gly Val Ala Pro Thr Lys
                    20                  25                  30

Ala Lys Arg Arg Val Val Ala Arg Glu Lys Arg Ala Ile Gly Met
                    35                  40                  45

Gly Ala Phe Phe Leu Gly Phe Leu Gly Ala Ala Gly Ser Thr Met
                    50                  55                  60

Gly Ala Ala Ser Ile Thr Leu Thr Val Gln Ala Arg Arg Leu Leu
                    65                  70                  75

Ser Gly Ile Val Gln Gln Gln Asn Asn Leu Leu Arg Ala Ile Glu
                    80                  85                  90

Ala Gln Gln His Leu Leu Lys Leu Thr Val Trp Gly Ile Lys Gln
                    95                  100                 105

Leu Gln Ala Arg Ile Leu Ala Val Glu Arg Tyr Leu Lys Asp Gln
                    110                 115                 120

Gln Leu Leu Gly Ile Trp Gly Cys Ser Gly Lys Ile Ile Cys Pro
                    125                 130                 135

Thr Asn Val Pro Trp Asn Ser Ser Trp Ser Asn Lys Ser Gln Ser
                    140                 145                 150

Asp Ile Trp Asp Lys Met Thr Trp Leu Glu Trp Asp Lys Glu Val
                    155                 160                 165

Ser Asn Tyr Thr Gln Val Ile Tyr Asn Leu Ile Glu Glu Ser Gln
                    170                 175                 180

Thr Gln Gln Glu Ile Asn Glu Arg Asp Leu Leu Ala Leu Asp Lys
                    185                 190                 195

Trp Ala Asn Leu Trp Asn Trp Phe Asp Ile Ser Asn Trp Leu Trp
                    200                 205                 210

Tyr Ile Lys Ile Phe Ile Met Ile Val Gly Gly Leu Ile Gly Leu
                    215                 220                 225

Arg Ile Val Phe Ala Val Leu Ser Ile Ile Asn Arg Val Arg Gln
                    230                 235                 240

Gly Tyr Ser Pro Leu Ser Phe Gln Thr Leu Thr His His Gln Arg
                    245                 250                 255

Glu Pro Asp Arg Pro Glu Arg Ile Glu Glu Gly Gly Gly
                    260                 265     268
```

(2) INFORMATION FOR SEQ ID NO: 71:

(i) SEQUENCE CHARACTERISTICS:

(A) LENGTH: 268 amino acids
                    (B) TYPE: Amino Acid
                    (D) TOPOLOGY: Linear (xi) SEQUENCE DESCRIPTION: SEQ ID NO: 71:

Gly Gly Gly Asn Met Arg Asp Asn Trp Arg Ser Glu Leu Tyr Lys
 1               5                  10                  15

Tyr Lys Val Val Lys Ile Glu Pro Leu Gly Val Ala Pro Ser Arg
            20                  25                  30

Ala Lys Arg Arg Val Val Glu Arg Glu Lys Arg Ala Val Gly Ile
            35                  40                  45

Gly Ala Val Phe Leu Gly Phe Leu Gly Ala Ala Gly Ser Thr Met
            50                  55                  60

Gly Ala Ala Ser Ile Thr Leu Thr Ala Gln Ala Arg Gln Leu Leu
            65                  70                  75

Ser Gly Ile Val Gln Gln Gln Ser Asn Leu Leu Arg Ala Ile Glu
            80                  85                  90

Ala Gln Gln His Met Leu Lys Leu Thr Val Trp Gly Ile Lys Gln
            95                  100                 105

Leu Gln Ala Arg Val Leu Ala Val Glu Arg Tyr Leu Lys Asp Gln
            110                 115                 120

Gln Leu Leu Gly Ile Trp Gly Cys Ser Gly Lys Leu Ile Cys Thr
            125                 130                 135

Thr Asn Val Pro Trp Asn Ser Ser Trp Ser Asn Lys Ser Met Asn
            140                 145                 150

Glu Ile Trp Asp Asn Met Thr Trp Leu Gln Trp Asp Lys Glu Ile
            155                 160                 165

Ser Asn Tyr Thr Gln Ile Ile Tyr Asn Leu Ile Glu Glu Ser Gln
            170                 175                 180

Asn Gln Gln Glu Lys Asn Glu Gln Asp Leu Leu Ala Leu Asp Lys
            185                 190                 195

Trp Ala Ser Leu Trp Asn Trp Phe Asp Ile Ser Arg Trp Leu Trp
            200                 205                 210

Tyr Ile Lys Ile Phe Ile Met Ile Val Gly Gly Leu Ile Gly Leu
            215                 220                 225

Arg Ile Val Phe Ala Val Leu Ser Val Ile Asn Arg Val Arg Gln
            230                 235                 240

Gly Tyr Ser Pro Leu Ser Phe Gln Ile Arg Thr Pro Asn Pro Lys
            245                 250                 255

Glu Pro Asp Arg Leu Gly Arg Ile Asp Gly Glu Gly Gly
            260                 265         268

(2) INFORMATION FOR SEQ ID NO: 72:

(i) SEQUENCE CHARACTERISTICS:
            (A) LENGTH: 268 amino acids
            (B) TYPE: Amino Acid
            (D) TOPOLOGY: Linear (xi) SEQUENCE DESCRIPTION: SEQ ID NO: 72:

Gly Gly Gly Asn Met Arg Asp Asn Trp Arg Ser Glu Leu Tyr Lys
 1               5                  10                  15

Tyr Lys Val Val Lys Ile Glu Pro Leu Gly Val Ala Pro Thr Arg
            20                  25                  30

Ala Lys Arg Arg Val Val Glu Arg Glu Lys Arg Ala Ile Gly Met
            35                  40                  45

```
Gly Ala Val Phe Ile Gly Phe Leu Gly Ala Ala Gly Ser Thr Met
                50                  55                  60

Gly Ala Ala Ser Ile Thr Leu Met Val Gln Ala Arg Gln Leu Leu
                65                  70                  75

Ser Gly Ile Val Gln Gln Gln Ser Asn Leu Leu Arg Ala Ile Glu
                80                  85                  90

Ala Gln Gln His Leu Leu Arg Leu Thr Val Trp Gly Ile Lys Gln
                95                 100                 105

Leu Gln Ala Arg Val Leu Ala Leu Glu Arg Tyr Leu Arg Asp Gln
               110                 115                 120

Gln Leu Leu Gly Ile Trp Gly Cys Ser Gly Lys Leu Ile Cys Thr
               125                 130                 135

Thr Asn Val Pro Trp Asn Ser Ser Trp Ser Asn Lys Ser Tyr Ser
               140                 145                 150

Glu Ile Trp Asp Asn Met Thr Trp Leu Gln Trp Asp Lys Glu Ile
               155                 160                 165

Asn Asn Tyr Thr Glu Leu Ile Tyr Ser Leu Ile Glu Asp Ser Gln
               170                 175                 180

Asn Gln Gln Glu Lys Asn Glu Gln Asp Leu Leu Ala Leu Asp Lys
               185                 190                 195

Trp Ala Asn Leu Trp Asn Trp Phe Asp Ile Ser Asn Trp Leu Trp
               200                 205                 210

Tyr Ile Lys Ile Phe Ile Met Ile Val Gly Gly Leu Ile Gly Leu
               215                 220                 225

Arg Ile Ile Phe Ala Val Leu Ser Ile Ile Asn Arg Val Arg Gln
               230                 235                 240

Gly Tyr Ser Pro Leu Ser Phe Gln Thr His Thr Pro Asn Pro Arg
               245                 250                 255

Gly Leu Asp Arg Pro Gly Arg Ile Glu Glu Glu Gly Gly
               260                 265         268

(2) INFORMATION FOR SEQ ID NO: 73:

(i) SEQUENCE CHARACTERISTICS:
        (A) LENGTH: 243 amino acids
        (B) TYPE: Amino Acid
        (D) TOPOLOGY: Linear (xi) SEQUENCE DESCRIPTION: SEQ ID NO: 73:

Gly Gly Gly Asp Met Arg Asp Asn Trp Arg Ser Glu Leu Tyr Lys
 1               5                  10                  15

Tyr Lys Asp Val Lys Ile Glu Pro Leu Gly Val Ala Pro Thr Arg
                20                  25                  30

Ala Lys Arg Arg Val Val Glu Arg Glu Lys Arg Ala Val Gly Leu
                35                  40                  45

Gly Ala Val Phe Leu Gly Phe Leu Gly Ala Ala Gly Ser Thr Met
                50                  55                  60

Gly Ala Ala Ser Ile Thr Leu Thr Val Gln Ala Arg Gln Leu Leu
                65                  70                  75

Ser Gly Ile Val Gln Gln Gln Ser Asn Leu Leu Met Ala Ile Glu
                80                  85                  90

Ala Gln Gln His Leu Leu Lys Leu Thr Val Trp Gly Ile Lys Gln
                95                 100                 105

Leu Gln Ala Arg Val Leu Ala Leu Glu Arg Tyr Leu Lys Asp Gln
               110                 115                 120
```

-continued

```
Gln Leu Leu Gly Ile Trp Gly Cys Ser Gly Lys Leu Ile Cys Thr
                125                 130                 135

Thr Thr Val Pro Trp Asn Ser Ser Trp Ser Asn Lys Thr Tyr Ser
                140                 145                 150

Asp Ile Trp Asp Asn Met Thr Trp Leu Gln Trp Asp Lys Glu Ile
                155                 160                 165

Ser Asn Tyr Thr Lys Ile Ile Tyr Ala Leu Ile Glu Glu Ser Ala
                170                 175                 180

Asn Gln Gln Glu Lys Asn Glu Gln Asp Leu Leu Ala Leu Asp Lys
                185                 190                 195

Trp Thr Ser Leu Trp Ser Trp Phe Asp Ile Thr Lys Trp Leu Trp
                200                 205                 210

Tyr Ile Arg Ile Phe Ile Met Ile Val Gly Gly Leu Ile Gly Leu
                215                 220                 225

Arg Ile Val Phe Ala Val Leu Asn Ile Ile Asn Arg Val Arg Gln
                230                 235                 240

Gly Tyr Ser
        243

(2) INFORMATION FOR SEQ ID NO: 74:

(i) SEQUENCE CHARACTERISTICS:
        (A) LENGTH: 104 amino acids
        (B) TYPE: Amino Acid
        (D) TOPOLOGY: Linear (xi) SEQUENCE DESCRIPTION: SEQ ID NO: 74:

Gly Gly Gly Asp Met Arg Asp Asn Trp Arg Ser Glu Leu Tyr Lys
 1               5                  10                  15

Tyr Lys Val Val Lys Ile Glu Pro Leu Gly Val Ala Pro Thr Arg
                20                  25                  30

Ala Lys Arg Arg Val Val Glu Arg Glu Lys Arg Ala Val Gly Leu
                35                  40                  45

Gly Ala Val Phe Ile Gly Phe Leu Gly Ala Ala Gly Ser Thr Met
                50                  55                  60

Gly Ala Ala Ser Ile Thr Leu Thr Val Gln Ala Arg Gln Leu Leu
                65                  70                  75

Ser Gly Ile Val Gln Gln Gln Ser Asn Leu Leu Arg Ala Ile Glu
                80                  85                  90

Ala Gln Gln His Leu Leu Lys Leu Thr Val Trp Gly Ile Lys
                95                  100                 104

(2) INFORMATION FOR SEQ ID NO: 75:

(i) SEQUENCE CHARACTERISTICS:
        (A) LENGTH: 54 amino acids
        (B) TYPE: Amino Acid
        (D) TOPOLOGY: Linear (xi) SEQUENCE DESCRIPTION: SEQ ID NO: 75:

Gly Gly Gly Asp Met Arg Asp Asn Trp Arg Ser Glu Leu Tyr Lys
 1               5                  10                  15

Tyr Lys Val Val Lys Ile Glu Pro Leu Gly Val Ala Pro Ser Arg
                20                  25                  30

Ala Lys Arg Arg Val Val Trp Arg Glu Lys Arg Ala Val Val Glu
                35                  40                  45

Ile Gly Ala Val Phe Leu Gly Phe Leu
                50              54
```

(2) INFORMATION FOR SEQ ID NO: 76:

(i) SEQUENCE CHARACTERISTICS:
        (A) LENGTH: 269 amino acids
        (B) TYPE: Amino Acid
        (D) TOPOLOGY: Linear (xi) SEQUENCE DESCRIPTION: SEQ ID NO: 76:

```
Gly Gly Gly Asp Met Arg Asp Asn Trp Arg Ser Glu Leu Tyr Lys
  1               5                  10                  15

Tyr Lys Val Val Glu Ile Lys Pro Leu Gly Val Ala Pro Thr Xaa
                 20                  25                  30

Ala Lys Arg Arg Val Val Glu Arg Glu Lys Arg Ala Val Gly Xaa
                 35                  40                  45

Ile Gly Ala Val Phe Leu Gly Phe Leu Gly Ala Ala Gly Ser Thr
                 50                  55                  60

Met Gly Ala Ala Ser Ile Thr Leu Thr Val Gln Ala Arg Gln Leu
                 65                  70                  75

Leu Ser Gly Ile Val Gln Gln Gln Ser Asn Leu Leu Arg Ala Ile
                 80                  85                  90

Glu Ala Gln Gln His Xaa Leu Gln Leu Thr Val Trp Gly Ile Lys
                 95                 100                 105

Gln Leu Gln Thr Arg Val Leu Ala Ile Glu Arg Tyr Leu Lys Asp
                110                 115                 120

Gln Gln Leu Leu Gly Ile Trp Gly Cys Ser Gly Lys Leu Ile Cys
                125                 130                 135

Thr Thr Xaa Val Pro Trp Asn Ser Ser Trp Ser Asn Arg Ser Gln
                140                 145                 150

Thr Asp Ile Trp Asp Asn Met Thr Trp Met Gln Trp Asp Arg Glu
                155                 160                 165

Ile Ser Asn Tyr Thr Asp Thr Ile Tyr Arg Leu Leu Glu Asp Ser
                170                 175                 180

Gln Asn Gln Gln Glu Arg Asn Glu Lys Asp Leu Leu Ala Leu Asp
                185                 190                 195

Ser Trp Lys Asn Leu Trp Asn Trp Phe Ser Ile Thr Asn Trp Leu
                200                 205                 210

Trp Tyr Ile Lys Ile Phe Ile Met Ile Val Gly Gly Leu Ile Gly
                215                 220                 225

Leu Arg Ile Ile Phe Ala Val Leu Ser Ile Val Asn Arg Val Arg
                230                 235                 240

Gln Gly Tyr Ser Pro Leu Ser Phe Gln Thr Leu Thr Pro Asn Pro
                245                 250                 255

Arg Gly Pro Asp Arg Leu Gly Arg Ile Glu Glu Glu Gly Gly
                260                 265             269
```

(2) INFORMATION FOR SEQ ID NO: 77:

(i) SEQUENCE CHARACTERISTICS:
        (A) LENGTH: 198 amino acids
        (B) TYPE: Amino Acid
        (D) TOPOLOGY: Linear (xi) SEQUENCE DESCRIPTION: SEQ ID NO: 77:

```
Gly Gly Gly Asp Met Arg Asp Asn Trp Arg Ser Glu Leu Tyr Lys
  1               5                  10                  15

Tyr Lys Val Val Glu Ile Lys Pro Leu Gly Val Ala Pro Thr Lys
```

```
                    20                  25                  30
Ala Lys Arg Arg Val Val Glu Arg Glu Lys Arg Ala Val Gly Ile
                35                  40                  45
Gly Ala Val Phe Leu Gly Phe Leu Gly Ala Ala Gly Ser Thr Met
                50                  55                  60
Gly Ala Ala Ser Val Thr Leu Thr Val Gln Ala Arg Gln Leu Leu
                65                  70                  75
Phe Gly Ile Val Gln Gln Gln Ser Asn Leu Leu Arg Ala Ile Glu
                80                  85                  90
Ala Gln His Gly Leu Leu Gln Leu Thr Val Trp Gly Ile Lys Gln
                95                 100                 105
Leu Gln Thr Arg Val Leu Ala Ile Glu Arg Tyr Leu Lys Asp Gln
               110                 115                 120
Gln Leu Leu Gly Ile Trp Gly Cys Ser Gly Lys Leu Ile Cys Thr
               125                 130                 135
Thr Ala Val Ala Trp Asn Ser Ser Trp Ser Asn Lys Ser Gln Ser
               140                 145                 150
Asp Ile Trp Asp Asn Met Thr Trp Met Glu Trp Asp Arg Glu Ile
               155                 160                 165
Ser Asn Tyr Thr Asp Ile Ile Tyr Lys Leu Leu Glu Asp Ser Gln
               170                 175                 180
Asn Gln Gln Glu Lys Asn Glu Lys Asp Leu Leu Ala Leu Asp Ser
               185                 190                 195
Trp Lys Asn
       198

(2) INFORMATION FOR SEQ ID NO: 78:

(i) SEQUENCE CHARACTERISTICS:
        (A) LENGTH: 198 amino acids
        (B) TYPE: Amino Acid
        (D) TOPOLOGY: Linear (xi) SEQUENCE DESCRIPTION: SEQ ID NO: 78:

Gly Gly Gly Asp Met Arg Asp Asn Trp Arg Ser Glu Leu Tyr Lys
  1               5                  10                  15
Tyr Lys Val Val Glu Ile Lys Pro Leu Gly Val Ala Pro Thr Glu
                20                  25                  30
Ala Lys Arg Arg Val Val Glu Arg Glu Lys Arg Ala Val Gly Ile
                35                  40                  45
Gly Ala Val Phe Leu Gly Phe Leu Gly Ala Ala Gly Ser Thr Met
                50                  55                  60
Gly Ala Ala Ser Ile Thr Leu Thr Val Gln Ala Arg Gln Leu Leu
                65                  70                  75
Ser Gly Ile Val Gln Gln Gln Ser Asn Leu Leu Arg Ala Ile Glu
                80                  85                  90
Ala Arg Gln Gly Met Leu Gln Leu Thr Val Trp Gly Ile Lys Gln
                95                 100                 105
Leu Gln Ala Arg Val Leu Ala Ile Glu Arg Tyr Leu Gln Asp Gln
               110                 115                 120
Gln Leu Leu Gly Leu Trp Gly Cys Ser Gly Lys Leu Ile Cys Thr
               125                 130                 135
Thr Thr Val Pro Trp Asn Ser Ser Trp Ser Asn Lys Ser Lys Thr
               140                 145                 150
Asp Ile Trp Asp Asn Met Thr Trp Met Gln Trp Asp Arg Glu Ile
```

```
                        155                 160                 165
Ser Asn Tyr Thr Asp Thr Ile Tyr Lys Leu Leu Glu Asp Ser Gln
                170                 175                 180

Asn Gln Gln Glu Lys Asn Glu Lys Asp Leu Leu Ala Leu Asp Ser
                185                 190                 195

Trp Asn Asn
        198

(2) INFORMATION FOR SEQ ID NO: 79:

(i) SEQUENCE CHARACTERISTICS:
        (A) LENGTH: 198 amino acids
        (B) TYPE: Amino Acid
        (D) TOPOLOGY: Linear (xi) SEQUENCE DESCRIPTION: SEQ ID NO: 79:

Gly Gly Gly Asp Met Arg Asn Asn Trp Arg Ser Glu Leu Tyr Lys
 1               5                  10                  15

Tyr Lys Val Val Glu Ile Lys Pro Leu Gly Val Ala Pro Thr Thr
                20                  25                  30

Ala Lys Arg Arg Val Val Glu Arg Glu Lys Arg Ala Val Gly Ile
                35                  40                  45

Gly Ala Val Phe Leu Gly Phe Leu Gly Ala Ala Gly Ser Thr Met
                50                  55                  60

Gly Ala Ala Ser Met Thr Leu Thr Val Gln Ala Arg Gln Leu Leu
                65                  70                  75

Ser Gly Ile Val Gln Gln Gln Ser Asn Leu Leu Arg Ala Ile Glu
                80                  85                  90

Ala Gln Gln Gly Leu Leu Gln Leu Thr Val Trp Gly Ile Lys Gln
                95                  100                 105

Leu Gln Thr Arg Val Leu Ala Ile Glu Arg Tyr Leu Lys Asp Gln
                110                 115                 120

Gln Leu Leu Gly Ile Trp Gly Arg Ser Gly Lys Leu Ile Cys Thr
                125                 130                 135

Thr Asn Val Pro Trp Asn Ser Ser Trp Ser Asn Arg Ser Gln Thr
                140                 145                 150

Asp Ile Trp Asp Asn Met Thr Trp Met Gln Trp Asp Arg Glu Ile
                155                 160                 165

Ser Asn Tyr Thr Asp Thr Ile Tyr Arg Leu Leu Glu Asp Ser Gln
                170                 175                 180

Asn Gln Gln Glu Arg Asn Glu Lys Asp Leu Leu Ala Leu Asp Ser
                185                 190                 195

Trp Lys Asn
        198

(2) INFORMATION FOR SEQ ID NO: 80:

(i) SEQUENCE CHARACTERISTICS:
        (A) LENGTH: 198 amino acids
        (B) TYPE: Amino Acid
        (D) TOPOLOGY: Linear (xi) SEQUENCE DESCRIPTION: SEQ ID NO: 80:

Gly Gly Gly Glu Met Arg Asp Asn Trp Arg Ser Glu Leu Tyr Lys
 1               5                  10                  15

Tyr Lys Val Val Glu Ile Lys Pro Leu Gly Val Ala Pro Thr Thr
                20                  25                  30
```

-continued

```
Ala Lys Arg Arg Val Val Glu Arg Glu Lys Arg Ala Val Gly Ile
                35                  40                  45

Gly Ala Val Phe Leu Gly Phe Leu Gly Ala Ala Gly Ser Thr Met
                50                  55                  60

Gly Ala Ala Ser Met Thr Val Thr Val Gln Ala Arg Gln Leu Leu
                65                  70                  75

Ser Gly Ile Val Gln Gln Gln Ser Asn Leu Leu Arg Ala Ile Glu
                80                  85                  90

Ala Gln Gln Gly Leu Leu Gln Leu Thr Ile Trp Gly Ile Lys Gln
                95                 100                 105

Leu Gln Ala Arg Val Leu Ala Ile Glu Arg Tyr Leu Lys Glu Gln
               110                 115                 120

Gln Leu Leu Gly Ile Trp Gly Cys Ser Gly Lys Leu Ile Cys Thr
               125                 130                 135

Thr Thr Val Pro Trp Asn Ser Ser Trp Ser Asn Arg Ser Gln Thr
               140                 145                 150

Asp Ile Trp Asp Asn Met Thr Trp Met Gln Trp Asp Arg Glu Ile
               155                 160                 165

Ser Asn Tyr Thr Glu Thr Ile Tyr Arg Leu Leu Glu Asp Ser Gln
               170                 175                 180

Asn Gln Gln Glu Arg Asn Glu Lys Asp Leu Leu Ala Leu Asp Ser
               185                 190                 195

Trp Lys Asn
       198

(2) INFORMATION FOR SEQ ID NO: 81:

(i) SEQUENCE CHARACTERISTICS:
        (A) LENGTH: 198 amino acids
        (B) TYPE: Amino Acid
        (D) TOPOLOGY: Linear (xi) SEQUENCE DESCRIPTION: SEQ ID NO: 81:

Gly Gly Gly Asp Met Arg Asp Asn Trp Arg Ser Glu Leu Tyr Lys
  1              5                  10                  15

Tyr Lys Val Val Glu Ile Lys Pro Leu Gly Val Ala Pro Thr Thr
                20                  25                  30

Ala Lys Arg Arg Val Val Glu Arg Glu Lys Arg Ala Val Gly Leu
                35                  40                  45

Gly Ala Val Phe Leu Gly Phe Leu Gly Ala Ala Gly Ser Thr Met
                50                  55                  60

Gly Ala Ala Ser Ile Thr Leu Thr Val Gln Ala Arg Gln Leu Leu
                65                  70                  75

Ser Gly Ile Val Gln Gln Gln Ser Asn Leu Leu Arg Ala Ile Glu
                80                  85                  90

Ala Gln Gln Gly Leu Leu Gln Leu Thr Val Trp Gly Ile Lys Gln
                95                 100                 105

Leu Gln Thr Arg Val Leu Ala Ile Glu Arg Tyr Leu Lys Asp Gln
               110                 115                 120

Gln Leu Leu Gly Met Trp Gly Cys Ser Gly Lys Leu Ile Cys Thr
               125                 130                 135

Thr Ala Val Pro Trp Asn Ser Ser Trp Ser Asn Arg Ser Gln Thr
               140                 145                 150

Asp Ile Trp Asp Asn Met Thr Trp Met Gln Trp Asp Arg Glu Ile
               155                 160                 165
```

```
Ser Asn Tyr Thr Asn Thr Ile Tyr Arg Leu Leu Glu Asp Ser Gln
                170                 175                 180

Asn Gln Gln Glu Arg Asn Glu Lys Asp Leu Leu Ala Leu Asp Ser
                185                 190                 195

Trp Lys Asn
        198

(2) INFORMATION FOR SEQ ID NO: 82:

(i) SEQUENCE CHARACTERISTICS:
        (A) LENGTH: 121 amino acids
        (B) TYPE: Amino Acid
        (D) TOPOLOGY: Linear (xi) SEQUENCE DESCRIPTION: SEQ ID NO: 82:

Gly Gly Gly Asn Met Lys Asp Asn Trp Arg Asn Glu Leu Tyr Lys
  1               5                  10                  15

Tyr Lys Val Val Glu Ile Lys Pro Leu Gly Ile Ala Pro Thr Gly
                 20                  25                  30

Ser Lys Arg Arg Val Val Glu Arg Glu Lys Arg Ala Val Gly Ile
                 35                  40                  45

Gly Ala Val Leu Leu Gly Phe Leu Gly Ala Ala Gly Ser Thr Met
                 50                  55                  60

Ala Ala Ala Ser Ile Thr Leu Thr Val Gln Ala Arg Gln Leu Leu
                 65                  70                  75

Ser Gly Ile Val Gln Gln Ser Asn Leu Leu Arg Ala Ile Glu
                 80                  85                  90

Ala Gln Gln Gly Met Leu Gln Leu Thr Val Trp Gly Ile Lys Gln
                 95                 100                 105

Leu Gln Thr Arg Val Leu Ala Ile Glu Arg Tyr Leu Lys Asp Gln
                110                 115                 120

Gln
121

(2) INFORMATION FOR SEQ ID NO: 83:

(i) SEQUENCE CHARACTERISTICS:
        (A) LENGTH: 72 amino acids
        (B) TYPE: Amino Acid
        (D) TOPOLOGY: Linear (xi) SEQUENCE DESCRIPTION: SEQ ID NO: 83:

Gly Gly Gly Asp Met Arg Asn Asn Trp Arg Ser Glu Leu Tyr Lys
  1               5                  10                  15

Tyr Lys Val Val Glu Ile Lys Pro Leu Gly Val Ala Pro Thr Thr
                 20                  25                  30

Pro Lys Arg Arg Val Val Glu Arg Glu Lys Arg Ala Val Gly Ile
                 35                  40                  45

Gly Ala Val Phe Leu Gly Phe Leu Gly Ala Ala Gly Ser Thr Met
                 50                  55                  60

Gly Ala Ala Ser Ile Thr Leu Thr Val Pro Leu Arg
                 65                  70  72

(2) INFORMATION FOR SEQ ID NO: 84:

(i) SEQUENCE CHARACTERISTICS:
        (A) LENGTH: 269 amino acids
        (B) TYPE: Amino Acid
        (D) TOPOLOGY: Linear
```

-continued (xi) SEQUENCE DESCRIPTION: SEQ ID NO: 84:

```
Gly Gly Gly Asp Met Arg Asp Asn Trp Arg Ser Glu Leu Tyr Lys
  1               5                  10                  15

Tyr Lys Val Val Arg Ile Glu Pro Leu Gly Xaa Ala Pro Thr Xaa
                 20                  25                  30

Ala Lys Arg Arg Val Val Glu Arg Glu Lys Arg Ala Ile Gly Leu
                 35                  40                  45

Gly Ala Xaa Phe Leu Gly Phe Leu Gly Ala Ala Gly Ser Thr Met
                 50                  55                  60

Gly Ala Ala Ser Leu Thr Leu Thr Val Gln Ala Arg Gln Leu Leu
                 65                  70                  75

Ser Gly Ile Val Gln Gln Gln Asn Asn Leu Leu Arg Ala Ile Glu
                 80                  85                  90

Ala Gln Gln His Leu Leu Gln Leu Thr Val Trp Gly Ile Lys Gln
                 95                 100                 105

Leu Gln Ala Arg Val Leu Ala Val Glu Arg Tyr Leu Lys Asp Gln
                110                 115                 120

Gln Leu Leu Gly Ile Trp Gly Cys Ser Gly Lys His Ile Cys Thr
                125                 130                 135

Thr Xaa Val Pro Trp Asn Ser Ser Trp Ser Asn Arg Ser Leu Asp
                140                 145                 150

Glu Ile Trp Gln Asn Met Thr Trp Met Glu Trp Glu Arg Glu Ile
                155                 160                 165

Asp Asn Tyr Thr Gly Leu Ile Tyr Ser Leu Ile Glu Glu Ser Gln
                170                 175                 180

Ile Gln Gln Glu Lys Asn Glu Lys Glu Leu Leu Glu Leu Asp Lys
                185                 190                 195

Trp Ala Ser Leu Trp Asn Trp Phe Ser Ile Thr Lys Trp Leu Trp
                200                 205                 210

Tyr Ile Lys Ile Phe Ile Met Ile Val Gly Gly Leu Ile Gly Leu
                215                 220                 225

Arg Ile Val Phe Ala Val Leu Ser Ile Val Asn Arg Val Arg Gln
                230                 235                 240

Gly Tyr Ser Pro Leu Ser Phe Gln Thr Leu Leu Pro Ala Pro Arg
                245                 250                 255

Gly Xaa Pro Asp Arg Pro Glu Gly Ile Glu Glu Gly Gly
                260                 265                 269
```

(2) INFORMATION FOR SEQ ID NO: 85:

(i) SEQUENCE CHARACTERISTICS:
        (A) LENGTH: 198 amino acids
        (B) TYPE: Amino Acid
        (D) TOPOLOGY: Linear (xi) SEQUENCE DESCRIPTION: SEQ ID NO: 85:

```
Gly Gly Gly Asp Met Lys Asp Asn Trp Arg Asn Glu Leu Tyr Lys
  1               5                  10                  15

Tyr Lys Val Val Arg Ile Glu Pro Leu Gly Ile Ala Pro Thr Arg
                 20                  25                  30

Ala Lys Arg Arg Val Val Glu Arg Glu Lys Arg Ala Ile Gly Leu
                 35                  40                  45

Gly Ala Val Phe Leu Gly Phe Leu Gly Ala Ala Gly Ser Thr Met
                 50                  55                  60

Gly Ala Val Ser Val Ala Leu Thr Gly Gln Ala Arg Gln Leu Leu
```

```
                         65                  70                  75
Ser Gly Ile Val Gln Gln Asn Asn Leu Leu Arg Ala Ile Glu
                80                  85                  90

Ala Gln Gln His Met Leu Gln Leu Thr Val Trp Gly Ile Lys Gln
                95                 100                 105

Leu Gln Ala Arg Val Leu Ala Val Glu Ser Tyr Leu Lys Asp Gln
               110                 115                 120

Gln Leu Leu Gly Ile Trp Gly Cys Ser Gly Lys His Ile Cys Thr
               125                 130                 135

Thr Thr Val Pro Trp Asn Ser Ser Trp Ser Asn Lys Ser Leu Glu
               140                 145                 150

Glu Ile Trp Asn Asn Met Thr Trp Ile Glu Trp Glu Arg Glu Ile
               155                 160                 165

Asp Asn Tyr Thr Gly Val Ile Tyr Ser Leu Ile Glu Asn Ser Gln
               170                 175                 180

Ile Gln Gln Glu Lys Asn Glu Gln Asp Leu Leu Gln Leu Asp Lys
               185                 190                 195

Trp Ala Ser
        198

(2) INFORMATION FOR SEQ ID NO: 86:

(i) SEQUENCE CHARACTERISTICS:
        (A) LENGTH: 198 amino acids
        (B) TYPE: Amino Acid
        (D) TOPOLOGY: Linear (xi) SEQUENCE DESCRIPTION: SEQ ID NO: 86:

Gly Gly Gly Asp Met Arg Asp Asn Trp Arg Ser Glu Leu Tyr Lys
 1               5                  10                  15

Tyr Lys Val Val Lys Ile Glu Pro Ile Gly Val Ala Pro Thr Lys
                20                  25                  30

Ala Arg Arg Arg Val Val Glu Arg Glu Lys Arg Ala Ile Gly Leu
                35                  40                  45

Gly Ala Val Phe Leu Gly Phe Leu Gly Ala Ala Gly Ser Thr Met
                50                  55                  60

Gly Ala Ala Ser Val Thr Leu Thr Val Gln Ala Arg Gln Leu Met
                65                  70                  75

Ser Gly Ile Val His Gln Gln Asn Asn Leu Leu Arg Ala Ile Glu
                80                  85                  90

Ala Gln Gln His Leu Leu Gln Leu Thr Val Trp Gly Ile Lys Gln
                95                 100                 105

Leu Gln Ala Arg Val Leu Ala Val Glu Arg Tyr Leu Arg Asp Gln
               110                 115                 120

Gln Leu Leu Gly Ile Trp Gly Cys Ser Gly Arg His Ile Cys Thr
               125                 130                 135

Thr Asn Val Pro Trp Asn Ser Ser Trp Ser Asn Arg Ser Leu Asp
               140                 145                 150

Glu Ile Trp Gln Asn Met Thr Trp Met Glu Trp Glu Arg Glu Ile
               155                 160                 165

Asp Asn Tyr Thr Gly Leu Ile Tyr Ser Leu Ile Glu Glu Ser Gln
               170                 175                 180

Ile Gln Gln Glu Lys Asn Glu Lys Glu Leu Leu Glu Leu Asp Lys
               185                 190                 195

Trp Ala Ser
```

198

(2) INFORMATION FOR SEQ ID NO: 87:

(i) SEQUENCE CHARACTERISTICS:
        (A) LENGTH: 198 amino acids
        (B) TYPE: Amino Acid
        (D) TOPOLOGY: Linear (xi) SEQUENCE DESCRIPTION: SEQ ID NO: 87:

```
Gly Gly Gly Asp Met Arg Asp Asn Trp Ile Ser Glu Leu Tyr Lys
  1               5                  10                  15

Tyr Lys Val Val Arg Ile Glu Pro Leu Gly Val Ala Pro Thr Lys
                 20                  25                  30

Ala Lys Arg Arg Val Val Glu Arg Glu Lys Arg Ala Ile Gly Leu
                 35                  40                  45

Gly Ala Met Phe Leu Gly Phe Leu Gly Ala Ala Gly Ser Thr Met
                 50                  55                  60

Gly Ala Ala Ser Leu Thr Leu Thr Val Gln Ala Arg Gln Leu Leu
                 65                  70                  75

Ser Gly Ile Val Gln Gln Gln Asn Asn Leu Leu Arg Ala Ile Glu
                 80                  85                  90

Ala Gln Gln His Leu Leu Gln Leu Thr Val Trp Gly Ile Lys Gln
                 95                 100                 105

Leu Gln Ala Arg Val Leu Ala Val Glu Arg Tyr Leu Gln Asp Gln
                110                 115                 120

Arg Leu Leu Gly Met Trp Gly Cys Ser Gly Lys His Ile Cys Thr
                125                 130                 135

Thr Phe Val Pro Trp Asn Ser Ser Trp Ser Asn Arg Ser Leu Asp
                140                 145                 150

Asp Ile Trp Asn Asn Met Thr Trp Met Gln Trp Glu Lys Glu Ile
                155                 160                 165

Ser Asn Tyr Thr Gly Ile Ile Tyr Asn Leu Ile Glu Glu Ser Gln
                170                 175                 180

Ile Gln Gln Glu Lys Asn Glu Lys Glu Leu Leu Glu Leu Asp Lys
                185                 190                 195

Trp Ala Ser
    198
```

(2) INFORMATION FOR SEQ ID NO: 88:

(i) SEQUENCE CHARACTERISTICS:
        (A) LENGTH: 198 amino acids
        (B) TYPE: Amino Acid
        (D) TOPOLOGY: Linear (xi) SEQUENCE DESCRIPTION: SEQ ID NO: 88:

```
Gly Gly Gly Asp Met Arg Asp Asn Trp Arg Ser Glu Leu Tyr Lys
  1               5                  10                  15

Tyr Lys Val Val Gln Ile Glu Pro Leu Gly Val Ala Pro Thr Arg
                 20                  25                  30

Ala Lys Arg Arg Val Val Glu Arg Glu Lys Arg Ala Ile Gly Leu
                 35                  40                  45

Gly Ala Met Phe Leu Gly Phe Leu Gly Ala Ala Gly Ser Thr Met
                 50                  55                  60

Gly Ala Arg Ser Val Thr Leu Thr Val Gln Ala Arg Gln Leu Met
                 65                  70                  75
```

```
Ser Gly Ile Val Gln Gln Gln Asn Asn Leu Leu Arg Ala Ile Glu
             80                  85                  90

Ala Gln Gln His Leu Leu Gln Leu Thr Val Trp Gly Ile Lys Gln
             95                 100                 105

Leu Gln Ala Arg Ile Leu Ala Val Glu Arg Tyr Leu Lys Asp Gln
            110                 115                 120

Gln Leu Leu Gly Ile Trp Gly Cys Ser Gly Lys His Ile Cys Thr
            125                 130                 135

Thr Asn Val Pro Trp Asn Ser Ser Trp Ser Asn Arg Ser Leu Asn
            140                 145                 150

Glu Ile Trp Gln Asn Met Thr Trp Met Glu Trp Glu Arg Glu Ile
            155                 160                 165

Asp Asn Tyr Thr Gly Leu Ile Tyr Ser Leu Ile Glu Glu Ser Gln
            170                 175                 180

Thr Gln Gln Glu Lys Asn Glu Lys Glu Leu Leu Glu Leu Asp Lys
            185                 190                 195

Trp Ala Ser
    198

(2) INFORMATION FOR SEQ ID NO: 89:

(i) SEQUENCE CHARACTERISTICS:
        (A) LENGTH: 198 amino acids
        (B) TYPE: Amino Acid
        (D) TOPOLOGY: Linear (xi) SEQUENCE DESCRIPTION: SEQ ID NO: 89:

Gly Gly Gly Asp Met Arg Asp Asn Trp Arg Ser Glu Leu Tyr Lys
 1               5                  10                  15

Tyr Lys Val Val Lys Ile Glu Pro Leu Gly Val Ala Pro Thr Arg
             20                  25                  30

Ala Lys Arg Arg Val Val Glu Arg Glu Lys Arg Ala Ile Gly Leu
             35                  40                  45

Gly Ala Met Phe Leu Gly Phe Leu Gly Ala Ala Gly Ser Thr Met
             50                  55                  60

Gly Ala Arg Ser Leu Thr Leu Thr Val Gln Ala Arg Gln Leu Leu
             65                  70                  75

Ser Gly Ile Val Gln Gln Gln Asn Asn Leu Leu Arg Ala Ile Glu
             80                  85                  90

Ala Gln Gln His Leu Leu Gln Leu Thr Val Trp Gly Ile Lys Gln
             95                 100                 105

Leu Gln Ala Arg Ile Leu Ala Val Glu Arg Tyr Leu Lys Asp Gln
            110                 115                 120

Gln Leu Leu Gly Ile Trp Gly Cys Ser Gly Lys Leu Ile Cys Thr
            125                 130                 135

Thr Thr Val Pro Trp Asn Ser Ser Trp Ser Asn Arg Ser Leu Asn
            140                 145                 150

Asp Ile Trp Gln Asn Met Thr Trp Met Glu Trp Glu Arg Glu Ile
            155                 160                 165

Asp Asn Tyr Thr Gly Leu Ile Tyr Arg Leu Ile Glu Glu Ser Gln
            170                 175                 180

Thr Gln Gln Glu Lys Asn Glu Gln Glu Leu Leu Glu Leu Asp Lys
            185                 190                 195

Trp Ala Ser
    198
```

(2) INFORMATION FOR SEQ ID NO: 90:

(i) SEQUENCE CHARACTERISTICS:
        (A) LENGTH: 198 amino acids
        (B) TYPE: Amino Acid
        (D) TOPOLOGY: Linear (xi) SEQUENCE DESCRIPTION: SEQ ID NO: 90:

```
Gly Gly Gly Asp Met Arg Asp Asn Trp Arg Ser Glu Leu Tyr Lys
 1               5                  10                  15

Tyr Lys Val Ile Lys Ile Glu Pro Leu Gly Leu Ala Pro Thr Arg
            20                  25                  30

Ala Lys Arg Arg Val Val Ala Arg Glu Lys Arg Ala Ile Gly Leu
            35                  40                  45

Gly Ala Val Phe Leu Gly Phe Leu Gly Ala Ala Gly Ser Thr Met
            50                  55                  60

Gly Ala Ala Ser Leu Thr Leu Thr Val Gln Ala Arg Gln Leu Met
            65                  70                  75

Ser Gly Ile Val Gln Gln Gln Asn Asn Leu Leu Arg Ala Ile Glu
            80                  85                  90

Ala Gln Gln His Leu Leu Gln Leu Thr Val Trp Gly Ile Lys Gln
            95                 100                 105

Leu Gln Ala Arg Val Leu Ala Val Glu Ser Tyr Leu Lys Asp Gln
           110                 115                 120

Gln Leu Leu Gly Ile Trp Gly Cys Ser Gly Arg His Ile Cys Pro
           125                 130                 135

Thr Gln Val Pro Trp Asn Ser Ser Trp Ser Asn Lys Ser Leu Asp
           140                 145                 150

Thr Ile Trp Gly Asn Met Thr Trp Met Glu Trp Glu Arg Glu Ile
           155                 160                 165

Ser Asn Tyr Thr Gly Leu Ile Tyr Asp Leu Ile Glu Glu Ser Gln
           170                 175                 180

Ile Gln Gln Glu Lys Asn Glu Lys Asp Leu Leu Glu Leu Asp Lys
           185                 190                 195

Trp Ala Ser
     198
```

(2) INFORMATION FOR SEQ ID NO: 91:

(i) SEQUENCE CHARACTERISTICS:
        (A) LENGTH: 104 amino acids
        (B) TYPE: Amino Acid
        (D) TOPOLOGY: Linear (xi) SEQUENCE DESCRIPTION: SEQ ID NO: 91:

```
Gly Gly Gly Asp Met Arg Asp Asn Trp Arg Asn Glu Leu Tyr Lys
 1               5                  10                  15

Tyr Lys Val Val Arg Ile Glu Pro Leu Gly Leu Ala Pro Thr Lys
            20                  25                  30

Ala Arg Arg Arg Val Val Glu Arg Glu Lys Arg Ala Ile Gly Leu
            35                  40                  45

Gly Ala Leu Phe Leu Gly Phe Leu Gly Ala Ala Gly Ser Thr Met
            50                  55                  60

Gly Ala Ala Ser Leu Thr Leu Thr Val Gln Ala Arg Gln Leu Leu
            65                  70                  75

Ser Gly Ile Val Gln Gln Gln Asn Asn Leu Leu Arg Ala Ile Glu
            80                  85                  90
```

```
Ala Gln Gln His Leu Leu Gln Leu Thr Val Trp Gly Ile Lys
                95                 100                104
```

(2) INFORMATION FOR SEQ ID NO: 92:

(i) SEQUENCE CHARACTERISTICS:
        (A) LENGTH: 70 amino acids
        (B) TYPE: Amino Acid
        (D) TOPOLOGY: Linear (xi) SEQUENCE DESCRIPTION: SEQ ID NO: 92:

```
Gly Gly Gly Asp Met Arg Asp Asn Trp Arg Ser Glu Leu Tyr Lys
 1               5                  10                  15

Tyr Lys Val Val Arg Ile Glu Pro Leu Gly Ile Ala Pro Thr Met
                20                  25                  30

Ser Lys Arg Arg Val Val Glu Arg Glu Lys Arg Ala Ile Gly Leu
                35                  40                  45

Gly Ala Leu Phe Leu Gly Phe Leu Gly Ala Ala Gly Ser Thr Met
                50                  55                  60

Gly Ala Ala Thr Leu Thr Leu Thr Val Xaa
                65                  70
```

(2) INFORMATION FOR SEQ ID NO: 93:

(i) SEQUENCE CHARACTERISTICS:
        (A) LENGTH: 70 amino acids
        (B) TYPE: Amino Acid
        (D) TOPOLOGY: Linear (xi) SEQUENCE DESCRIPTION: SEQ ID NO: 93:

```
Gly Gly Gly Asp Met Arg Asp Asn Trp Arg Ser Glu Leu Tyr Lys
 1               5                  10                  15

Tyr Lys Val Val Arg Ile Glu Pro Leu Gly Leu Ala Pro Thr Glu
                20                  25                  30

Ala Lys Arg Arg Val Val Glu Arg Glu Lys Arg Ala Ile Gly Leu
                35                  40                  45

Gly Ala Met Phe Leu Gly Phe Leu Gly Ala Ala Gly Ser Thr Met
                50                  55                  60

Gly Ala Ala Ser Met Thr Leu Thr Val Xaa
                65                  70
```

(2) INFORMATION FOR SEQ ID NO: 94:

(i) SEQUENCE CHARACTERISTICS:
        (A) LENGTH: 53 amino acids
        (B) TYPE: Amino Acid
        (D) TOPOLOGY: Linear (xi) SEQUENCE DESCRIPTION: SEQ ID NO: 94:

```
Gly Gly Gly Asp Met Arg Asp Asn Arg Arg Ser Glu Leu Tyr Lys
 1               5                  10                  15

Tyr Lys Val Val Lys Ile Glu Pro Leu Gly Val Ala Pro Thr Lys
                20                  25                  30

Thr Lys Arg Arg Val Val Glu Arg Glu Glu Arg Ala Ile Gly Leu
                35                  40                  45

Gly Ala Met Phe Leu Gly Phe Leu
                50      53
```

(2) INFORMATION FOR SEQ ID NO: 95:

(i) SEQUENCE CHARACTERISTICS:
    (A) LENGTH: 41 amino acids
    (B) TYPE: Amino Acid
    (D) TOPOLOGY: Linear (xi) SEQUENCE DESCRIPTION: SEQ ID NO: 95:

```
Gly Gly Gly Asp Met Arg Asp Asn Trp Arg Ser Glu Leu Tyr Lys
 1               5                  10                  15

Tyr Lys Val Val Arg Ile Glu Pro Leu Gly Ile Ala Pro Thr Met
                20                  25                  30

Ala Lys Arg Arg Val Val Glu Arg Glu Lys Arg
                35                  40  41
```

(2) INFORMATION FOR SEQ ID NO: 96:

(i) SEQUENCE CHARACTERISTICS:
    (A) LENGTH: 269 amino acids
    (B) TYPE: Amino Acid
    (D) TOPOLOGY: Linear (xi) SEQUENCE DESCRIPTION: SEQ ID NO: 96:

```
Gly Gly Gly Asn Ile Lys Asp Asn Trp Arg Ser Glu Leu Tyr Lys
 1               5                  10                  15

Tyr Lys Val Val Gln Ile Glu Pro Leu Gly Ile Ala Pro Thr Arg
                20                  25                  30

Ala Lys Arg Arg Val Val Glu Arg Glu Lys Arg Ala Val Gly Xaa
                35                  40                  45

Ile Gly Ala Met Ile Phe Gly Phe Leu Gly Ala Ala Gly Ser Thr
                50                  55                  60

Met Gly Ala Ala Ser Ile Thr Leu Thr Val Gln Ala Arg Gln Leu
                65                  70                  75

Leu Ser Gly Ile Val Gln Gln Gln Ser Asn Leu Leu Arg Ala Ile
                80                  85                  90

Glu Ala Gln Gln His Leu Leu Gln Leu Thr Val Trp Gly Ile Lys
                95                  100                 105

Gln Leu Gln Ala Arg Val Leu Ala Val Glu Arg Tyr Leu Lys Asp
                110                 115                 120

Gln Lys Phe Leu Gly Leu Trp Gly Cys Ser Gly Lys Ile Ile Cys
                125                 130                 135

Thr Thr Ala Val Pro Trp Asn Ser Thr Trp Ser Asn Arg Ser Phe
                140                 145                 150

Glu Glu Ile Trp Asn Asn Met Thr Trp Ile Glu Trp Glu Arg Glu
                155                 160                 165

Ile Ser Asn Tyr Thr Asn Gln Ile Tyr Glu Ile Leu Thr Glu Ser
                170                 175                 180

Gln Asn Gln Gln Asp Arg Asn Glu Lys Asp Leu Leu Glu Leu Asp
                185                 190                 195

Lys Trp Ala Ser Leu Trp Asn Trp Phe Asp Ile Thr Asn Trp Leu
                200                 205                 210

Trp Tyr Ile Lys Ile Phe Ile Met Ile Val Gly Gly Leu Ile Gly
                215                 220                 225

Leu Arg Ile Ile Phe Ala Val Leu Ser Ile Val Asn Arg Val Arg
                230                 235                 240

Gln Gly Tyr Ser Pro Leu Ser Phe Gln Thr Pro Xaa His His Gln
                245                 250                 255

Arg Glu Pro Asp Arg Pro Glu Arg Ile Glu Glu Gly Gly Gly
                260                 265             269
```

(2) INFORMATION FOR SEQ ID NO: 97:

(i) SEQUENCE CHARACTERISTICS:
        (A) LENGTH: 198 amino acids
        (B) TYPE: Amino Acid
        (D) TOPOLOGY: Linear (xi) SEQUENCE DESCRIPTION: SEQ ID NO: 97:

```
Gly Gly Gly Asn Ile Lys Asp Asn Trp Arg Ser Glu Leu Tyr Lys
 1               5                  10                  15

Tyr Lys Val Val Gln Ile Glu Pro Leu Gly Ile Ala Pro Thr Arg
                20                  25                  30

Ala Lys Arg Arg Val Val Glu Arg Glu Lys Arg Ala Val Gly Ile
                35                  40                  45

Gly Ala Met Ile Phe Gly Phe Leu Gly Ala Ala Gly Ser Thr Met
                50                  55                  60

Gly Ala Ala Ser Ile Thr Leu Thr Val Gln Ala Arg Gln Leu Val
                65                  70                  75

Ser Gly Ile Val Gln Gln Gln Ser Asn Leu Leu Arg Ala Ile Glu
                80                  85                  90

Ala Gln Gln His Leu Leu Gln Leu Thr Val Trp Gly Ile Lys Gln
                95                 100                 105

Leu Gln Ala Arg Val Leu Ala Val Glu Arg Tyr Leu Lys Asp Gln
               110                 115                 120

Lys Phe Leu Gly Leu Trp Gly Cys Ser Gly Lys Ile Ile Cys Thr
               125                 130                 135

Thr Ala Val Pro Trp Asn Ser Thr Trp Ser Asn Arg Ser Phe Glu
               140                 145                 150

Glu Ile Trp Ser Asn Met Thr Trp Ile Glu Trp Glu Arg Glu Ile
               155                 160                 165

Ser Asn Tyr Thr Asn Gln Ile Tyr Glu Ile Leu Thr Glu Ser Gln
               170                 175                 180

Asn Gln Gln Asp Arg Asn Glu Lys Asp Leu Leu Glu Leu Asp Lys
               185                 190                 195

Trp Ala Ser
       198
```

(2) INFORMATION FOR SEQ ID NO: 98:

(i) SEQUENCE CHARACTERISTICS:
        (A) LENGTH: 198 amino acids
        (B) TYPE: Amino Acid
        (D) TOPOLOGY: Linear (xi) SEQUENCE DESCRIPTION: SEQ ID NO: 98:

```
Gly Gly Gly Asn Ile Lys Asp Asn Trp Arg Ser Glu Leu Tyr Lys
 1               5                  10                  15

Tyr Lys Val Val Gln Ile Glu Pro Leu Gly Ile Ala Pro Thr Arg
                20                  25                  30

Ala Lys Arg Arg Val Val Glu Arg Glu Lys Arg Ala Val Gly Ile
                35                  40                  45

Gly Ala Met Ile Phe Gly Phe Leu Gly Ala Ala Gly Ser Thr Met
                50                  55                  60

Gly Ala Ala Ser Ile Thr Leu Thr Val Gln Ala Arg Gln Leu Leu
                65                  70                  75

Ser Gly Ile Val Gln Gln Gln Ser Asn Leu Leu Arg Ala Ile Glu
```

```
                  80                  85                  90
Ala Gln Gln His Leu Leu Gln Leu Thr Val Trp Gly Ile Lys Gln
                  95                 100                 105

Leu Gln Ala Arg Val Leu Ala Val Glu Arg Tyr Leu Lys Asp Gln
                 110                 115                 120

Lys Phe Leu Gly Leu Trp Gly Cys Ser Gly Lys Ile Ile Cys Thr
                 125                 130                 135

Thr Ala Val Pro Trp Asn Ser Thr Trp Ser Asn Arg Ser Phe Glu
                 140                 145                 150

Glu Ile Trp Asn Asn Met Thr Trp Thr Glu Trp Arg Glu Ile
                 155                 160                 165

Ser Asn Tyr Thr Asn Gln Ile Tyr Asp Ile Leu Thr Glu Ser Gln
                 170                 175                 180

Asn Gln Gln Asp Arg Asn Glu Lys Asp Leu Leu Gly Leu Asp Lys
                 185                 190                 195

Trp Ala Ser
      198
```

(2) INFORMATION FOR SEQ ID NO: 99:

(i) SEQUENCE CHARACTERISTICS:
        (A) LENGTH: 198 amino acids
        (B) TYPE: Amino Acid
        (D) TOPOLOGY: Linear (xi) SEQUENCE DESCRIPTION: SEQ ID NO: 99:

```
Gly Gly Gly Asn Ile Lys Asp Asn Trp Arg Ser Glu Leu Tyr Lys
 1               5                  10                  15

Tyr Lys Val Val Gln Ile Glu Pro Leu Gly Ile Ala Pro Thr Arg
                  20                  25                  30

Ala Lys Arg Arg Val Val Glu Arg Glu Lys Arg Ala Val Gly Ile
                  35                  40                  45

Gly Ala Met Ile Phe Gly Phe Leu Gly Ala Ala Gly Ser Thr Met
                  50                  55                  60

Gly Ala Ala Ser Ile Thr Leu Thr Val Gln Ala Arg Gln Leu Leu
                  65                  70                  75

Ser Gly Ile Val Gln Gln Ser Asn Leu Leu Arg Ala Ile Glu
                  80                  85                  90

Ala Gln Gln His Met Leu Gln Leu Thr Val Trp Gly Ile Lys Gln
                  95                 100                 105

Leu Gln Ala Arg Val Leu Ala Val Glu Arg Tyr Leu Lys Asp Gln
                 110                 115                 120

Lys Phe Leu Gly Leu Trp Gly Cys Ser Gly Lys Ile Ile Cys Thr
                 125                 130                 135

Thr Ala Val Pro Trp Asn Ser Thr Trp Ser Asn Lys Ser Phe Glu
                 140                 145                 150

Glu Ile Trp Asn Asn Met Thr Trp Thr Glu Trp Arg Glu Ile
                 155                 160                 165

Ser Asn Tyr Thr Asn Gln Ile Tyr Glu Ile Leu Thr Glu Ser Gln
                 170                 175                 180

Asn Gln Gln Asp Arg Asn Glu Lys Asp Leu Leu Glu Leu Asp Lys
                 185                 190                 195

Trp Ala Ser
      198
```

(2) INFORMATION FOR SEQ ID NO: 100:

(i) SEQUENCE CHARACTERISTICS:
        (A) LENGTH: 189 amino acids
        (B) TYPE: Amino Acid
        (D) TOPOLOGY: Linear (xi) SEQUENCE DESCRIPTION: SEQ ID NO: 100:

```
Gly Gly Gly Asn Ile Lys Asp Asn Trp Arg Ser Glu Leu Tyr Lys
 1               5                  10                  15

Tyr Lys Val Val Gln Ile Glu Pro Leu Gly Ile Ala Pro Thr Arg
                20                  25                  30

Ala Lys Arg Arg Val Val Glu Arg Glu Lys Arg Ala Val Gly Ile
                35                  40                  45

Gly Ala Met Ile Phe Gly Phe Leu Gly Ala Ala Gly Ser Thr Met
                50                  55                  60

Gly Ala Ala Ser Ile Thr Leu Thr Val Gln Ala Arg Gln Leu Leu
                65                  70                  75

Ser Gly Ile Val Gln Gln Ser Asn Leu Leu Arg Ala Glu Ala Gln
                80                  85                  90

Gln His Leu Leu Gln Leu Thr Val Trp Gly Gln Leu Gln Ala Arg
                95                 100                 105

Val Ala Val Glu Arg Tyr Leu Lys Asp Gln Lys Leu Gly Leu Trp
               110                 115                 120

Cys Ser Gly Lys Ile Ile Cys Thr Thr Ala Val Pro Trp Asn Ser
               125                 130                 135

Thr Trp Ser Asn Arg Ser Phe Glu Glu Ile Trp Asn Asn Met Trp
               140                 145                 150

Ile Glu Trp Arg Glu Ile Ser Asn Tyr Thr Asn Gln Ile Tyr Glu
               155                 160                 165

Ile Leu Thr Glu Ser Gln Asn Gln Gln Asp Arg Asn Glu Lys Asp
               170                 175                 180

Leu Leu Glu Leu Asp Lys Trp Ala Ser
               185                 189
```

(2) INFORMATION FOR SEQ ID NO: 101:

(i) SEQUENCE CHARACTERISTICS:
        (A) LENGTH: 198 amino acids
        (B) TYPE: Amino Acid
        (D) TOPOLOGY: Linear (xi) SEQUENCE DESCRIPTION: SEQ ID NO: 101:

```
Gly Gly Gly Asn Ile Lys Asp Asn Trp Arg Ser Glu Leu Tyr Lys
 1               5                  10                  15

Tyr Lys Val Val Gln Ile Glu Pro Leu Gly Ile Ala Pro Thr Arg
                20                  25                  30

Ala Lys Arg Arg Val Val Glu Arg Glu Lys Arg Ala Val Gly Ile
                35                  40                  45

Gly Ala Met Ile Phe Gly Phe Leu Gly Ala Ala Gly Ser Thr Met
                50                  55                  60

Gly Ala Ala Ser Ile Thr Leu Thr Val Gln Ala Arg Gln Leu Leu
                65                  70                  75

Ser Gly Ile Val Gln Gln Gln Ser Asn Leu Leu Arg Ala Ile Glu
                80                  85                  90

Ala Gln Gln His Leu Leu Gln Leu Thr Val Trp Gly Ile Lys Gln
                95                 100                 105
```

```
Leu Gln Ala Arg Val Leu Ala Val Glu Arg Tyr Leu Lys Asp Gln
                110                 115                 120

Lys Phe Leu Gly Leu Trp Gly Cys Ser Gly Lys Ile Ile Cys Thr
                125                 130                 135

Thr Ala Val Pro Trp Asn Ser Thr Trp Ser Asn Arg Ser Leu Glu
                140                 145                 150

Glu Ile Trp Asn Asn Met Thr Trp Ile Glu Trp Glu Arg Glu Ile
                155                 160                 165

Ser Asn Tyr Thr Asn Arg Ile Tyr Glu Ile Leu Thr Lys Ser Gln
                170                 175                 180

Asp Gln Gln Asp Arg Asn Glu Lys Asp Leu Leu Glu Leu Asp Lys
                185                 190                 195

Trp Ala Ser
        198

(2) INFORMATION FOR SEQ ID NO: 102:

(i) SEQUENCE CHARACTERISTICS:
        (A) LENGTH: 70 amino acids
        (B) TYPE: Amino Acid
        (D) TOPOLOGY: Linear (xi) SEQUENCE DESCRIPTION: SEQ ID NO: 102:

Gly Gly Gly Asn Ile Lys Asp Asn Trp Arg Ser Glu Leu Tyr Lys
 1               5                  10                  15

Tyr Lys Val Val Gln Ile Glu Pro Leu Gly Ile Ala Pro Thr Arg
                20                  25                  30

Ala Lys Arg Arg Val Val Glu Arg Glu Lys Arg Ala Val Gly Ile
                35                  40                  45

Gly Ala Met Ile Phe Gly Phe Leu Gly Ala Ala Gly Ser Thr Met
                50                  55                  60

Gly Ala Pro Ser Ile Thr Leu Thr Val Xaa
                65                  70

(2) INFORMATION FOR SEQ ID NO: 103:

(i) SEQUENCE CHARACTERISTICS:
        (A) LENGTH: 213 amino acids
        (B) TYPE: Amino Acid
        (D) TOPOLOGY: Linear (xi) SEQUENCE DESCRIPTION: SEQ ID NO: 103:

Xaa Gly Gly Asp Met Lys Asp Ile Trp Arg Thr Glu Leu Tyr Asn
 1               5                  10                  15

Tyr Lys Val Val Arg Ile Lys Pro Xaa Ser Val Ala Pro Thr Lys
                20                  25                  30

Xaa Xaa Arg Pro Xaa Ile Xaa Xaa Xaa Xaa His Arg Xaa Lys
                35                  40                  45

Arg Ala Val Gly Xaa Leu Gly Met Leu Phe Leu Gly Val Leu Ser
                50                  55                  60

Ala Ala Gly Ser Thr Met Gly Ala Ala Ala Thr Xaa Leu Thr Val
                65                  70                  75

Gln Thr Xaa Xaa Leu Leu Lys Gly Ile Val Gln Gln Gln Asp Asn
                80                  85                  90

Leu Leu Arg Ala Ile Xaa Ala Gln Gln His Leu Leu Xaa Leu Ser
                95                  100                 105

Val Trp Gly Xaa Xaa Gln Leu Xaa Ala Arg Leu Leu Ala Xaa Glu
                110                 115                 120
```

```
Thr Xaa Leu Gln Xaa Gln Gln Leu Leu Ser Leu Trp Gly Cys Lys
            125                 130                 135

Gly Lys Leu Val Cys Tyr Thr Xaa Val Xaa Trp Asn Asn Ser Trp
            140                 145                 150

Xaa Xaa Xaa Xaa Xaa Xaa Xaa Xaa Asn Ser Ser Xaa Xaa Xaa
            155                 160                 165

Xaa Ile Trp Asp Asn Leu Thr Trp Gln Xaa Trp Asp Arg Leu Xaa
            170                 175                 180

Ser Asn Xaa Xaa Xaa Xaa Ile Tyr Xaa Glu Xaa Gln Xaa Ala Gln
            185                 190                 195

Xaa Gln Gln Glu Lys Asn Glu Lys Xaa Leu Leu Glu Leu Asp Glu
            200                 205                 210

Trp Ala Ser
        213

(2) INFORMATION FOR SEQ ID NO: 104:

(i) SEQUENCE CHARACTERISTICS:
        (A) LENGTH: 200 amino acids
        (B) TYPE: Amino Acid
        (D) TOPOLOGY: Linear (xi) SEQUENCE DESCRIPTION: SEQ ID NO: 104:

Ile Gly Gly Asp Met Lys Asp Ile Trp Arg Thr Glu Leu Phe Asn
 1               5                  10                  15

Tyr Lys Val Val Arg Val Lys Pro Phe Ser Val Ala Pro Thr Arg
            20                  25                  30

Ile Ala Arg Pro Val Ile Ser Thr Arg Thr His Arg Glu Lys Arg
            35                  40                  45

Ala Val Gly Leu Gly Met Leu Phe Leu Gly Val Leu Ser Ala Ala
            50                  55                  60

Gly Ser Thr Met Gly Ala Ala Ala Thr Thr Leu Ala Val Gln Thr
            65                  70                  75

His Thr Leu Leu Lys Gly Ile Val Gln Gln Gln Asp Asn Leu Leu
            80                  85                  90

Arg Ala Ile Gln Ala Gln Gln Gln Leu Leu Arg Leu Ser Xaa Trp
            95                  100                 105

Gly Ile Arg Gln Leu Arg Ala Arg Leu Leu Ala Leu Glu Thr Leu
            110                 115                 120

Leu Gln Asn Gln Gln Leu Leu Ser Leu Trp Gly Cys Lys Gly Lys
            125                 130                 135

Leu Val Cys Tyr Thr Ser Val Lys Trp Asn Arg Thr Trp Ile Gly
            140                 145                 150

Asn Glu Ser Ile Trp Asp Thr Leu Thr Trp Gln Glu Trp Asp Arg
            155                 160                 165

Gln Ile Ser Asn Ile Ser Ser Thr Ile Tyr Glu Glu Ile Gln Lys
            170                 175                 180

Ala Gln Val Gln Gln Glu Gln Asn Glu Lys Lys Leu Leu Glu Leu
            185                 190                 195

Asp Glu Trp Ala Ser
        200

(2) INFORMATION FOR SEQ ID NO: 105:

(i) SEQUENCE CHARACTERISTICS:
        (A) LENGTH: 204 amino acids
```

```
            (B) TYPE: Amino Acid
            (D) TOPOLOGY: Linear (xi) SEQUENCE DESCRIPTION: SEQ ID NO: 105:

Val Gly Gly Asp Met Lys Asp Ile Trp Arg Thr Lys Leu Tyr Asn
 1               5                  10                  15

Tyr Lys Val Val Gln Ile Lys Pro Phe Ser Val Ala Pro Thr Lys
                20                  25                  30

Met Ser Arg Pro Ile Ile Asn Ile His Thr Pro His Arg Glu Lys
                35                  40                  45

Arg Ala Val Gly Leu Gly Met Leu Phe Leu Gly Val Leu Ser Ala
                50                  55                  60

Ala Gly Ser Thr Met Gly Ala Ala Thr Ala Leu Thr Val Arg
                65                  70                  75

Thr His Ser Val Leu Lys Gly Ile Val Gln Gln Gln Asp Asn Leu
                80                  85                  90

Leu Arg Ala Ile Gln Ala Gln Gln His Leu Leu Arg Leu Ser Val
                95                 100                 105

Trp Gly Ile Arg Gln Leu Arg Ala Arg Leu Gln Ala Leu Glu Thr
               110                 115                 120

Leu Ile Gln Asn Gln Gln Arg Leu Asn Leu Trp Gly Cys Lys Gly
               125                 130                 135

Lys Leu Ile Cys Tyr Thr Ser Val Lys Trp Asn Thr Ser Trp Ser
               140                 145                 150

Gly Arg Tyr Asn Asp Asp Ser Ile Trp Asp Asn Leu Thr Trp Gln
               155                 160                 165

Gln Trp Asp Gln His Ile Asn Asn Val Ser Ser Ile Ile Tyr Asp
               170                 175                 180

Glu Ile Gln Ala Ala Gln Asp Gln Gln Glu Lys Asn Val Lys Ala
               185                 190                 195

Leu Leu Glu Leu Asp Glu Trp Ala Ser
               200                 204

(2) INFORMATION FOR SEQ ID NO: 106:

(i) SEQUENCE CHARACTERISTICS:
        (A) LENGTH: 204 amino acids
        (B) TYPE: Amino Acid
        (D) TOPOLOGY: Linear (xi) SEQUENCE DESCRIPTION: SEQ ID NO: 106:

Thr Gly Gly Asn Met Lys Asp Ile Trp Arg Ser Glu Leu Tyr Lys
 1               5                  10                  15

Tyr Lys Val Val Arg Ile Glu Pro Leu Ser Val Ala Pro Thr Lys
                20                  25                  30

Ala Arg Arg His Thr Val Ala Arg Gln Lys Asp Arg Gln Lys Arg
                35                  40                  45

Ala Ala Phe Gly Leu Gly Ala Leu Phe Leu Gly Phe Leu Gly Ala
                50                  55                  60

Ala Gly Ser Thr Met Gly Ala Ala Ala Val Thr Leu Thr Val Gln
                65                  70                  75

Ala Arg Gln Leu Leu Ser Gly Ile Val Gln Gln Gln Asn Asn Leu
                80                  85                  90

Leu Lys Ala Ile Glu Ala Gln Gln His Leu Leu Gln Leu Ser Ile
                95                 100                 105

Trp Gly Val Lys Gln Leu Gln Ala Arg Leu Leu Ala Val Glu Arg
```

-continued

```
                110                 115                 120
Tyr Leu Gln Asp Gln Gln Ile Leu Gly Leu Trp Gly Cys Ser Gly
                125                 130                 135
Lys Ala Val Cys Tyr Thr Thr Val Pro Trp Asn Asn Ser Trp Pro
                140                 145                 150
Gly Ser Asn Ser Thr Asp Asp Ile Trp Gly Asn Leu Thr Trp Gln
                155                 160                 165
Gln Trp Asp Lys Leu Val Ser Asn Tyr Thr Gly Lys Ile Phe Gly
                170                 175                 180
Leu Leu Glu Glu Ala Gln Ser Gln Gln Glu Lys Asn Glu Arg Asp
                185                 190                 195
Leu Leu Glu Leu Asp Gln Trp Ala Ser
                200             204
```

(2) INFORMATION FOR SEQ ID NO: 107:

(i) SEQUENCE CHARACTERISTICS:
        (A) LENGTH: 30 amino acids
        (B) TYPE: Amino Acid
        (D) TOPOLOGY: Linear (xi) SEQUENCE DESCRIPTION: SEQ ID NO: 107:

```
Glu Trp Asp Arg Glu Ile Asn Asn Tyr Thr Ser Leu Ile His Ser
 1               5                  10                  15
Leu Ile Glu Glu Ser Gln Asn Gln Gln Glu Lys Asn Glu Gln Glu
                20                  25                  30
```

(2) INFORMATION FOR SEQ ID NO: 108:

(i) SEQUENCE CHARACTERISTICS:
        (A) LENGTH: 36 amino acids
        (B) TYPE: Amino Acid
        (D) TOPOLOGY: Linear (xi) SEQUENCE DESCRIPTION: SEQ ID NO: 108:

```
Tyr Thr Ser Leu Ile His Ser Leu Ile Glu Glu Ser Gln Asn Gln
 1               5                  10                  15
Gln Glu Lys Asn Glu Gln Glu Leu Leu Glu Leu Asp Lys Trp Ala
                20                  25                  30
Ser Leu Trp Asn Trp Phe
                35  36
```

(2) INFORMATION FOR SEQ ID NO: 109:

(i) SEQUENCE CHARACTERISTICS:
        (A) LENGTH: 46 amino acids
        (B) TYPE: Amino Acid
        (D) TOPOLOGY: Linear (xi) SEQUENCE DESCRIPTION: SEQ ID NO: 109:

```
Trp Met Glu Trp Glu Arg Glu Ile Asp Asn Tyr Thr Xaa Leu Ile
 1               5                  10                  15
Tyr Thr Leu Ile Glu Glu Ser Gln Asn Gln Gln Glu Lys Asn Glu
                20                  25                  30
Gln Glu Leu Leu Glu Leu Asp Lys Trp Ala Ser Leu Trp Asn Trp
                35                  40                  45
Phe
 46
```

(2) INFORMATION FOR SEQ ID NO: 110:

(i) SEQUENCE CHARACTERISTICS:
    (A) LENGTH: 46 amino acids
    (B) TYPE: Amino Acid
    (D) TOPOLOGY: Linear (xi) SEQUENCE DESCRIPTION: SEQ ID NO: 110:

Trp Leu Gln Trp Asp Lys Glu Ile Ser Asn Tyr Thr Xaa Ile Ile
 1               5                  10                  15

Tyr Asn Leu Ile Glu Glu Ser Gln Asn Gln Gln Glu Lys Asn Glu
                 20                  25                  30

Gln Asp Leu Leu Ala Leu Asp Lys Trp Ala Asn Leu Trp Asn Trp
                 35                  40                  45

Phe
46

(2) INFORMATION FOR SEQ ID NO: 111:

(i) SEQUENCE CHARACTERISTICS:
        (A) LENGTH: 46 amino acids
        (B) TYPE: Amino Acid
        (D) TOPOLOGY: Linear (xi) SEQUENCE DESCRIPTION: SEQ ID NO: 111:

Trp Met Gln Trp Asp Arg Glu Ile Ser Asn Tyr Thr Asp Thr Ile
 1               5                  10                  15

Tyr Arg Leu Leu Glu Asp Ser Gln Asn Gln Gln Glu Arg Asn Glu
                 20                  25                  30

Lys Asp Leu Leu Ala Leu Asp Ser Trp Lys Asn Leu Trp Asn Trp
                 35                  40                  45

Phe
46

(2) INFORMATION FOR SEQ ID NO: 112:

(i) SEQUENCE CHARACTERISTICS:
        (A) LENGTH: 46 amino acids
        (B) TYPE: Amino Acid
        (D) TOPOLOGY: Linear (xi) SEQUENCE DESCRIPTION: SEQ ID NO: 112:

Trp Met Glu Trp Glu Arg Glu Ile Asp Asn Tyr Thr Gly Leu Ile
 1               5                  10                  15

Tyr Ser Leu Ile Glu Glu Ser Gln Ile Gln Gln Glu Lys Asn Glu
                 20                  25                  30

Lys Glu Leu Leu Glu Leu Asp Lys Trp Ala Ser Leu Trp Asn Trp
                 35                  40                  45

Phe
46

(2) INFORMATION FOR SEQ ID NO: 113:

(i) SEQUENCE CHARACTERISTICS:
        (A) LENGTH: 40 amino acids
        (B) TYPE: Amino Acid
        (D) TOPOLOGY: Linear (xi) SEQUENCE DESCRIPTION: SEQ ID NO: 113:

```
Trp Ile Glu Trp Glu Arg Glu Ile Ser Asn Tyr Thr Asn Gln Ile
 1           5                  10                      15

Tyr Glu Ile Leu Thr Glu Ser Gln Asn Gln Gln Asp Arg Asn Glu
            20                  25                      30

Lys Asp Leu Leu Glu Leu Asp Lys Trp Ala
                35              40
```

What is claimed is:

1. A compound selected from the group consisting of:

the compound represented by Formula (1):

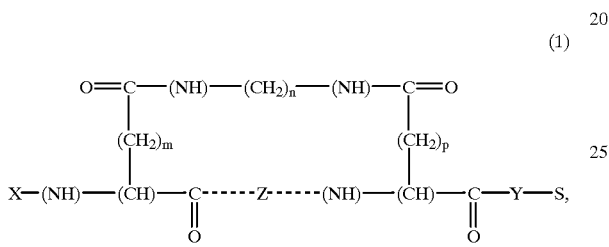

(1)

wherein S is absent or is a macromolecule, X is hydrogen or is any amino acid or amino acid sequence, Y is absent, or is hydroxyl if S is absent, or is any amino acid or amino acid sequence, m and p are independently selected from the integers 0 to 6 inclusive, provided that m+p is less than or equal to 6, and n is any integer in the range defined by (7−(m+p)) to (9−(m+p)) inclusive, provided that n is greater than 1;

the compound represented by Formula (6):

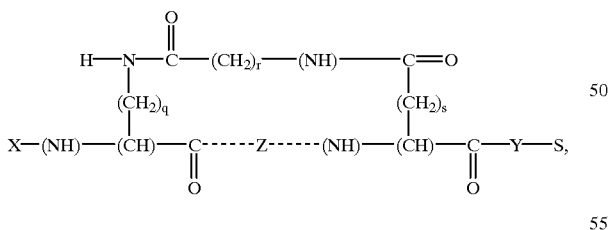

(6)

wherein S is absent or is a macromolecule, X is hydrogen or is any amino acid or amino acid sequence, Y is absent, or is hydroxyl if S is absent, or is any amino acid or amino acid sequence, q is selected from the integers 1 to 7 inclusive, s is selected from the integers 0 to 6 inclusive, provided that q+s is less than or equal to 7, and r is any integer in the range defined by (7−(q+s)) to (9−(q+s)) inclusive, provided that r is greater than 0;

the compound represented by Formula (11):

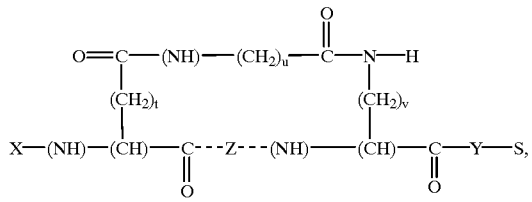

(11)

wherein S is absent or is a macromolecule, X is hydrogen or is any amino acid or amino acid sequence, Y is absent, or is hydroxyl if S is absent, or is any amino acid or amino acid sequence, t is selected from the integer 0 to 6 inclusive, and v is selected from the integers 1 to 7 inclusive, provided that t+v is less than or equal to 7; and u is any integer in the range defined by (7−(t+v)) to (9−(t+v)) inclusive, provided that u is greater than 0; and the compound represented by Formula (16):

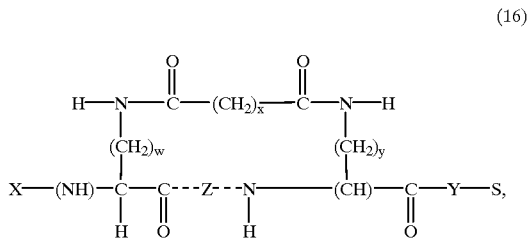

(16)

wherein S is absent or is a macromolecule, X is hydrogen or is any amino acid or amino acid sequence, Y is absent, or is hydroxyl if S is absent, or is any amino acid or amino acid sequence, w and y are independently selected from the integers 1 to 7 inclusive, provided that w+y is less than or equal to 8, and x is any integer in the range defined by (7−(w+y)) to (9−(w+y)) inclusive, provided that x is greater than or equal to 0, wherein Z is an amino acid sequence consisting of six amino acids, wherein the internal sequence of six amino acids has the form gabcde, defgab, or cdefga and is selected from the group of sequences consisting of a sequence of six contiguous amino acids in HIV-1LAI strain gp41 amino acid sequence 633 to 678, in its homolog sequence from another HIV strain, in a consensus sequence of its homolog sequences from any one HIV clade, and amino acid substituted variant thereof, in which amino acid 633 or its corresponding amino acid in the homolog, consensus or variant sequence is assigned position a of a repeating abcdefg assignment.

2. The compound of claim 1, further comprising S' when S is absent and X is any amino acid or amino sequence, wherein S' is a macromolecule attached to X.

3. A method to therapeutically treat a mammal at risk for or infected with HIV, comprising administering a therapeutically effective amount of a compound of claim 1.

4. The method of claim 3, wherein the compound comprises internal six amino acid sequences from different HIV strains or HIV clades.

* * * * *

UNITED STATES PATENT AND TRADEMARK OFFICE
CERTIFICATE OF CORRECTION

PATENT NO. : 6,271,198 B1
DATED : August 7, 2001
INVENTOR(S) : Andrew C. Braisted et al.

It is certified that error appears in the above-identified patent and that said Letters Patent is hereby corrected as shown below:

Column 9,
Line 29, "FIGS 23A and 23D" should read -- FIGS. 23A through 23D --.
Lines 30-31, "series I-VII (FIG. 23A) and VIII-XII (FIG. 23B)" should read
-- series I-III (FIG. 23A), IV-VI (FIG. 23B), VII-IX (FIG. 23C) X-XII (FIG. 23D) --.

Column 69,
Line 64, "(see FIGS. 16A-16G and 17)." should read -- (see FIGS. 16A-16M and 17). --.

Column 70,
Line 42, "FIGS 16A-16G." should read -- FIGS. 16A-16M. --.

Column 72,
Line 59, "FIGS 22 and 23A and B." should read -- FIGS. 22 and 23A through 23D. --.
Line 67, "FIG. 23A and 23D." should read -- FIG. 23A through 23D. --.

Column 73,
Line 1, "FIG. 23A and 23D." should read -- FIG. 23A through 23D. --.
Lines 5-6, 10-11 and 18-19, "FIG. 23A and 23D." should read -- FIG. 23A through 23D --.
Lines 15-16, "FIGS. 23A and 23B." should read -- FIG. 23A through 23D --.

Signed and Sealed this

Seventh Day of May, 2002

JAMES E. ROGAN
Director of the United States Patent and Trademark Office

Attest:

Attesting Officer